US007795260B2

(12) United States Patent
Barrasa et al.

(10) Patent No.: US 7,795,260 B2
(45) Date of Patent: *Sep. 14, 2010

(54) SYNTHESIS OF NATURALLY OCCURRING ECTEINASCIDINS AND RELATED COMPOUNDS

(75) Inventors: Valentin Martinez Barrasa, Madrid (ES); Pilar Gallego, Madrid (ES); Carmen Cuevas, Madrid (ES); Simon Munt, Madrid (ES); Ignacio Manzanares, Madrid (ES); Roberto Menchaca, Madrid (ES); Natividad Rodriguez, Madrid (ES); Alberto Rodriguez, Madrid (ES)

(73) Assignee: Pharma Mar, S.A., Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 12/273,919

(22) Filed: Nov. 19, 2008
(Under 37 CFR 1.47)

(65) Prior Publication Data
US 2009/0163507 A1 Jun. 25, 2009

Related U.S. Application Data

(63) Continuation of application No. 10/503,106, filed as application No. PCT/GB03/00481 on Feb. 4, 2003.

(30) Foreign Application Priority Data
Feb. 4, 2002 (GB) ................ 0202544.3

(51) Int. Cl.
*A01N 43/58* (2006.01)
*A01N 43/30* (2006.01)
*A61K 31/50* (2006.01)
*A61K 31/495* (2006.01)
*C07D 241/36* (2006.01)
*C07D 271/00* (2006.01)
*C07D 487/00* (2006.01)
*C07D 491/00* (2006.01)
*C07D 495/00* (2006.01)
*C07D 497/00* (2006.01)
*C07D 498/00* (2006.01)
*C07D 513/00* (2006.01)

(52) U.S. Cl. .................... 514/250; 544/338
(58) Field of Classification Search ............... None
See application file for complete search history.

(56) References Cited

U.S. PATENT DOCUMENTS

| 5,089,273 | A | 2/1992 | Rinehart et al. |
| 5,149,804 | A | 9/1992 | Rinehart et al. |
| 5,256,663 | A | 10/1993 | Rinehart et al. |
| 5,478,932 | A | 12/1995 | Rinehart et al. |
| 5,552,544 | A | 9/1996 | Brana et al. |
| 5,654,426 | A | 8/1997 | Rinehart et al. |
| 5,721,362 | A | 2/1998 | Corey et al. |
| 5,908,835 | A | 6/1999 | Bissery |
| 5,985,876 | A | 11/1999 | Rinehart et al. |
| 6,124,292 | A | 9/2000 | Corey |
| 6,124,293 | A | 9/2000 | Rinehart et al. |
| 6,153,590 | A | 11/2000 | Andersen et al. |
| 6,316,214 | B1 | 11/2001 | Rinehart et al. |
| 6,348,467 | B1 | 2/2002 | Corey |
| 6,544,560 | B1 | 4/2003 | Bullent et al. |
| 6,569,859 | B1 | 5/2003 | Corey |
| 6,686,470 | B2 | 2/2004 | Danishefsky et al. |
| 6,712,023 | B2 | 3/2004 | Bullent et al. |
| 6,815,544 | B2 | 11/2004 | Corey |
| 6,867,334 | B2 | 3/2005 | Floriano et al. |
| 7,115,743 | B2 | 10/2006 | Rinehart |
| 7,202,361 | B2 | 4/2007 | Flores et al. |
| 7,241,892 | B1 | 7/2007 | Cuevas et al. |
| 7,247,629 | B2 | 7/2007 | Manzanares et al. |
| 7,309,601 | B2 | 12/2007 | Perez Esteban et al. |
| 7,410,969 | B2 | 8/2008 | Manzanares et al. |
| 7,420,051 | B2 | 9/2008 | Francesch |
| 7,524,956 | B2 | 4/2009 | Cuevas et al. |
| 7,622,458 | B2 | 11/2009 | Rybak |
| 2002/0137663 | A1 | 9/2002 | Forman et al. |
| 2003/0216397 | A1 | 11/2003 | Flores et al. |
| 2004/0002602 | A1 | 1/2004 | Francesch |
| 2004/0019027 | A1 | 1/2004 | Forman et al. |
| 2004/0019056 | A1 | 1/2004 | Manzanares et al. |
| 2004/0108086 | A1 | 6/2004 | Takahashi et al. |
| 2006/0030571 | A1 | 2/2006 | Rinehart et al. |

(Continued)

FOREIGN PATENT DOCUMENTS

EP 0 309 477 B1 11/1991

(Continued)

OTHER PUBLICATIONS

Arai, T. et al., "The Structure of a Novel Antitumor Antibiotic, Saframycin A", *Experientia*, vol. 36, pp. 1025-1027 (1980).
Arai, Tadashi et al., "Directed Biosynthesis of New Saframycin Derivatives with Resting Cells of *Streptomyces lavendulae*", *Antimicrobial Agents and Chemotherapy*, vol. 28, No. 1, pp. 5-11 (1985).
Arai, Tadashi et al., "Increased Production of Saframycin A and Isolation of Saframycin S", *The Journal of Antibiotics*, vol. XXXIII, No. 9, pp. 951-960 (1980).
Arai, Tadashi et al., "Isoquinolineinones from Actinomycetes and Sponges", *The Alkaloids Chemistry and Pharmacology*, vol. XXI, pp. 56-100 (1983).
Arai, Tadashi et al., "New Antibiotics, Safraycins A, B, C, D and E", *The Journal of Antibiotics*, vol. XXX, No. 11, pp. 1015-1018 (1977).
Asaoka, Takemitsu et al., "A New Saframycin, Saframycin R", *The Journal of Antibiotics*, vol. XXXV, No. 12, pp. 1708-1710 (1982).

(Continued)

*Primary Examiner*—James O Wilson
*Assistant Examiner*—Noble Jarrell
(74) *Attorney, Agent, or Firm*—Kenneth H. Sonnenfeld; King & Spalding LLP

(57) ABSTRACT

Ecteinascidin compounds with a quinone ring for ring E are active as anti-cancer agents. Related processes and compounds are provided.

22 Claims, No Drawings

U.S. PATENT DOCUMENTS

| | | | |
|---|---|---|---|
| 2006/0094687 | A1 | 5/2006 | Beijnen et al. |
| 2006/0106021 | A1 | 5/2006 | Martinez et al. |
| 2007/0004691 | A1 | 1/2007 | Donald et al. |
| 2007/0082856 | A1 | 4/2007 | Gianni et al. |
| 2007/0128201 | A1 | 6/2007 | D'Incalci et al. |
| 2008/0234279 | A1 | 9/2008 | Rinehart et al. |

FOREIGN PATENT DOCUMENTS

| | | |
|---|---|---|
| JP | 59-225189 | 12/1984 |
| JP | 60-84288 | 5/1985 |
| WO | WO 87/07610 | 12/1987 |
| WO | WO 92/09607 | 6/1992 |
| WO | WO 98/12198 | 3/1998 |
| WO | WO 98/46080 | 10/1998 |
| WO | WO 99/52138 | 10/1999 |
| WO | WO 99/58125 | 11/1999 |
| WO | WO 00/18233 | 4/2000 |
| WO | WO 00/69441 | 11/2000 |
| WO | WO 00/69862 | 11/2000 |
| WO | WO 01/77115 | 10/2001 |
| WO | WO 01/87894 | 11/2001 |
| WO | WO 01/87895 | 11/2001 |
| WO | WO 02/36135 | 5/2002 |
| WO | WO 02/064843 | 8/2002 |
| WO | WO 03/008423 | 1/2003 |
| WO | WO 03/020259 | 3/2003 |
| WO | WO 03/039571 | 5/2003 |
| WO | WO 2005/049029 | 6/2005 |
| WO | WO 2005/049030 | 6/2005 |
| WO | WO 2005/049031 | 6/2005 |
| WO | WO 2006/035244 | 4/2006 |
| WO | WO 2006/046080 | 5/2006 |
| WO | WO 2009/050303 | 4/2009 |
| WO | WO 2009/138509 | 11/2009 |
| WO | WO 2009/140675 | 11/2009 |

OTHER PUBLICATIONS

Barton, Derek H.R. et al, "Synthesis and Properties of a Series of Sterically Hindered Guanidine Bases[1]", *Journal of the Chemical Society Perkin Transactions I*, No. 9, pp. 2085-2090 (1982).

Brown, J.M., "NCI's Anticancer Drug Screening Program May Not Be Selecting for Clinically Active Compounds," Oncol. Res. 9(5):213-215 (1997).

Cable, Karl M. et al., "The Biosynthesis of Tuberin from Tyrosine and Glycine; Observations on the Stereochemistry Associated with the Conversion of Glycine through Methylenetetrahydrofolate into Methylenetetrahydrofolate", *Journal of the Chemical Society Perkins Transactions I*, No. 7, pp. 1593-1598 (1987).

Cancer definition, http://www.medterms.com/script/main/art.asp?articlekey=2580, accessed Nov. 27, 2007.

Cecil Texbook of Medicine, 21st Edition (2000), Goldman & Bennett (Editors), W.B. Saunders Company (Publisher), Chapter 198, pp. 1060-1074.

Cooper, Raymond et al., "Structure of the Quinone Antibiotic EM5519 and the Behavior of Quinones in Fast Atom Bombardment Mass Spectrometry", *The Journal of Antibiotics*, vol. XXXVIII, No. 1, pp. 24-30 (1985).

Corey, E.J. et al., "Enantioselective Total Synthesis of Ecteinascidin 743", *Journal of the American Chemical Society*, vol. 118, No. 38, pp. 9202-9203 (1996).

Cuevas, Carmen et al., "Synthesis of Ecteinascidin ET-743 and Phthalascidin Pt-650 from Cyanosafracin B", *Organic Letters*, vol. 2, No. 16, pp. 2545-2548 (2000).

Draetta, G. and Pagano, M., "Annual Reports in Medicinal Chemistry vol. 31," Academic Press, San Diego, pp. 241-246 (1996).

Eckhardt, S.G. et al., "Activity of ecteinascidin, a novel marine cytotoxic, against primary human tumor colony-forming units ", *Proceedings of the American Association for Cancer Research*, vol. 37, #2791, pp. 409 (1996).

Faircloth, G. et al., "Ecteinascidin-743 (ET743): in vitro (IVT) and in vivo (INV) Results in Tumor Models", *The European Journal of Cancer*, vol. 32A, Supp. 1, #24 O, pp. S5 (1996).

Flam, Faye, "Chemical Prospectors Scour the Seas for Promising Drugs", *Science*, vol. 266, pp. 1324-1325 (1994).

Frincke, James M. et al., "Antimicrobial Metabolites of the Sponge Reniera sp.", *Journal of the American Chemical Society*, vol. 104, pp. 265-269 (1982).

Fukuyama, Tohru et al., "Stereocontrolled Total Synthesis of (±)-Saframycin B", *Journal of American Chemical Society*, vol. 104, pp. 4957-4958 (1982).

Fukuyama, Tohru et al., "Total Synthesis of (±)-Saframycin A", *Journal of American Chemical Society*, vol. 112, pp. 3712-3713 (1990).

Garcia-Rocha, M. et al., "Characterisation of antimitotic products from marine organisms that disorganize the microtubule network: ecteinascidin 743, isohomohalichondrin-B and LL-15", *British Journal of Cancer*, vol. 73, pp. 875-883 (1996).

Greene et al., "Protective Groups in Organic Synthesis", 1999, table of contents for chapters 2 and 7.

Goldwasser, F, et al. "Characterization of ecteinascidin 743-induced DNA damages in cells", *Proceedings of the American Association for Cancer Research*, vol. 39, #4066, pp. 598 (1998).

Guan, Yue et al., "Molecular and Crystal Structures of Ecteinascidins: Potent Antitumor Compounds from the Caribbean Tunicate Ecteinascidia Turbinata", *Journal of Biomolecular Structure & Dynamics*, vol. 10, No. 5, pp. 793-818 (1993).

Gulavita, Nanda K., et al., "Antimicrobial Constituents of a Sponge-Nudibranch Pair from Sri Lanka", *Bioactive Compounds from Marine Organisms*, Oxford & IBH Publishing Co. Pvt. Ltd., pp. 229-233 (1991).

He, Hai-yin et al., "Renieramycins E and F from the Sponge Reniera sp.: Reassignment of the Stereochemistry of the Renieramycins", *The Journal of Organic Chemistry*, vol. 54, No. 24, pp. 5822-5824 (1989).

Hendriks, H.R. et al., "High antitumor activity of ET743 in human tumor xenograft models", *Proceedings of the American Association for Cancer Research*, vol. 37, #2653, pp. 389 (1996).

Ikeda, Yoshifumi et al., "Safracins, New Antitumor Antibiotics I. Producing Organism, Fermentation and Isolation", *The Journal of Antibiotics*, vol. XXXVI, No. 10, pp. 1279-1283 (1983).

Ikeda, Yoshifumi et al., "Safracins, New Antitumor Antibiotics I. Producing Organism, Fermentation and Isolation", *The Journal of Antibiotics*, vol. XXXVI, No. 10, pp. 1284-1289 (1983).

Internal Medicine, 4th Edition, Editor-in-Chief Jay Stein, Chapters 71-72, pp. 699-715.

Ito, Yoichiro, "High-Speed Countercurrent Chromatography", *Critical Reviews in Analytical Chemistry*, vol. 17, No. 1, pp. 65-143 (1986).

IUPAC Gold Book, http:/goldbook.iupac.org/A00123.html, accessed Dec. 26, 2007.

Koenig, Karl E., "The Applicability of Asymmetric Homogeneous Catalytic Hodrogenation", *Asymmetric Synthesis*, Ed. Morrison, Academic Press, Inc., Orlando, FL, vol. 5, pp. 71 (1985).

Kofron, William G. et al., "A Convenient Method for Estimation of Alkyllithium Concentrations", *The Journal of Organic Chemistry*, vol. 41, No. 10, pp. 1879-1880 (1976).

Kubo, Akinori et al., "Structure of Saframycin D, A New Dimeric Isoquinolinequinone Antibiotic", *Chem. Pharm. Bull.*, vol. 35, No. 1, pp. 440-442 (1987).

Kuffel, M.J. et al., "Cytochrome P450 catalyzed metabolism of Ecteinascidin 743 by rat and human liver microsomes", *Proceedings of the American Association for Cancer Research*, vol. 38, #4003, pp. 596 (1997).

Lichter, W. et al., "Biological Activities Exerted by Extracts of Ecteinascidia Turbinata", *Food and Drugs from the Sea Proceedings*, pp. 117-127 (1972).

Lown, J. William et al., "Molecular Mechanisms of Binding and Single-Strand Scission of Deoxyribonucleic Acid by the Antitumor Antibiotics Saframycins A and C", *Biochemistry*, vol. 21, No. 3, pp. 419-428 (1982).

Lown, J. William et al., "Structure and Confirmation of Saframycin R Determined by High Field $^1$H and $^{13}$C NMR and its Interactions with DNA in Soloution", *The Journal of Antibiotics*, vol. XXXVI, No. 9, pp. 1184-1194 (1983).

Martinez et al., "A New, More Efficient, and Effective Process for the Synthesis of a Key Pentacyclic Intermediate for Production of Ecteinascidin and Phthalascidin Antitumor Agents", *Organic Letters*, 2(7):993-996 (2000).

Martinez et al., "Enantioselective Synthesis of Saframycin A and Evaluation of Antitumor Activity Relative to Ecteinascidin/Saframycin Hybirds", *Organic Letters*, 1(7):75-77 (1999).

Martinez, Eduardo J. et al., "Phthalascidin, a synthetic antitumor agent with potency and mode of action comparable to ecteinascidin 743", *Chemistry*, vol. 96, pp. 3496-3501 (1999).

Mikami, Yuzuru et al., "Structural Studies on Minor Components of Saframycin Group Antibiotics Saframycins F, G and H", *The Journal of Antibiotics*, vol. XLI, No. 6, pp. 734-740 (1988).

Mirsalis, J.C. et al., "Toxicity of Ecteinascidin 743 in female Fischer-344 rats administered i.v. in a multiple-dose regimen", *Proceedings of the American Association for Cancer Research*, vol. 38, #2073, pp. 309 (1997).

Moore, B.M. et al., "The NMR model of an ecteinascidin 743-DNA adduct", *Proceedings of the American Association for Cancer Research*, vol. 38, #2105, pp. 314 (1997).

Myers et al., "A Concise, Stereocontrolled Syntheis of (-)-Saframycin A by the Directed Condensation of α–Amino Aldehyde Precursors", *J. Am. Chem. Soc.*, 121:10828-10829 (1999).

Nakagawa, Masako et al., "Total Synthesis of (−)-Eudistomin L and (−-Debromoeudistomin L", *Journal of the American Chemical Society*, vol. 111, No. 7, pp. 2721-2722 (1989).

Parulekar, A.H. et al., "Bioactivity and Chemical Ecology of Some Interdial Animals", *Bioactivity and Chemical Ecology*, pp. 29-35.

Pommier, Yves et al., "DNA Sequence- and Structure-Selective Alkylation of Guanine N2 in the DNA Minor Groove by Ecteinascidin 743, a Potent Antitumor Compound from the Caribbean Tunicate Ecteinascidia Turbinata", *Biochemistry*, vol. 35, pp. 13303-13309 (1996).

Pretsch et al., *Tables of Spectral Data for Structure Determination of Organic Compounds*, pp. H125 (1983).

Reid, Joel M. et al., "Preclinical pharmacology of ecteinascidin 729, a marine natural product with potent antitumor activity", *Cancer Chemotherapy and Pharmacology*, vol. 38, No. 4, pp. 329-334 (1996).

Remers, William A., "Saframycins, Renieramycins, and Safracins", *The Chemistry of Antitumor Antibiotics*, vol. 2, pp. 93-119 (1988).

Rinehart et al., "Novel Bioactive Natural Products from Marine Organisms", *Topics in Pharmaceutical Sciences 1989*, pp. 613-626, D.D. Breimer, D.J.A. Cromwelin, K.K. Midha, Eds., Amsterdam Medical Press B.V. Noordwijk, The Netherlands (1989).

Rinehart, Kenneth L. et al., "Applications of High-Resolution Tandem FAB Mass Spectrometry", *Biological Mass Spectrometry*, eds. Burlingame et al., Elsevier Amsterdam, pp. 233-258 (1990).

Rinehart, Kenneth L. et al., "Bioactive Compounds from Aquatic and Terrestrial Sources", *Journal of Natural Products*, vol. 53, No. 4, pp. 771-792 (1990).

Rinehart, Kenneth L. et al., "Biologically active natural products", *Pure and Applied Chemistry*, vol. 62, No. 7, pp. 1277-1280 (1990).

Rinehart, Kenneth L. et al., "Ecteinascidins 729, 743, 759A , 759B, and 770: Potent Antitumor Agents from the Caribbean Tunicate Exteinascidia Turbinata", *The Journal of Organic Chemistry*, vol. 55, No. 15, pp. 4512-4515 (1990).

Rinehart, Kenneth L., "Antitumor Compounds from Tunicates", *Medicinal Research Reviews*, vol. 20, No. 1, pp. 1-27 (2000).

Saito, Naoki et al., "Synthesis of Saframycins. 3. Preparation of a Key Tricyclic Lactam Intermediate to Saframycin A", *The Journal of Organic Chemistry*, vol. 54, No. 22, pp. 5391-5395 (1989).

Sakai, Ryuichi et al., "Additional antitumor ecteinascidins from a Caribbean tunicate: Crystal structures and activities in vivo", *Proceedings of the National Academy of Sciences*, vol. 89, No. 23, pp. 11456-11460 (1992).

Sakai, Ryuichi et al., "Ecteinascidins: Putative Biosynthetic Precursors and Absolute Stereochemistry", *Journal of the American Chemical Society*, vol. 118, No. 38, pp. 9017-9023 (1996).

Shamma, Maurice et al., *Carbon-13 NMR Shift Assignments of Amines and Alkaloids*, pp. 206 (1979).

Still, W. Clark et al., "Rapid Chromatographic Technique for Preparative Separations with Moderate Resolution", *Journal of Organic Chemistry*, vol. 43, No. 14, pp. 2923-2925 (1978).

Takahaski, Katsuhiro et al., "Microbial Conversion of Saframycin A to 25-Dihydrosaframycin A and 21-Decyano-25-Dihydrosaframycin A (25-Dihydrosaframycin B) and Their Biological Activities", *The Journal of Antibiotics*, vol. XXXV, No. 2, pp. 196-202 (1982).

Takahaski, Katsuhiro, "New Antibiotics, Saframycins A, B, C, D and E", *The Journal of Antibiotics*, vol. XXX, No. 11, pp. 1015-1018 (1977).

Trowitzsch-Kienast, Wolfram et al., "Isolierung und Strukturaufklarung der Saframycine Mx 1 und Mx 2, neue antitumoraktive Antibiotika aus Myxococcus xanthus", Liebigs Ann. Chem., vol. XXXV, pp. 475-481 (1988).

Witten, Jane L. et al., "Structures of Two Cockroach Neuropeptides Assigned by Fast Atom bombardment Mass Spectrometry", *Biochemical and Biophysical Research Communications*, vol. 124, No. 2, pp. 350-358 (1984).

Calabresi et al., "Chemotherapy of Neoplastic Diseases", Goodman & Gilman's The Pharmacological Basis of Therapeutics, 9th ed. New York: McGraw-Hill, 1996, pp. 1225-1229.

Cecil Textbook of Medicine (Bennet, J.C. and Plum, F., eds.) 20th Edition, vol. 1, pp. 1004-1010 (1996).

Cecil Textbook of Medicine (Goldman & Bennett, eds.) 21st Edition, Chapter 198, 2000, pp. 1060-1074.

Fregeau, Nancy Louise, "Biologically Active Compounds froma Clam and a Tunicate", Thesis, University of Illinois art Urbana-Champaign, 1992.

Holt, Tom Grady, "The Isolation and Structural Characterization of the Ecteinascidins", Thesis, University of Illinois art Urbana-Champaign, 1986.

Internal Medicine, $4^{th}$ Edition, Editor-in-Chief Jay Stein, Chapters 71-72, 1994, pp. 699-715.

Kania, "The first Enantioselective Total Synthesis of Dolabellatrienone and Ecteinascidin 743", Harvard University, Sep. 1997, pp. 1-225.

Morales, Jose Javier, "Marine Natural Products Chemistry of a Caribbean Tunicate and a Palau Sponge", University of Illinois art Urbana-Champaign, 1999.

Sakai, Ryuichi, "Biologically Active Compounds from Tunicates and a Sponge", Thesis, University of Illinois art Urbana-Champaign, 1991.

Sparidans, Rolf W. et al., "Search for metabolites of ecteinascidin 743, a novel, marine-derived, anti-cancer agent, in man." *Anti-Cancer Drugs*, vol. 12, pp. 653-666.

Valoti et al. Clin. Cancer Res. 4(8): 1977-83 (1998).

Wright, Amy E. et al., "Antitumor Tetrahydroisoquinoline Alkaloids from the Colonial Ascidian Ecteinascidia Turbinata", *The Journal of Organic Chemistry*, vol. 55, No. 15, pp. 4508-4512 (1990).

Yazawa, Katsukiyo et al., "Bioconversions of Saframycin A Specific to some Genera of Actinomycetes", *The Journal of Antibiotics*, vol. XXXV, No. 7, pp. 915-917 (1982).

Yazawa, Katsukiyo et al., "Isolation and Structural Elucidation of New Saframycins Y3, Yd-1, Yd-2, Ad-1, Y2b and Y2b-d", *The Journal of Antibiotics*, vol. XXXIX, No. 12, pp. 1639-1650 (1986).

Zmijewski, Milton J., Jr. et al., "The in vitro Interaction of Naphthyridinomycin with Deoxyribonucleic Acids", *Chemico-Biological Interactions*, vol. 52, No. 3, pp. 361-375 (1985).

Bonfanti et al., Effect of Ecteinascidin-743 on the Interaction Between DNA Binding Proteins and DNA. Anticancer Drug Des. 14, 179-86, 1999.

Chabner, "Cytotoxic agents in the era of molecular targets and genomics," The Oncologist, vol. 7, suppl. 3, pp. 34-41, 2002.

Committee on Risk Assessment Methodology, "Issues in Risk Assessment. Appendix A: Workshop Summary- Maximum Tolerated Dose: Implications for Risk Assessment," National Research Council, National Academy of Sciences, National Academies Press, Washington DC, pp. 79-89, 1993.

Cvitkovic, E. et al., "Ecteinascidin-743 (ET-743) 24 hour continuous intravenous infusion (CI) phase I study in solid tumors (ST) patients," Annals Oncology, Abstract 456, 1998.

Delaloge, S. et al., "Ecteinascidin-743: A Marine-Derived Compound in Advanced Pretreated Sarcoma Patients-Preliminary Evidence of Activity", J. of Clinical Oncology, vol. 19, No. 5, pp. 1248-1255, 2001.

DeVita et al., "Combination Versus Single Agent Chemotherapy: A Review of the Basis for Selection of Drug Treatment of Cancer", Cancer, vol. 35, pp. 98-110, 1975.

D'Incalci et al., "Mode of action of Ecteinascidin-743 (ET-743)," Proceedings of the 1999 AACR-NCI-EORTC International Conference, Clinical Cancer Research, vol. 5, Supplement, pp. 3872s-3873s, Abstract of Plenary Session 7, Nov. 16-19, 1999.

D'Incalci et al., "Preclinical and Clinical Results with the Natural Marine Product ET-743," Expert Opin. Investig. Drugs, 12(11):1843-1853 (2003).

D'Incalci et al., "Unique Features of the Mode of Action of ET-743", The Oncologist, 7, p. 210-216, Jun. 2002.

Dorwald, Florencio Zaragoza, Side Reactions in Organic Synthesis: A Guide to Syccessfull Synthesis Design, Wiley, VCH, Weinheim, pp. IX of Preface, 2005.

Drugs Fut., "Ecteinascidin-743" vol. 22, No. 11, p. 1279, 1997.

Eckhardt et al., "In vitro Studies of a Novel Marine Cytotoxic, Ecteinascidin (ET-743)," New Drugs and Pharmacology, Annals of Oncology, 7 (Suppl. 5), 131, Abstract 632P (1996).

Endo et al., "Total Synthesis of Ecteinascidin 743", J. Am. Chem. Soc., 124, 6552-6554, 2002.

Erba et al., "ET-743 and Cisplatin (DDP) Show in vitro and in vivo Synergy Against Human Sarcoma and Ovarian Carcinoma Cell Lines," from the AACR-NCI-EORTC Conference on Molecular Targets and Cancer Therapeutics of Oct. 29-Nov. 2, 2001, Abstract 406.

Erlichman, C., "18: Pharmacology of Anticancer Drugs," The Basic Science of Oncology, 2nd edition, Tannock et al., editors, McGraw-Hill, New York, pp. 317-337, 1992.

European Agency for the Evaluation of Medicinal Products, "Committee for Proprietary Medicinal Products Summary of Opinion for Yondelis", Nov. 20, 2003.

Faircloth et al., "In Vivo Combinations of Chemotherapeutic Agents with Ecteinascidin 743 (ET743) Against Solid Tumors," from the Proceedings AACR-NCI-EORTC of Nov. 2001, Abstract 387.

Faulkner et al., "Symbiotic Bacteria in Sponges: Sources of Bioactive Substances," Drugs from the Sea, Fusetani, N. (ed.), Basel Karger, 2000, pp. 107-119.

Fayette et al., "ET-743: A Novel Agent with Activity in Soft-Tissue Sarcomas," Current Opinion in Oncology, 18:347-353 (2006).

Friereich et al., "Quantitative Comparison of Toxicity of Anticancer Agents in Mouse, Rat, Hamster, Dog, Monkey, and Man," Cancer Chemotherapy Reports, 50:4, May 1966, pp. 219-245.

Garcia Gravalos, M.D., et al., "In vitro schedule-dependent cytotoxicity by ecteinascidin 743 (ET-743) against human tumor cells," 23rd European Society for Medical Oncology Congress, Abstract No. 652, Nov. 6-10, 1998.

Gourley C. et al., "Malignant mixed Mesodermal Tumours—Biology and Clinical Aspects," European Journal of Cancer, 2002, vol. 38, No. 11, pp. 1437-1446.

Grever et al., "The National Cancer Institute: Cancer Drug Discovery and Development Program", Seminars in Oncology, vol. 19, No. 6, 622-638, Dec. 1992.

Grosso et al., "Steroid Premedication Markedly Reduces Liver and Bone Marrow Toxicity of Trabectedin in Advanced Sarcoma," European Journal of Cancer 42:10, 1484-1490 (2006).

Hornicek et al., "In vitro effect of the tetrahydroisoquinoline alkaloid Ecteinascidin-743 (ET-743) on chondrosarcoma (CHSA) cells," Proceedings of the 1999 AACR-NCI-EORTC International Conference, Clinical Cancer Research, vol. 5, Supplement, p. 3790s Abstract 304, Nov. 16-19, 1999.

Hornicek et al., "Effect of Ecteinascidin-743 and Plasminogen related Protein B on a Human Chondrosarcoma Xenograft Tumor in Mice," Clinical Cancer Research, vol. 7 Supplement P3734S-3734S, Abstract 398 (Nov. 2001).

Horstmann et al., "Risks and Benefits of Phase I Oncology Trials, 1991 through 2002," New England Journal of Medicine, vol. 352, pp. 895-904; Mar. 3, 2005.

Izbicka, E. et al., "In vitro antitumor activity of the novel marine agent, Ecteinascidin-743 (ET-743, NSC- 648766) against human tumors explanted from patients," Annals of Oncology, vol. 9, pp. 981-987, 1998.

Jimeno, J.M. et al., "Enhancing the preclinical in vivo antitumor activity of ecteinascidin 743, a marine natural product currently in phase II clinical trials," Proceedings of the 1999 AACR-NCI-EORTC International Conference, Clinical Cancer Research, vol. 5, p. 3790S, Abstract No. 306, Nov. 16-19, 1999.

Jimeno et al., "Pharmacokinetics (PK)/Pharmacodynamic (PD) Relationships in Patients (PT) Treated with Ecteinascidin-743 (ET-743) Given As 24 Hours Continuous Infusion (CI)," Journal of Clinical Oncology, ASCO Annual Meeting Proceedings, Abstract No. 744, May 15-18, 1999.

Jimeno, J. et al., "Phase I and pharmacokinetic (PK) study of Et-743, a novel minor groove binder of marine origin on a daily [times] 5 schedule," 1998 ASCO Annual Meeting Proceedings, Abstract No. 737, 1998.

Jimeno, Jose et al., "Adding Pharmacogenomics to the Development of New Marine-Derived Anticancer Agents," Journal of Translational Medicine, vol. 4, issue 3, Jan. 9, 2006, downloaded from the internet website: <<http://www.translational-medicine.com/content/4/1/3>>.

Jin et al., "The antitumor agent Ecteinascidin 743 (ET743), inhibits transcriptional activation of the MDR1 Gene by multiple inducers," Proceedings of the 1999 AACR-NCI-EORTC International Conference, Clinical Cancer Research, vol. 5, Supplement, p. 3790s, Abstract 203, Nov. 16-19, 1999.

Jin et al., Ecteinascidin-743, A Transcription-Targeted Chemotherapeutic that Inhibits MDR I Activation. Proc. Natl. Acad. Sci. USA, 97, 6775-9, 2000.

Kubo et al., "Stereoselective Total Synthesis of (.+−.) Saframycim B", J. Org. Chem., vol. 53, No. 18, 1988, pp. 4295-4310.

Leonetti et al., "Antitumoral Effect of the G-quadraplex Interactive Compound RHPS4 on Human Melanoma Cells Possessing Relatively Long Telomeres," from the Proceedings of the AACR, vol. 45, Mar. 2004.

Maier et al., "In vitro inhibition of endothelial cell growth by the antiangiogenic drug AGM-1470 (TNP-470) and the antiendoglin antibody TEC-11," Anti-Cancer Drugs, vol. 8, pp. 238-244, 1997.

Magro et al., "The Role of PARP and PARP Inhibitors in Yondelis (Trabectedin) Mediated Cytotoxicity," Abstract and Presentation from the AACR Annual Meeting, Apr. 17, 2007.

Manzanares et al., "Advances in the Chemistry and Pharmacology of Ecteinascidins, A Promising New Class of Anticancer Agents," Curr. Med. Chem. -Anti-Cancer Agents, 2001, vol. 1, pp. 257-276.

Martinez, E. J. et al., "A New, More Efficient, and Effective Process for the Synthesis of a Key Pentacyclic Intermediate for Production of Ecteinascidin and Phthalascidin Antitumor Agents." Org. Lett. 2, 993-6, 2000.

McMahon, Gerald, "VEGF Receptor Signaling in Tumor Angiogenesis," The Oncologist, 2005; 5 (Suppl. 1): 3-10.

Menchaca et al., "Synthesis of Natural Ecteinascidins (ET-729, ET-745, ET-759B, ET-736, ET-637, ET-594) from Cyanosafracin B," J. Org. Chem., published on web Oct. 21, 2003, pp. 8859-8866.

Minuzzo, M. et al., "Interference of Transcriptional Activation by the Antineoplastic Drug Ecteinascidin.743." Proc. Natl. Acad. Sci. USA 97, 6780-4, 2000.

Moore et al., "Sequencing evaluation of ET-743 combinations with standard chemotherapy agents against a panel of human tumor cell lines," Clinical Cancer Research, vol. 6, Abstract 504 (Nov. 2000).

Moore et al., "NMR-Based Model of an Ecteinascidin 743-DNA Adduct," J. Am. Chem. Soc., vol. 119, 1997, pp. 5475-5476.

Morioka et al., "Antiangiogenesis Treatment Combined with Chemotherapy Produces Chondrosarcoma Necrosis," Clinical Cancer Research, vol. 9, 1211-1217, Mar. 2003.

Pinedo et al., "Translation Research: The Role of VEGF in Tumor Angiogenesis," The Oncologist, 2000; 5 (suppl. 1): 1-2.

Riofrio, M. et al., "Ecteinascidin-743 (ET-743) 24 hours continuous infusion (CI): Clinical and pharmacokinetic phase I study progressive report," 23rd European Society for Medical Oncology Congress, Abstract 639P, Nov. 6-10, 1998.

Rosing et al., "Pharmacokinetics (PK) of Ecteinascidin-743 (ET-743) in three different phase I trials," Proceedings of the American Association for Cancer Research, vol. 40, pp. 81, abstract No. 542, Mar. 1999.

Ryan, D.P. "Studies with Ecteinascidin-743 (ET-743) A Marine Alkaloid," Cancer Invest, vol. 18 (suppl 1), pp. 112, abstract No. 87, Jan. 2000, from the Chemotherapy Foundation Symposium XVII Innovative Cancer Therapy for Tomorrow, Nov. 3-6, 1999, New York, NY.

Schwartsmann G. et al., "Marine Organisms as a Source of New Anticancer Agents," The Lancet Oncology, 2001, vol. 2, No. 4, pp. 221-225.

Scotlandi et al., "Effectiveness of Ecteinascidin-743 against Drug-sensitive and—resistant Bone Tumor Cells," Clinical Cancer Research, 8:3893-3903 (Dec. 2002).

Scotto et al., "Ecteinascidin 743, a novel chemotherapeutic agent that targets transcriptional activation of a subset of genes, including MDR1," Clinical Cancer Research, vol. 6, Supplement, Abstract 210, p. 4508s, NCI-EORTC-AACR Symposium On New Drugs In Cancer Therapy, Nov. 7-10, 2000.

Sessa et al., "Trabectedin for Women with Ovarian Carcinoma After Treatment with Platinum and Taxane Falls," Journal of Clinical Oncology, vol. 23, No. 9, pp. 1867-1874, Mar. 20, 2005.

Smyth, "Rationale for Drug Combiantions," European Journal of Cancer, 39, 1816-1817 (2003).

Suggitt et al., "50 years of Preclinical Anticancer Drug Screening: Empiracal to Target-Driven Approaches," Clinical Cancer Research, vol. 11, pp. 971-981, Feb. 1, 2005.

Tabor et al., "Anti oxidation Potential of Indole Compounds-Structure Activity Studies," Biological Reactive Intermediates IV, p. 833-836, 1990.

Takebayashi et al., "Poisoning of Human DNA Topoisomerase I by Ecteinascidin 743, An Anticancer Drug That Selectively Alkylates DNA in the Minor Groove," Proc. Natl. Acad. Sci. USA 96, 7196-201 1999.

Takebayashi et al., "Multidrug Resistance Induced by DNA Minor Groove Alkylation of Ecteinascidin 743 (Et743)," Proceedings of the 1999 AACR-NCI-EORTC International Conference, Clinical Cancer Research, vol. 5, Supplement, p. 3851s, Abstract 602, Nov. 16-19, 1999.

Takebayashi et al., "Nucleotide excision repair-dependent cytotoxicity of Ecteinascidin 743," Clinical Cancer Research, vol. 6, Supplement, Abstract 207, p. 4508s, NCI-EORTC-AACR Symposium On New Drugs In Cancer Therapy, Nov. 7-10, 2000.

Valoti, G., et al., "Ecteinascidin-743 (ET-743), a marine natural compound, shows antitumor activity against human ovarian carcinoma xenografts," European Journal of Cancer (Novel Therapeutics and Pharmacology), vol. 34, Supp. 2, p. S39, Abstract PP179, 1998.

van Kesteren et al., "Pharmacokinetics and Pharmacodynamics of the Novel Marine-derived Anticancer Agent Ecteinascidin 743 in a Phase I Dose-finding Study," Clinical Cancer Research, vol. 6, pp. 4725-2732, Dec. 2000.

van Kesteren et al., "Clinical Pharmacology of the Novel Marine-derived Anticancer Agent Ecteinascidin 743 Administered as a 1- and 3-h Infusion in a Phase I Study," Anti-Cancer Drugs, vol. 13, No. 4, pp. 381-393, Apr. 2002.

van Kesteren et al. "Yondelis® (trabectedin, ET-743): The Development of an Anticancer Agent of Marine Origin" Anti-Cancer Drugs, vol. 14, No. 7, pp. 487-502, Aug. 2003.

Weiwei et al., "Potent antitumor activity of ET-743 against human soft tissue sarcoma cell lines," Proceedings of the 1999 AACR-NCI-EORTC International Conference, Clinical Cancer Research, vol. 5, Supplement, p. 3790s, Abstract 305, Nov. 16-19, 1999.

Wiesenthal, "Is one 'sensitive' drug better an another!" downloaded from internet website <<http://weisenthal.org/feedback.html>>, Feb. 4, 2002.

Zewail-Foote et al., "Echteinascidin 743: A Minor Groove Alkylator that Bends DNA Toward the Major Groove," J. Med. Chem. 42, 2493-7, Jul. 15, 1999.

U.S. Appl. No. 10/484,060, filed Mar. 2, 2005, Martinez et al.
U.S. Appl. No. 10/485,536, filed May 18, 2005, Gallego et al.
U.S. Appl. No. 10/503,106, filed Jun. 8, 2005, Barrasa et al.
U.S. Appl. No. 11/645,356, filed Dec. 22, 2006, Manzanares et al.
U.S. Appl. No. 11/733,606, filed Apr. 10, 2007, Flores et al.

SYNTHESIS OF NATURALLY OCCURRING ECTEINASCIDINS AND RELATED COMPOUNDS

CROSS-REFERENCE TO RELATED APPLICATION

This application is a continuation of U.S. Ser. No. 10/503,106, filed Jul. 29, 2004, which is the National Stage of International Application No. PCT/GB03/00481 filed on Feb. 4, 2003, which claims the benefit of United Kingdom Patent Application No. 0202544.3, filed on Feb. 4, 2002, all of which are incorporated herein by reference in their entirety.

FIELD OF THE INVENTION

The present invention relates to synthetic processes, compounds obtained with these processes and their use as antitumor agents. In particular it relates to synthetic processes for producing naturally occurring ecteinascidin compounds and related analogues, including novel intermediates that form a part of such synthetic processes.

In addition, the present invention relates to novel, previously undisclosed indications of the ecteinascidin analogues.

BACKGROUND OF THE INVENTION

U.S. Pat. No. 5,089,273, describes novel compositions of matter extracted from the tropical marine invertebrate, *Ecteinascidia turbinata*, and designated therein as ecteinascidins 729, 743, 745, 759A, 759B and 770. These compounds are useful as antibacterial and/or antitumor agents in mammals. Ecteinascidin 743 is undergoing clinical trials as an antitumour agent.

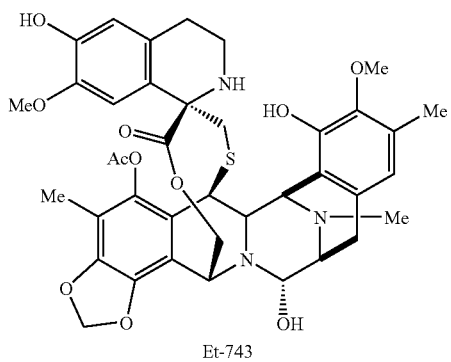

Et-743

The limited availability of natural material has resulted in the search for alternative synthetic methods being sought for the natural compounds and related analogs.

A synthetic process for producing ecteinascidin compounds is described in U.S. Pat. No. 5,721,362. The claimed method involves many steps, there being 38 Examples each describing one or more steps in the synthetic sequence to arrive at ecteinascidin 743.

Shorter synthetic processes for producing Ecteinascidin 743 are described in WO 0069862 and WO 0187895 and involve the use of cyanosafracin B as starting material.

However, there is still a need to provide synthetic routes to other ecteinascidins, in particular to provide more economic paths to the known antitumour agents such as ET-729, as well as permitting the preparation of new compounds.

Synthetic ecteinascidin compounds are known from various earlier PCT filings, including for example WO 0018233, WO 0177115, WO 0187894, WO 0187895, WO 99 51238, and WO 9846080. All of these patent specifications are specifically incorporated by reference, especially for the guidance they give in the design and synthesis of ecteinascidin compounds. In particular, they reveal structure-activity relationships which may be applied to the compounds of the present invention. See also *J. Am. Chem. Soc.*, 1996, vol. 118, no. 38, pages 9017-9023 for ecteinascidin compounds. The synthetic compounds and the natural ecteinascidins have a fused ring system:

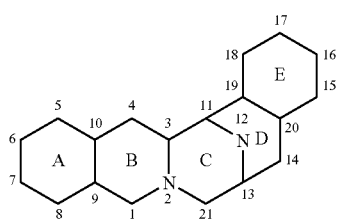

In many ecteinascidins, there is a 1,4 bridge across the fused ring system. With the natural ecteinascidins, the 1,4 bridge is sometimes a 1,4-spiroamine bridge, as for instance in ecteinascidin 729, 736 or 743.

SUMMARY OF THE INVENTION

In one aspect, the present invention provides quinone ecteinascidin compounds having a quinone group in ring E. Such compounds are typically of the formula (Ab):

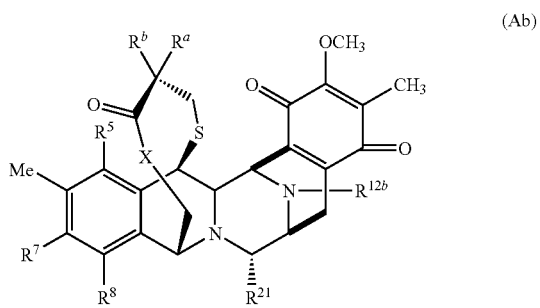

(Ab)

where $R^a$, $R^b$, $R^5$, $R^7$, $R^8$, $R^{21}$, X and ring E are as defined, the sulphur in the 1,4 bridge may be oxidised, and $R^{12b}$ is as defined for $R^{12}$ or $R^{12a}$.

These quinone compounds are of special interest for their activity, notably the activity of ecteinascidin 637 quinone. They can be made by oxidation of an ecteinascidin compound having a ring E which is phenolic, as for example in ecteinascidin 743 with a 16-methyl, 17-methoxy, 18-hydroxy phenyl ring for ring E. Other substituents can be employed. Suitable oxidising agents include Fremy's salt.

In a related aspect, the present invention provides a process for making ecteinascidin 729 and related compounds having a hydrogen at the N-12 position. To this end, the present invention provides a process which comprises providing an ecteinascidin with a substituent at the N-12 position, and removing that substituent. Thereafter the N—H group at the 12-position can be derivatised, for example with a group R12$^a$.

The invention also provides a process which is a modification of the process for preparing an ecteinascidin product as described in our WO 0187895. Thus, the present invention provides a process for preparing an ecteinascidin compound wherein a 1,4 bridge is formed using a 1-labile, 10-hydroxy, 12-protected, 18-protected hydroxy, di-6,8-enone fused ring precursor compound.

The 1,4 bridge can be a spiroamine, for example as in ecteinascidin 729, but need not be such a group. Typically the 1,4 bridge is of the formula:

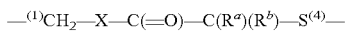

where the —CH$_2$— is at the 1-position and the —S— is at the 4-position, of the ecteinascidin compound, with the groups X, R$^a$ and R$^b$ being as herein defined.

As a related part of this invention, the invention provides an ecteinascidin compound which is of the formula (A):

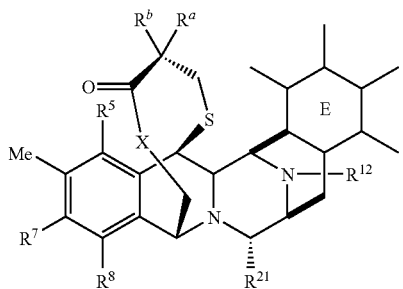

wherein:

R$^a$ and R$^b$ together with the carbon to which they are attached form a group —C(=O)—; a group —CH(R$^c$)— where R$^c$ is OX$^1$ or N(X$^1$X$^2$) where the or each X$^1$, X$^2$ is independently H, —C(=O)R', substituted or unsubstituted hydrocarbyl; or a spiro ring;

R$^5$ is —OH or a protected or derivatised version of such a group;

R$^7$ is —OCH$_3$ and R$^8$ is —OH or R$^7$ and R$^8$ together form a group —O—CH$_2$—O—;

R$^{12}$ is a protecting group;

R$^{21}$ is —H, —OH or —CN;

X is —NH— or —O—;

ring E is of the formula:

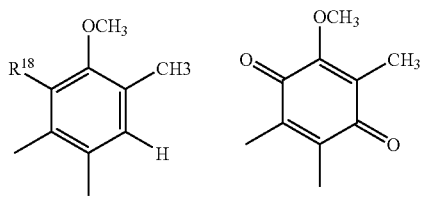

where R$^{18}$ is —OH or a protected or derivatised version of such a group; and the sulphur in the 1,4 bridge may be oxidised.

The 1,4-bridge can be omitted, especially for the new quinone compounds. In that instance, the substituent at the 1-position, R$^1$, can be as in our WO 0187894.

The protecting group on N-12 can be removed to give a hydrogen, and optionally replaced with another substituent to give other compounds of this invention. Examples of such derivatised compounds include those where the group at N-12 is alkyl such as methyl or ethyl, especially methyl, or is acyl, especially acetyl.

In this respect, the present invention further provides compounds of formula (Aa):

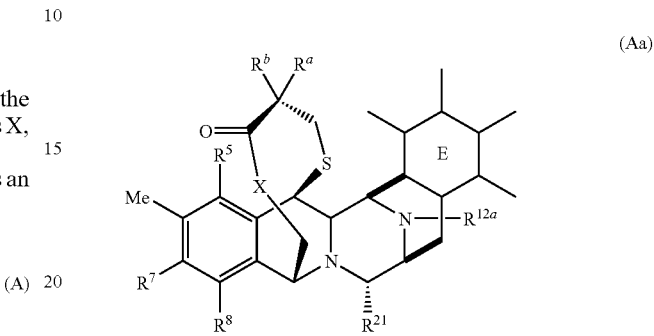

where R$^a$, R$^b$, R$^5$, R$^7$, R$^8$, R$^{21}$, X and ring E are as defined, the sulphur in the 1,4 bridge may be oxidised, and R$^{12a}$ is hydrogen, substituted or unsubstituted hydrocarbyl, or substituted or unsubstituted acyl, but is preferably not methyl.

In another aspect, the present invention provides ecteinascidin compounds having a 1,4 bridge where the oxygen β to the 1-position is replaced by an isostere. Suitable isosteres include —NH—.

Thus, according to the present invention, there are provided 1,4-bridged ecteinascidin compounds wherein the 1,4 bridge is of the formula:

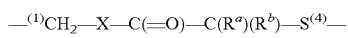

where the —CH$_2$— is at the 1-position, and the —S— is at the 4-position, of the ecteinascidin compound, with the group X being NH, and R$^a$ and R$^b$ being as herein defined.

Such compounds include those of the formula (Ac):

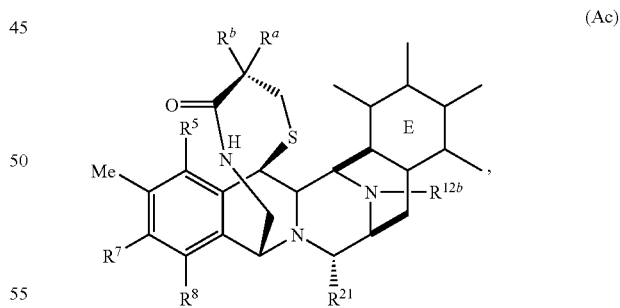

where R$^a$, R$^b$, R$^5$, R$^7$, R$^8$, R$^{12b}$, R$^{21}$, and ring E are as defined and the sulphur in the 1,4 bridge may be oxidised.

These compounds can be prepared by a process of this invention which is a modification of the process of WO 0187895, with a 1-labile substituent which is suitably a group of formula:

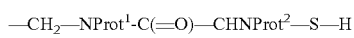

where Prot$^1$ and Prot$^2$ are amine protecting groups.

The protecting groups can then be removed separately or together, and the respective nitrogen atoms derivatised as appropriate.

Suitable procedures can be devised in the light of the disclosure in WO 0187894, WO 0187895, WO 0177115, which are incorporated herein by specific reference.

PREFERRED EMBODIMENTS

The quinone compounds of this invention are preferably made by a process which involves oxidation of an ecteinascidin having a phenol for ring E, where the hydroxy function of the phenol is at position 18 and may be substituted.

Such a reaction be in accordance with the following scheme:

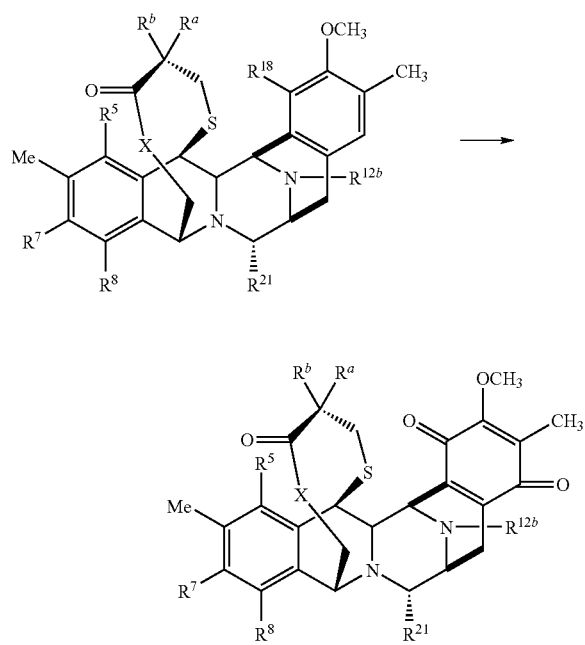

Alternatively, the quinone compounds of this invention can be made by modification of the synthetic procedures known from our earlier patent applications and which start from safracin B or a related compound. In particular, the present invention provides a process based on that disclosed in our WO 0069862 where ring E is a quinone ring in the starting material, and the ring E is not converted into the phenol system, as mentioned at the bottom of printed page 24 of the WO 00699862.

The 1,4 bridge need not be present in the quinone compounds.

In the compounds of this invention with a 1,4-bridge, preferred examples of the group formed by Ra and Rb together with the carbon to which they are attached include:

—C(=O)—;

—CHNH$_2$ or a protected or derivatised version of such a group;

—CHOH or a protected or derivatised version of such a group;

a group of formula:

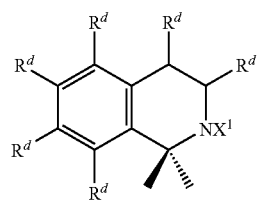

where $R^d$ and $X^1$ are as defined;

a group of formula:

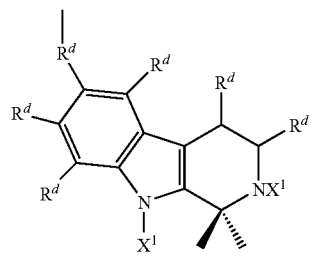

where $R^d$ and $X^1$ are as defined.

$R^d$ and $X^1$ in these groups are preferably chosen from hydrogen or substituted or unsubstituted R', OR', —(C=O)R', hydrocarbyl, hydrocarbyloxy or hydrocarboyl, especially hydrogen, unsubstituted or substituted alkyl or alkoxy, unsubstituted or substituted alkenyl, substituted or unsubstituted alkynyl, unsubstituted or substituted aryl, unsubstituted or substituted aralkyl; preferably hydrogen, alkyl or alkoxy, more preferably hydrogen, methyl or methoxy, most preferably both hydrogen.

Preferred definitions include those which give a group of formula:

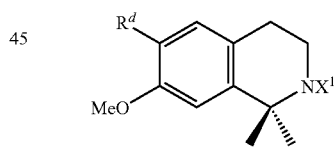

where $R^d$ and $X^1$ are as defined; or a group of formula:

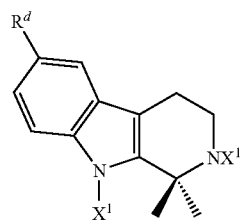

where $R^d$ and $X^1$ are as defined.

In particular, $R^a$ and $R^b$ can be chosen to give a group of formula:

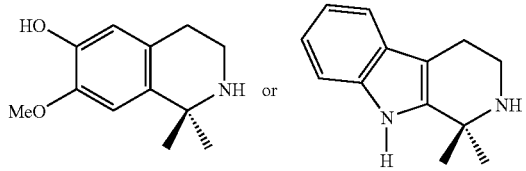

Where $R^a$ and $R^b$ together with the carbon to which they are attached form a group —CHNH$_2$ or a protected or derivatised version of such a group, the group can be of the formula —CHNHX$^1$ or —CHN(X$^1$X$^2$) where X$^1$, X$^2$ is H, C(=O)R', substituted or unsubstituted C$_1$-C$_{18}$ alkyl, substituted or unsubstituted C$_2$-C$_{18}$ alkenyl, substituted or unsubstituted C$_2$-C$_{18}$ alkynyl, substituted or unsubstituted aryl, or a protecting group. Preferred definitions include hydrogen, acyl such as acetyl or a protecting group.

One of $R^a$ or $R^b$ is often hydrogen and the other is preferably H; —NHCOalkyl, particularly where the alkyl has up to 16 carbon atoms, such as 1, 4, 7, 15 carbon atoms and may be halo substituted optionally perhalosubstituted; —NHalkyl-COOH particularly where the alkyl has up to 4 carbon atoms; protected —NHCOCH(NH$_2$)CH$_2$SH where the NH$_2$ and/or the SH are protected; —NHbiotin; —NHaryl; —NH(aa)y where aa is an amino acid acyl and y is suitably 1, 2 or 3 and wherein any NH$_2$ is optionally derivatised or protected, as with an amide terminal group or a Doc group; phthalimido formed —NX$^2$—; alkyl preferably having 1 to 4 carbon atoms; arylalkenyl, especially cinnamoyl which may be substituted as with 3-trifluoromethyl.

Preferred examples of the group $R^a$ or $R^b$ include NHAc, NHCO(CH$_2$)$_2$COOH, NHCOCH(NHAlloc)CH$_2$SFm, NHCO(CH$_2$)$_{14}$CH$_3$, NHTFA, NHCO(CH$_2$)$_2$CH$_3$, NHCOCH$_2$CH(CH$_3$)$_2$, NHCO(CH$_2$)$_6$CH$_3$, NHBiotin, NHBz, NHCOCinn, NHCO-(p-F$_3$C)—Cinn, NHCOVal-NH$_2$, NHCOVal-N—Ac, NHCOVal-N—COCinn, NHCO-Val-Ala-NH$_2$, NHCOVal-Ala-N—Ac, NHCOAla-NH$_2$, OH, OAc, NHAc, NHCO(CH$_2$)$_2$COOH, NHCOCH(NHAlloc)CH$_2$SFm, NHCOCH(NH$_2$)CH$_2$SFm, NPhth, NH-(m-CO$_2$Me)-Dz, NHCO(CH$_2$)$_{14}$CH$_3$, NMe$_2$, NHTFA, NHCO(CH$_2$)$_2$CH$_3$, NHCOCH$_2$CH(CH$_3$)$_2$, NHCO(CH$_2$)$_6$CH$_3$, NHAlloc, NHTroc, NHBiotin, NHBz, NHCOCinn, NHCO—(P—F3C)—Cinn, NHCOVal-NH$_2$, NHCOVal-N—Ac, NHCOVal-N—COCinn, NHCOVal-Ala-NH$_2$, NHCO-Val-Ala-N—Ac, NHCOVal-Ala-N—COCinn, NHCOAla-NH$_2$, NHCOAla-N—Ac, NHCOAla-N—COCinn, OH, OAc, NHAc, NHCO(CH$_2$)$_2$COOH, NHCOCH(NHAlloc)CH2SFm, Nphth, along with similar groups where the number of carbon atoms is varied or the amino acid is changed or another change of this kind is made to give a similar group.

Where $R^a$ and $R^b$ together with the carbon to which they are attached form a group —CHOH or a protected or derivatised version of such a group, the group can be of the formula —CHOX$^1$, where X$^1$ is as defined.

Other preferred examples include OH, OAc, OCOCF$_3$, OCOCH$_2$CH$_2$CH$_3$, OCO(CH$_2$)$_6$CH$_3$, OCO(CH$_2$)$_{14}$CH$_3$, OCOCH=CHPh, OSO$_2$CH$_3$ along with similar groups where the number of carbon atoms is varied or different substituent groups are introduced or another change of this kind is made to give a similar group.

The sulphur in the 1,4 bridge may be oxidised to give, for example a group —S(=O)—.

Where the 1,4 bridge is not present, the group at the 1-position, $R^1$, is suitably an optionally protected or derivatised aminomethylene group, or an optionally protected or derivatised hydroxymethylene group; and the group at the 4-position, $R^4$, is typically hydrogen.

$R^1$ is suitably a hydrophobic group and which thus lacks free amino, hydroxy or other hydrophilic function. Typically $R^1$ is a group —CH$_2$—NH$_2$—CO—R', where R' is as defined but preferably has a linear chain length of less than 20 atoms, more preferably less than 15 or 10 atoms, where a 1,4-phenyl is counted as a chain length of four atoms and similar considerations apply to other cyclic groups (for example, 1,2-cyclohexyl is chain length of two), and the linear chain of less than 10, 15 or 20 atoms can itself be substituted. In particular, data suggests there is a balance to be achieved between having no such group Ra—CO— and having a large, bulky group.

In particularly preferred compounds, the group $R^1$ is acylated on an —NH$_2$ group, and for example N-acyl derivatives can be formed from groups —CH$_2$NH$_2$ and —CH$_2$—NH-aa, where aa is amino acid. The acyl derivatives can be N-acyl or N-thioacyl derivatives thereof. The acyl groups can be of formula —CO—R', where R' is as defined and is chosen to meet the indicated criteria. Suitable acyl groups include alanyl, arginyl, aspartyl, asparagyl, cystyl, glutamyl, glutaminyl, glycyl, histidyl, hydroxyprolyl, isoleucyl, leucyl, lysyl, methionyl, phenylalanyl, prolyl, seryl, threonyl, thyronyl, tryptophyl, tyrosyl, valyl, as well as other amino acid acyl groups, which may be L- or D-. Such amino acid acyl groups are preferred derivatised on the amino group to give hydrophobicity.

In a variation, the group $R^1$ is a derivatised hydroxymethylene group. Similar considerations apply as with the derivatised aminomethylene group.

In one preferred aspect, at least one of $R^5$, $R^{18}$ and R' in the group $R^d$ is selected from hydrogen, R', C=OR', or COOR', where R' is optionally substituted alkyl or alkenyl, the optional substituents being chosen from halo, amino including amino derived from amino acid, aryl or heterocyclic.

$R^5$ is preferably —OH or a protected or derivatised version of such a group. In particular, it can be a group —OX$^1$. Particularly preferred for $R^5$ is an acyloxy group, especially an acetyloxy group. Other examples include cinnamoyloxy and heptanoyloxy.

$R^7$ is —OCH$_3$ and $R^8$ is —OH or more preferably $R^7$ and $R^8$ together form a group —O—CH$_2$—O—.

$R^{12}$ is a protecting group for the nitrogen atom of the amine function. Suitable protecting groups for such amines include carbamates, amides, and other protecting groups, such as alkyl, arylalkyl, sulpho- or halo-arylalkyl, haloalkyl, alkylsilylalkyl, arylalkyl, cycloalkylalkyl, alkylarylalkyl, heterocyclylalkyl, nitroarylalkyl, acylaminoalkyl, nitroaryldithioarylalkyl, dicycloalkylcarboxamidoalkyl, cycloalkyl, alkenyl, arylalkenyl, nitroarylalkenyl, heterocyclylalkenyl, heterocyclyl, hydroxyheterocyclyl, alkyldithio, alkoxy- or halo- or alkylsulphinyl arylalkyl, heterocyclylacyl, and other carbamates, and alkanoyl, haloalkanoyl, arylalkanoyl, alkenoyl, heterocyclylacyl, aroyl, arylaroyl, haloaroyl, nitroaroyl, and other amides, as well as alkyl, alkenyl, alkylsilylalkoxyalkyl, alkoxyalkyl, cyanoalkyl, heterocyclyl, alkoxyarylalkyl, cycloalkyl, nitroaryl, arylalkyl, alkoxy- or hydroxy-arylalkyl, and many other groups. Such groups may optionally be substituted. Further examples are given in our earlier patent specifications.

A preferred class of compounds comprise an ecteinascidin compound wherein the N-12 protecting group $R^{12}$ is chosen from haloalkyl, alkoxyalkyl, haloalkoxyalkyl, arylalkylene, haloalkylarylakylene, acyl, haloacyl, optionally halo alkoxyalkyl, optionally halo or alkyl arylalkenylacyl, alkenylacyl, carbonate, carbamate, arylalkyl, alkenyl, acid anhydride and amino acid.

Especially preferred is an ecteinascidin compound wherein the N-12 protecting group $R^{12}$ is chosen from allyl, acetyl, trifluoroacetyl, 2,2,2-trichloroethoxycarbonyl, isovalerylcarbonyl, trans-3-(trifluoromethyl)cinnamoylcarbonyl, heptafluorobutyrylcarbonyl, decanoylcarbonyl, trans-cinnamoylcarbonyl, butyrylcarbonyl, 3-chloropropionylcarbonyl, cinnamoylcarbonyl, 4-methylcinnamoylcarbonyl, hydrocinnamoylcarbonyl, or trans-hexenoylcarbonyl, or alanyl, arginyl, aspartyl, asparagyl, cystyl, glutamyl, glutaminyl, glycyl, histidyl, hydroxyprolyl, isoleucyl, leucyl, lysyl, methionyl, phenylalanyl, prolyl, seryl, threonyl, thyronyl, tryptophyl, tyrosyl, valyl, or other amino acid acyl group, phthalimido or other cyclic amido group.

$R^{18}$ is suitably as defined for $R^5$, though the most preferred definition is hydroxy.

$R^{21}$ is —H, or more preferably —OH or —CN.

Ring E is of the formula:

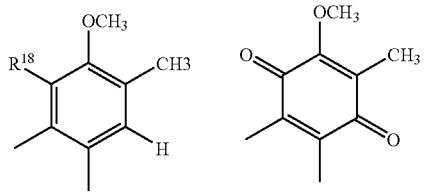

where $R^{18}$ is —OH or a protected or derivatised version of such a group and is suitably of the formula —$OX^1$. Examples apart from —OH include cinnamoyloxy.

$X^1$ or $X^2$ when an amine protecting group, and $Prot^1$ and $Prot^2$ can be as defined for $R^{12}$, and reference is made to WO 0187895 for more information.

$X^1$ when a hydroxy protecting group, and $Prot^3$ can be known protecting groups for a hydroxy function. Suitable protecting groups for hydroxy groups include ethers and esters, such as alkyl, alkoxyalkyl, aryloxyalkyl, alkoxyalkoxyalkyl, alkylsilylalkoxyalkyl, alkylthioalkyl, arylthioalkyl, azidoalkyl, cyanoalkyl, chloroalkyl, heterocyclic, arylacyl, haloarylacyl, cycloalkylalkyl, alkenyl, cycloalkyl, alyklarylalkyl, alkoxyarylalkyl, nitroarylalkyl, haloarylalkyl, alkylaminocarbonylarylalkyl, alkylsulfinylarylalkyl, alkylsilyl and other ethers, and arylacyl, aryl alkyl carbonate, aliphatic carbonate, alkylsulfinylarlyalkyl carbonate, alkyl carbonate, aryl haloalkyl carbonate, aryl alkenyl carbonate, aryl carbamate, alkyl phosphinyl, alkylphosphinothioyl, aryl phosphinothioyl, aryl alkyl sulphonate and other esters. Such groups may optionally be substituted ether examples are given in our earlier patent specifications.

Each group R' is independently selected from the group consisting of H, OH, $NO_2$, $NH_2$, SH, CN, halogen, =O, C(=O)H, C(=O)$CH_3$, $CO_2$H, $CO_2CH_3$, $C_1$-$C_6$ alkyl, alkynyl, alkenyl, aryl, aralkyl and heterocyclic. Preferred definitions include H, acyl, alkyl, especially H and alkanoyl or cinnamoyl.

Preferred compounds of this invention include those complying with one or more of the following definitions:

$R^1$ is —$CH_2NH_2$ or —$CH_2OH$, or a protected or derivatised version of such a group (for which especially see WO 0187894, incorporated by specific reference at this point for its teaching of $R^1$ and thus all the teaching in WO 0187894 on $R^1$ forms part of the present text) and $R^4$ is —H; or $R^1$ and $R^4$ together form a group of formula (II), (III), (IV), (V) or (VI) wherein X is O, NH or NR and Y is O, S or S=O and R is a nitrogen protecting group and R' is H or OH or OMe or Me.

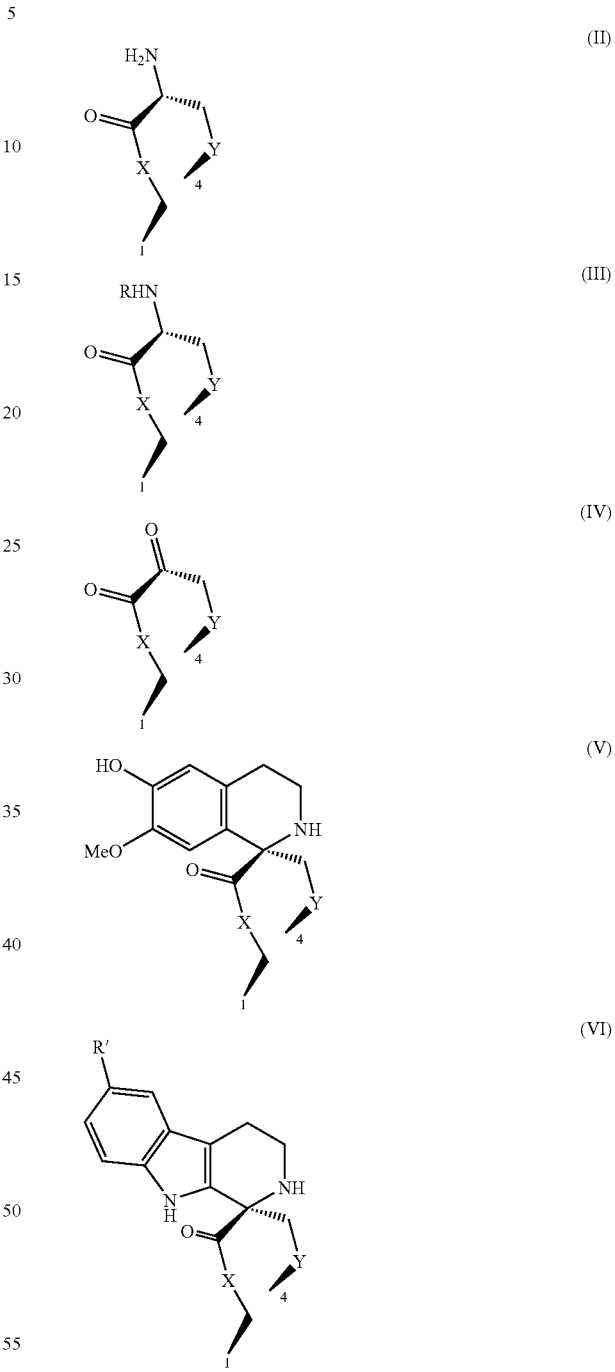

$R^5$ is —OH, —OAc or —OAllyl or —OCinnamoyl or —OOctanoyl;

$R^7$ and $R^8$ together form a group —O—$CH_2$—O—;

$R^{12b}$ is H, alkyl, haloalkyl, alkoxyalkyl, haloalkoxyalkyl, arylalkylene, haloalkylarylakylene, acyl, haloacyl, carbonate, carbamate, arylalkyl, alkenyl and amino acid. Preferably $R^{12b}$ is H, methyl, allyl, acetyl, trifluoroacetyl, 2,2,2-trichloroethoxycarbonyl, isovalerylcarbonyl, trans-3-(trifluoromethyl)

cinnamoylcarbonyl, heptafluorobutyrylcarbonyl, decanoyl-carbonyl, trans-cinnamoylcarbonyl, butyrylcarbonyl, 3-chloropropyonylcarbonyl, cinnamoylcarbonyl, 4-methyl-cinnamoylcarbonyl, hydrocinnamoylcarbonyl, or trans-hex-enoylcarbonyl, or alanyl, arginyl, aspartyl, asparagyl, cystyl, glutamyl, glutaminyl, glycyl, histidyl, hydroxyprolyl, isole-ucyl, leucyl, lysyl, methionyl, phenylalanyl, prolyl, seryl, threonyl, thyronyl, tryptophyl, tyrosyl, valyl, as well as other less common amino acid acyl groups, as well as phthalimido and other cyclic amides.

Ring E is of the formula:

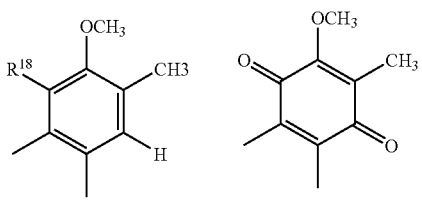

Suitable halogen substituents in the compounds of the present invention include F, Cl, Br and I.

Alkyl groups preferably have from 1 to 24 carbon atoms. One more preferred class of alkyl groups has 1 to about 12 carbon atoms, yet more preferably 1 to about 8 carbon atoms, still more preferably 1 to about 6 carbon atoms, and most preferably 1, 2, 3 or 4 carbon atoms. Another more preferred class of alkyl groups has 12 to about 24 carbon atoms, yet more preferably 12 to about 18 carbon atoms, and most preferably 13, 15 or 17 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members.

Preferred alkenyl and alkynyl groups in the compounds of the present invention have one or more unsaturated linkages and from 2 to about 12 carbon atoms, more preferably 2 to about 8 carbon atoms, still more preferably 2 to about 6 carbon atoms, even more preferably 1, 2, 3 or 4 carbon atoms. The terms alkenyl and alkynyl as used herein refer to both cyclic and noncyclic groups, although straight or branched noncyclic groups are generally more preferred.

Preferred alkoxy groups in the compounds of the present invention include groups having one or more oxygen linkages and from 1 to about 12 carbon atoms, more preferably from 1 to about 8 carbon atoms, and still more preferably 1 to about 6 carbon atoms, and most preferably 1, 2, 3 or 4 carbon atoms.

Preferred alkylthio groups in the compounds of the present invention have one or more thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred.

Preferred alkylsulfinyl groups in the compounds of the present invention include those groups having one or more sulfoxide (SO) groups and from 1 to about 12 carbon atoms, more preferably from 1 to about 8 carbon atoms, and still more preferably 1 to about 6 carbon atoms. Alkylsulfinyl groups having 1, 2, 3 or 4 carbon atoms are particularly preferred.

Preferred alkylsulfonyl groups in the compounds of the present invention include those groups having one or more sulfonyl ($SO_2$) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred.

Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties.

Heterocylic groups include heteroaromatic and heteroali-cyclic groups. Suitable heteroaromatic groups in the compounds of the present invention contain one, two or three heteroatoms selected from N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofura-nyl and benzothiazol. Suitable heteroalicyclic groups in the compounds of the present invention contain one, two or three heteroatoms selected from N, O or S atoms and include, e.g., tetrahydrofuranyl, tetrahydropyranyl, piperidinyl, mor-pholino and pyrrolindinyl groups.

Suitable carbocyclic aryl groups in the compounds of the present invention include single and multiple ring compounds, including multiple ring compounds that contain separate and/or fused aryl groups. Typical carbocyclic aryl groups contain 1 to 3 separate or fused rings and from 6 to about 18 carbon ring atoms. Specifically preferred carbocy-clic arykl groups include phenyl including substituted phenyl, such as 2-substituted phenyl, 3-substituted phenyl, 2,3-sub-stituted phenyl, 2,5-substituted phenyl, 2,3,5-substituted and 2,4,5-substituted phenyl, including where one or more of the phenyl substituents is an electron-withdrawing group such as halogen, cyano, nitro, alkanoyl, sulfinyl, sulfonyl and the like; naphthyl including 1-naphthyl and 2-naphthyl; biphenyl; phenanthryl; and anthracyl.

Preferred acyl groups are R'—CO— including alkyl-CO, alkenyl-CO, alkynyl-CO, aryl-CO, heterocyclic-CO, amongst others.

References herein to substituted groups in the compounds of the present invention refer to the specified moiety that may be substituted at one or more available positions by one or more suitable groups as mentioned above, e.g., halogen such as fluoro, chloro, bromo and iodide; cyano; hydroxyl; nitro; azido; alkanoyl such as a C1-6 alkanoyl group such as acyl and the like; carboxamido; alkyl groups including those groups having 1 to about 2 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having those having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfinyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocyclic aryl having 6 or more carbons, particularly phenyl (e.g., R being a substituted or unsubstituted biphenyl moiety); and aralkyl such as benzyl.

Preferred R' groups are present in groups of formula R', COR' or OCOR' and include alkyl or alkenyl, that may be substituted at one or more available positions by one or more suitable groups, e.g., halogen such as fluoro, chloro, bromo and iodo, especially ω-chloro or perfluoro; aminoalkyl groups such as groups having one or more N atoms and from 1 to about 12 carbon atoms or from 1 to about 6 carbon atoms, and especially including amino acid, notably glycine, alanine, arginine, asparagine, asparaginic acid, cystein, glutamine, glutamic acid, histidine, isoleucine, leucine, lysine, methionine, phenylalanine, proline, serine, threonine, tryptophan, tyrosine or valine, especially protected forms of such amino acids; carbocylic aryl having 6 or more carbons, particularly phenyl; and aralkyl such as benzyl; heterocyclic groups including heteroalicyclic and heteroaromatic groups, especially with 5 to 10 ring atoms of which 1 to 4 are heteroatoms, more preferably heterocyclic groups with 5 or 6 ring atoms and 1 or 2 heteratoms or with 10 ring atoms and 1 to 3 heteroatoms, the heterocyclic groups optionally being substituted with one or more of the substituents permitted for R' and especially amino such as dimethylamino or with keto.

The acyl derivatives such as —CO—R' can be N-acyl or N-thioacyl derivatives thereof, as well as cyclic amides. The acyl groups can illustratively be alkanoyl, haloalkanoyl, arylalkanoyl, alkenyl, heterocyclylacyl, aroyl, arylaroyl, haloaroyl, nitroaroyl, or other acyl groups. R' or similar group of an acyl can be various groups such as alkyl, alkoxy, alkylene, arylalkyl, arylalkylene, amino acid acyl, or heterocyclyl, each optionally substituted with halo, cyano, nitro, carboxyalkyl, alkoxy, aryl, aryloxy, heterocyclyl, heterocycyloxy, alkyl, amino or substituted amino. Other acylating agents include isothiocyanates, such as aryl isothiocyanates, notably phenyl isocyanate. The alkyl, alkoxy or alkylene groups suitably have 1 to 6 or 12 to 24 carbon atoms, and can be linear, branched or cyclic. Aryl groups are typically phenyl, biphenyl or naphthyl. Heterocyclyl groups can be aromatic or partially or completely unsaturated and suitably have 4 to 8 ring atoms, more preferably 5 or 6 ring atoms, with one or more heteroatoms selected from nitrogen, sulphur and oxygen.

Without being exhaustive, typical R' groups in acyl groups include alkyl, haloalkyl, alkoxyalkyl, haloalkoxyalkyl, arylalkylene, haloalkylarylakylene, acyl, haloacyl, arlyalkyl, alkenyl and amino acid. For example, R'—CO— can be acetyl, trifluoroacetyl, 2,2,2-trichloroethoxycarbonyl, isovalerylcarbonyl, trans-3-(trifluoromethyl)cinnamoylcarbonyl, heptafluorobutyrylcarbonyl, decanoylcarbonyl, trans-cinnamoylcarbonyl, butyrylcarbonyl, 3-chloropropyonylcarbonyl, cinnamoylcarbonyl, 4-methylcinnamoylcarbonyl, hydrocinnamoylcarbonyl, or trans-hexenoylcarbonyl, or alanyl, arginyl, aspartyl, asparagyl, cystyl, glutamyl, glutaminyl, glycyl, histidyl, hydroxyprolyl, isoleucyl, leucyl, lysyl, methionyl, phenylalanyl, prolyl, seryl, threonyl, thyronyl, tryptophyl, tyrosyl, valyl, as well as other less common amino acid acyl groups, as well as phthalimido and other cyclic amides.

One class of preferred compounds of this invention includes compounds of this invention which have one or more of the following substituents:

$R^1$ and $R^4$ form a bridge as defined, or $R^1$ is as defined and $R^4$ is hydrogen.

$R^5$ is hydrogen;

alkyl, more preferably alkyl of 1 to 6 carbon atoms;

C(=O)R', where R' is alkyl, more preferably alkyl of 1 to 24 carbon atoms, especially 1 to 8 or 12 to 18 carbon atoms; haloalkyl, more preferably ω-chloro- or perfluoro-alkyl of 1 to 4 carbon atoms, especially ω-chloroethyl or perfluoromethyl, ethyl or propyl;

heterocylicalkyl, more preferably an aylkyl of 1 to 6 carbon atoms with an ω-heterocyclic substituent suitably having 5 to 10 ring atoms and 1 to 4 heteroatoms, including fused heteroalicyclic with 3 hetero atoms, such as biotin; aminoalkyl, more preferably alkyl of 1 to 6 carbon atoms, especially 2 carbon atoms, with an ω-amino group optionally protected for example with alkoxycarbonyl such as $(CH_3)_3C$—O—C=O— or other protecting group;

arylalkylene, especially cinnamoyl; alkylene, especially vinyl or allyl; aralkyl, such as benzyl; or C(=O)OR', where R' is alkyl, more preferably alkyl of 1 to 6 carbon atoms, especially branched alkyl; alkenyl, more preferably allyl;

$R^{12}$ is hydrogen, methyl, or a protecting group including alkoxycarbonyl such as $(CH_3)_3C$—O—C=O—.

$R^{18}$ when present is hydrogen;

alkyl, more preferably alkyl of 1 to 6 carbon atoms;

(C=O)R', where R' is alkoxy, especially with an alkyl group of 1 to 6 carbon atoms; alkyl, more preferably alkyl of 1 to 24 carbon atoms, preferably 1 to 8 or 12 to 18 carbon atoms; haloalkyl, more preferably perfluoroalkyl of 1 to 4 carbon atoms, especially perfluoromethyl, ethyl or propyl; arylalkylene, especially cinnamoyl; heterocylicalkyl, more preferably an alkyl of 1 to 6 carbon atoms with an c heterocyclic substituent suitably having 5 to 12 ring atoms and 1 to 4 heteroatoms, including fused heterocyclic with 3 ring atoms, such as biotin; heterocyclicalkyl, with preferably 1 carbon atom in the alkyl group, and more preferably heteroalicylicmethyl with 5 to 10 ring atoms and 1 to 4 ring atoms, especially fused heterocylic with 1 to 4 heteroatoms, such as dimethylaminocoumarin or coumarin; alkylene, especially allyl; aralkyl, such as benzyl;

(C=O)OR', where R' is alkyl, more preferably alkyl of 1 to 6 carbon atoms; alkylene, especially vinyl or allyl; aralkyl, such as benzyl.

$R^d$ is OC(=O)R', where R' is alkyl, more preferably alkyl of 1 to 24 carbon atoms, preferably 1 to 8 or 12 to 18 carbon atoms; haloalkyl, more preferably ω-chloro- or perfluoroalkyl of 1 to 4 carbon atoms, especially ω-chloroethyl or perfluoromethyl, ethyl or propyl; aralkyl, such as benzyl or phenethyl; arylalkylene, especially cinnamoyl; aminoalkyl, especially amino acid, more especially protected amino acid, including protected cysteinine, notably Fm—S CH₂CH(NH-BOC)-cys or protected alanine, notably $(CH_3)_3C$—O—C=O-ala; heterocyclicalkyl, more preferably an alkyl of 1 to 6 carbon atoms with an ω-heterocyclic substituent suitably having 5 to 12 ring atoms and 1 to 4 heteroatoms, including fused heterocyclic with 3 ring atoms, such as biotin; heterocyclicalkyl, with preferably 1 carbon atom in the alkyl group, and more preferably heteroalicyclicmethyl with 5 to 10 ring atoms and 1 to 4 ring atoms, especially fused heterocylic with 1 to 4 heteroatoms, such as coumarin or dimethylaminocoumarin;

O(C=O)OR', where R' is alkyl, more preferably alkyl of 1 to 6 carbon atoms; alkylene, especially vinyl or allyl; aralkyl, such as benzyl;

OP=O(OR')₂, where R' is benzyl.

$X^1$ is hydrogen;

alkyl, more preferably alkyl of 1 to 6 carbon atoms;

(C=O)OR', where R' is alkylene, especially vinyl.

$R^{21}$ is hydrogen, hydroxy, or cyano.

Compounds with changes at $R^5$ are part of this invention, especially ester groups, $R_1$=R'CO—, with R' a long aliphatic or aromatic group.

There are compounds that have good ADME properties (absorption-distribution-metabolism-excretion) which are good indicative of pharmacokinetics.

In a related aspect of this invention, the compounds have one or more of the following features:

$R^1$ is —$CH_2$—N(R')$_2$ or —$CH_2$—OR', where each R' is H; alkyl-CO—; haloalkyl-CO—; cycloalkylalkyl-CO—; haloalkyl-O—CO—; arylalkyl-CO—; arylalkenyl-CO—; heteroaryl-CO—; alkenyl-CO—; alkenyl; amino acid acyl; or a protecting group;

$R^5$ is acetyl or another acyl. Preferably it has at least 4, 5 or 6 carbon atoms, for example up to 18 or 24 carbon atoms. Suitable substituents include esters COR', where R' is alkyl, alkenyl, often with one or more substituents. Alkyl, substituted alkyl, alkenyl and arylalkenyl are preferred, with suitable substituents including aryl, heterocyclic. Other definitions for $R^5$ include esters of formula COR' derived from an amino acid, optionally a protected amino acid.

$R^{18}$ is hydroxy or it is OR', OCOR' or OCOOR' where R' is a substituent with some bulk. Such bulky substituents include those with branched chain groups, unsaturated groups or cyclic groups including aromatic groups. Thus, branched alkyl, cycloalkyl, branched alkenyl, aryl, heteroaromatic and related groups are preferred for inclusion within the structure of the substituent $R^{18}$. Preferably the total number of carbon atoms is 2 to 24, more preferably 6 to 18 carbon atoms. Typically $R^{18}$ is an ester, ether or carbonate, being of formula OCOR', OR' or OCOOR'.

$R^d$ is hydroxy or methoxy. Alternatively, it is OR', OCOR' or OCOOR' where R' is a substituent with some bulk. Such bulky substituents include those with branched chain groups, unsaturated groups or cyclic groups including aromatic groups. Thus, branched alkyl, cycloalkyl, branched alkenyl, aryl, heteroaromatic and related groups are preferred for inclusion within the structure of the substituent. Preferably the total number of carbon atoms is 2 to 24, more preferably 6 to 18 carbon atoms.

Without being exhaustive, another class of preferred compounds of this invention have one or more of the following definitions:

$R^{21}$ is H, —CN or —OH, most especially —OH or —CN.

$R^5$ is preferably H or acetyl; arylalkyl, especially benzyl; alkyl-CO— (alkyl being up to 25 carbon atoms, such as up to 17, 19 or 21 carbon atoms and preferably an odd number of carbon atoms corresponding to a fatty acid carboxylic acid of even number of carbon atoms or else a low number of carbon atoms such as 1 to 6) especially $CH_3$—(CH$_2$)$_n$—CO— where n is for example 1.2.4.6.12.14 or 16; haloalkyl-CO—, especially trifluoromethylcarbonyl; arylalkyl-CO—, especially benzyl-CO—; arylalkenyl-CO—, especially cinnamoyl-CO—; most especially $R_1$ is H, acetyl or cinnamoyl.

$R^{12}$ is H; alkyl, especially methyl; alkyl-O—CO—, especially t-butyl-O—CO— or alkenyl-O—CO—, especially allyl-O—CO—.

$R^{18}$ is preferably H or acetyl; alkyl (alkyl being 1 to 6 carbon atoms), especially $C_1$ to $C_3$ alkyl; alkenyl, especially allyl; arylalkyl, especially benzyl; alkyl-CO— (alkyl being up to 25 carbon atoms, such as up to 17, 19 or 21 carbon atoms and preferably an odd number of carbon atoms corresponding to a fatty acid carboxylic acid of even number of carbon atoms or else a low number of carbon atoms such as 1 to 6) especially $CH_3$—(CH$_2$)$_n$—CO— where n is for example 1.2.4.6.12.14 or 16 and derivatives thereof, as in Biotin-(CH$_2$)$_4$—CO—; arylalkenyl-CO—, especially cinnamoyl-CO—; alkyl-O—CO—, especially t-butyl-O—CO—; arylalkyl-O—CO—, especially benzyl-O—CO—; alkenyl-O—CO, especially allyl-O—CO—.

$R^d$ is preferably OH, O-acetyl, O-alkyl (alkyl being 1 to 6 carbon atoms) especially $C_1$ to $C_3$ alkyl; O-alkenyl, especially allyl; arylalkyl-O—, especially benzyl; alkyl-CO—O— (alkyl being up to 25 carbon atoms, such as up to 17, 19 or 21 carbon atoms and preferably an odd number of carbon atoms corresponding to a fatty acid carboxylic acid of even number of carbon atoms or else a low number of carbon atoms such as 1 to 6) especially $CH_3$—(CH$_2$)$_n$—CO—O— where n is for example 1, 2, 4, 6, 12, 14 or 16 and derivatives thereof, as in Biotin-(CH$_2$)$_4$—COO—; haloalkyl-CO—O—, especially trifluoromethylcarbonyl; amino acid acyl or a derivative thereof, as in FmSCH$_2$CH(NHBOC)CO—O—; arylalkenyl-CO—O—, especially cinnamoyl-CO—O—; alkyl-O—CO—O—, especially tert-butyl-O—CO—O—; alkenyl-O—CO—O—, especially allyl-O—CO—O—; arylalkyl-O—CO—O—, especially benzyl-O—CO—O—; protecting group as in PO(OBn)$_2$; most especially $R_4$ is OH, acyloxy as cinnamoyloxy.

$X^1$ is H or alkyl (alkyl being 1 to 6 carbon atoms) and $R_5$ is most especially H or $C_1$ to $C_3$ alkyl.

The process which comprises providing an ecteinascidin with a substitutent at the N-12 position, and removing that substituent, is typically carried out using an ecteinascidin compound with an N-12 methyl group. Examples of such compounds are to be found in our published and copending PCT patent applications relating to ecteinascidin compounds. These applications are incorporated herein in full by specific reference. Removal of the N-12 methyl group can be achieved using known demethylation procedures.

Within the generality of this reaction we also include the process where the substituent is a protecting group, and the protecting group is removed.

The N—H group at the 12-position can be derivatised with a group $R12^a$. Suitable examples are as defined for $R^d$ with the exception of hydrogen. Preferred examples include acyl, especially alkyl-CO—; alkenyl, especially allyl; or alkyl-O—CO—. especially tBOC.

The process for making ecteinascidin 729 and related compounds can be modelled on the synthetic procedures given in WO 0187895. Typically, the process can employ a starting compound with a methyl group at N-12, which is replaced by a protecting group.

For example, in accordance with a process of this invention, a compound of formula (B):

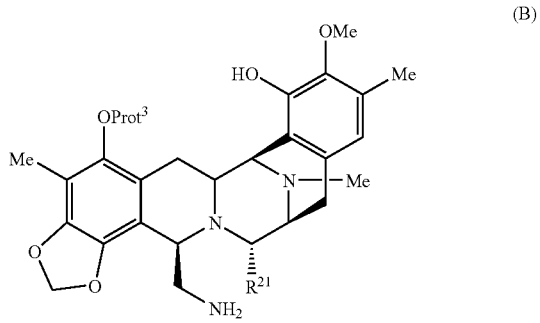

where $R^{21}$ is as defined, and $Prot^3$ is a protecting group, is subjected to converting —CH$_2$NH$_2$ at the 1-position to —CH$_2$OH, protecting the —CH$_2$OH at the 1-position, protecting the —OH at the 18-position, removing the methyl group at the 12-position, deprotecting the 5-position, forming a 10-hydroxy-di-6,8-enone, protecting the 12-position, removing the protecting group at the 1-position, forming a labile group at the 1-position set up for giving a 1,4 bridge, forming the 1,4 bridge, deprotecting the 18-position, optionally modifying the 1,4 bridge, removing the protecting group at the 12-position, and optionally further modifying the structure.

The —CH$_2$OH at the 1-position is protected for example with a tert-butyldiphenylsilyloxy group. The —OH at the 18-position is protected for example with a methoxyethoxymethyl group. The 12-position is protected for example with an allyl group. A labile group at the 1-position is typically formed using a reagent of formula:

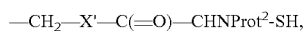

where X' is —O— or —NProt$^1$-, and Prot$^1$ and Prot$^2$ are as defined. The 1,4 bridge can be modified, as for example by removing protection from —NProt$^1$- to give —NH— which may then be further derivatised, deprotecting —NProt$^2$- to —NH— and optionally converting to —C(=O)— which may then be further derivatised, thus giving the range of possibilities for the 1,4 bridge defined by the given formula —$^{(1)}$CH$_2$—X—C(=O)—C(R$^a$)(R$^b$)—S$^{(4)}$—.

Examples of further modifications which may be carried out on the structure include one or more of altering the 1-substituent such as converting a 21-nitrile group to a 21-hydroxy group. altering the 5-substituent, altering the 18-substituent, oxidising the sulphur in the 1,4 bridge, adding a substituent at the 12-position, and converting ring E to a quinone.

FURTHER DETAILS OF THE INVENTION

Intermediates 1 and 16 (denoted as intermediates 21 and 36 respectively in patent applications WO 0069862 and WO 0187895) are useful for the preparation of other ecteinascidin compounds as detailed herein. Also other quinone related analogues are described herein from intermediate 16 and 18 (denoted as intermediate 35 in patent applications WO 0069862 and WO 0187895).

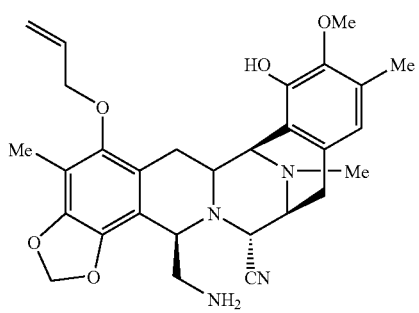

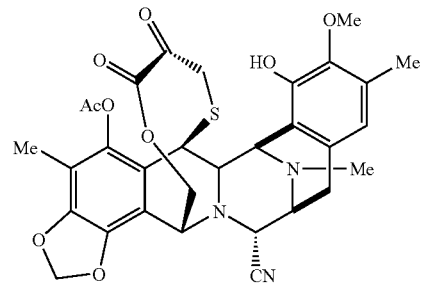

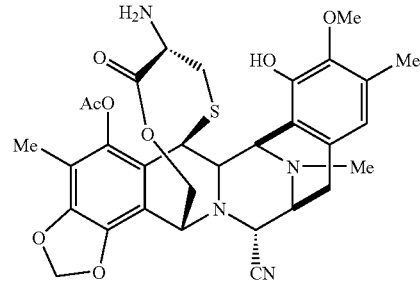

In particular, from intermediate 1 it is possible to synthesize the naturally occurring ecteinascidin compound ET729.

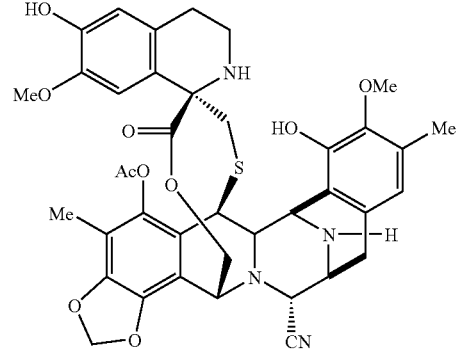

Similarly, from intermediate 16 it is possible to synthesize the naturally occurring compounds ET594, ET745 and ET759B (via ET770 and ET743 as intermediates)) and the quinones related to ET594 and ET736, respectively. The quinone related to ET637 is obtained from intermediate 18.

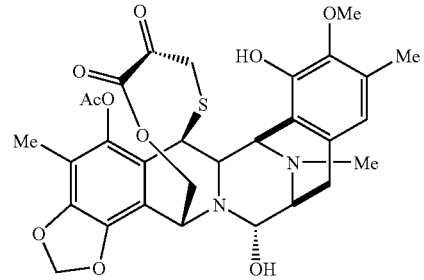

Et-745
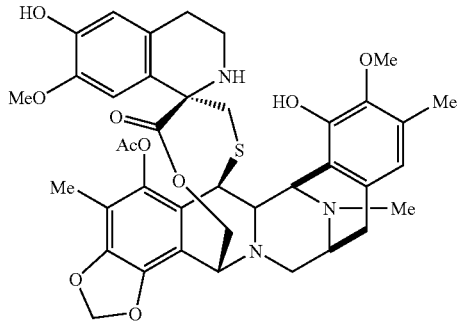

Et-759B
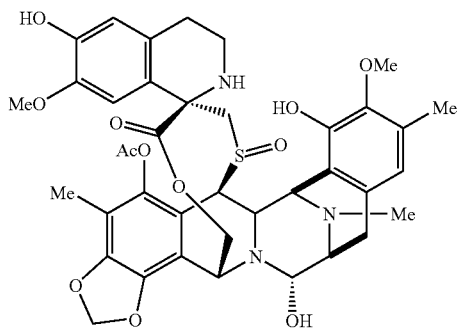

Et-594-quinone
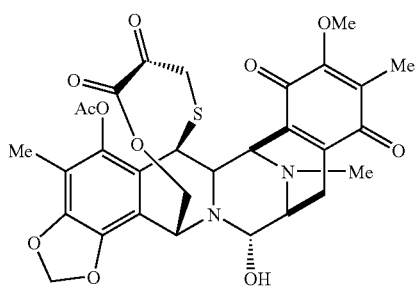

Et-736
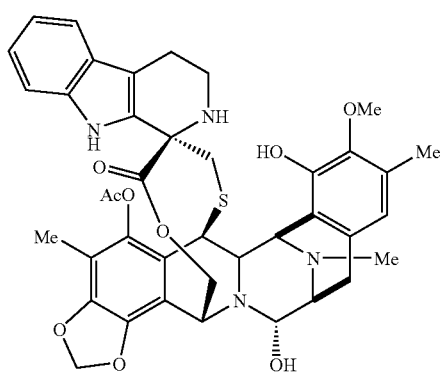

Et-736-quinone
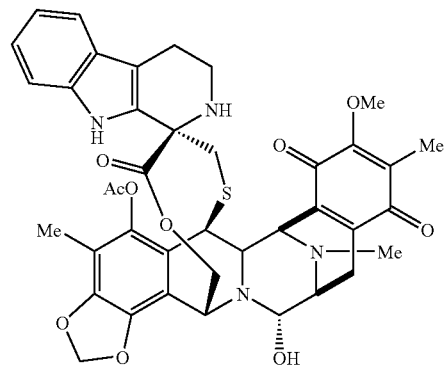

Et-637
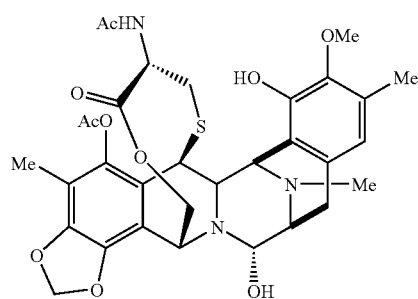

Et-637-quinone
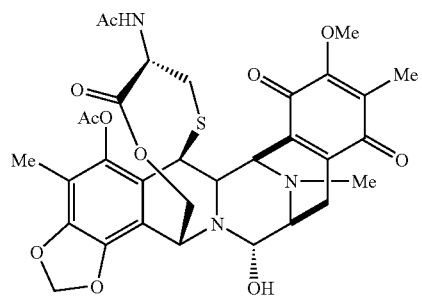

The synthesis of ET729 is described herein; the current invention is also directed at the preparation of new analogues of ET729 from intermediate 12 following a similar synthetic sequence.

In a further aspect of the current invention, intermediate 1 is used in the synthesis of a new family of ecteinascidin analogues (such as 77) in which the 1,4 bridge includes an amide linkage rather than the lactone linkage found in ET-743.

I
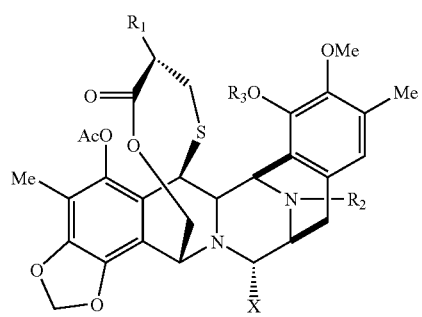

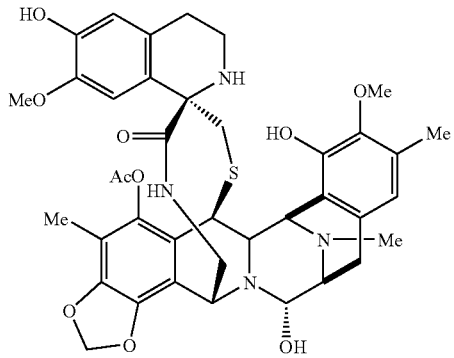

Thus according to the present invention, we provide ecteinascidin derivatives having an amide linkage rather than the lactone linkage found in ET-743, or lacking the bridge. The definition of the new compounds excludes the known ecteinascidin compounds. The new compounds include those in the table at the end of this specification, and analogues thereof. The analogues may differ by one or more substituents from those exemplified in our WO0187894, WO0187895 or WO0069862, and generally are within the relevant formulae given in our WO0187894, WO0187895 or WO0069862.

Thus, a general formula for the compounds of this invention is arrived at by identifying a new compound in the present specification, especially the table, and generalising in accordance with the definitions of the rest of the molecule based on a general formula of the preceding applications. Preferred definitions given in our earlier WO filings will then also apply.

The synthetic methods of the present invention provide the first methods for the preparation of ET729, ET594, ET745 and ET759B; and the quinones related of ET594, ET637, ET736 and the bridged lactam analog of ET743 and related intermediates. Furthermore the present invention provides the first synthetic methods for preparation of different analogs of ET729.

Such synthetic routes may provide more economic paths to the known antitumour agents, as well as permitting preparation of new active compounds.

Suitable starting materials for the new synthetic processes include compounds related to the natural bis(tetrahydroisoquinoline) alkaloids. Such starting materials may be prepared either from the different classes of saframycin and safracin antibiotics available from different culture broths as detailed in patent applications WO 0187894 and WO 0187895 or by other synthetic or biochemical processes.

In one particular aspect, the present invention is directed at the use of the Intermediate 1 (intermediate 21 in patent applications WO 0187894 and WO 0187895) in a new synthetic process for the preparation of ecteinascidin 729 as detailed in Scheme I.

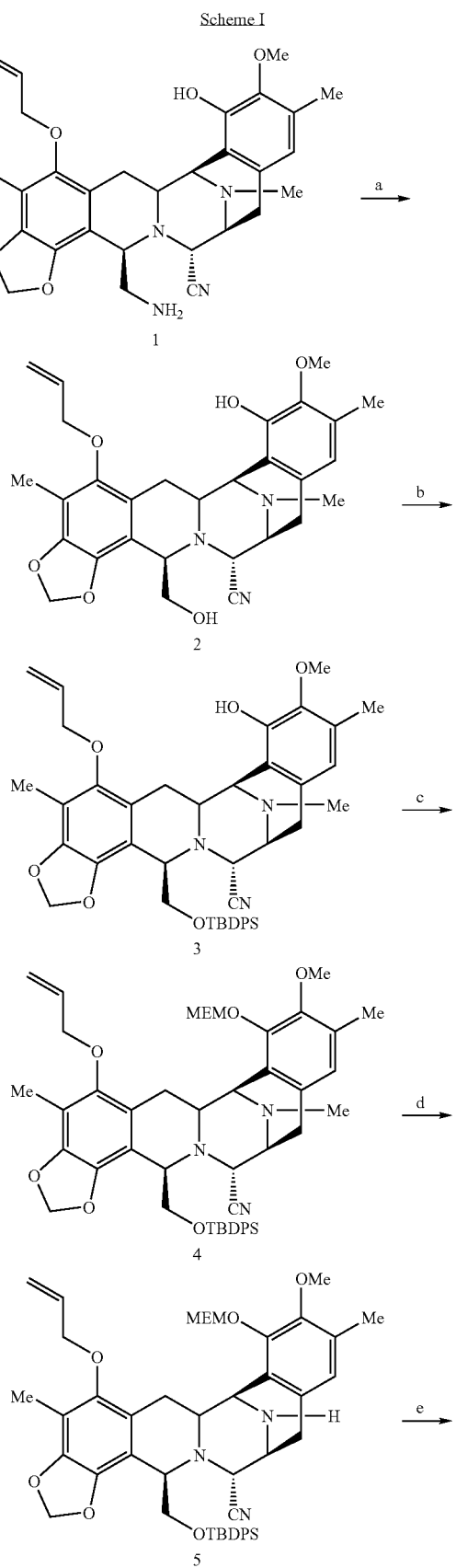

Scheme I

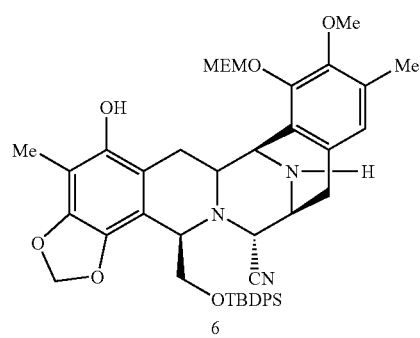
6
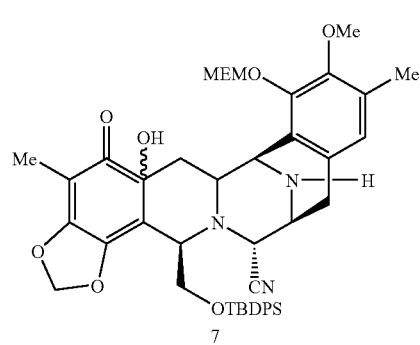
7
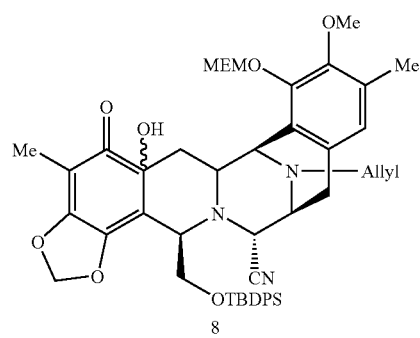
8
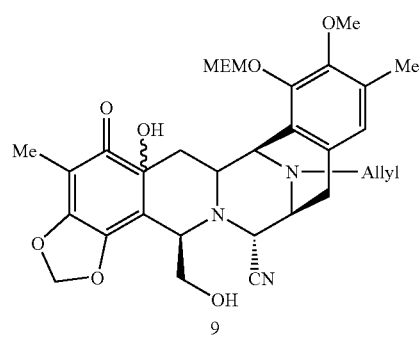
9
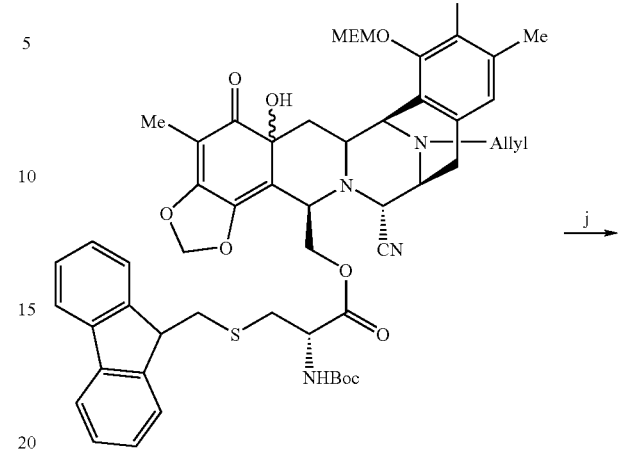
10
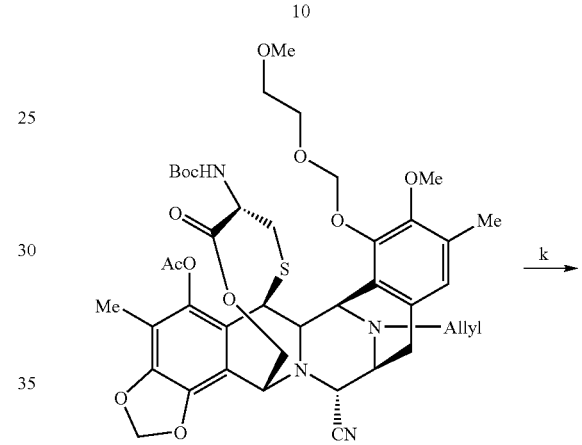
11
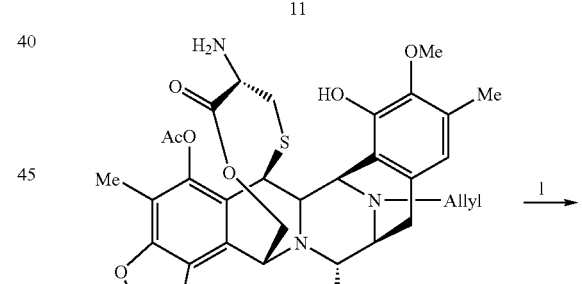
12
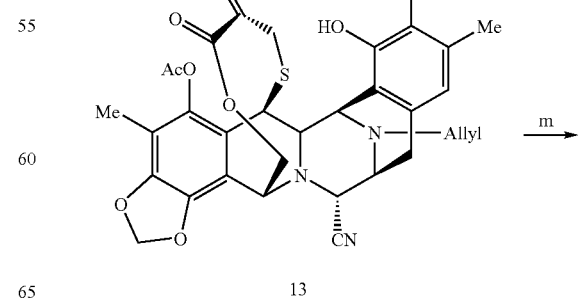
13

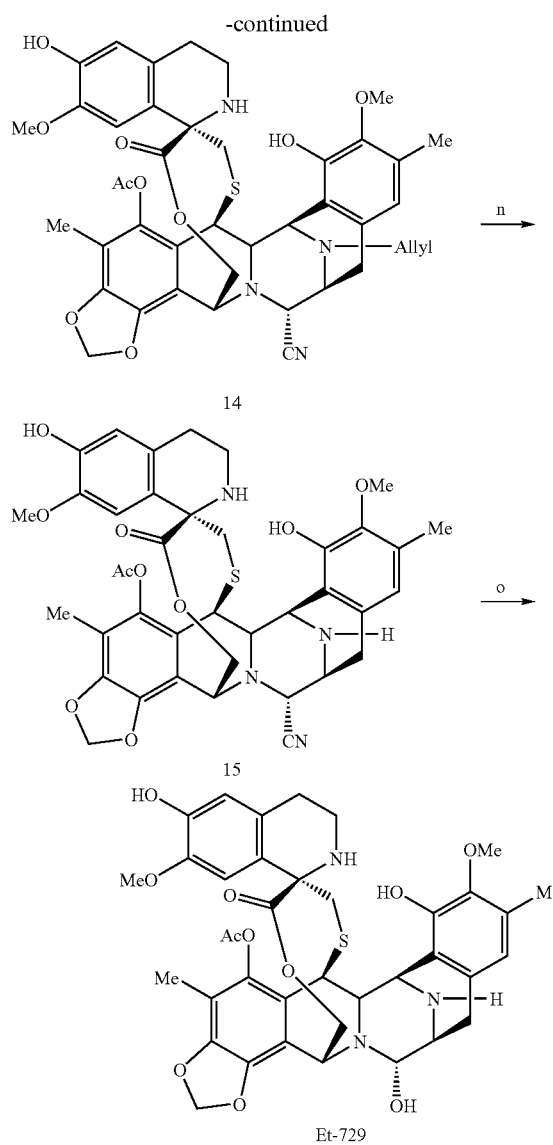

Reagents:
a) NaNO₂, AcOH, THF
b) TBDPSCl, Im, DMAP, DMF;
c) MEMCl, NaH, THF/H₂O;
d) m-CPBA, TEA, TFFA, DCM;
e) HSnBu₃, AcOH, (PPh₃)₂PdCl₂, DCM;
f) (PhSeO)₂O, DCM;
g) Cs₂CO₃, AllylBr, DMF;
h) TBAF, THF;
i) Cysteine derivative, EDC·HCl, DMAP, DIPEA, DCM;
j) DMSO; Tf₂O, DIPEA, t-BuOH, t-Butyl-tetramethyl guanidine, Ac₂O, DCM;
k) p-TsOH, CHCl₃;
l) N-methyl pyridin-4-carboxaldehyde iodide, DBU, oxalic acid;
m) 3-hydroxy-4-metoxy-phenethyl amine, silica gel, EtOH;
n) HSnBu₃, (PPh₃)₂PdCl₂, AcOH, DCM;
o) AgNO₃, CH₃CN, H₂O In general, the conversion of Intermediate 1, or a related compound, to an ecteinascidin product such as ET729 involves the following transformations:

(a) Conversion of the NH₂ to OH by reaction, for example with sodium nitrite in acetic acid.

(b) Protection of the primary OH and the E-ring phenol.

(c) Demethylation of the bridged secondary amine followed by deprotection and oxidation of the A-ring phenol and subsequent allylation of the bridged amine.

(d) Deprotection and esterification of the primary alcohol with a protected cysteine sidechain to give intermediate 10.

(e) Creation of the bridged ring by cyclization reaction (to give 11) and subsequent N and O deprotection reactions to give intermediate 12.

(f) Introduction of the dopamine residue by transamination and Pictect-Spengler reactions to give intermediate 14.

(g) Removal of the N allyl protecting group and conversion of the CN to OH.

Therefore in summary, it is now feasible to transform intermediate 1 (obtainable from cyanosafracin B) into ET-729, resulting in the first synthetic approach to this naturally occurring ecteinascidin.

The high functionality of the intermediate compounds necessitates the use of protecting groups for the E-ring phenol, the cysteine sidechain, the bridged nitrogen and the primary alcohol in order to prevent unwanted side reactions.

As such, a number of alternative intermediates can be generated dependent on the particular selection of protecting groups. The use of other protecting group strategies not detailed is also part of this invention.

In a further aspect, the current invention provides new processes for the conversion of intermediate 16 (denoted as intermediate 36 in patent applications WO 0069862 and WO 0187895) into the naturally occurring ecteinascidin compounds ET594, ET745 and ET759B as detailed in Scheme 2.

Intermediate 16 is obtained from intermediate 1 as described in the above mentioned patent applications, and has the same structure of intermediate 13 of scheme 1 with -Me bonded to N instead of -Allyl.

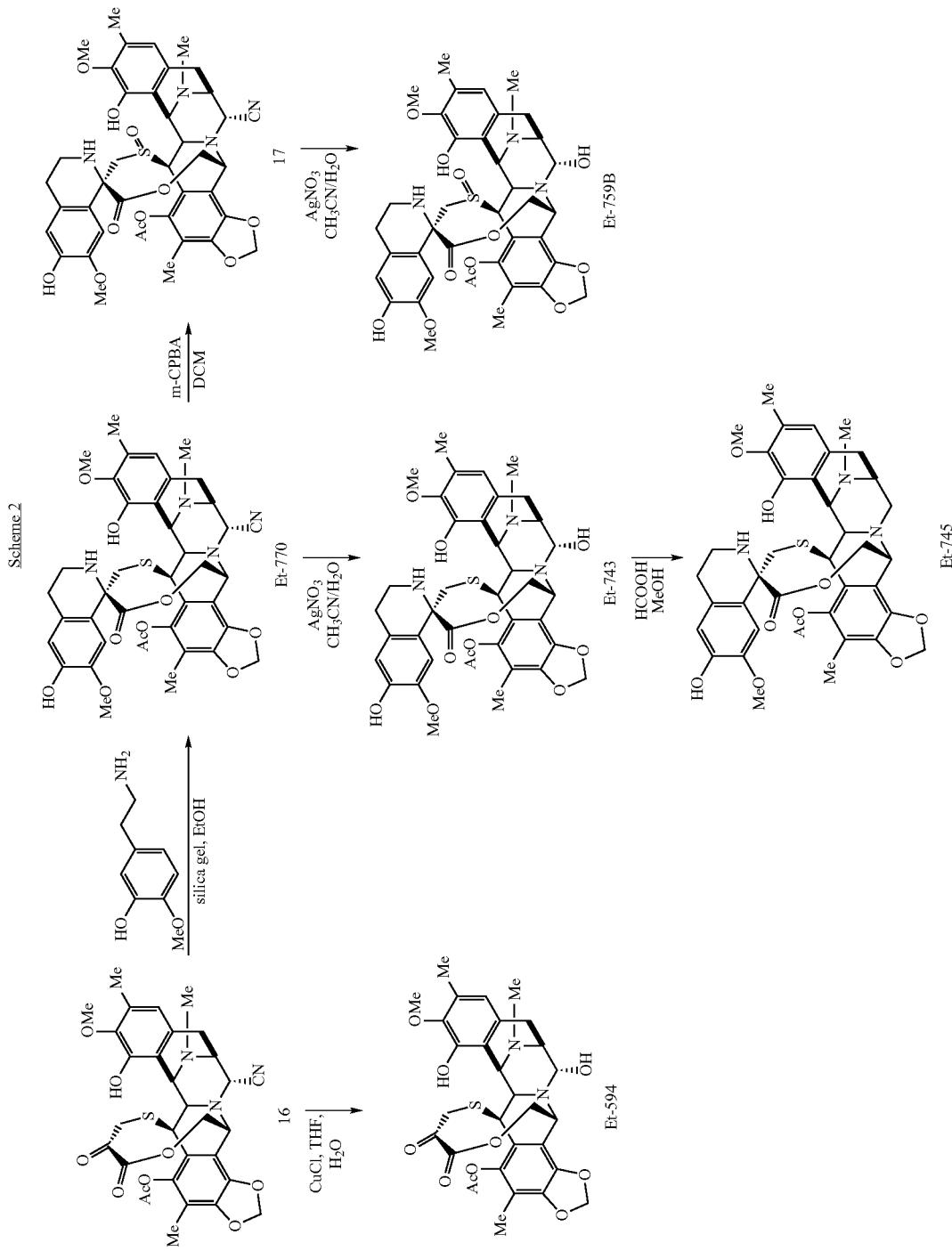

In more detail such processes involve the following conversions.
(a) Generation of ET594 from intermediate 16 in a single step by conversion of the CN group into an OH group.
(b) Synthesis of ET745 from ET743 (obtained in two steps from intermediate 16) by reductive cleavage of the secondary alcohol functionality.
(c) Generation of ET759B from intermediate 16 in three steps involving the formation of ET770 followed by oxidation and conversion of the nitrile group into a hydroxy group.

Thus, the current invention also provides simple new methods for producing the naturally occurring ecteinascidin compounds ET594, ET745 and ET759B from intermediate 16 (obtainable from cyanosafracin B).

Furthermore, the current invention provides a process for the synthesis of the quinone derivatives of ET594, ET637 and ET736 from intermediate 16 (denoted as intermediate 36 in patent applications WO 0187894 and WO 0187895) and intermediate 18 (denoted as intermediate 35 in patent applications WO 0069862 and WO 0187895). (Scheme 3).

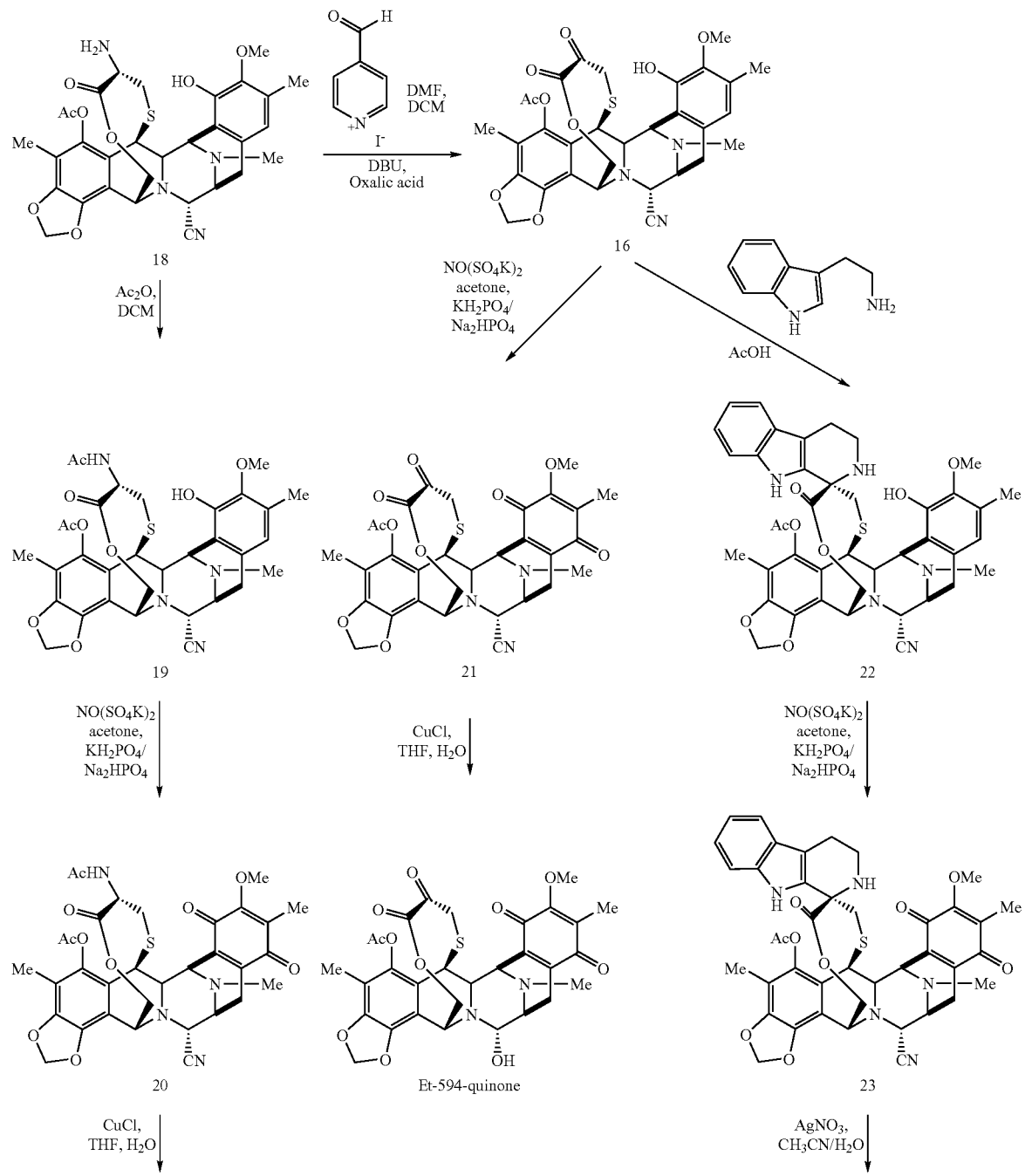

Scheme 3

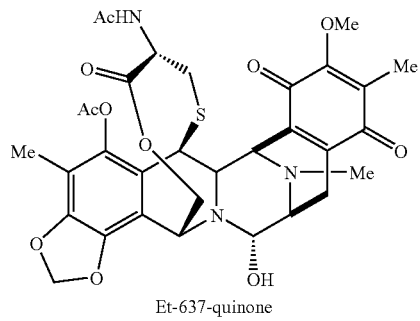

Et-637-quinone

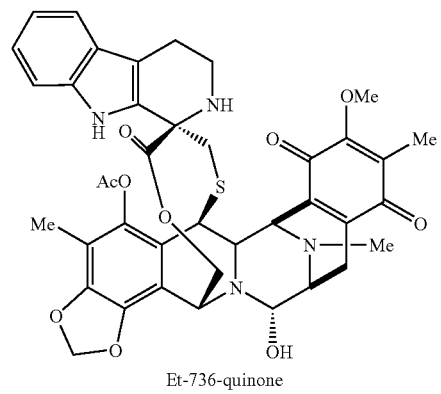

Et-736-quinone

In more detail, such processes involve the following conversions.

(a) Generation of ET637-quinone from intermediate 18 in three steps involving the formation of intermediate 19 by acetylation of the amine group, followed by oxidation of the phenolic ring and conversion of the nitrile group into a hydroxyl group.

(b) Synthesis of ET594-quinone in two steps from intermediate 16 through an oxidation reaction of the phenolic ring and conversion of the nitrile group into a hydroxyl group.

(c) Synthesis of ET736-quinone in three steps from intermediate 16 involving the introduction of the tryptamine moiety to generate intermediate 22, oxidation reaction and conversion of the nitrile group into a hydroxyl group.

Thus, the current invention provides short and new methods for producing the oxidized derivatives of the naturally occurring ecteinascidin compounds Et594, ET637 and ET736 from intermediates 16 and 18 (both obtainable from cyanosafracin B).

In a further embodiment and following the synthetic sequence of ET729, the present invention provides processes for producing new and different analogues of ET729 from intermediate 12. The preferred methods of producing the compounds of formula I, II and III are described below in the following reaction schemes with examples of typical substituent groups.

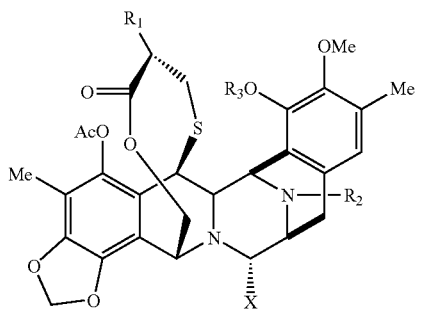

I

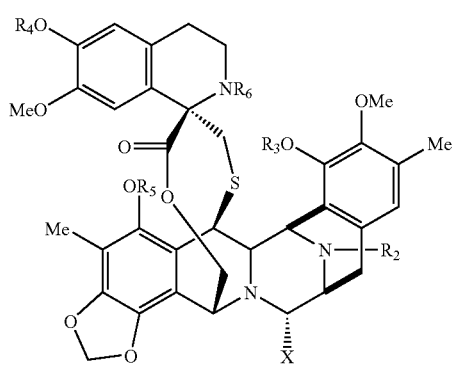

II

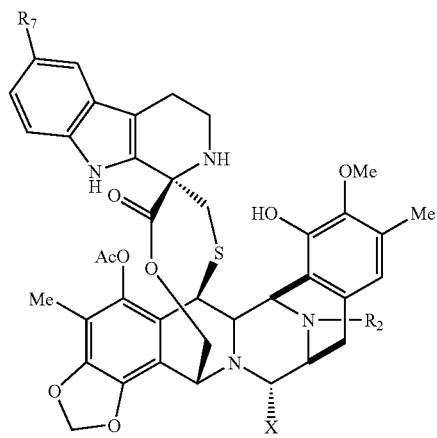

III

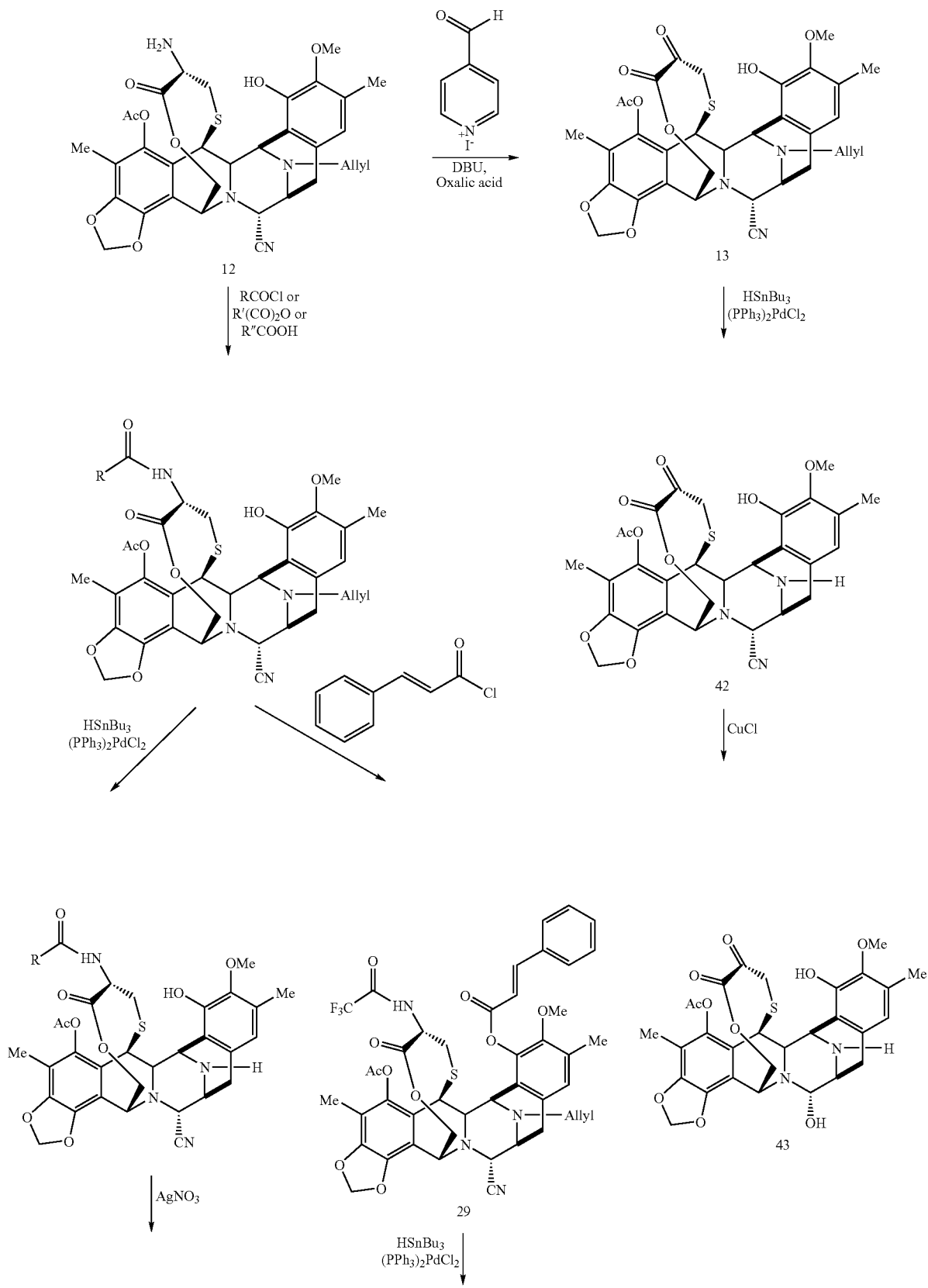

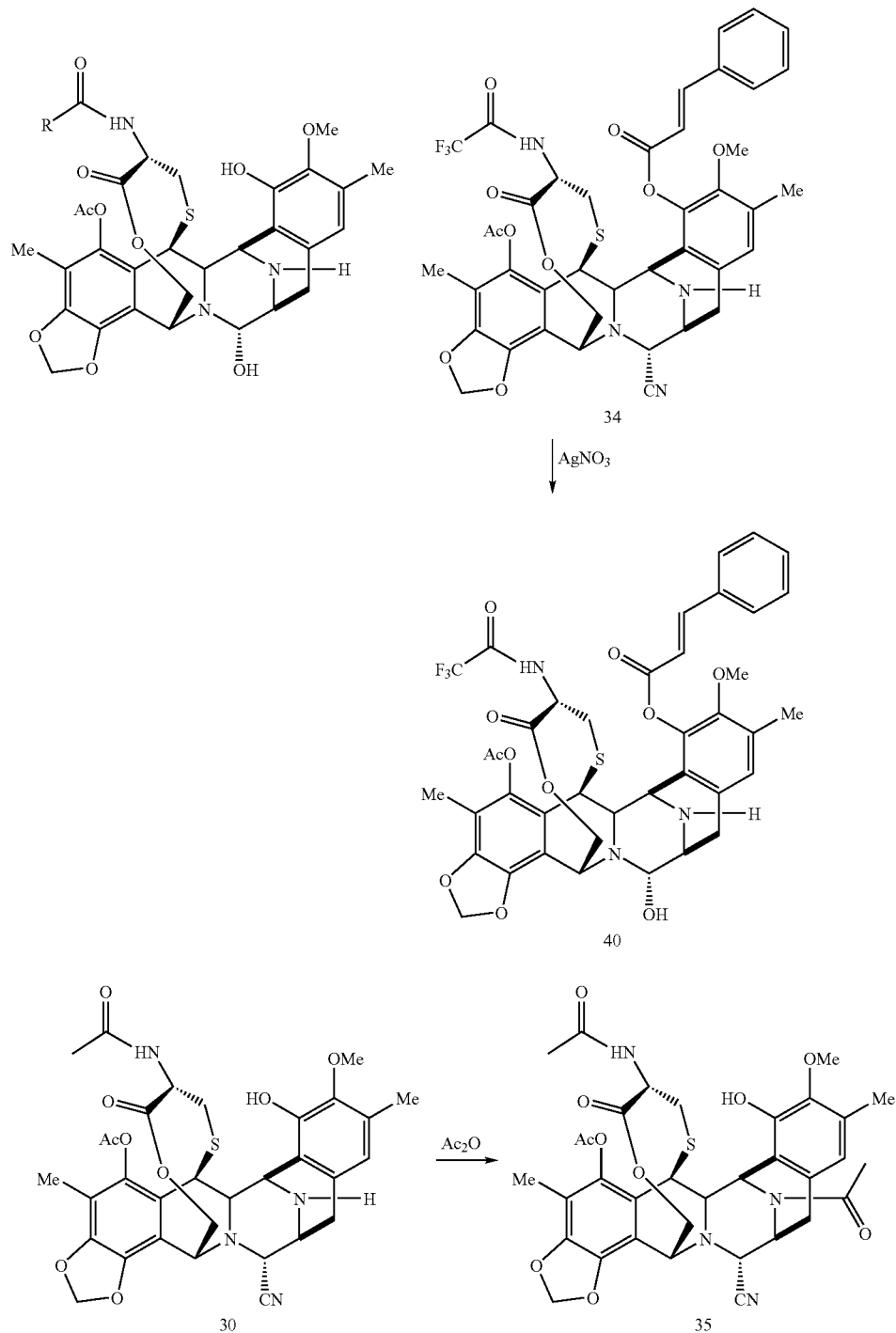

In general, the conversion of Intermediate 12 or 13, to different analogues of ET729 involves the following transformations:

(a) Acylation reactions through the different procedures described in the experimental part, deallylation reactions at N-12 and interconversion of the nitrile group into the hydroxyl group. Compound 40 is an example of intermediate with typical substituent groups wherein two consecutive acylation reactions has placed, followed by the two last steps described above.

(b) Generation of compound 35 form intermediate 30 in a single step by acetylation reaction at N-12.

(c) Synthesis of compound 43 from compound 13 by deallylation reaction and conversion of the nitrile group into the hydroxyl group with CuCl.

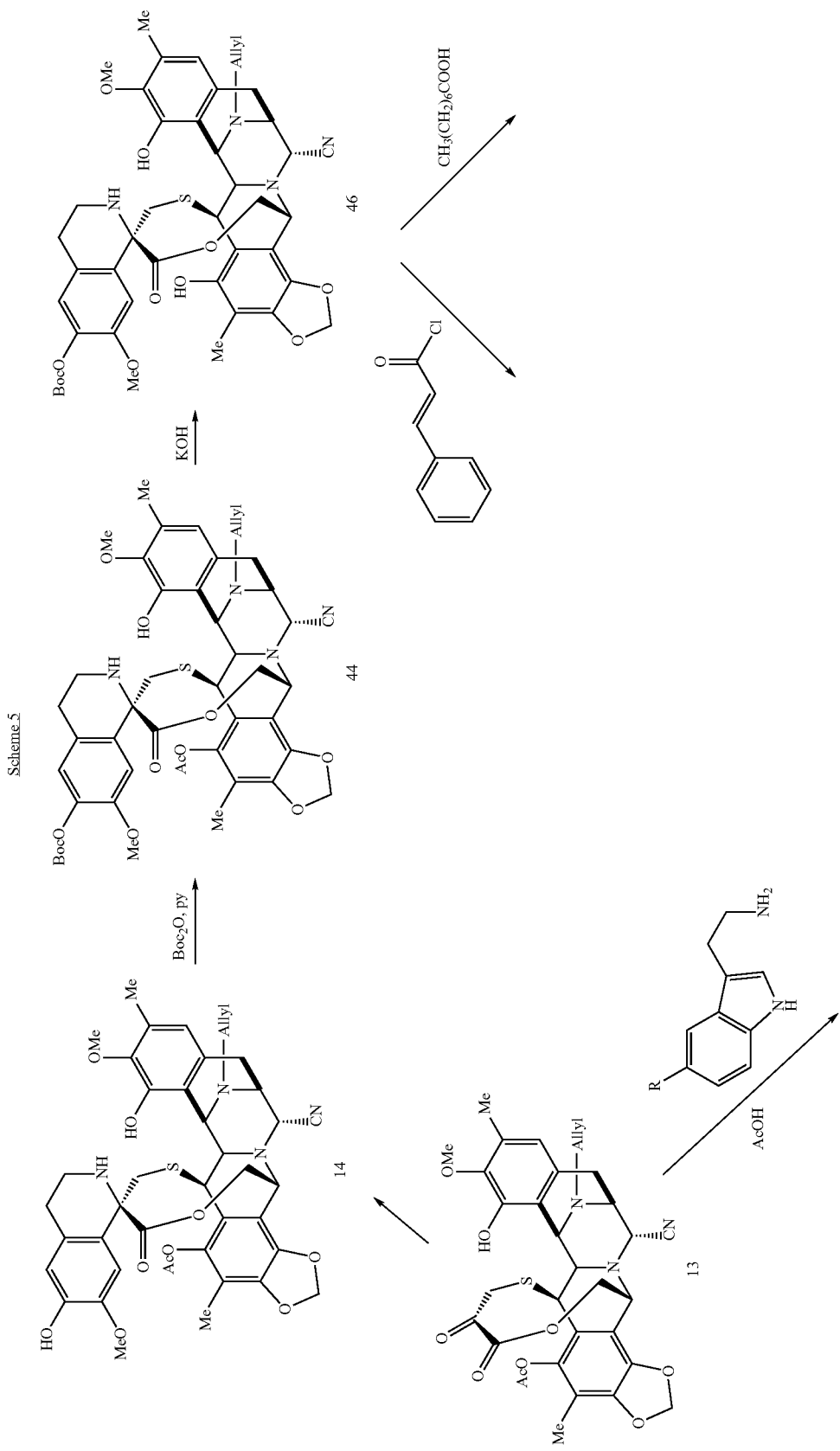

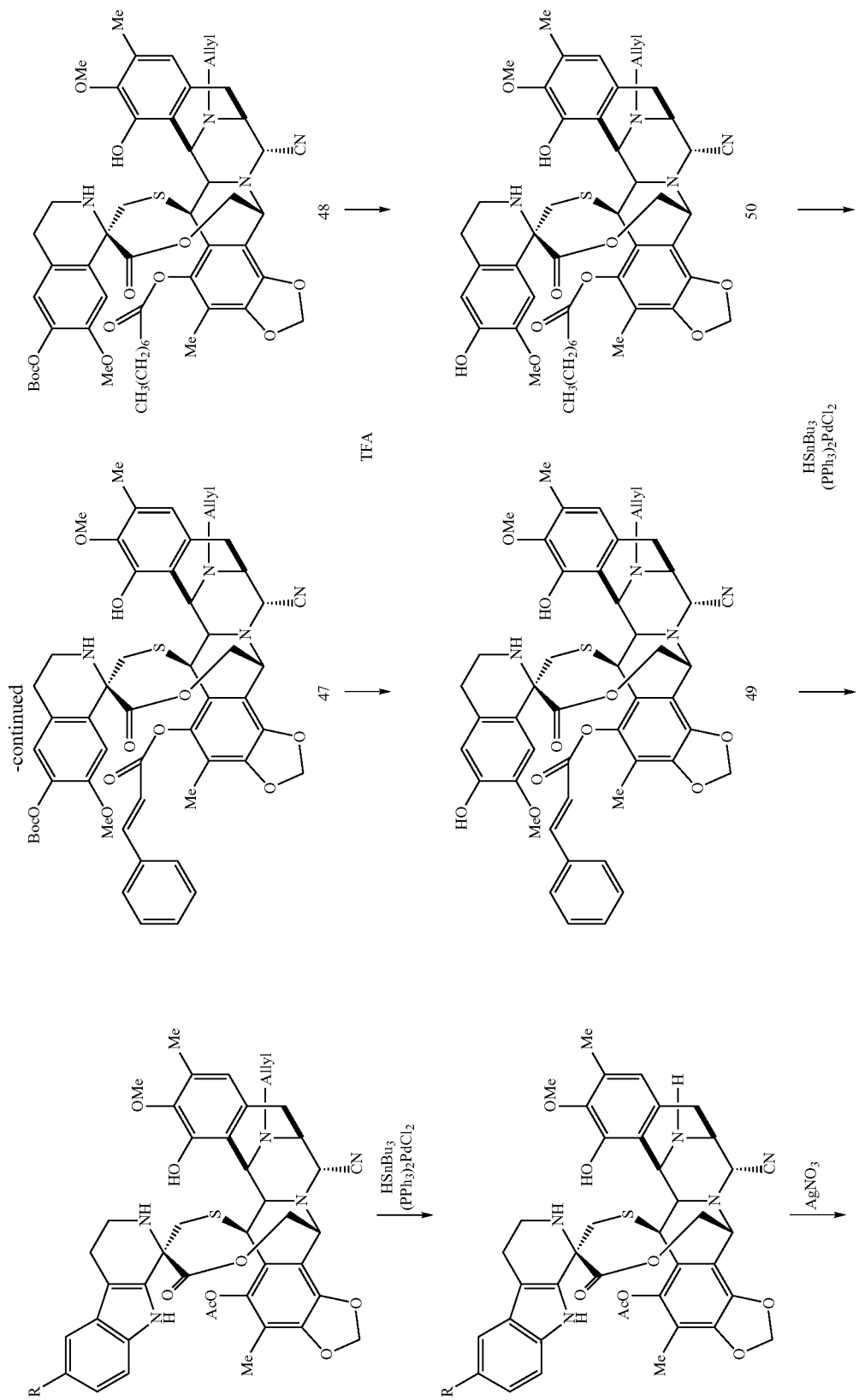

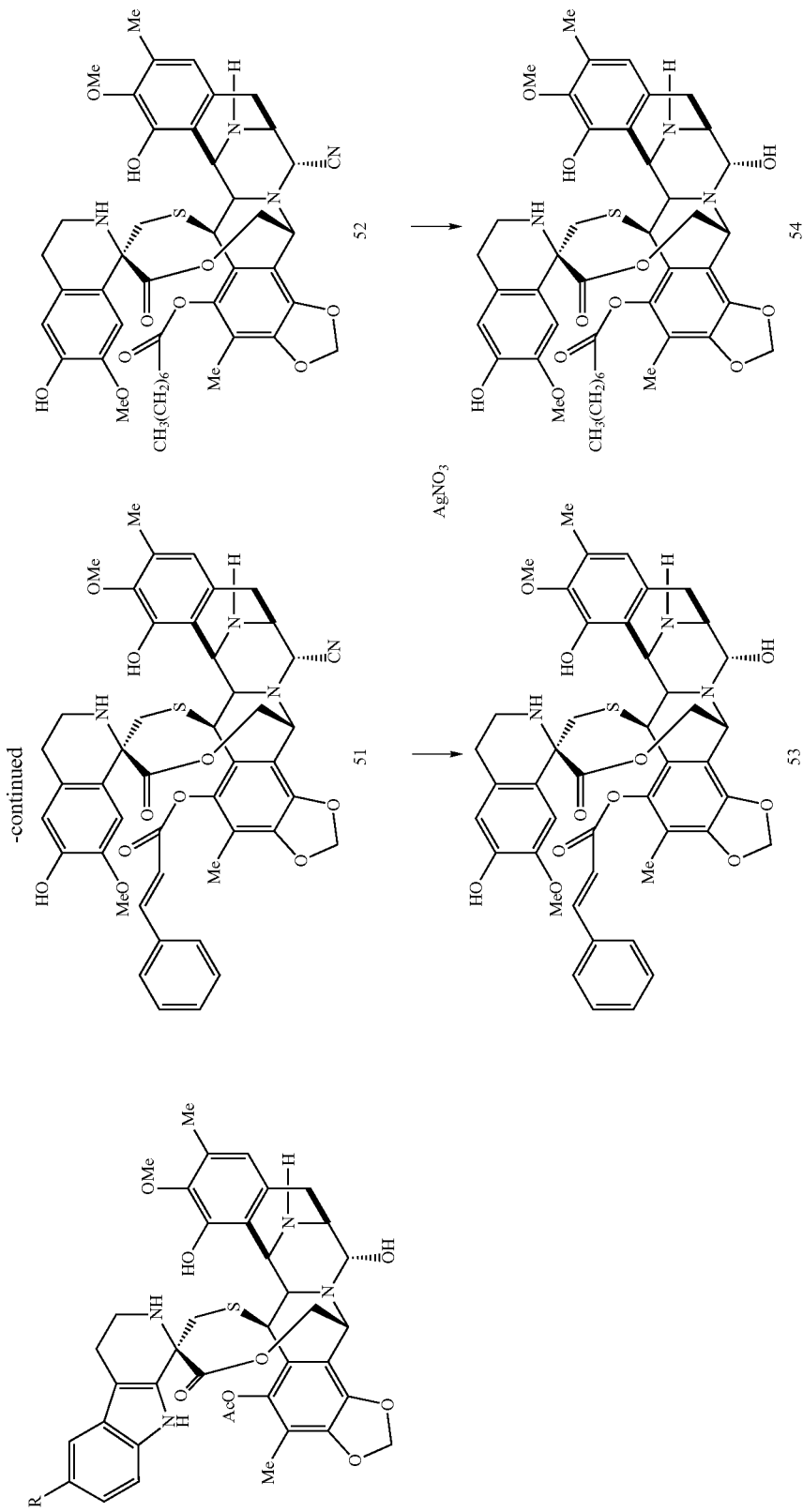

In more detail, such processes involve the following transformations from intermediate 13.

(a) Generation of intermediate 46 in two steps from compound 14 by protection of the hydroxyl group as Boc carbonate and deacetyllation at C-5 with KOH.

(b) Synthesis of compounds 53 and 54 from intermediate 46 following the same synthetic sequence: Acylation reaction at C-5 with cinnamoyl chloride or octanoic acid, deprotection of the carbonate group, deallylation reaction at N-12 and finally conversion of the nitrile group into the hydroxyl group.

(c) Synthesis of different analogues of ET729 from intermediate 13 involving three steps: introduction of the triptamine moiety, deallylation reaction and conversion of the nitrile group into the hydroxyl group.

Scheme 6

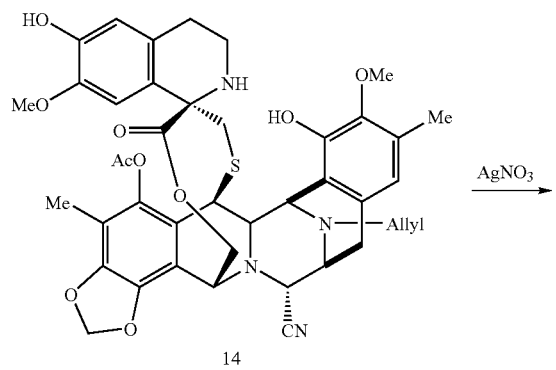

14

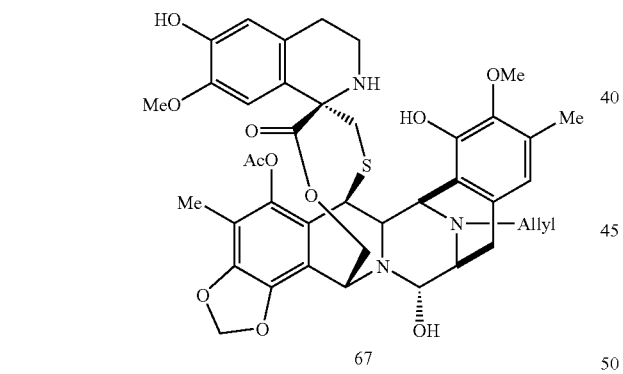

67

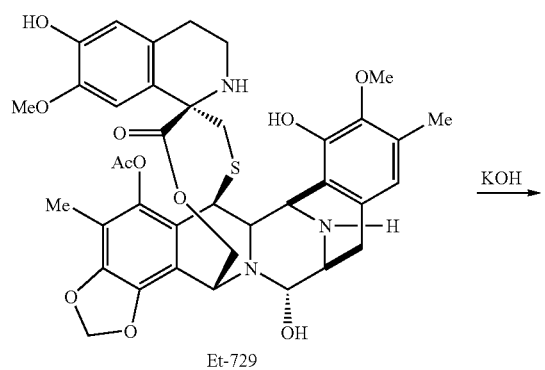

Et-729

-continued

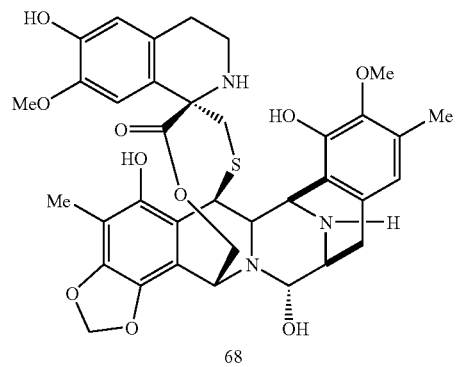

68

In more detail, scheme 6 describes the synthesis of compound 67 and 68 from intermediate 14 and ET729 respectively.

In a further embodiment, the current invention provides a process for the synthesis of a new family of ecteinascidin compounds wherein the lactone linkage of the 1,4 bridge of ET743 and related intermediates is replaced with an amide linkage, as detailed in Scheme 7.

Scheme 7

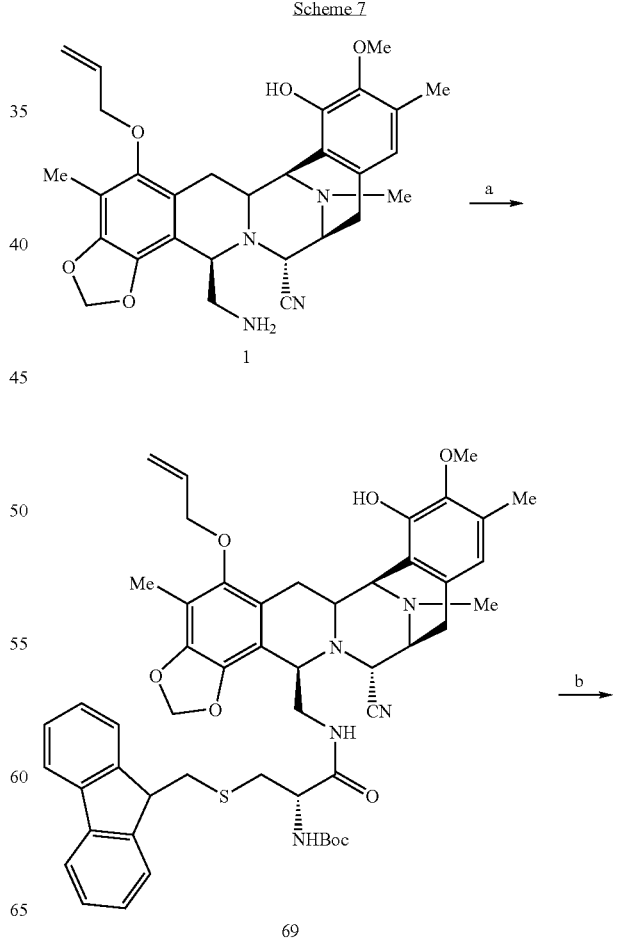

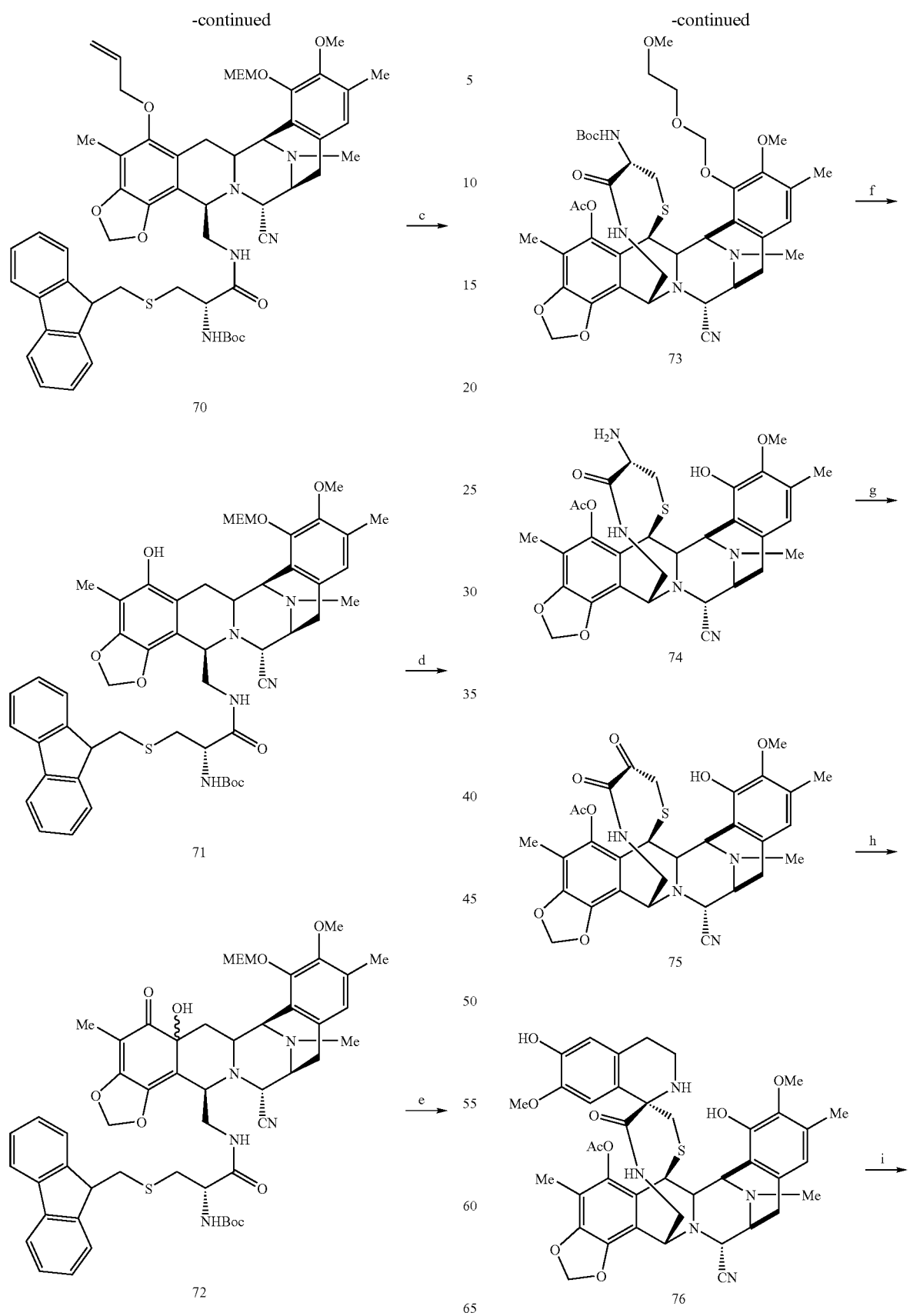

-continued

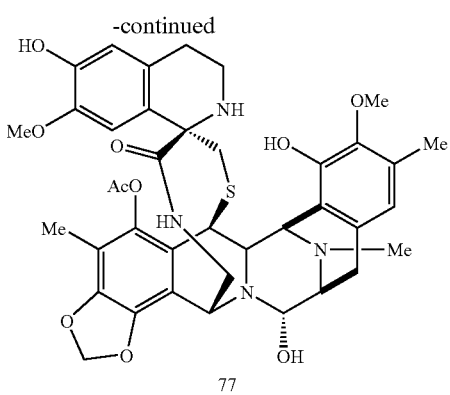

77

In more detail, intermediate 1 (intermediate 21 in patent applications WO 0069862 and WO 0187895) can be converted to such compounds through the following sequence of steps:
(a) Introduction of a protected cysteine fragment in a single step by coupling with the primary amine functionality of intermediate 1.
(b) Protecting group manipulations and an oxidation reaction to generate intermediate 72.
(c) Cyclization to generate the desired lactam bridge structure followed by deprotection of the primary amine.
(d) Completion of the synthesis through transamination, Pictect-Spengler reaction and conversion of the nitrile into a hydroxyl group.

Thus this invention provides a process for the synthesis of a large family of compounds related to ET743 in which the lactone linkage of the bridge structure has been replaced by a lactam linkage.

As the skilled artisan will readily appreciate, the reaction schemes described herein may be modified and/or combined in various ways, and the alternative sequences of steps and the compounds generated therefrom are part of this invention.

Thus, by these and other routes, it is possible to transform cyanosafracin B into a number of intermediates and derivatives with potential antitumor therapeutic activity. These intermediates can be made starting from already described compounds, or using alternative routes.

Novel Active Compounds

We have additionally found that certain of the compounds of the invention which we initially prepared as intermediates have exceptional activity in the treatment of cancers, such as leukaemias, lung cancer, colon cancer, kidney cancer and melanoma.

Thus, the present invention provides a method of treating any mammal, notably a human, affected by cancer which comprises administering to the affected individual a therapeutically effective amount of a compound of the invention, or a pharmaceutical composition thereof.

The present invention also relates to pharmaceutical preparations, which contain as active ingredient a compound or compounds of the invention, as well as the processes for their preparation.

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

Administration of the compounds or compositions of the present invention may be by any suitable method, such as intravenous infusion, oral preparations, intraperitoneal and intravenous administration. We prefer that infusion times of up to 24 hours are used, more preferably 2-12 hours, with 2-6 hours most preferred. Short infusion times which allow treatment to be carried out without an overnight stay in hospital are especially desirable. However, infusion may be 12 to 24 hours or even longer if required. Infusion may be carried out at suitable intervals of say 2 to 4 weeks. Pharmaceutical compositions containing compounds of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of this invention may be used with other drugs to provide a combination therapy. The other drugs may form part of the same composition, or be provided as a separate composition for administration at the same time or a different time. The identity of the other drug is not particularly limited, and suitable candidates include:

a) drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine);

b) antimetabolite drugs such as 5-fluorouracil, cytarabine, gemcitabine, purine analogues such as pentostatin, methotrexate);

c) alkylating agents such as nitrogen mustards (such as cyclophosphamide or ifosphamide);

d) drugs which target DNA such as the antracycline drugs adriamycin, doxorubicin, pharmorubicin or epirubicin;

e) drugs which target topoisomerases such as etoposide;

f) hormones and hormone agonists or antagonists such as estrogens, antiestrogens (tamoxifen and related compounds) and androgens, flutamide, leuprorelin, goserelin, cyprotrone or octreotide;

g) drugs which target signal transduction in tumour cells including antibody derivatives such as herceptin;

h) alkylating drugs such as platinum drugs (cis-platin, carbonplatin, oxaliplatin, paraplatin) or nitrosoureas;

i) drugs potentially affecting metastasis of tumours such as matrix metalloproteinase inhibitors;

j) gene therapy and antisense agents;

k) antibody therapeutics;

l) other bioactive compounds of marine origin, notably the didemnins such as aplidine;

m) steroid analogues, in particular dexamethasone;

n) anti-inflammatory drugs, in particular dexamethasone; and o) anti-emetic drugs, in particular dexamethasone.

The present invention also extends to the compounds of the invention for use in a method of treatment, and to the use of the compounds in the preparation of a composition for treatment of cancer.

EXAMPLES

The present invention is illustrated by the following examples.

Experimental Part

Example 1

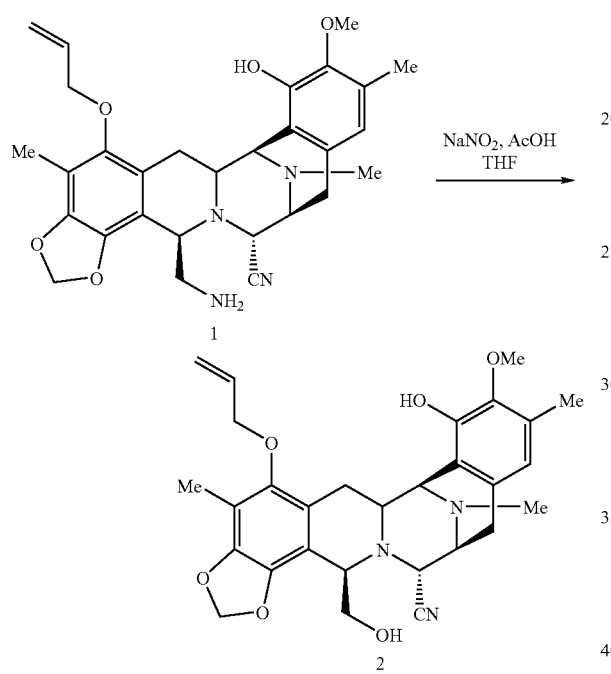

A solution of 1 (9.84 g, 18.97 mmol) in THF (569 mL) and H$_2$O (285 mL) was cooled at 0° C. with an ice bath. Then, NaNO$_2$ (1.96 g, 28.45 mmol) and 90% aq. AcOH (18.97 mL, 0.33 mol) were added at 0° C. and the mixture was stirred at 23° C. for 18 h. After cooling down the reaction to 0° C., a saturated aqueous sodium bicarbonate solution (300 mL, basic pH) and dichloromethane (500 mL) were added. After extraction, the aqueous phase was further extracted with dichloromethane (2×300 mL). The combined organic extracts were dried over sodium sulphate and evaporated to dryness under reduced pressure. The crude solid was then dissolved in MeOH (379 mL), and 1M NaOH (38 mL) was added at 0° C. The mixture was stirred at 23° C. for 4 h. After dilution with EtOAc (600 mL) at 0° C., the organic layer was washed with a mixture of water (400 mL) and, a saturated aqueous sodium bicarbonate solution (100 mL, basic pH). After extraction, the aqueous phase was further extracted with EtOAc (3×300 mL). The combined organic extracts were dried over Na$_2$SO$_4$, filtered and concentrated in vacuo. The residue was purified by flash column chromatography (SiO$_2$, Hex:EtOAc gradient from 3:1 to 2:1) to afford 2 (4.55 g, 46%) as a white solid.

R$_f$: 0.33 (Hex:EtOAc 1:1).

$^1$H NMR (300 MHz, CDCl$_3$) 6.48 (s, 1H), 6.15-6.02 (m, 1H), 5.92 (d, 1H), 5.86 (d, 1H), 5.77 (s, 1H), 5.39 (dd, 1H), 5.26 (dd, 1H), 4.24-4.15 (m, 3H), 4.04 (d, 1H), 3.97 (t, 1H), 3.74 (s, 3H), 3.64 (dt, 1H), 3.43 (dd, 1H), 3.38-3.34 (m, 2H), 3.31 (t, 1H), 3.22 (dd, 1H), 3.10 (dd, 1H), 2.49 (d, 1H), 2.34 (s, 3H), 2.24 (s, 3H), 2.11 (s, 3H), 1.88 (dd, 1H).

$^{13}$C NMR (75 MHz, CDCl$_3$) 148.6, 146.7, 144.4, 143.0, 138.9, 133.9, 130.2, 129.1, 121.1, 120.9, 117.7, 117.4, 116.8, 113.3, 112.3, 101.1, 74.3, 63.7, 60.6, 60.1, 58.1, 56.9, 56.7, 55.4, 41.7, 26.2, 25.7, 15.7, 9.3.

ESI-MS m/z: Calcd. for C$_{29}$H$_{33}$N$_3$O$_6$: 519.59. Found (M+1)$^+$: 520.3.

Example 2

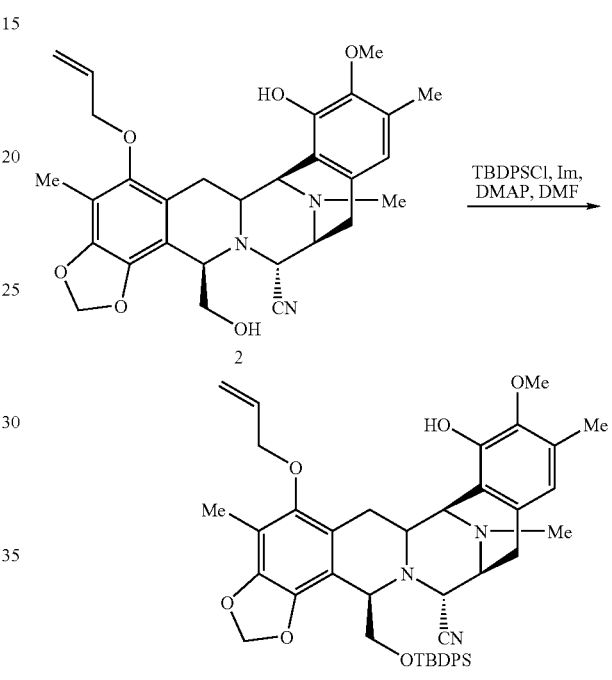

To a solution of 2 (9.33 g, 0.018 mol), in anhydrous DMF (40 mL, 0.45 M) was added at 23° C. imidazole (3.05 g, 0.045 mol) and DMAP (219 mg, 0.0018 mol). The solution was cooled at 0° C. and TBDPSCl (7.0 mL, 0.027 mol) was dropwise added under argon atmosphere. The reaction mixture was allowed to reach 23° C. and left at this temperature for 1 hour and 15 minutes. After this time, water (350 mL) and a mixture of ethyl acetate/hexane (3:2, 250 mL) were added. The organic phase was separated, dried over sodium sulphate and filtered and the solvent was eliminated under reduced pressure. The crude material was purified by flash column chromatography (eluent mixtures of ethyl acetate/hexane in gradient from 15:85 to 2:3) to afford 3 (11.8 g, 87%) as a yellow solid.

R$_f$: 0.36 (ethyl acetate/hexane 2:3)

$^1$H-RMN (300 MHz, CDCl$_3$): δ 7.55 (d, 2H), 7.41-7.22 (m, 8H), 6.45 (s, 1H), 6.18-6.02 (m, 1H), 6.78 (s, 2H), 6.61 (s, 1H), 5.35 (d, 1H), 5.21 (d, 1H), 4.42 (d, 1H), 4.18 (m, 2H), 4.05 (m, 2H), 3.78 (s, 3H), 3.64 (dd, 1H), 3.41-3.31 (m, 2H), 3.29-3.20 (m, 2H); 3.02 (dd, 1H), 2.70 (d, 1H), 2.30 (s, 3H), 2.28 (s, 3H), 2.08 (s, 3H), 2.02 (dd, 1H), 0.90 (s, 9H).

$^{13}$C-RMN (75 MHz, CDCl$_3$): δ 148.69, 146.94, 144.33, 142.90, 139.35, 135.98, 135.67, 134.27, 133.56, 132.94, 131.49, 129.84, 129.70, 128.59, 127.79, 127.73, 122.13, 121.24, 118.94, 117.61, 117.55, 113.22, 112.04, 101.12, 74.52, 68.24, 61.89, 60.93, 59.29, 57.68, 57.06, 55.73, 42.01, 26.93, 26.79, 25.84, 19.19, 16.07, 9.56.

ESI-MS m/z: Calcd. for C$_{45}$H$_{51}$N$_3$O$_6$Si: 757.3. Found (M+Na)$^+$: 780.3.

Example 3

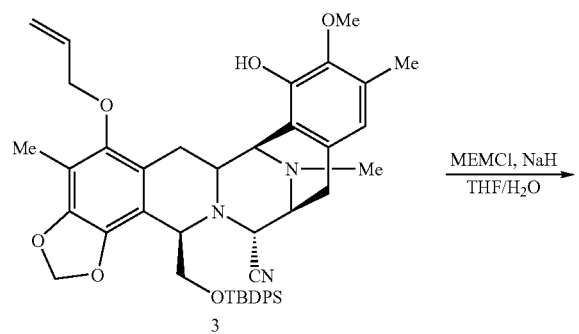
3

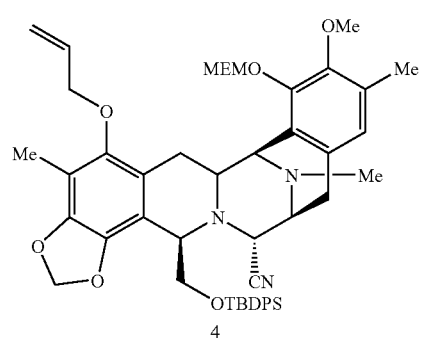
4

118.45, 117.55, 113.23, 111.97, 101.13, 98.49, 95.79, 74.26, 71.98, 71.95, 69.57, 67.44, 67.37, 66.95, 61.32, 59.85, 59.18, 59.10, 57.50, 57.16, 55.58, 41.69, 29.87, 26.83, 26.83, 26.12, 19.05, 16.07, 9.46.

ESI-MS m/z: Calcd. for C$_{49}$H$_{59}$N$_3$O$_8$Si: 845.4. Found (M+1)$^+$: 846.3.

Example 4

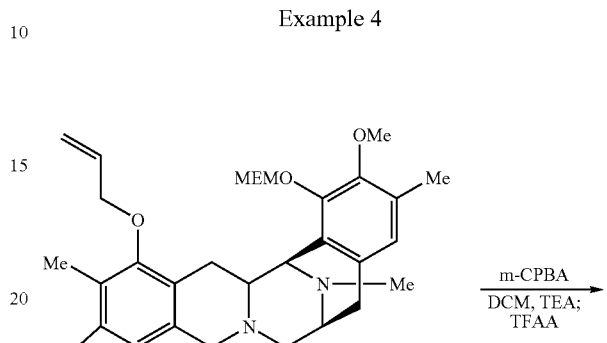
4

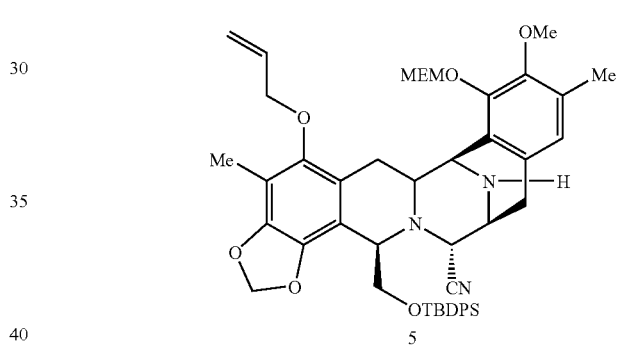
5

To a solution of intermediate 3 (11.75 g, 0.016 mol) in THF/H$_2$O (113 mL/0.31 mL, 0.14 M) was added MEM-chloride (3.0 mL, 0.026 mol). The solution was cooled at 0° C. and sodium hydride (930 mg, 0.023 mol) was portionwise added (1 hour and 15 minutes for the addition). The reaction mixture was left at 0° C. under Argon atmosphere for 1 hour. After this time water (150 mL) was added and the aqueous phase was extracted with dichloromethane (2×150 mL). The combined organic layers were dried over sodium sulphate, filtered and the solvent was eliminated under reduced pressure to afford intermediate 4 (13.4 g, 100%) as a yellow solid. This compound is used for the next step without purification.

R$_f$: 0.32 (ethyl acetate/hexane 1:2)

$^1$H-RMN (300 MHz, CDCl$_3$): δ 7.58 (d, 2H), 7.38 (m, 6H), 7.27 (m, 2H), 6.70 (s, 1H), 6.18-6.02 (m, 1H), 5.75 (s, 1H), 5.60 (s, 1H), 5.40 (d, 1H), 5.28 (d, 1H), 5.24 (d, 1H), 5.19 (d, 1H), 4.50 (broad s, 1H), 4.38 (broad s, 1H), 4.20-3.97 (m, 4H), 3.85 (m, 1H), 3.70 (s, 3H), 3.58 (m, 3H), 3.38 (s, 3H), 3.38 (m, 2H), 3.22 (m, 2H), 3.02 (dd, 1H), 2.70 (d, 1H), 2.38 (s, 3H), 2.24 (s, 3H), 2.05 (s, 3H), 1.93 (dd, 1H), 0.84 (s, 9H).

$^{13}$C-RMN (75 MHz, CDCl$_3$): δ 148.76, 148.60, 148.49, 139.29, 135.87, 135.63, 134.18, 133.23, 132.89, 130.85, 130.49, 129.89, 129.77, 127.82, 127.73, 125.45, 121.76,

To a solution of intermediate 4 (2.51 g, 0.003 mol) in anhydrous dichloromethane (25 mL, 0.12 M) was added at −20° C. under Argon atmosphere m-CPBA (1.33 g, 0.006 mol). The solution was allowed to reach −10° C. for 25 minutes, TEA (4.14 mL, 0.03 mol) was added and the reaction mixture was left at 0° C., finally TFAA (6.29 mL, 0.045 mol) was dropwise added and the solution kept at 0° C. for 30 minutes. After this time water was added and the aqueous phase was separated, dried over sodium sulphate, filtered and the solvent was eliminated under reduced pressure. The crude was purified by flash column chromatography (eluent mixtures of ethyl acetate/hexane in gradient from 1:4 to 6:1 and final washes with methanol) to afford intermediate 5 (2.1 g, 85%) as a yellow solid.

R$_f$: 0.19 (ethyl acetate/hexane 1:1)

$^1$H-RMN (300 MHz, CDCl$_3$): δ 7.55 (d, 2H), 7.45-7.28 (m, 8H), 6.70 (s, 1H), 6.14-6.02 (m, 1H), 5.81 (d, 1H), 5.67 (d, 1H), 5.43-5.35 (m, 2H), 5.26 (m, 2H), 5.03 (broad s, 1H), 4.73 (broad s, 1H), 4.68 (m, 1H), 4.22-4.09 (m, 3H), 3.81 (broad s, 2H), 3.73 (s, 3H), 3.61 (dd, 1H), 3.53 (broad s, 4H), 3.46-3.28 (m, 2H), 3.34 (s, 3H), 2.97 (d, 1H), 2.25 (s, 3H), 2.11 (s, 3H), 1.95 (dd, 1H), 0.94 (s, 9H).

ESI-MS m/z: Calcd. for C$_{48}$H$_{57}$N$_3$O$_8$Si: 831.4. Found (M+Na)$^+$: 832.3.

Example 5

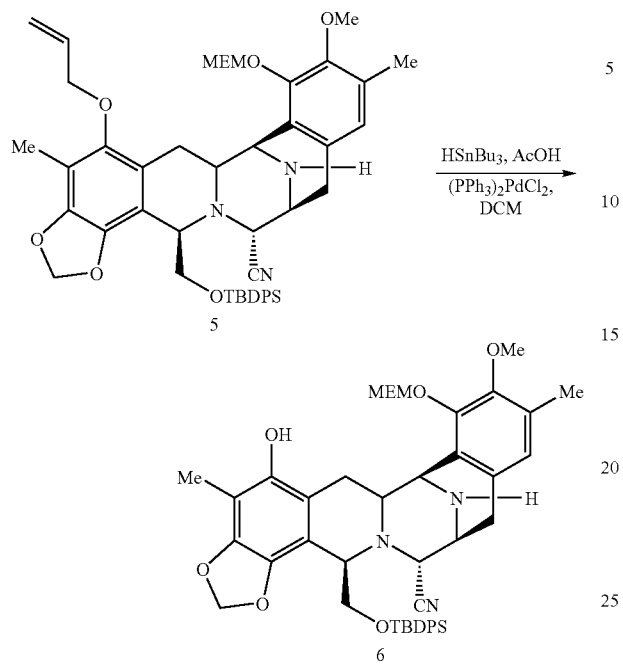

To a solution of intermediate 5 (5.9 g, 7.09 mmol), (PPh$_3$)$_2$PdCl$_2$ (399 mg, 0.57 mmol), acetic acid (2.03 mL, 35.47 mmol) in anhydrous dichloromethane (45 mL, 0.16 M) was dropwise added at 23° C. tributyltin hydride (6.7 mL, 24.83 mmol). The reaction mixture was left at 23° C. and under Argon atmosphere for 35 minutes. The reaction mixture was poured onto column (eluent mixtures of ethyl acetate/hexane in gradient from 1:4 to 8:1) to afford intermediate 6 (3.97 g, 71%) as a yellow solid.

R$_f$: 0.17 (ethyl acetate/hexane 1:1)

$^1$H-RMN (300 MHz, CDCl$_3$): δ 7.57 (d, 2H), 7.43-7.24 (m, 8H), 6.68 (s, 1H), 5.73 (d, 1H), 5.58 (d, 1H), 5.47 (d, 1H), 5.22 (d, 1H), 4.54 (d, 1H), 4.47 (d, 1H), 4.14 (m, 1H), 4.04 (dd, 1H), 3.94 (m, 1H), 3.73-3.65 (m, 4H), 3.70 (s, 3H), 3.39 (s, 3H), 3.38-3.30 (m, 2H), 3.25 (m, 1H), 3.11 (dd, 1H); 2.91 (d, 1H), 2.24 (s, 3H), 2.06 (s, 3H), 1.84 (dd, 1H), 0.91 (s, 9H).

ESI-MS m/z: Calcd. for C$_{45}$H$_{53}$N$_3$O$_8$Si: 791.4. Found (M+Na)$^+$: 814.3.

Example 6

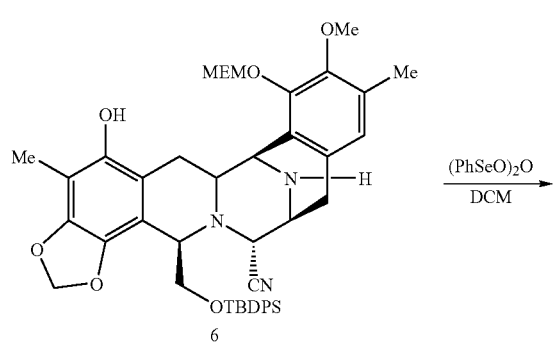

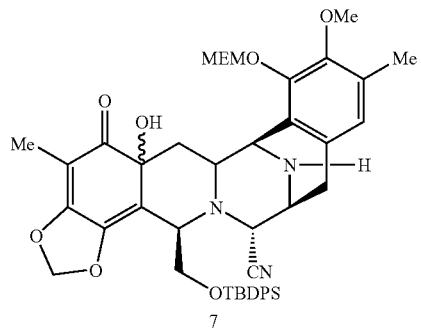

To a solution of intermediate 6 (1.87 g, 2.36 mmol) in anhydrous dichloromethane (20 mL, 0.12 M) was dropwise added at −15° C. under Argon atmosphere a solution of benceneseleninic anhydride (1.82 g, 3.53 mmol) in anhydrous dichloromethane (20 mL). The solution was left at −15° C. for 25 minutes. The reaction mixture was diluted with dichloromethane, and a saturated solution of sodium bicarbonate was added at −10° C. The aqueous phase was extracted with dichloromethane, the combined organic layers were dried over sodium sulphate, filtered and the solvent was eliminated under reduced pressure. The crude of the reaction was purified by flash column chromatography (eluent mixtures of ethyl acetate/hexane in gradient from 1:6 to 6:1) to afford intermediate 7 (1.53 g, 80%) as a yellow solid and as a mixture of isomers 3:1 by $^1$H-RMN.

R$_f$: 0.24 (ethyl acetate/hexane 2:1)

$^1$H-RMN (300 MHz, CDCl$_3$): δ 7.64 (dd, 6H), 7.57 (d, 2H), 7.40-7.25 (m, 12H), 6.65 (s, 1H), 6.53 (s, 1H), 5.65 (s, 1H), 5.42 (s, 1H), 5.25 (s, 1H), 5.23 (s, 1H), 5.22 (m, 1H), 5.19 (d, 1H), 5.11 (d, 1H), 5.06 (d, 1H), 4.80 (s, 1H), 4.73 (s, 1H), 4.43 (d, 1H), 4.36 (m, 1H), 4.32 (m, 1H), 4.25 (d, 1H), 3.97 (dd, 1H); 3.89 (s, 3H), 3.86-3.77 (m, 4H), 3.74-3.60 (m, 4H), 3.59 (s, 3H), 3.55-3.48 (m, 4H), 3.38-3.35 (m, 2H), 3.34 (s, 3H), 3.31 (s, 3H), 3.18-3.03 (m, 2H), 2.96 (dd, 1H), 2.73 (d, 1H), 2.57 (d, 1H), 2.21 (s, 3H), 2.14 (s, 3H), 2.17-1.86 (m, 2H), 1.75 (s, 3H), 1.70 (s, 3H), 1.07 (s, 9H), 0.99 (s, 9H).

$^{13}$C-RMN (75 MHz, CDCl$_3$): δ 201.05, 197.78, 160.43, 158.64, 148.81, 147.84, 146.88, 146.70, 140.01, 137.97, 135.99, 135.97, 135.79, 133.64, 133.00, 132.80, 131.33, 131.25, 130.61, 130.41, 130.05, 129.98, 129.91, 129.04, 127.95, 127.91, 127.77, 127.60, 125.98, 125.82, 117.38, 117.26, 113.51, 111.22, 104.50, 104.37, 101.39, 100.55, 98.16, 95.84, 92.51, 73.09, 71.96, 71.94, 71.92, 70.48, 69.67, 69.60, 67.65, 66.99, 64.65, 60.68, 60.23, 60.12, 60.02, 59.35, 59.26, 59.24, 59.22, 59.19, 59.03, 56.81, 56.44, 50.30, 49.99, 49.73, 49.61, 43.24, 36.30, 31.30, 27.10, 19.57, 19.23, 16.03, 16.01, 7.55, 7.27.

ESI-MS m/z: Calcd. for C$_{45}$H$_{53}$N$_3$O$_9$Si: 807.4. Found (M+1)$^+$: 808.3.

Example 7

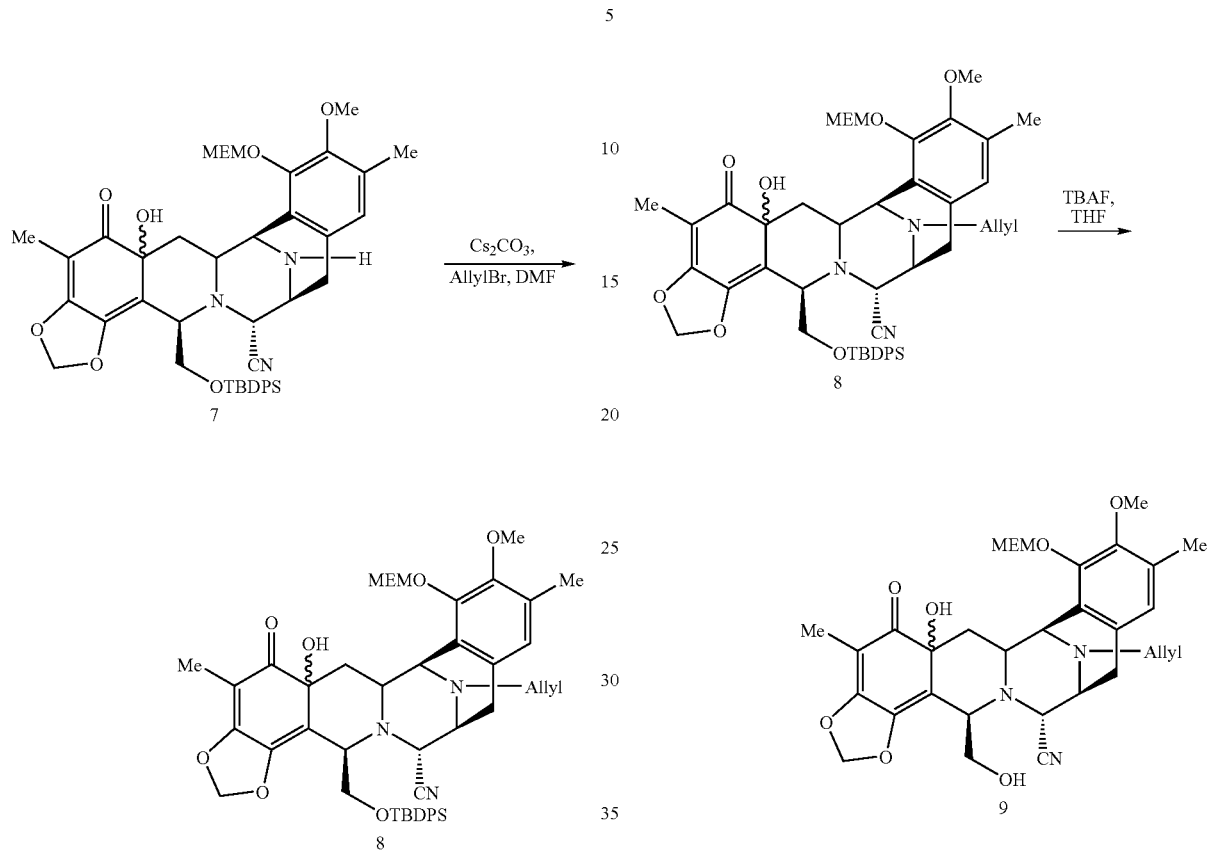

To a solution of intermediate 7 (3.78 g, 4.68 mmol) in anhydrous DMF (30 mL, 0.16 M) was added at 23° C. and under Argon atmosphere cesium carbonate (5.35 g, 16.39 mmol) and allyl bromide (2.03 mL, 23.42 mmol). The reaction mixture was left at 23° C. for 16 hours, cooled at 0° C. and dropwise added acetic acid to destroy the excess of base. The solution was diluted with dichloromethane and a saturated solution of sodium bicarbonate was dropwise added. The aqueous phase was extracted with dichloromethane, the combined organic layers were dried over sodium sulphate, filtered and the solvent was eliminated under reduced pressure. The crude was purified by flash column chromatography (eluent mixtures of hexane/ethyl acetate in gradient from 100/0 to 2:1) to afford intermediate 8 (3.62 g, 91%) as a yellow solid.

$R_f$: 0.40 (ethyl acetate/hexane 1:1)

$^1$H-RMN (300 MHz, CDCl$_3$): δ 7.65 (m, 3H), 7.43-7.28 (m, 7H), 6.54 (s, 1H), 5.88 (m, 1H), 5.31-5.10 (m, 2H), 5.24 (s, 1H), 5.19 (s, 1H), 5.12 (d, 1H), 5.02 (d, 1H), 4.47 (d, 1H), 4.34 (dd, 1H), 3.99 (dd, 1H), 3.93-3.86 (m, 2H), 3.81-3.73 (m, 2H), 3.62-3.53 (m, 2H), 3.61 (s, 3H), 3.41 (m, 1H), 3.37 (s, 3H), 3.23 (m, 1H), 3.08-2.97 (m, 2H), 2.79 (ddd, 2H), 2.39 (d, 1H), 2.24-1.95 (m, 1H), 2.17 (s, 3H), 1.71 (s, 3H), 1.07 (s, 9H).

ESI-MS m/z: Calcd. for C$_{48}$H$_{57}$N$_3$O$_9$Si: 847.4. Found (M+1)$^+$: 848.2.

Example 8

To a solution of intermediate 8 (942 mg, 1.11 mmol) in anhydrous THF (10 mL, 0.1 M) and under Argon atmosphere was dropwise added TBAF (3.33 mL, 3.33 mmol) at 23° C. The reaction mixture was left at 23° C. under Argon atmosphere for 2 hours and 20 minutes. The solution was diluted with ethyl acetate and a saturated solution of brine was added. The organic phase was separated, dried over sodium sulphate, filtered and the solvent was eliminated under reduced pressure. The crude was purified by flash column chromatography (eluent mixtures of ethyl acetate/hexane in gradient from 1:2 to 2:1) to afford intermediate 9 (461 mg, 68%) as a yellow solid.

$R_f$: 0.26 (ethyl acetate/hexane 2:1)

$^1$H-RMN (300 MHz, CDCl$_3$): δ 6.66 (s, 1H), 6.60 (s, 1H), 5.88-5.80 (m, 1H), 5.81 (s, 3H), 5.80 (s, 3H), 5.20 (d, 2H), 5.12 (d, 1H), 5.07 (d, 1H), 4.12 (m, 1H), 4.07 (m, 1H), 3.91-3.67 (m, 4H), 3.85 (s, 3H), 3.59-3.49 (m, 4H), 3.41 (broad d, 1H), 3.34 (m, 1H), 3.31 (s, 3H), 3.24 (dt, 1H), 3.09 (dd, 1H), 2.86 (ddd, 2H), 2.53 (d, 2H), 2.18 (s, 3H), 2.05 (d, 2H), 1.75 (s, 3H).

$^{13}$C-RMN (75 MHz, CDCl$_3$): δ 198.81, 159.04, 149.01, 148.23, 140.94, 135.34, 131.42, 130.99, 125.74, 123.58, 117.99, 117.21, 111.06, 104.41, 101.86, 98.52, 71.86, 70.57, 69.43, 62.25, 60.63, 59.22, 59.19, 58.46, 56.68, 56.22, 55.74, 51.89, 36.57, 25.79, 15.98, 7.52.

ESI-MS m/z: Calcd. for C$_{32}$H$_{39}$N$_3$O$_9$: 609.3. Found (M+Na)$^+$: 632.3.

Example 9

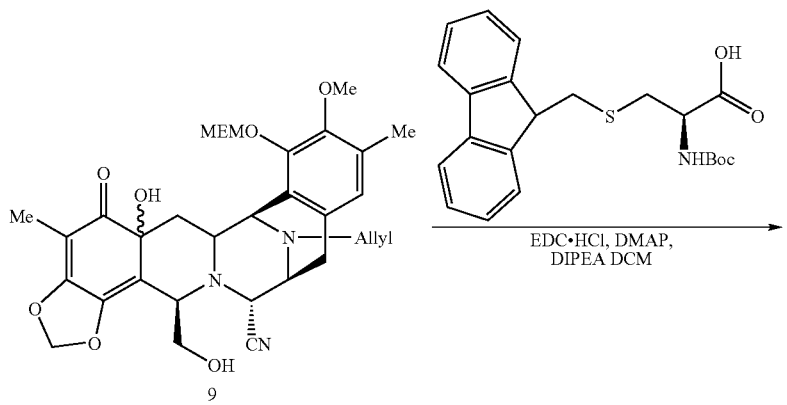

To a solution of intermediate 9 (1.43 g, 2.34 mmol) and cysteine derivative (1.40 g, 3.51 mmol) in anhydrous dichloromethane (20 mL, 0.12 M), was added at 23° C. EDC.HCl (1.12 g, 5.85 mmol), DMAP (144 mg, 1.17 mmol) and DIPEA (0.24 mL, 1.36 mmol). The reaction mixture was left under Argon atmosphere for 2 hours. A saturated solution of sodium bicarbonate was added and the aqueous phase was extracted with dichloromethane, the combined organic layers were dried over sodium sulphate, filtered and the solvent was eliminated under reduced pressure. The crude was purified by flash column chromatography (eluent mixtures of ethyl acetate/hexane in gradient from 1:4 to 2:1) to afford intermediate 10 (1.42 g, 61%, some starting material was recuperated) as a yellow solid and as a mixture of 4 isomers.

$R_f$: 0.26 (ethyl acetate/hexane 2:1)

$^1$H-RMN (300 MHz, CDCl$_3$): δ 7.70 (d, 8H), 7.66-7.58 (m, 8H), 7.37-7.23 (m, 16H), 6.59 (broad s, 2H), 6.49 (s, 1H), 6.47 (s, 1H), 5.87-5.79 (m, 4H), 5.69, 5.67, 5.65 (broad s, 6H), 5.56 (s, 2H), 5.38-4.97 (m, 20H), 4.61-4.37 (m, 12H), 4.18-3.85 (m, 28H), 3.78 (s, 3H), 3.77-3.66 (m, 2H), 3.59 (s, 3H), 3.58 (s, 3H), 3.58 (s, 3H), 3.53 (m, 8H), 3.35 (m, 2H), 3.35 (s, 3H), 3.35 (s, 3H), 3.32 (s, 3H), 3.31 (s, 3H), 3.21-2.55 (m, 36H), 2.43-2.30 (m, 4H), 2.17 (s, 6H), 2.12 (s, 3H), 2.10 (s, 3H), 1.74, 1.74, 1.73 (s, 12H), 1.22 (s, 36H).

ESI-MS m/z: Calcd. for C$_{54}$H$_{62}$N$_4$O$_{12}$S: 990.4. Found (M+1)$^+$: 991.2.

Example 10

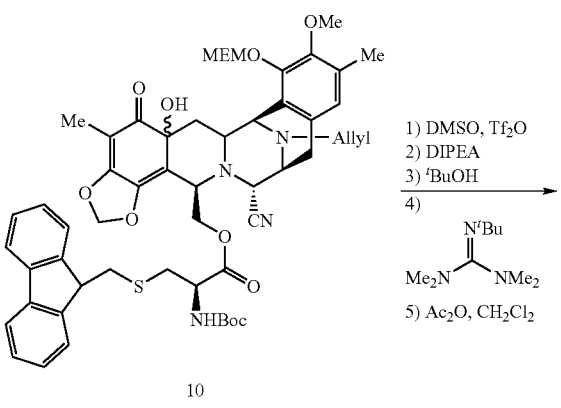

Example 11

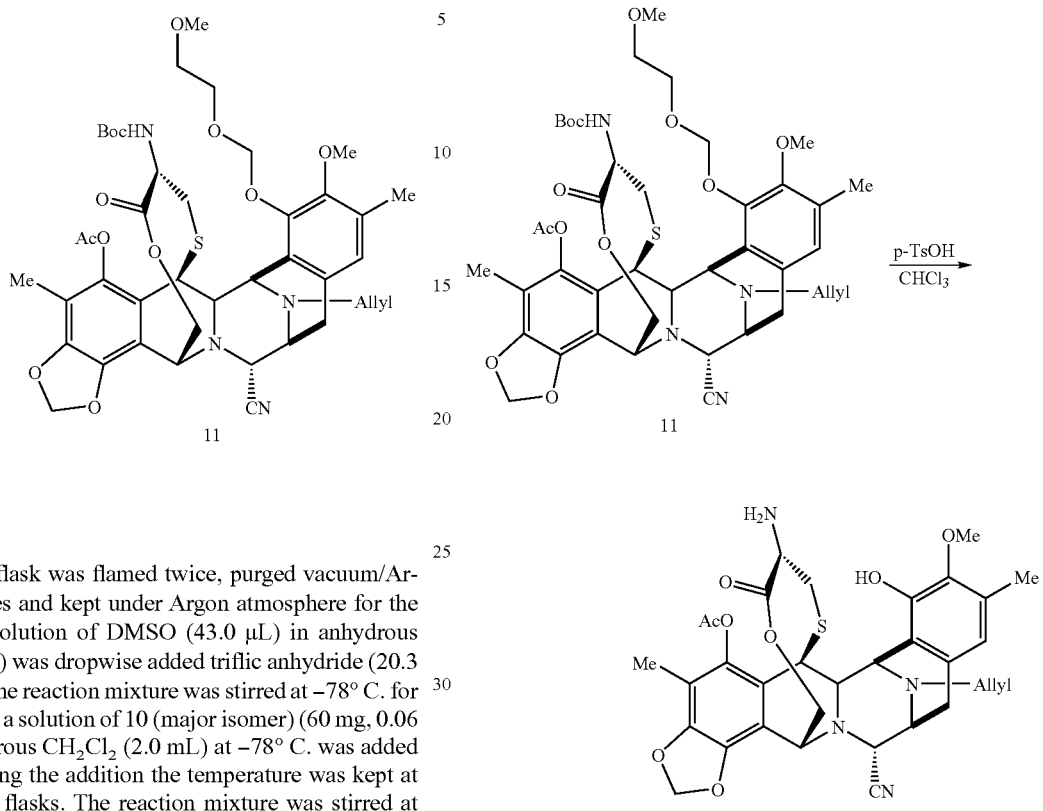

The reaction flask was flamed twice, purged vacuum/Argon several times and kept under Argon atmosphere for the reaction. To a solution of DMSO (43.0 µL) in anhydrous CH$_2$Cl$_2$ (4.0 mL) was dropwise added triflic anhydride (20.3 µL) at −78° C. The reaction mixture was stirred at −78° C. for 20 minutes, then a solution of 10 (major isomer) (60 mg, 0.06 mmol) in anhydrous CH$_2$Cl$_2$ (2.0 mL) at −78° C. was added via canula. During the addition the temperature was kept at −78° C. in both flasks. The reaction mixture was stirred at −40° C. for 35 minutes. After this time, $^i$Pr$_2$Net (160 µL) was dropwise added and the reaction mixture was kept at 0° C. for 45 minutes. Then $^t$BuOH (57 µL) and guanidine (96 µL) were dropwise added and the reaction mixture was stirred at 23° C. for 40 minutes. After this time, acetic anhydride (86 µL) was dropwise added and the reaction mixture was kept at 23° C. for 1 hour more. Then the reaction mixture was diluted with CH$_2$Cl$_2$ and washed with an aqueous saturated solution of NH$_4$Cl, NaHCO$_3$ and NaCl. The combined organic layers were dried over Na$_2$SO$_4$, filtered and concentrated.

The residue was purified by a flash column chromatography (eluent mixtures of ethyl acetate/hexane in gradient from 1:4 to 1:1) to afford 11 (34 mg, 67%) as a pale yellow solid.

R$_f$: 0.43 (ethyl acetate/hexane 1:1)

$^1$H-RMN (300 MHz, CDCl$_3$): δ 6.79 (s, 1H), 6.08 (d, 1H), 5.98 (d, 1H), 5.92-5.82 (m, 1H), 5.32 (d, 1H), 5.18 (m, 1H), 5.17 (d, 1H), 5.12 (d, 1H), 5.01 (d, 1H), 4.62 (d, 1H), 4.52 (broad s, 1H), 4.41 (d, 1H), 4.28 (m, 2H), 4.20 (d, 1H), 4.14 (dd, 1H), 3.91 (oct, 2H), 3.76 (s, 3H), 3.59 (t, 2H), 3.54 (m, 1H), 3.44 (d, 1H), 3.37 (s, 3H), 3.00 (m, 2H), 2.90-2.72 (m, 3H), 2.37-2.24 (m, 1H), 2.31 (s, 3H), 2.29 (s, 3H), 2.02 (s, 3H), 1.45 (s, 9H).

$^{13}$C-RMN (75 MHz, CDCl$_3$): δ 170.89, 168.86, 155.36, 149.40, 148.60, 145.97, 141.19, 140.64, 135.47, 131.65, 131.15, 125.54, 125.24, 120.68, 118.18, 118.09, 113.78, 113.54, 102.21, 98.33, 79.95, 71.93, 69.35, 61.60, 60.60, 60.44, 59.93, 59.39, 59.30, 55.90, 54.14, 54.03, 51.18, 41.95, 33.06, 28.72, 28.45, 23.93, 20.59, 16.11, 14.42, 9.83.

ESI-MS m/z: Calcd. for C$_{42}$H$_{52}$N$_4$O$_{12}$S: 836.3. Found (M+1)$^+$: 837.1

To a solution of intermediate 11 (29 mg, 0.035 mmol) in CHCl$_3$ (1 mL, 0.03 M) was added at 23° C. p-TsOH (40 mg, 0.21 mmol). The reaction mixture was left at 23° C. and under Argon atmosphere for 15 hours. The reaction was diluted with dichloromethane and a saturated solution of sodium bicarbonate was added. The aqueous phase was extracted with dichloromethane, the combined organic layers were dried over sodium sulphate, filtered and the solvent was eliminated under reduced pressure. The crude was purified by flash column chromatography (eluent mixtures of ethyl acetate/hexane in gradient from 1:4 to 2:1 and final washes with methanol) to afford intermediate 12 (16 mg, 71%) as a yellow solid.

R$_f$: 0.07 (ethyl acetate/hexane 1:1)

$^1$H-RMN (300 MHz, CDCl$_3$): δ 6.52 (s, 1H), 6.07 (d, 1H), 5.98 (d, 1H), 5.85 (m, 1H), 5.13-5.06 (m, 2H), 5.01 (d, 1H), 4.52 (broad s, 1H), 4.33 (d, 1H), 4.26 (s, 1H), 4.19 (d, 1H), 4.12 (m, 1H), 3.77 (s, 3H), 3.53 (broad d, 1H), 3.40 (d, 1H), 3.28 (m, 1H), 2.95-2.75 (m, 4H), 2.30 (s, 3H), 2.28 (s, 3H), 2.21 (broad s, 2H), 2.03 (s, 3H).

$^{13}$C-RMN (75 MHz, CDCl$_3$): δ 174.59, 168.91, 147.85, 145.86, 143.10, 141.22, 140.56, 135.21, 131.27, 129.53, 121.11, 120.72, 118.93, 118.30, 114.01, 113.54, 102.15, 61.55, 60.44, 60.30, 59.73, 59.53, 56.09, 54.22, 53.31, 52.07, 41.95, 34.58, 24.23, 20.82, 15.89, 9.86.

ESI-MS m/z: Calcd. for C$_{33}$H$_{36}$N$_4$O$_8$S: 648.2. Found (M+1)$^+$: 649.1

Example 12

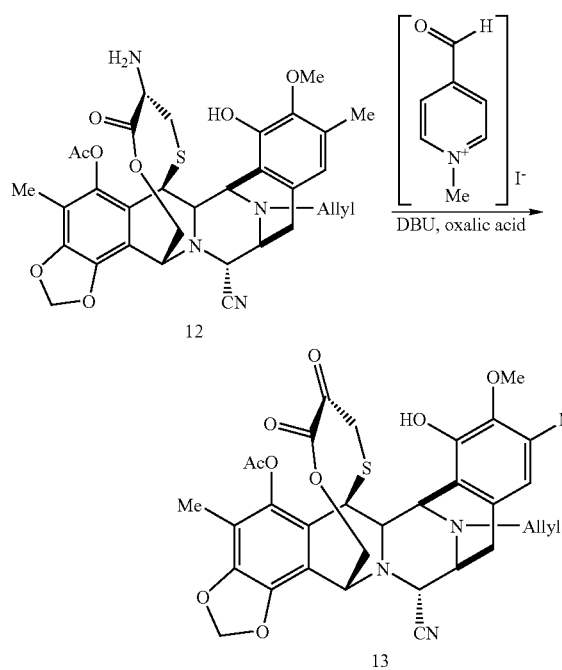

To a solution of the pyiridinium salt (211 mg, 0.85 mmol) in DMF (2.3 mL) was added at 23° C. a solution of intermediate 12 (55 mg, 0.085 mmol) in dichloromethane (2.9 mL, 0.016 M final concentration). The reaction mixture was left at 23° C. and under Argon atmosphere for 4 hours and 15 minutes, then DBU (13 µL, 0.085 mmol) was added and the solution was stirred at 23° C. and under Argon atmosphere for 15 minutes. After this time a saturated solution of oxalic acid (2 mL) was added, and the reaction mixture was left at 23° C. under Argon atmosphere for 30 minutes. The reaction mixture was cooled at 0° C., was diluted with $Et_2O$ and a saturated solution of sodium bicarbonate was added until to reach pH=5. The aqueous phase was extracted with $Et_2O$ (×4), further basified with more sodium bicarbonate and extracted with more $Et_2O$ (×4). The combined organic layers were dried over sodium sulphate, filtered and the solvent was eliminated under reduced pressure. The crude was purified by flash column chromatography (eluent mixtures ethyl acetate/hexane in gradient from 1:2 to 2:1) to afford intermediate 13 (28 mg, 51%) as a yellow solid.

$R_f$: 0.66 (ethyl acetate/hexane 2:1)

$^1$H-RMN (300 MHz, $CDCl_3$): δ 6.49 (s, 1H), 6.11 (d, 1H), 6.01 (d, 1H), 5.88-5.77 (m, 1H), 5.70 (s, 1H), 5.09 (m, 3H), 4.66 (broad s, 1H), 4.40 (s, 1H), 4.36 (d, 1H), 4.20 (dd, 1H), 4.17 (d, 1H), 3.75 (s, 3H), 3.55 (m, 2H), 2.88-2.67 (m, 5H), 2.56 (d, 1H), 2.32 (s, 3H), 2.25 (s, 3H), 2.04 (s, 3H).

ESI-MS m/z: Calcd. for $C_{33}H_{33}N_3O_9S$: 647.1. Found $(M+1)^+$: 648.1.

Example 13

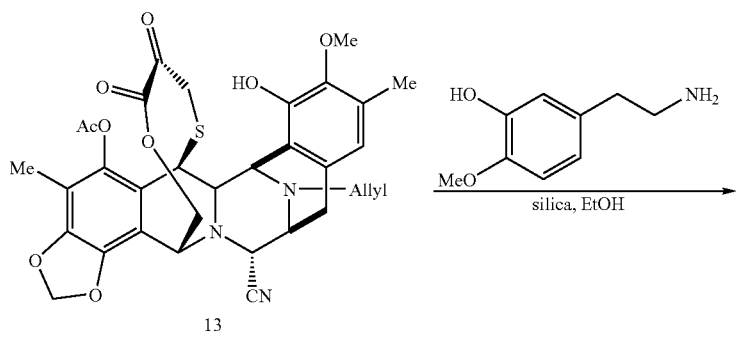

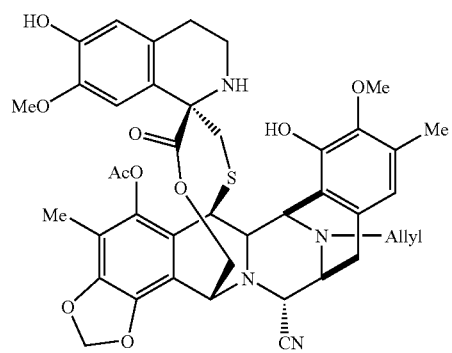

To a solution of intermediate 13 (26 mg, 0.04 mmol) and dopamine derivative (24 mg, 0.14 mmol) in EtOH (0.7 mL, 0.06 M) was added at 23° C. silica gel (56 mg). The reaction mixture was left at 23° C. and under Argon atmosphere for 15 hours. The solvent of the reaction was eliminated under reduced pressure and the crude was purified by flash column chromatography (eluent mixtures of ethyl acetate/hexane in gradient from 1:1 to 4:1) to afford intermediate 14 (30 mg, 94%) as a pale yellow solid.

$R_f$: 0.37 (ethyl acetate/hexane 2:1)

$^1$H-RMN (300 MHz, CDCl$_3$): δ 6.60 (s, 1H), 6.46 (s, 1H), 6.44 (s, 1H), 6.04 (d, 1H), 5.96 (d, 1H), 5.94-5.80 (m, 1H), 5.73 (s, 1H), 5.48 (broad s, 1H), 5.11 (m, 2H), 5.02 (d, 1H), 4.57 (broad s, 1H), 4.36 (d, 1H), 4.33 (s, 1H), 4.19 (d, 1H), 4.11 (dd, 1H), 3.78 (s, 3H), 3.61 (s, 3H), 3.55 (m, 1H), 3.50 (d, 1H9, 3.09 (m, 1H), 2.99-2.74 (m, 5H), 2.59 (m, 1H), 2.47 (dt, 1H), 2.32 (s, 3H), 2.25 (s, 3H), 2.23-2.13 (m, 2H), 2.04 (s, 3H).

ESI-MS m/z: Calcd. for C$_{42}$H$_{44}$N$_4$O$_{10}$S: 796.3. Found (M+1)$^+$: 797.2.

Example 14

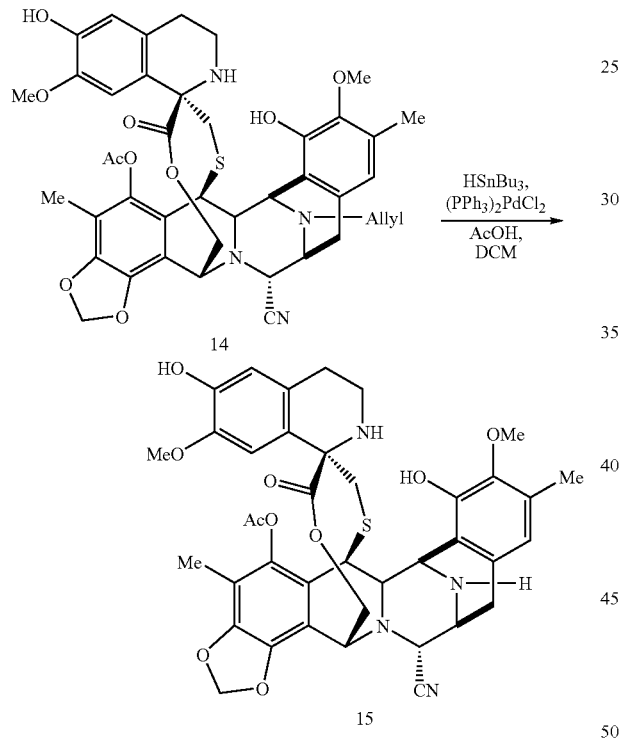

To a solution of intermediate 14 (30 mg, 0.038 mmol), (PPh$_3$)$_2$PdCl$_2$ (3 mg, 0.003 mmol), acetic acid (11 μL, 0.188 mmol) in anhydrous dichloromethane (1 mL, 0.04 M) was dropwise added at 23° C. and under Argon atmosphere HSnBu$_3$ (36 μL, 0.13 mmol). The reaction mixture was left at 23° C. under Argon atmosphere for 20 minutes. After this time the reaction mixture was poured onto column (eluent mixtures of dichloromethane/methanol in gradient from 100/0 to 30:1 to afford intermediate 15 (12 mg, 42%) as a pale yellow solid. Some starting material (17 mg) was isolated impurified with traces of butyltinderivatives.

$R_f$: 0.22 (dichloromethane/methanol 20:1)

$^1$H-RMN (300 MHz, CDCl$_3$): δ 6.62 (s, 1H), 6.47 (s, 1H), 6.44 (s, 1H), 6.06 (d, 1H), 5.98 (d, 1H), 5.03 (d, 1H), 4.57 (broad s, 1H), 4.50 (d, 1H), 4.34 (s, 1H), 4.20 (d, 1H), 4.15 (dd, 1H), 3.85 (d, 1H), 3.78 (s, 3H), 3.62 (s, 3H), 3.52 (d, 1H), 3.15-2.95 (m, 3H), 2.77 (m, 1H), 2.60 (m, 1H), 2.46 (dt, 1H), 2.35 (d, 1H), 2.31 (s, 3H), 2.26 (s, 3H), 2.15 (d, 1H), 2.04 (s, 3H).

$^{13}$C-RMN (75 MHz, CDCl$_3$): δ 172.84, 172.12, 145.98, 145.60, 144.77, 144.53, 142.98, 141.59, 140.36, 131.49, 129.81, 129.36, 125.84, 124.60, 121.57, 121.32, 118.34, 114.33, 114.17, 109.99, 102.10, 64.79, 61.46, 60.66, 60.17, 59.25, 59.01, 55.40, 48.84, 47.86, 42.13, 39.87, 29.00, 28.33, 20.67, 16.01, 9.97.

ESI-MS m/z: Calcd. for C$_{39}$H$_{40}$N$_4$O$_{10}$S: 756.2. Found (M+1)$^+$: 757.3.

Example 15

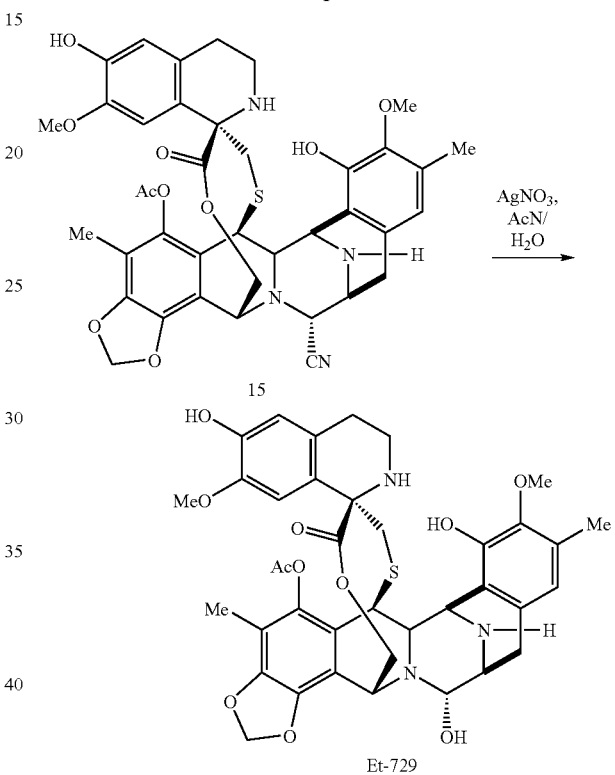

To a solution of intermediate 15 (12 mg, 0.016 mmol) in acetonitrile (0.66 mL) was added at 23° C. water (0.44 mL, 0.015 M, final concentration) and AgNO$_3$ (81 mg, 0.47 mmol). The reaction mixture was left under Argon atmosphere at 23° C. for 23 hours. The reaction was diluted with dichloromethane and a saturated solution of sodium bicarbonate and a saturated solution of sodium chloride was added. The aqueous phase was extracted with dichloromethane and the combined organic layers were dried over sodium sulphate, filtered and the solvent was eliminated under reduced pressure. The crude Et-729 was purified by flash column chromatography (eluent dichloromethane/methanol in gradient from 100/0 to 3:1) to afford the final product (8.3 mg, 70%) as a white solid.

$R_f$: 0.07 (dichloromethane/methanol 95:5)

$^1$H-RMN (300 MHz, CD$_3$OD): δ 6.59 (s, 1H), 6.44 (s, 1H), 6.40 (s, 1H), 6.13 (s, 1H), 6.02 (s, 1H), 5.20 (d, 1H), 4.73 (s, 1H), 4.58 (d, 2H), 4.26 (d, 1H), 4.13 (dd, 1H), 3.80 (broad d, 1H), 3.73 (s, 3H), 3.67 (d, 1H), 3.59 (s, 3H), 3.22-3.02 (m, 3H), 2.78 (m, 1H), 2.59 (m, 1H), 2.42 (m, 2H), 2.31 (s, 3H), 2.30 (s, 3H), 2.05 (m, 1H), 2.04 (s, 3H).

$^{13}$C-RMN (75 MHz, CD$_3$OD): δ 173.52, 170.26, 148.13, 147.01, 146.92, 146.86, 145.04, 142.67, 141.95, 132.04, 129.28, 125.79, 122.77, 122.42, 121.40, 116.29, 115.89, 111.63, 103.54, 90.94, 65.53, 61.80, 60.38, 58.23, 57.23, 55.76, 47.35, 43.15, 40.70, 28.85, 27.79, 20.49, 16.07, 9.38.

ESI-MS m/z: Calcd. for C$_{38}$H$_{41}$N$_3$O$_{11}$S: 747.2. Found (M+1)$^+$: 748.1.

Example 16

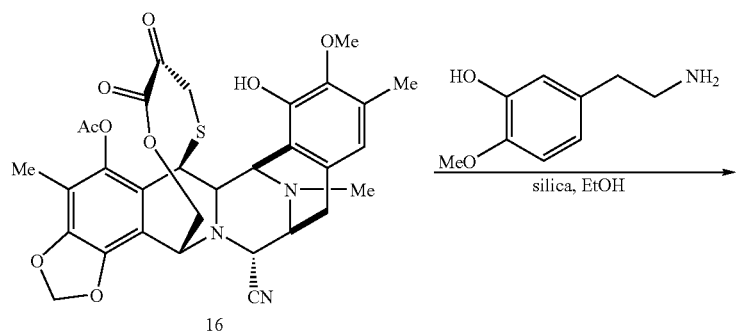

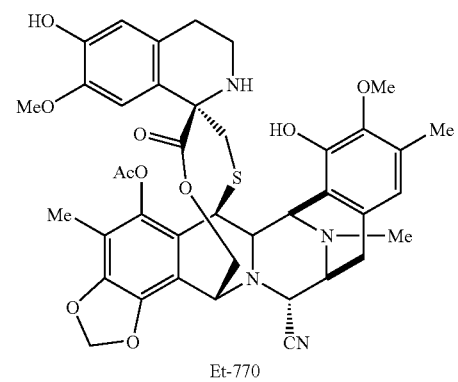

To a solution of compound 16 (0.5 g, 0.80 mmol), 3-hydroxy-4-metoxy-phenethyl amine (924 mg, 2.8 mmol) in ethyl alcohol was added at 23° C. silica gel (1 g). The reaction mixture was stirred at 23° C. under Argon atmosphere for 16 hours. After this time the solvent is eliminated under reduced pressure and the crude of the reaction is purified by flash column chromatography (eluent mixtures of ethyl acetate/methylene chloride in gradient from 1:2 to 100% in ethyl acetate, final washes in methylene chloride/methyl alcohol 9:1) to afford Et-770 (564 mg, 91%) as a pale yellow solid.

$^1$H-NMR (300 MHz, CDCl$_3$): 6.60 (s, 1H), 6.47 (s, 1H), 6.45 (s, 1H), 6.05 (s, 1H), 5.98 (s, 1H), 5.02 (d, 1H), 4.57 (bs, 1H), 4.32 (bs, 1H), 4.28 (d, 1H), 4.18 (d, 1H), 4.12 (dd, 1H), 3.78 (s, 3H), 3.62 (s, 3H), 3.50 (d, 1H), 3.42 (m, 1H), 3.10 (ddd, 1H), 2.94 (m, 2H), 2.79 (m, 1H), 2.61 (m, 1H), 2.47 (m, 1H), 2.35 (m, 1H), 2.32 (s, 3H), 2.27 (s, 3H), 2.20 (s, 3H), 2.09 (m, 1H), 2.04 (s, 3H).

ESI-MS m/z: Calcd. for C$_{40}$H$_{42}$N$_4$O$_{10}$S: 770.7. Found (M+H)$^+$: 771.2.

Example 17

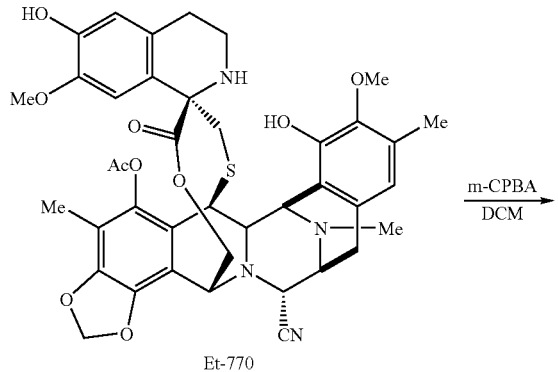

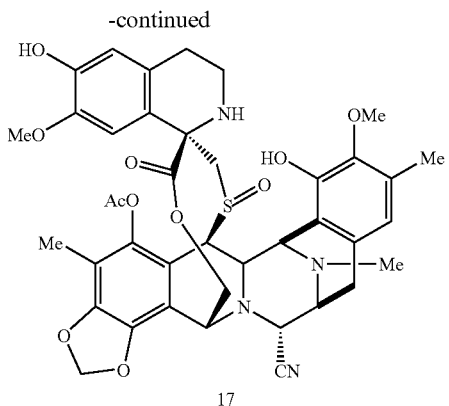

17

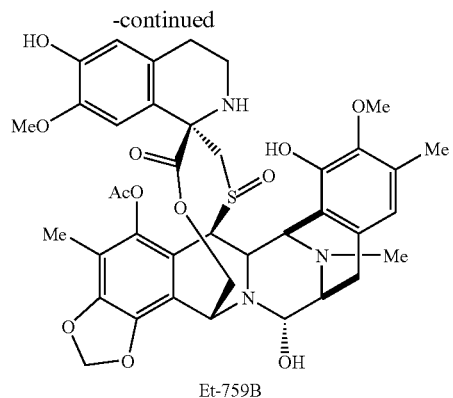

Et-759B

To a solution of Et-770 (45 mg, 0.058 mmol.) in $CH_2Cl_2$ (3 mL, 0.03 M) was added at 0° C. under Argon atmosphere m-CPBA (15.1 mg, 0.087 mmol). The reaction was stirred at 0° C. for 30 minutes, then a saturated aqueous solution of sodium bicarbonate was added, then aqueous phase was extracted with $CH_2Cl_2$, the organic layers dried over sodium sulphate and the solvent was eliminated under reduced pressure. The crude was purified by flash column chromatography (eluent: ethyl acetate/hexane 3:1) to afford compound 17 (45.6 mg, 99%).

$R_f$: 0.18 (ethyl acetate/hexane 2:1)

$^1$H-RMN (300 MHz, $CDCl_3$): δ 6.63 (s, 1H); 6.51 (s, 1H); 6.47 (s, 1H); 6.19 (s, 1H); 6.05 (s, 1H); 6.00 (s, 1H); 4.66 (d, 1H); 4.61 (d, 1H); 4.30-4.28 (m, 1H); 4.19 (s, 1H); 4.07 (s, 1H); 3.82 (s, 1H); 3.73 (d, 1H); 3.65 (d, 1H); 3.60 (s, 3H); 3.43 (d, 1H); 3.04-2.95 (m, 2H); 2.88-2.81 (m, 1H); 2.72-2.55 (m, 3H); 2.48-2.41 (m, 1H); 2.30 (s, 3H); 2.25 (s, 3H); 2.23 (s, 3H); 2.05 (s, 3H).

$^{13}$C-RMN (75 MHz, $CDCl_3$): δ 172.0, 169.2, 148.2, 146.8, 146.3, 145.1, 144.8, 142.3, 140.8, 130.8, 129.6, 129.5, 124.5, 122.6, 120.2, 120.0, 117.8, 114.6, 111.8, 109.5, 102.4, 70.9, 67.8, 61.8, 61.7, 60.9, 60.6, 60.0, 55.3, 54.9, 54.7, 41.9, 40.0, 29.9, 29.1, 25.0, 21.0, 16.2, 10.3

ESI-MS m/z: Calcd. for $C_{40}H_{42}N_4O_{11}S$: 786.2. Found (M+Na)$^+$: 809.3.

Example 18

To a solution of compound 17 (45 mg, 0.057 mmol) in $CH_3CN/H_2O$ (6 mL/2 mL, 0.007 M) was added at 23° C. $AgNO_3$ (287.1 mg, 1.71 mmol). The reaction mixture was stirred under Argon atmosphere and protected from the light for 24 hours. The reaction was diluted with $CH_2Cl_2$ and quenched with an aqueous saturated solution of sodium bicarbonate and an aqueous saturated solution of brine 1:1. The aqueous phase was extracted with $CH_2Cl_2$, the organic layers were dried over sodium sulphate and the solvent was eliminated under reduced pressure. The crude was purified by flash column chromatography to afford Et-759B (23.2 mg, 52%) as a pale yellow solid and some starting material (18.7 mg, 42%) was recuperated.

$R_f$: 0.36 ($CH_2Cl_2$/MeOH 8:0.5)

1H-RMN (300 MHz, $CDCl_3$): δ 6.65 (s, 1H); 6.48 (s, 1H); 6.43 (s, 1H); 6.20 (s, 1H); 6.04 (d, 1H); 5.97 (s, 1H); 4.78 (s, 1H); 4.70 (d, 1H); 4.55 (d, 1H); 4.36 (d, 1H); 4.07-3.98 (m, 1H); 3.83 (s, 3H); 3.77 (d, 1H); 3.69-3.63 (m, 1H); 3.61 (s, 3H); 3.46 (d, 1H); 3.22 (d, 1H); 3.06-2.82 (m, 4H); 2.66-2.43 (m, 4H); 2.31 (s, 3H); 2.26 (s, 3H); 2.21 (s, 3H); 2.04 (s, 3H).

$^{13}$C-RMN (75 MHz, $CDCl_3$): δ 171.9, 169.3, 148.0, 146.9, 145.0, 144.7, 142.2, 141.0, 130.7, 130.1, 129.6, 124.9, 123.0, 120.9, 120.1, 114.6, 113.7, 109.5, 102.2, 82.9, 67.9, 63.1, 61.8, 60.5, 57.7, 57.6, 55.9, 55.3, 55.1, 41.7, 40.0, 29.9, 29.2, 24.7, 21.0, 16.1, 14.3, 10.2.

ESI-MS m/z: Calcd. for $C_{39}H_{43}N_3O_{12}S$: 777.84. Found (M−H$_2$O+H)$^+$: 760.2.

Example 19

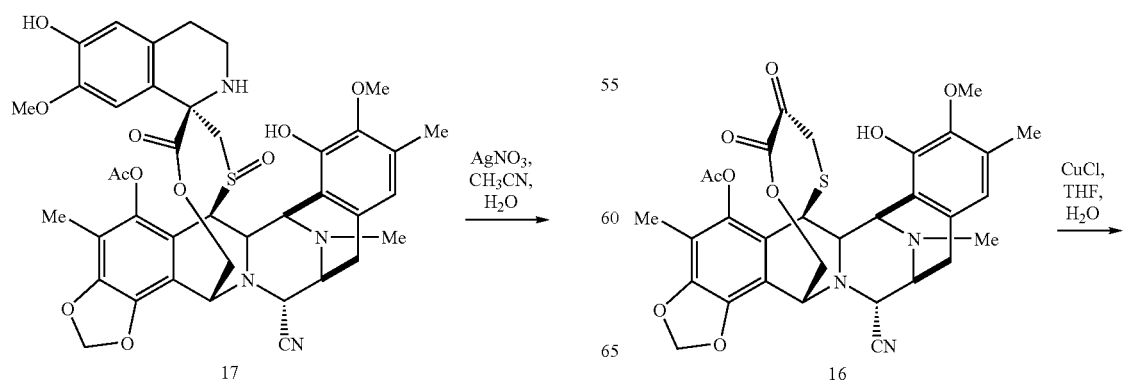

17     16

-continued

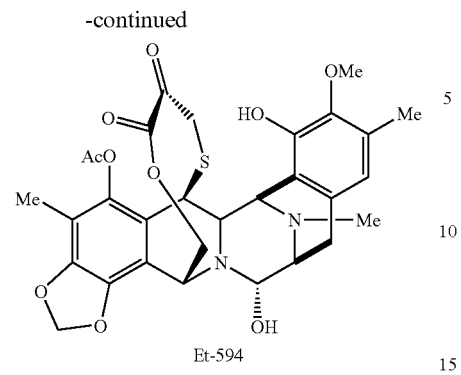

Et-594

To a solution of compound 16 (100 mg, 0.16 mmol) in THF/H$_2$O (4.26 mL/1.06 mL, 0.03 M) was added at 23° C. under Argon atmosphere CuCl (79.5 mg, 0.80 mmol). The reaction was stirred at 23° C. under Argon atmosphere and protected from the light for 24 hours. The reaction was diluted with CH$_2$Cl$_2$, quenched with an aqueous saturated solution of ammonium chloride. The aqueous phase was separated and the organic phase was washed with an aqueous saturated solution of sodium bicarbonate. The aqueous phase was extracted with CH$_2$Cl$_2$, the organic layers were dried over sodium sulphate and the solvent was eliminated under reduced pressure. The crude was purified by flash column chromatography (eluent CH$_2$Cl$_2$/MeOH 60:1) to afford Et-594 (70 mg, 71%) as a yellow solid.

R$_f$: 0.44 (CH$_2$Cl$_2$/MeOH 60:1)

$^1$H-RMN (300 MHz, CDCl$_3$): δ 6.53 (s, 1H); 6.49 (s, 1H); 6.07 (s, 1H); 6.05 (s, 1H); 5.98 (s, 1H); 5.94 (s, 1H); 5.71 (s, 2H); 5.18 (d, 1H); 5.12 (d, 1H); 4.85 (s, 1H); 4.77 (s, 1H) 4.55-4.36 (m, 3H); 4.17-4.11 (m, 4H); 3.77 (s, 3H); 3.75 (s, 3H); 3.58 (d, 1H); 3.47 (s, 4H); 3.19 (s, 2H); 3.07 (s, 3H); 2.87-2.54 (m, 6H); 2.31 (s, 3H); 2.30 (s, 3H); 2.28 (s, 3H); 2.23 (s, 3H); 2.18-2.05 (m, 2H); 2.15 (s, 3H); 2.11 (s, 3H); 2.05 (s, 3H); 1.98 (s, 3H).

ESI-MS m/z: Calcd. for C$_{30}$H$_{32}$N$_2$O$_{10}$S: 612.1. Found (M−H$_2$O+H)$^+$: 595.5.

Example 20

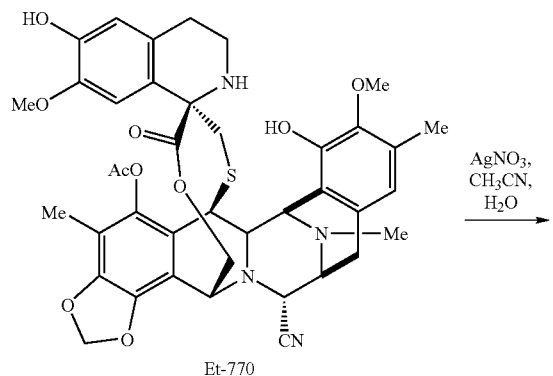

Et-770

-continued

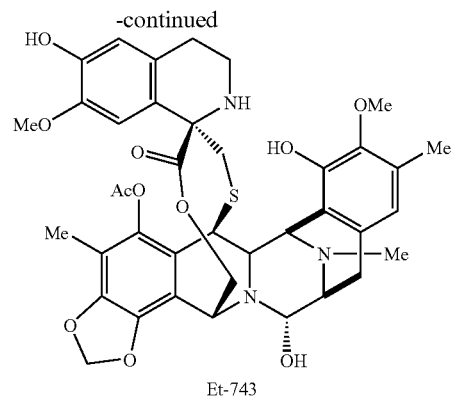

Et-743

To a solution of Et-770 (1.25 g, 1.62 mmol) in CH$_3$CN/H$_2$O (64.8 mL/43.2 mL, 0.015 M) was added at 23° C. AgNO$_3$ (8.27 g, 1.71 mmol). The reaction mixture was stirred under Argon atmosphere and protected from the light for 24 hours. The reaction was diluted with CH$_2$Cl$_2$ and quenched with an aqueous saturated solution of sodium bicarbonate and an aqueous saturated solution of brine 1:1. The aqueous phase was extracted with CH$_2$Cl$_2$, the organic layers were dried over sodium sulphate and the solvent was eliminated under reduced pressure. The crude was purified by flash column chromatography (CHCl$_3$/EtOAc/MeOH in gradient from 49:49:2 to 48:40:12) to afford Et-743 (1.09 g, 88%) as a yellow solid and some starting material (75 mg, 6%) was recuperated.

R$_f$: 0.2 (CHCl$_3$/EtOAc/MeOH 49:49:2)

$^1$H-RMN (300 MHz, CDCl$_3$): δ 6.60 (s, 1H), 6.46 (s, 1H), 6.44 (s, 1H), 6.02 (d, 1H), 5.94 (broad d, 1H), 5.13 (d, 1H), 4.81 (broad s, 1H), 4.50 (broad s, 1H), 4.49 (broad s, 1H), 4.16 (dd, 1H), 4.04 (dd, 1H), 3.79 (s, 3H), 3.61 (s, 3H), 3.57 (broad d, 1H), 3.22 (broad, d, 1H), 3.12 (ddd, 1H), 2.87 (broad s, 1H), 2.85 (broad s, 1H), 2.80 (m, 1H), 2.60 (ddd, 1H), 2.47 (ddd, 1H), 2.38 (broad s, 1H), 2.26 (s, 3H), 2.18 (m, 1H), 2.17 (s, 3H), 2.03 (s, 3H).

$^{13}$C-RMN (75 MHz, CDCl$_3$): δ 172.6, 168.3, 147.7, 145.1, 144.4, 143.0, 141.3, 140.5, 131.5, 129.2, 126.1, 121.9, 120.9, 118.0, 116.0, 114.0, 112.5, 109.8, 101.6, 82.1, 64.7, 61.3, 60.3, 57.8, 56.0, 55.1, 54.9, 42.2, 41.4, 39.7, 28.8, 24.0, 20.4, 15.8, 9.6.

ESI-MS m/z: Calcd. for C$_{39}$H$_{43}$N$_3$O$_{11}$S: 761.3. Found (M−H$_2$O+H)$^+$: 744.4.

Example 21

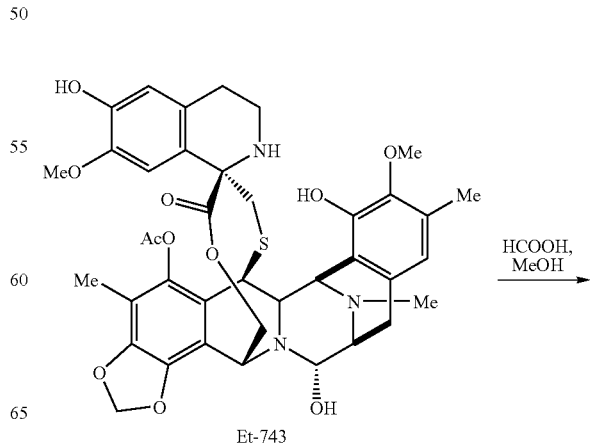

Et-743

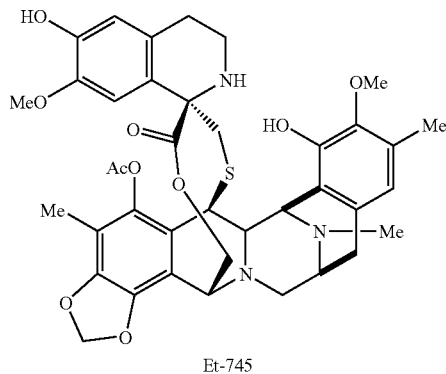

Et-745

To a solution of Et-743 (25 mg, 0.03 mmol) in methyl alcohol (1.5 mL, 0.02 M) was added at 23° C. formic acid (11 μL, 0.3 mmol). The solution was stirred at 23° C. for 6 hours, then the solvent was eliminated under reduced pressure and the crude was purified by flash column chromatography (CHCl$_3$/EtOAc/MeOH 49:49:2) to afford Et-745 (15.8 mg, 64%).

$R_f$: 0.17 (CHCl$_3$/EtOAc/MeOH 49:49:2)

$^1$H-RMN (300 MHz, CDCl$_3$): δ 6.61 (s, 1H), 6.49 (s, 1H), 6.42 (s, 1H), 6.00 (d, 1H), 5.95 (d, 1H), 5.10 (d, 1H), 4.50 (broad s, 1H), 4.38 (d, 1H), 4.09 (dd, 1H), 3.79 (s, 3H), 3.60 (s, 3H), 3.38-3.21 (m, 3H), 3.17-2.81 (m, 5H), 2.71 (m, 1H), 2.52 (m, 2H), 2.41 (d, 1H), 2.33 (s, 3H), 2.24 (s, 3H), 2.22 (s, 3H), 2.12 (m, 1H), 2.02 (s, 3H).

$^{13}$C-RMN (75 MHz, CDCl$_3$): δ 172.43, 168.19, 147.72, 144.79, 144.60, 144.50, 142.64, 141.03, 139.77, 131.61, 128.61, 126.07, 122.09, 120.50, 118.51, 115.41, 114.50, 112.63, 109.94, 101.41, 64.26, 64.06, 62.21, 60.83, 60.01, 55.00, 42.39, 41.76, 40.78, 39.29, 31.39, 29.50, 28.53, 25.45, 22.45, 20.30, 15.62, 13.92, 9.48.

ESI-MS m/z: Calcd. for C$_{39}$H$_{43}$N$_3$O$_{10}$S: 745.3. Found (M+H)$^+$: 746.2.

Example 22

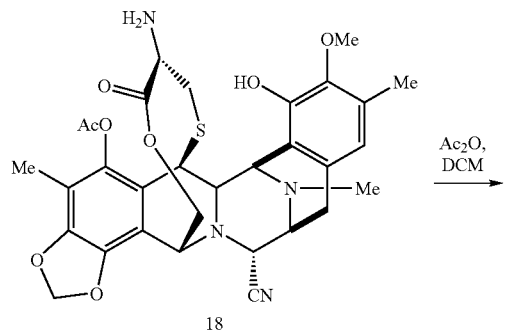

18

$\xrightarrow{\text{Ac}_2\text{O, DCM}}$

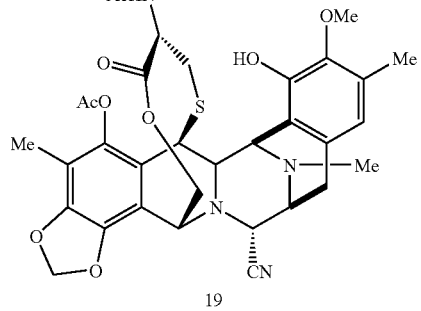

19

To a solution of compound 18 (520.8 mg, 0.84 mmol) in CH$_2$Cl$_2$ (17 mL, 0.05M) under Argon at room temperature, was added acetic anhydride (0.08 mL, 0.88 mmol). The reaction was stirred for 30 min and then quenched with an aqueous saturated solution of NaHCO$_3$. The aqueous layer was extracted with CH$_2$Cl$_2$ and the organic layer was dried over Na$_2$SO$_4$. Flash chromatography (hexane/EtOAc, 1:2, 2:5, 1:3,) gives pure compound 19 (96%).

$R_f$: 0.2 (Hexane/ethyl acetate 2:3)

$^1$H-RMN (300 MHz, CDCl$_3$): δ 6.56 (s, 1H), 6.04 (dd, 2H), 5.78 (s, 1H), 5.52 (bd, 1H), 5.02 (d, 1H), 4.58 (ddd, 1H), 4.53 (bs, 1H), 4.27-4.25 (m, 2H), 4.19-4.15 (m, 2H), 3.77 (s, 3H), 3.44-3.43 (m, 2H), 2.92-2.90 (m, 2H), 2.36-2.02 (m, 2H), 2.36 (s, 3H), 2.30 (s, 3H), 2.16 (s, 3H), 2.02 (s, 3H), 1.88 (s, 3H).

$^{13}$C-RMN (75 MHz, CDCl$_3$): δ 170.5, 168.8, 168.4, 148.1, 145.8, 143.1, 141.0, 140.3, 130.7, 129.9, 129.0, 120.3, 119.0, 117.9, 113.5, 102.0, 61.3, 60.3, 60.2, 59.3, 58.9, 54.7, 54.5, 51.9, 41.8, 41.4, 32.4, 23.7, 22.8, 20.4, 16.0, 9.5.

ESI-MS m/z: Calcd. for C$_{33}$H$_{36}$N$_4$O$_9$S: 664.2. Found (M+H)$^+$: 665.2.

Example 23

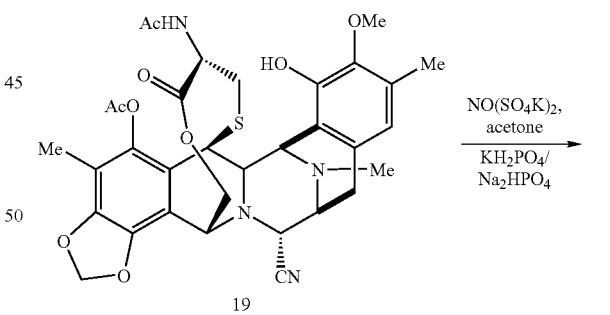

19

$\xrightarrow[\text{KH}_2\text{PO}_4/\text{Na}_2\text{HPO}_4]{\text{NO(SO}_4\text{K)}_2, \text{acetone}}$

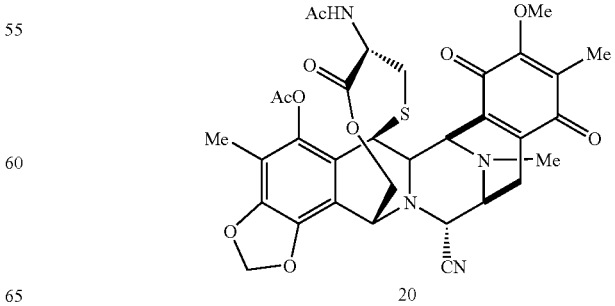

20

To a solution of compound 19 (100 mg, 0.15 mmol) in acetone (15 mL, 0.01M) was added a solution of Fremy's salt (141 mg, 0.52 mmol) in a buffer solution of $KH_2PO_4$/$Na_2HPO_4$ (15 mL, 0.035M). After 24 h at 23° C. the reaction mixture was extracted with $CH_2Cl_2$ and dried over $Na_2SO_4$. Chromatography (hexane/erhyl acetate 1:2) gives pure compound 20 (101 mg, 99%).

$R_f$: 0.38 (Hexane/ethyl acetate 1:1)

$^1$H-RMN (300 MHz, $CDCl_3$): δ 6.10 (d, 1H); 6.01 (d, 1H); 5.68 (d, 1H); 4.98 (d, 1H); 4.54-4.50 (m, 1H); 4.43 (s, 1H); 4.21 (s, 1H); 4.15-4.07 (m, 3H); 4.09 (s, 3H); 3.47 (s, 1H); 3.42 (d, 1H); 2.88-2.78 (m, 2H); 2.47 (d, 1H); 2.25 (s, 3H); 2.22-2.18 (m, 1H); 2.18 (s, 3H); 2.02 (s, 3H); 2.01 (s, 3H); 1.87 (s, 3H).

ESI-MS m/z: Calcd. for $C_{33}H_{34}N_4O_{10}S$: 678.2. Found $(M+H)^+$: 679.1.

Example 24

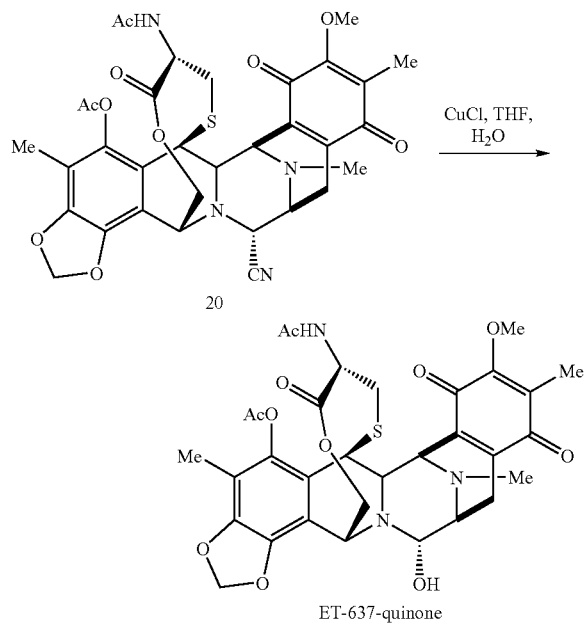

To a solution of compound 20 (100 mg, 0.14 mmol) in $THF/H_2O$ 4:1 (5.6 mg, 0.009M) was added CuCl (145 mg, 1.47 mmol). After 24 h at 23° C. the reaction was quenched with an aqueous saturated solution of $NH_4Cl$, and washed with brine and an aqueous saturated solution of $NaHCO_3$, diluted and extracted with $CH_2Cl_2$. The organic layer was dried over $Na_2SO_4$. Chromatography ($CH_2Cl_2$/MeOH 32:1) gives pure compound ET-637-quinone (60 mg, 61%).

$R_f$: 0.54 ($CH_2Cl_2$/MeOH 32:1)

$^1$H-RMN (300 MHz, $CDCl_3$): δ 6.07 (d, 1H); 5.97 (d, 1H); 5.72 (d, 1H); 5.08 (d, 1H); 4.71 (s, 1H); 4.52-4.33 (m, 3H); 4.08 (s, 3H); 4.08-4.01 (m, 3H); 3.53 (d, 1H); 3.24 (d, 1H); 2.83-2.69 (m, 2H); 2.46-2.33 (m, 1H); 2.24 (s, 3H); 2.16 (s, 3H); 2.02 (s, 3H); 2.00 (s, 3H); 1.87 (s, 3H).

$^{13}$C-RMN (75 MHz, $CDCl_3$): δ 175.5, 162.6, 162.2, 150.0, 138.9, 134.2, 133.7, 130.9, 129.9, 119.9, 111.7, 107.5, 94.9, 75.2, 55.3, 53.6, 50.4, 48.6, 46.0, 45.8, 34.1, 33.6, 26.8, 22.6, 15.9, 13.4, 12.7

ESI-MS m/z: Calcd. for $C_{32}H_{35}N_3O_{11}S$: 669.2. Found $(M-H_2O+H)^+$: 652.1.

Example 25

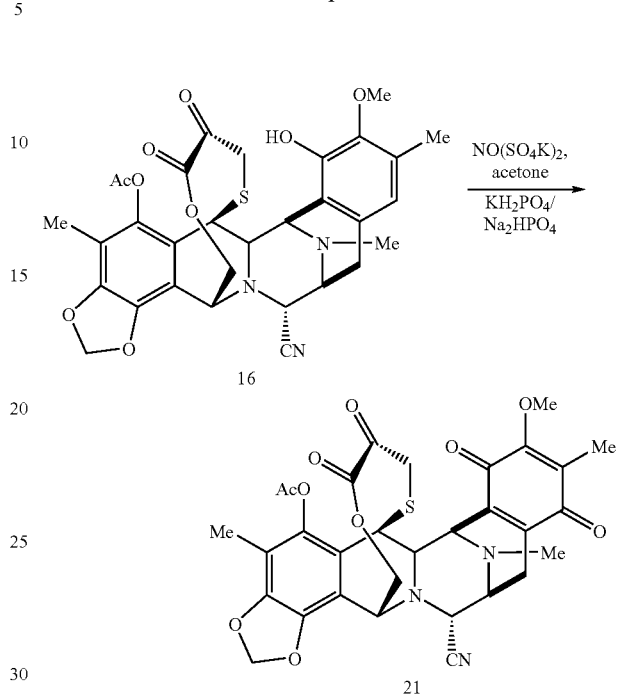

To a solution of compound 16 (100 mg, 0.16 mmol) in acetona (16 mL, 0.01M) was added a solution of Fremy's salt (151 mg, 0.56 mmol) in a buffer solution of $KH_2PO_4$/$Na_2HPO_4$ (16 mL, 0.035M). After 24 h at 23° C. the reaction mixture was extracted with $CH_2Cl_2$ and dried over $Na_2SO_4$. Chromatography (hexane/ethyl acetate 1:1) gives pure compound 21 (79 mg, 78%).

$R_f$: 0.3 (hexane/ethyl acetate 1:1)

$^1$H-RMN (300 MHz, $CDCl_3$): δ 6.12 (d, 1H); 6.03 (d, 1H); 5.05 (d, 1H); 4.48 (s, 1H); 4.28 (d, 1H); 4.24 (s, 1H); 4.20-4.16 (m, 1H); 4.05-4.00 (m, 1H); 3.98 (s, 3H); 3.59 (t, 1H); 3.38 (d, 1H); 3.35 (d, 1H); 2.84-2.64 (m, 2H); 2.40-2.27 (m, 1H); 3.30 (s, 3H); 2.18 (s, 3H); 2.03 (s, 3H); 2.02 (s, 3H).

ESI-MS m/z: Calcd. for $C_{31}H_{29}N_3O_{10}S$: 635.2. Found $(M+H)^+$: 636.1.

Example 26

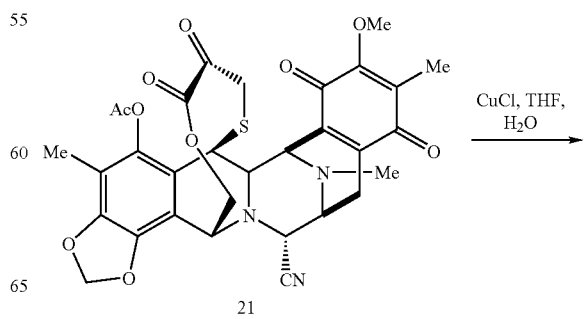

-continued

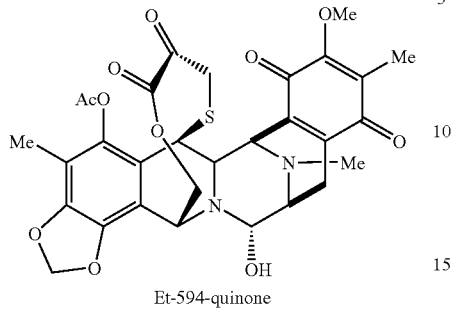
Et-594-quinone

-continued

[structure labeled 22]

To a solution of compound 21 (79 mg, 0.12 mmol) in THF/H₂O 4:1 (4.4 mL, 0.009M) was added CuCl (123 mg, 1.24 mmol). After 24 h at 23° C. the reaction was quenched with an aqueous saturated solution of NH₄Cl, and washed with brine and an aqueous saturated solution of NaHCO₃, diluted and extracted with CH₂Cl₂. The organic layer was dried over Na₂SO₄. Chromatography (CH₂Cl₂/MeOH 32:1) gives pure compound Et-594-quinone (45 mg, 59%).

$R_f$: 0.6 (CH₂Cl₂/MeOH 32:1)

¹H-RMN (300 MHz, CDCl₃): δ 6.10-5.97 (m, 4H); 5.12 (d, 1H); 5.05 (d, 1H); 4.74-4.63 (m, 2H); 4.43-4.26 (m, 2H); 4.22-4.11 (m, 2H); 4.06 (s, 6H); 4.05-3.91 (m, 2H); 3.82-3.71 (m, 2H); 3.55-3.20 (m, 2H); 3.03 (s, 4H); 2.75-2.62 (m, 2H); 2.56-2.42 (m, 2H); 2.35-2.23 (m, 2H); 2.29 (s, 3H); 2.27 (s, 3H); 2.18 (s, 3H); 2.17 (s, 3H); 2.03 (s, 3H); 2.02 (s, 3H); 2.00 (s, 3H); 1.98 (s, 3H).

¹³C-RMN (75 MHz, CDCl₃): δ 187.6, 187.2, 186.3, 186.1, 170.0, 169.3, 158.5, 158.4, 156.5, 146.6, 146.6, 142.0, 141.9, 140.9, 140.7, 137.4, 137.1, 136.7, 129.7, 129.4, 118.6, 117.9, 117.7, 115.1, 114.9, 102.5, 102.4, 92.4, 83.0, 82.7, 65.3, 64.6, 60.7, 60.6, 58.8, 58.5, 58.1, 57.5, 57.4, 56.0, 55.8, 55.1, 53.7, 53.3, 53.1, 52.6, 42.6, 42.4, 40.9, 40.8, 35.5, 35.2, 29.9, 20.9, 20.8, 20.2, 9.9, 9.8

ESI-MS m/z: Calcd. for $C_{30}H_{30}N_2O_{11}S$: 626.2. Found (M–H₂O+H)⁺: 609.1.

To a solution of compound 16 (75 mg, 0.12 mmol) in acetic acid (1.5 mL, 0.08 M) under Argon at 23° C. was added tryptamine (68 mg, 0.42 mmol). The reaction mixture was stirred at 23° C. for 24 h and then the acetic acid was evaporated. An aqueous saturated solution of NaHCO₃ was added and the mixture was extracted with CH₂Cl₂. The combined organic layers were dried over Na₂SO₄. Flash chromatography (hexane/ethyl acetate 1:1) gives pure compound 22 (90 mg, 99%).

$R_f$: 0.4 (hexane/ethyl acetate 1:1)

¹H-RMN (300 MHz, CDCl₃): δ 7.74 (s, 1H); 7.38 (d, 1H); 7.25 (d, 1H); 7.08 (t, 1H); 7.00 (t, 1H); 6.66 (s, 1H); 6.22 (d, 1H); 6.02 (d, 1H); 5.79 (s, 1H); 5.08 (d, 1H); 4.55 (s, 1H); 4.32 (s, 1H); 4.27 (d, 1H); 4.21 (s, 1H); 4.19 (d, 1H); 3.81 (s, 3H); 3.44-3.40 (m, 2H); 3.18-2.78 (m, 4H); 2.71-2.51 (m, 3H); 2.37 (s, 3H); 2.26 (s, 3H); 2.21 (s, 3H); 2.06 (s, 3H).

¹³C-RMN (75 MHz, CDCl₃): δ 171.7, 168.9, 148.2, 145.9, 143.2, 141.3, 140.5, 135.7, 130.8, 130.6, 129.5, 127.0, 122.2, 120.9, 120.8, 119.5, 118.6, 118.4, 113.8, 111.1, 110.5, 102.2, 62.5, 61.5, 60.8, 60.5, 59.7, 55.9, 54.8, 42.1, 41.7, 40.0, 39.5, 29.9, 24.0, 21.7, 20.8, 16.1, 9.9.

ESI-MS m/z: Calcd. for $C_{41}H_{41}N_5O_8S$: 763.3. Found (M+H)⁺: 764.2.

Example 28

Example 27

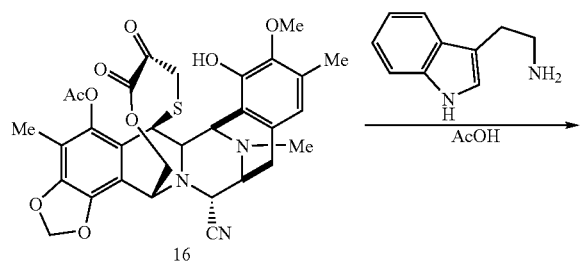

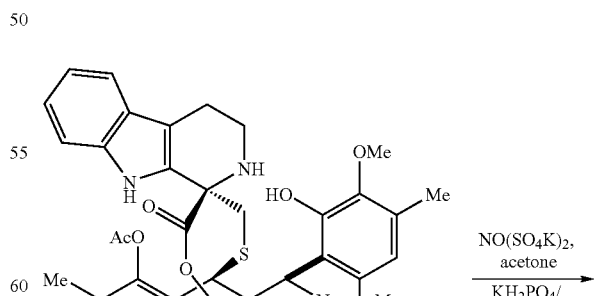

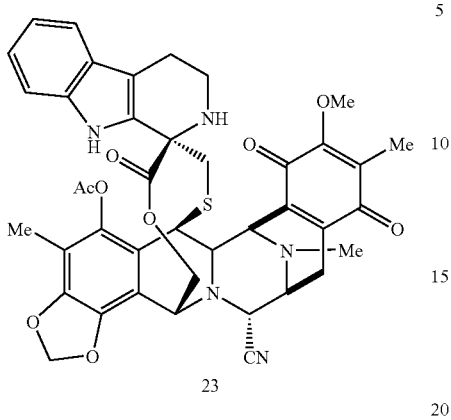

23

To a solution of compound 22 (100 mg, 0.13 mmol) in acetone (13 mL, 0.01M) was added a solution of Fremy's salt (122 mg, 0.45 mmol) in a buffer solution of $KH_2PO_4/Na_2HPO_4$ (13 mL, 0.035M). After 24 h at 23° C. the reaction mixture was extracted with $CH_2Cl_2$ and dried over $Na_2SO_4$. Chromatography (hexane/ethyl acetate 1:1) gives pure compound 23 (85 mg, 85%)

$R_f$: 0.4 (hexane/ethyl acetate 1:1)

$^1$H-RMN (300 MHz, $CDCl_3$): δ 7.76 (s, 1H); 7.39 (d, 1H); 7.24 (d, 1H); 7.09 (ddd, 1H); 7.01 (ddd, 1H); 6.22 (d, 1H); 6.02 (d, 1H); 4.98 (d, 1H); 4.44 (s, 1H); 4.22 (s, 1H); 4.19-4.18 (m, 1H) 3.13 (d, 1H); 4.11 (s, 3H); 4.04 (d, 1H); 3.48 (s, 1H); 3.39 (d, 1H); 3.16-3.09 (m, 1H); 2.88-2.78 (m, 2H); 2.70-2.47 (m, 5H); 2.23 (s, 3H); 2.21 (s, 3H); 2.08 (s, 3H); 2.05 (s, 3H).

ESI-MS m/z: Calcd. for $C_{41}H_{39}N_5O_9S$: 777.3. Found $(M+H)^+$: 778.2.

Example 29

To a solution of compound 23 (85 mg, 0.10 mmol) in $CH_3CN/H_2O$ 3:2 (5.8 mL, 0.009M) was added $AgNO_3$ (549 mg, 3.27 mmol). After 24 h at 23° C. the reaction was quenched with a mixture 1:1 of an aqueous saturated solution of brine and $NaHCO_3$, stirred for 10 min and diluted and extracted with $CH_2Cl_2$. The organic layer was dried over $Na_2SO_4$. Chromatography ($CH_2Cl_2$/MeOH 32:1) gives pure compound ET-736-quinone (40 mg, 50%)

$R_f$: 0.6 ($CH_2Cl_2$/MeOH 32:1)

$^1$H-RMN (300 MHz, $CDCl_3$): δ 7.71 (s, 1H); 7.39 (d, 1H); 7.26 (d, 1H); 7.10 (ddd, 1H); 7.01 (ddd, 1H); 6.22 (d, 1H); 6.01 (d, 1H); 5.12 (d, 1H); 4.76 (s, 1H); 4.42-4.37 (m, 2H); 4.11-4.04 (m, 2H) 4.10 (s, 3H); 3.56 (s, 1H); 3.35-3.11 (m, 2H); 2.85-2.65 (m, 3H); 2.60-2.36 (m, 4H); 2.23 (s, 3H); 2.19 (s, •3H); 2.09 (s, 3H); 2.05 (s, 3H).

$^{13}$C-RMN (75 MHz, $CDCl_3$): δ 186.6, 182.8, 170.9, 169.0, 157.1, 146.1, 141.7, 140.9, 137.5, 136.9, 135.7, 130.6, 128.2, 127.0, 122.4, 119.2, 119.4, 118.7, 115.3, 111.2, 82.7, 62.9, 62.8, 60.9, 58.6, 57.7, 55.9, 53.3, 41.5, 41.1, 40.9, 40.3, 29.9, 22.0, 20.8, 20.0, 14.4, 9.9, 9.1

ESI-MS m/z: Calcd. for $C_{40}H_{40}N_4O_{10}S$: 768.3. Found $(M-H_2O+H)^+$: 751.2.

Example 30

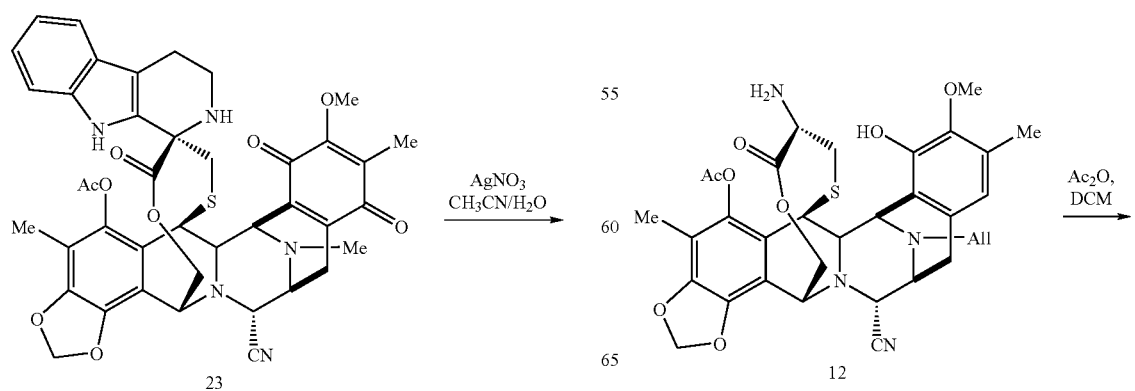

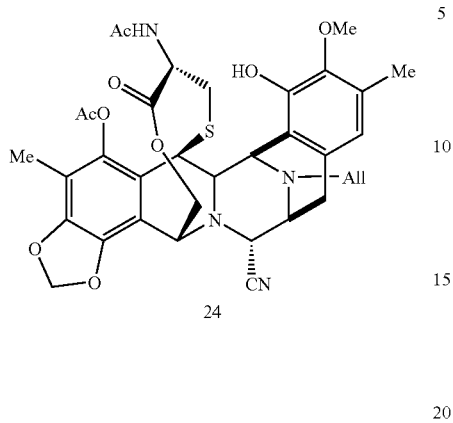

24

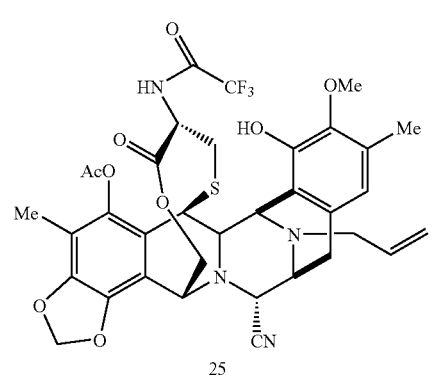

25

To a solution of compound 12 (99.1 mg, 0.15 mmol) in $CH_2Cl_2$ (3 mL, 0.05M) under Argon at 23° C., was added acetic anhydride (0.015 mL, 0.16 mmol). The reaction mixture was stirred for 45 min and then quenched with an aqueous saturated solution of $NaHCO_3$. The aqueous layer was extracted with $CH_2Cl_2$ and the organic layer was dried over $Na_2SO_4$. Flash chromatography (hexane/EtOAc, in gradient from 3:2 to 1:2) gives pure compound 24 (97 mg, 91%).

$R_f$: 0.3 (hexane/ethyl acetate 3:2)

$^1$H-RMN (300 MHz, $CDCl_3$): δ 6.54 (s, 1H), 6.02 (d, 2H), 5.96 (s, 1H), 5.89-5.76 (m, 1H), 5.52 (d, 1H), 5.11-4.99 (m, 3H), 4.58-4.55 (m, 1H), 4.52 (m, 1H), 4.33 (d, 1H), 4.26 (s, 1H), 4.18 (s, 1H), 4.16 (d, 1H), 3.74 (s, 3H), 3.54 (bd, 1H), 3.41 (d, 1H), 2.94-2.71 (m, 4H), 2.30-2.25 (m, 1H), 2.30 (s, 3H), 2.25 (s, 3H), 2.10 (d, 1H), 2.00 (s, 3H), 1.87 (s, 3H).

$^{13}$C-RMN (75 MHz, $CDCl_3$): δ 170.5, 168.8, 168.4, 147.8, 145.7, 143.0, 140.9, 140.3, 134.8, 131.1, 129.0, 120.3, 120.1, 119.4, 118.1, 117.8, 113.4, 113.3, 101.9, 61.2, 60.3, 60.2, 59.4, 59.1, 55.7, 53.0, 51.8, 51.7, 41.7, 32.4, 23.8, 22.8, 20.4, 16.0, 9.5.

ESI-MS m/z: Calcd. for $C_{35}H_{38}N_4O_9S$: 690.2. Found $(M+H)^+$: 691.5.

Example 31

To a solution of compound 12 (130 mg, 0.20 mmol) in $CH_2Cl_2$ (3 mL, 0.03M) under Argon atmosphere was added trifluoroacetic anhydride (0.057 mL, 0.40 mmol). The reaction mixture was stirred for 30 min at 23° C., then diluted with $CH_2Cl_2$, washed with an aqueous saturated solution of $NaHCO_3$ and the organic phase dried over $Na_2SO_4$. Flash chromatography (hexane/EtOAc, 3:2) gives pure compound 25 (104 mg, 73%).

$R_f$: 0.68 (hexane/ethyl acetate 1:1)

$^1$H-RMN (300 MHz, $CDCl_3$): δ 6.55 (s, 1H), 6.41 (d, 1H), 6.09 (d, 1H), 5.99 (d, 1H); 5.90-5.77 (m, 1H); 5.72 (s, 1H), 5.12-5.03 (m, 3H), 4.60 (bp, 1H), 4.54-4.51 (m, 1H), 4.34 (dd, 1H), 4.33 (s, 1H); 4.21 (dd, 1H), 4.19 (d, 1H), 3.73 (s, 3H), 3.57-3.55 (m, 1H), 3.44 (d, 1H); 2.87-2.71 (m, 4H), 2.43-2.38 (m, 1H), 2.28 (s, 3H), 2.27 (s, 3H), 2.11-2.04 (m, 1H); 2.02 (s, 3H).

ESI-MS m/z: Calcd. for $C_{35}H_{35}F_3N_4O_9S$: 744.2. Found $(M+H)^+$: 745.5.

Example 32

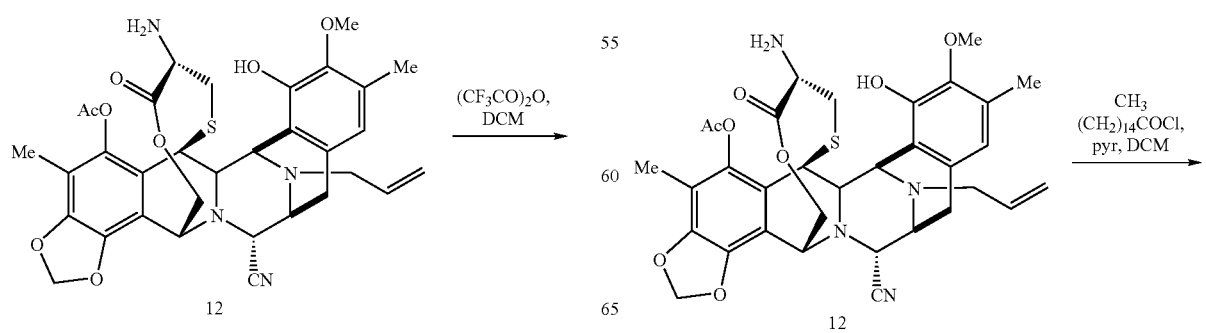

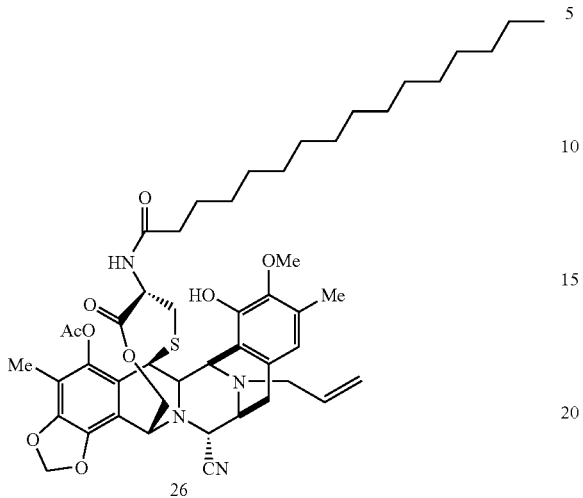

26

To a solution of compound 12 (60 mg, 0.09 mmol) in CH₂Cl₂ (3.2 mL, 0.03M) under Argon atmosphere were added pyridine (0.008 mL, 0.09 mmol) and palmitoyl chloride (0.03 mL, 0.09 mmol). The reaction mixture was stirred for 30 min at 23° C., then diluted with CH₂Cl₂ and washed with an aqueous saturated solution of NaHCO₃. The organic phase was dried over Na₂SO₄. Flash chromatography (hexane/EtOAc, 3:2) gives pure compound 26 (71 mg, 90%).

$R_f$: 0.62 (hexane/ethyl acetate 1:1)

¹H-RMN (300 MHz, CDCl₃): δ 6.55 (s, 1H), 6.08 (d, 1H), 5.98 (d, 1H), 5.89-5.77 (m, 1H); 5.75 (s, 1H); 5.47 (d, 1H), 5.11 (d, 1H); 5.07 (d, 1H); 5.02 (d, 1H), 4.62-4.58 (m, 1H), 4.53 (s, 1H), 4.34 (d, 1H), 4.28 (s, 1H), 4.19 (d, 1H); 4.17 (dd, 1H); 3.76 (s, 3H), 3.55 (d, 1H), 3.43 (d, 1H); 2.96-2.72 (m, 4H), 2.32 (s, 3H), 2.27 (s, 3H), 2.14-1.98 (m, 1H); 2.02 (s, 3H), 1.62-1.56 (m, 2H), 1.32-1.28 (m, 24H), 0.87 (t, 3H).

ESI-MS m/z: Calcd. for $C_{49}H_{66}N_4O_9S$: 886.5. Found (M+H)⁺: 887.9.

Example 33

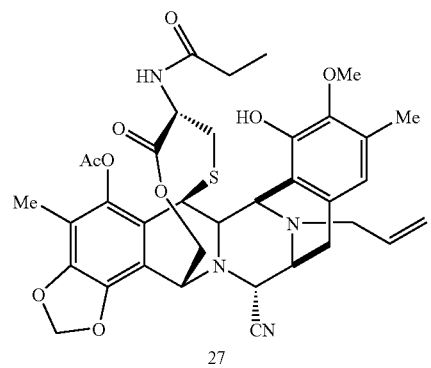

27

To a solution of compound 12 (65 mg, 0.1 mmol) in CH₂Cl₂ (1.6 mL, 0.06M) under Argon atmosphere were added pyridine (0.009 mL, 0.11 mmol) and propionyl chloride (0.009 mL, 0.11 mmol). The reaction mixture was stirred for 15 min at 23° C. then diluted with CH₂Cl₂ and washed with an aqueous saturated solution of NaHCO₃. The organic phase was dried over Na₂SO₄. Flash chromatography (hexane/EtOAc in gradient from 1:1 to 1:2) gives pure compound 27 (41 mg, 59%).

$R_f$: 0.66 (hexane/ethyl acetate 1:4)

¹H-RMN (300 MHz, CDCl₃): δ 6.55 (s, 1H), 6.08 (d, 1H), 5.98 (d, 1H); 5.90-5.77 (m, 1H), 5.51 (d, 1H), 5.12 (d, 2H), 5.03 (d, 2H), 4.61-4.54 (m, 2H), 4.36 (d, 1H), 4.29 (s, 1H), 4.16 (dd, 2H), 3.76 (s, 3H), 3.55 (d, 1H), 3.43 (d, 1H), 2.89-2.76 (m, 5H), 2.31 (s, 3H), 2.24 (s, 3H), 2.15-2.04 (m, 2H), 2.02 (s, 3H), 1.10 (t, 3H).

ESI-MS m/z: Calcd. for $C_{36}H_{40}N_4O_9S$: 704.3. Found (M+H)⁺: 705.6.

Example 34

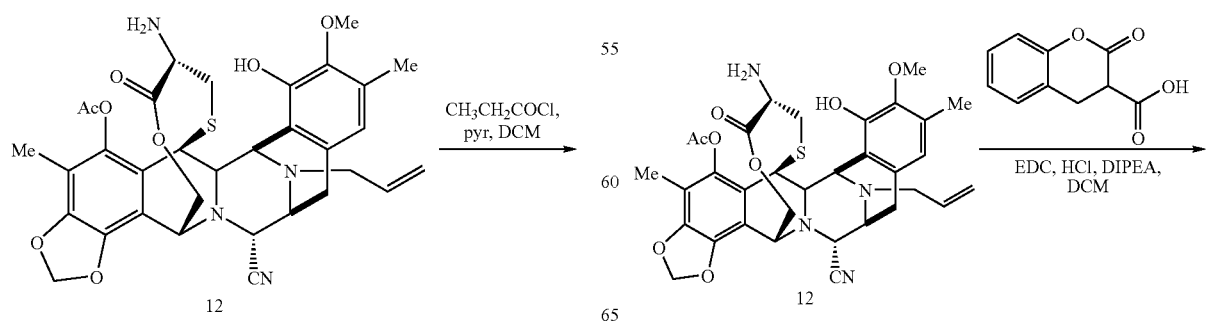

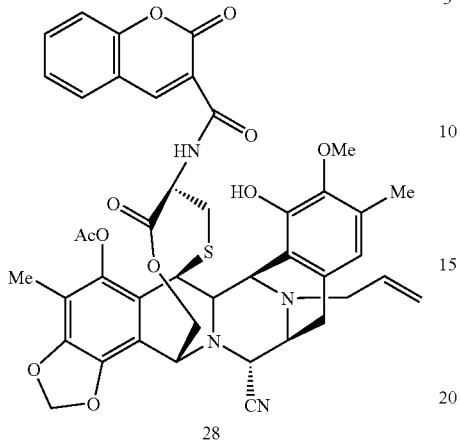

28

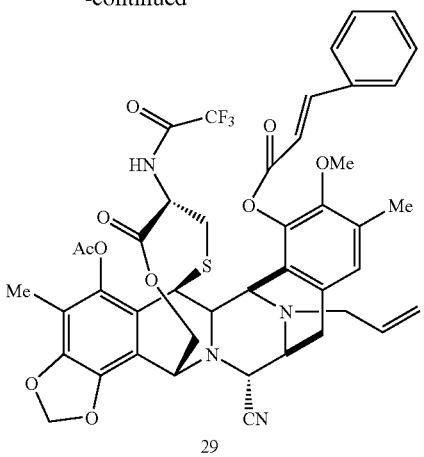

29

To a solution of compound 25 (40 mg, 0.05 mmol) in CH$_2$Cl$_2$ (1.5 mL, 0.03M) under Argon atmosphere were added Et$_3$N (0.035 mL, 0.24 mmol) and cinnamoyl chloride (27.7 mg, 0.016 mmol). After 30 min at 23° C., the reaction was diluted with CH$_2$Cl$_2$, washed with an aqueous saturated solution of NaHCO$_3$ and the organic phase dried over Na$_2$SO$_4$. Flash chromatography (hexane/EtOAc, 3:2) gives pure compound 29 (46 mg, 99%).

R$_f$: 0.5 (hexane/ethyl acetate 2:1)

$^1$H-RMN (300 MHz, CDCl$_3$): δ 7.93 (d, 1H); 7.62-7.59 (m, 2H); 7.46-7.44 (m, 3H); 6.91 (s, 1H); 6.63 (d, 1H); 6.44 (d, 1H), 6.11 (d, 1H), 6.01 (d, 1H); 5.84-5.71 (m, 1H); 5.19-5.05 (m, 3H), 4.59-4.53 (m, 1H), 4.35 (s, 1H); 4.25-4.21 (m, 2H); 4.00 (d, 1H); 3.71 (s, 3H); 3.64-3.62 (m, 1H); 3.49 (d, 1H); 2.95-2.88 (m, 3H), 2.77-2.70 (m, 1H); 2.52-2.48 (m, 1H), 2.36 (s, 3H), 2.30 (s, 3H), 2.14-2.04 (m, 1H); 2.06 (s, 3H).

ESI-MS m/z: Calcd. for C$_{44}$H$_{41}$F$_3$N$_4$O$_{10}$S: 874.3. Found (M+H)$^+$: 875.6.

To a solution of compound 12 (64 mg, 0.1 mmol) in CH$_2$Cl$_2$ (2 mL, 0.05M) under Argon atmosphere were added coumarine acid (23 mg, 0.13 mmol), DIPEA (0.05 mL, 0.15 mmol) and EDC.HCl (60 mg, 0.15 mmol). The reaction mixture was stirred under Argon atmosphere at 23° C. for 4 hours, then diluted with CH$_2$Cl$_2$, washed with an aqueous saturated solution of NaHCO$_3$. The organic phase was dried over Na$_2$SO$_4$. Flash chromatography (hexane/EtOAc, 1:1) gives pure compound 28 (40 mg, 49%).

R$_f$: 0.5 (hexane/ethyl acetate 1:2)

$^1$H-RMN (300 MHz, CDCl$_3$): δ 8.98 (d, 1H), 7.69-7.62 (m, 2H), 7.44 (7.33 (m, 2H), 6.65 (s, 1H), 6.10 (s, 1H), 5.99 (s, 1H), 5.89-5.80 (m, 1H), 5.60 (d, 1H), 5.11-5.05 (m, 4H), 4.69 (dd, 1H), 4.59 (bs, 1H), 4.35-416 (m, 5H), 3.67 (3H), 3.58 (d, 1H), 3.45 (d, 2H), 2.93-2.62 (m, 5H), 2.27 (s, 3H), 2.13 (s, 3H), 2.03 (s, 3H).

ESI-MS m/z: Calcd. for C$_{43}$H$_{40}$N$_4$O$_{11}$S: 820.2. Found (M+H)$^+$: 821.8.

General Experimental Procedure for the Synthesis of Compounds 30, 32, 32, 33 and 34: Deallylation Reaction To a solution of starting material in CH$_2$Cl$_2$ (0.04M) were added (PPh$_3$)$_2$PdCl$_2$ (0.08 equiv) and acetic acid (5 equiv). HSnBu$_3$ (initial amount 8 equiv) was dropwise added at 23° C. and under Argon atmosphere Additional HSnBu$_3$ (final amount 48 equiv) was dropwise added during the reaction time (1 hour to 1 hour and 45 min). After this time, the solution was poured onto a column. Flash chromatography (mixtures hexane/ethyl acetate) gives pure compounds.

Example 35

Example 36

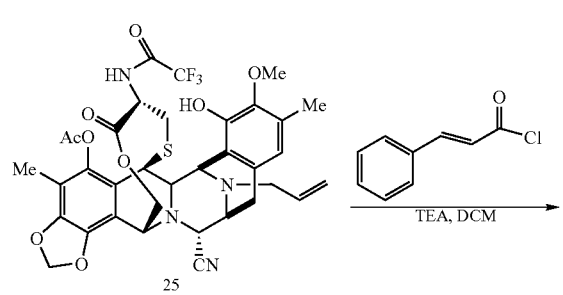

25

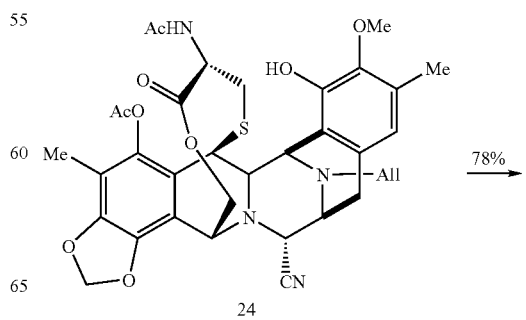

24

78%

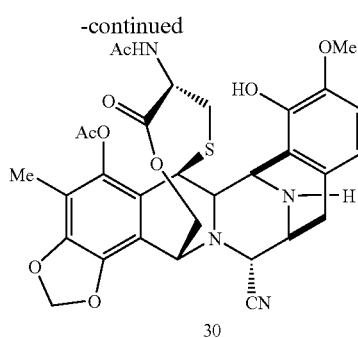

$R_f$: 0.3 (hexane/ethyl acetate 2:5)

$^1$H-RMN (300 MHz, CDCl$_3$): δ 6.57 (s, 1H), 6.04 (d, 2H), 5.51 (d, 1H), 5.03 (d, 1H), 4.60-4.57 (m, 1H), 4.52 (bp, 1H), 4.47 (d, 1H), 4.27 (s, 1H), 4.19-4.15 (m, 2H), 3.84 (bd, 1H), 3.75 (s, 3H), 3.43 (d, 1H), 3.07 (s, 1H), 2.96 (q, 1H), 2.34-2.27 (m, 1H), 2.30 (s, 3H), 2.27 (s, 3H), 2.13 (d, 1H), 2.02 (s, 3H), 1.87 (s, 3H)

ESI-MS m/z: Calcd. for $C_{32}H_{34}N_4O_9S$: 650.2. Found (M+H)$^+$: 651.4.

Example 37

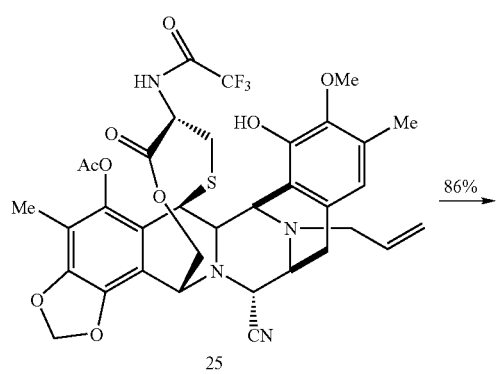

$R_f$: 0.3 (hexane/ethyl acetate 1:1)

$^1$H-RMN (300 MHz, CDCl$_3$): δ 6.54 (s, 1H), 6.40 (d, 1H), 6.10 (d, 1H), 6.00 (d, 1H); 5.05 (d, 1H), 4.60 (bp, 1H), 4.54-4.51 (m, 1H), 4.48 (d, 1H), 4.32 (s, 1H); 4.22 (dd, 1H), 4.19 (d, 1H); 3.86-3.84 (m, 1H); 3.73 (s, 3H), 3.46 (d, 1H); 2.99-2.98 (m, 2H), 2.44-2.39 (m, 1H), 2.29 (s, 3H), 2.26 (s, 3H), 2.13-2.08 (m, 1H); 2.03 (s, 3H).

ESI-MS m/z: Calcd. for $C_{32}H_{31}F_3N_4O_9S$: 704.2. Found (M+H)$^+$: 705.6.

Example 38

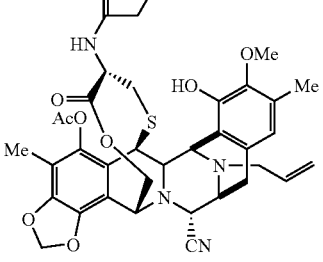

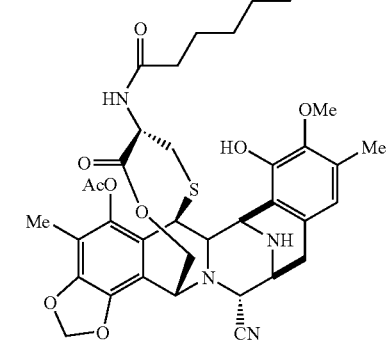

$R_f$: 0.4 (hexane/ethyl acetate 1:1)

$^1$H-RMN (300 MHz, CDCl$_3$): δ 6.57 (s, 1H), 6.09 (d, 1H), 5.99 (d, 1H), 5.78 (s, 1H); 5.47 (d, 1H), 5.03 (d, 1H); 4.62-4.60 (m, 1H), 4.53 (s, 1H), (d, 1H), 4.28 (s, 1H), 4.19 (d, 1H); 4.17 (dd, 1H); 3.85 (d, 1H); 3.76 (s, 3H), 3.44 (d, 1H); 3.11-2.91 (m, 2H), 2.31 (s, 3H), 2.28 (s, 3H), 2.16-1.96 (m, 3H); 2.02 (s, 3H), 1.62-1.56 (m, 2H), 1.38-1.28 (m, 24H), 0.87 (t, 3H).

ESI-MS m/z: Calcd. for $C_{46}H_{62}N_4O_9S$: 846.4. Found (M+H)$^+$: 847.0.

Example 39

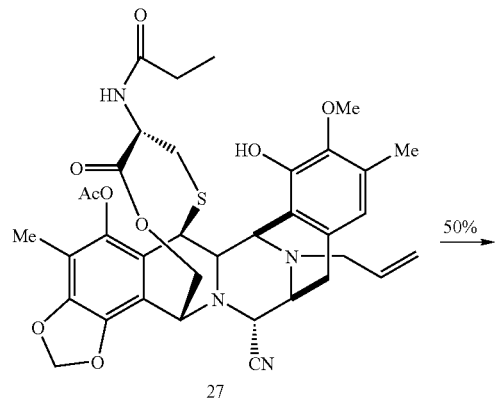

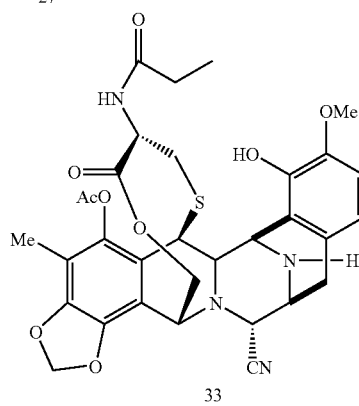

$R_f$: 0.2 (hexane/ethyl acetate 1:1)
$^1$H-RMN (300 MHz, CDCl$_3$): δ 6.57 (s, 1H), 6.01 (s, 1H), 5.74 (d, 1H), (d, 1H), 5.10-4.83 (m, 2H), 4.61-4.54 (m, 1H), 4.48 (d, 1H), 4.34-4.15 (m, 4H), 3.76 (s, 3H), 3.59-3.34 (m, 3H), 3.10-2.89 (m, 3H), 2.30 (s, 3H), 2.29 (s, 3H), 2.12 (dd, 2H), 2.03 (s, 3H), 1.10 (t, 3H).
ESI-MS m/z: Calcd. for C$_{33}$H$_{36}$N$_4$O$_9$S: 664.2. Found (M+H)$^+$: 665.6.

Example 40

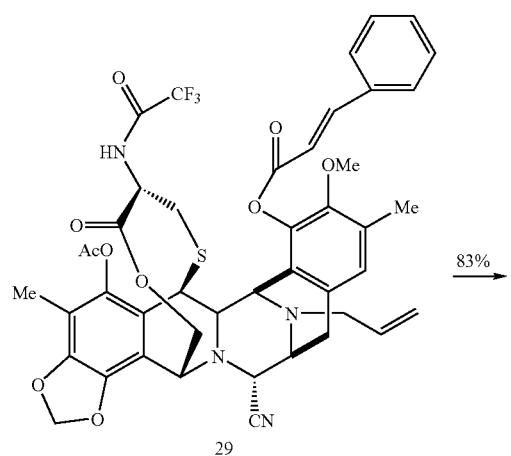

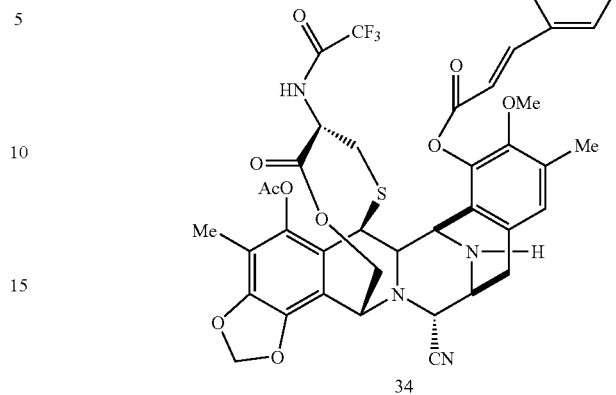

$R_f$: 0.4 (hexane/ethyl acetate 1:1)
$^1$H-RMN (300 MHz, CDCl$_3$): δ 7.93 (d, 1H); 7.62-7.59 (m, 2H); 7.46-7.44 (m, 3H); 6.87 (s, 1H), 6.65 (d, 1H); 6.43 (d, 1H), 6.12 (d, 1H), 6.03 (d, 1H); 5.03 (d, 1H); 4.56-4.49 (m, 1H), 4.35 (s, 1H); 4.23-4.1 (m, 3H); 3.72 (s, 3H), 3.49 (d, 1H); 3.19-2.90 (m, 3H), 2.52-2.43 (m, 1H), 2.30 (s, 3H), 2.147-2.08 (m, 1H); 2.06 (s, 3H), 2.03 (s, 3H).
ESI-MS m/z: Calcd. for C$_{41}$H$_{37}$F$_3$N$_4$O$_{10}$S: 834.2. Found (M+H)$^+$: 836.0.

Example 41

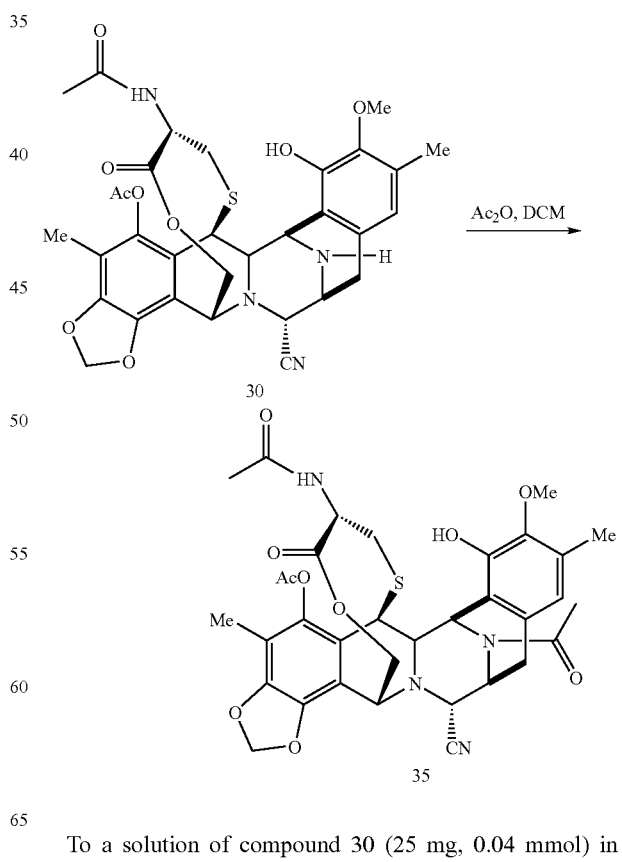

To a solution of compound 30 (25 mg, 0.04 mmol) in CH$_2$Cl$_2$ (0.8 mL, 0.05M) under Argon atmosphere was added at 23° C. acetic anhydride (0.005 mL, 0.042 mmol). After 1 h at 23° C. more acetic anhydride was added (0.005 mL, 0.042 mmol). The reaction was stirred for 4 h more and then quenched with an aqueous saturated solution of NaHCO$_3$. The aqueous layer was extracted with CH$_2$Cl$_2$ and the organic layer was dried over Na$_2$SO$_4$. Flash chromatography (hexane/EtOAc, in gradient from 2:5 to 1:5,) gives pure compound 35 (24 mg, 90%)

R$_f$: 0.15 (hexane/ethyl acetate 2:7)

$^1$H-RMN (300 MHz, CDCl$_3$): δ 6.56, 6.54 (2s, 1H), 6.36, 6.15-6.00 (m, 3H), 5.52-5.42 (m, 1.6H), 5.29-5.25 (m, 0.6H), 5.07-5.01 (m, 1H), 4.71-4.58 (m, 2.4H), 4.30-4.16 (m, 3.4H), 3.76, 3.74 (2s, 3H), 3.41-3.13 (m, 3H), 2.40-2.35 (m, 1H), 2.13 (d, 1H), 2.28, 2.27, 2.19, 2.07, 2.02, 1.98, 1.87, 1.86 (8s, 15H).

ESI-MS m/z: Calcd. for C$_{34}$H$_{36}$N$_4$O$_{10}$S: 692.2. Found (M+H)$^+$: 693.3.

General Experimental Procedure for the Synthesis of Compounds 36, 32, 38, 39, 40 and 41: Conversion of the Nitrile Group into Hydroxyl Group.

To a solution of starting material in THF/H$_2$O 4:1 (0.03M) were added 10 equiv. of CuCl. The reaction was stirred for 24 h protected from the light. After this time, the reaction was quenched with an aqueous saturated solution of NH$_4$Cl and diluted with CH$_2$Cl$_2$. The organic phase is washed with brine and an aqueous saturated solution of NaHCO$_3$ and the aqueous phase extracted with CH$_2$Cl$_2$. The combined organic layers were dried over Na$_2$SO$_4$. Flash chromatography (mixtures CH$_2$Cl$_2$/MeOH) gives pure compounds.

Example 42

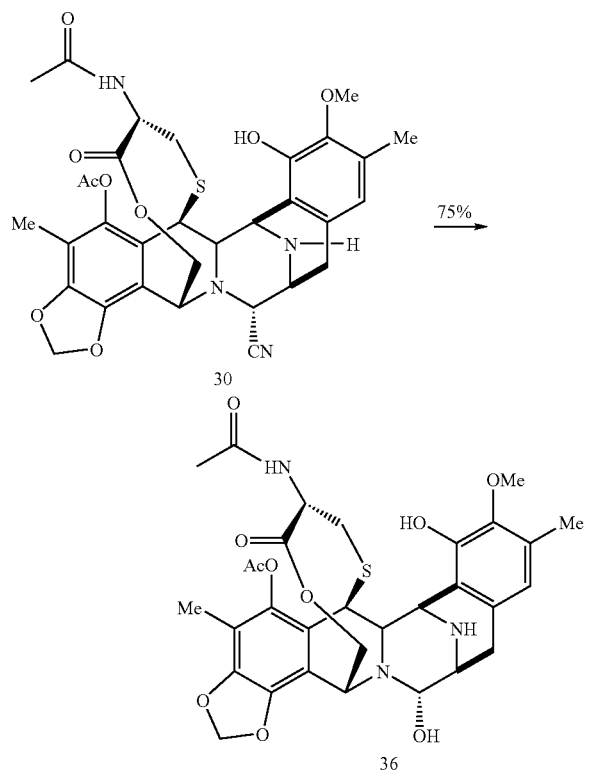

R$_f$: 0.11 (CH$_2$Cl$_2$/MeOH 30:1)

$^1$H-RMN (300 MHz, CD$_3$OD): δ 6.56 (s, 1H), 6.05 (d, 2H), 5.23 (d, 1H), 4.71 (s, 1H), 4.51 (m, 1H), 4.50-4.40 (m, 2H), 4.14-4.11 (m, 2H), 3.71 (s, 3H), 3.62-3.60 (m, 1H), 3.52-3.50 (m, 1H), 3.00 (d, 2H), 2.30 (s, 3H), 2.28 (s, 3H), 2.28-2.05 (m, 2H), 2.00 (s, 3H), 1.90 (s, 3H).

ESI-MS m/z: Calcd. for C$_{31}$H$_{35}$N$_3$O$_{10}$S: 641.2. Found (M−H$_2$O+H)$^+$: 624.3.

Example 43

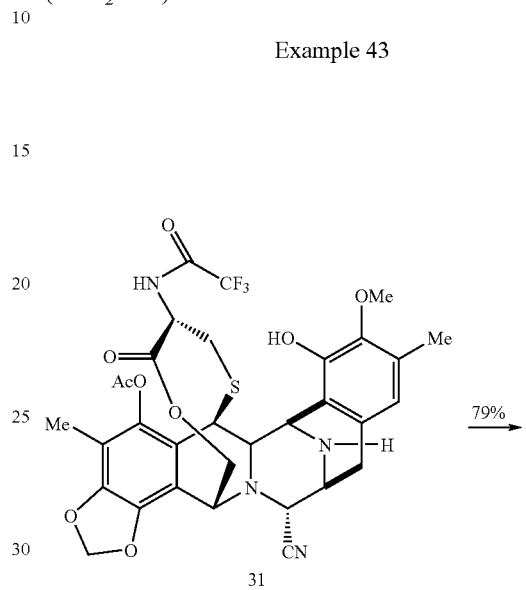

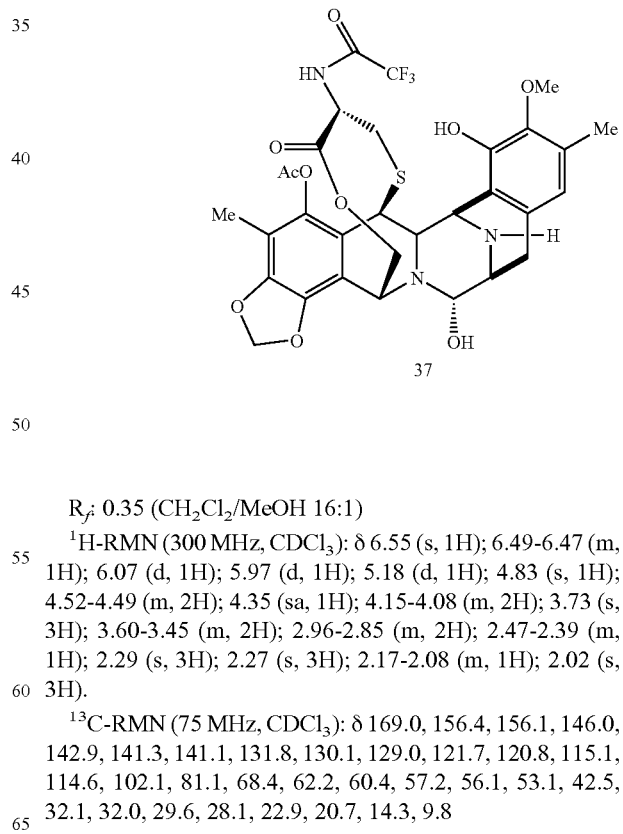

R$_f$: 0.35 (CH$_2$Cl$_2$/MeOH 16:1)

$^1$H-RMN (300 MHz, CDCl$_3$): δ 6.55 (s, 1H); 6.49-6.47 (m, 1H); 6.07 (d, 1H); 5.97 (d, 1H); 5.18 (d, 1H); 4.83 (s, 1H); 4.52-4.49 (m, 2H); 4.35 (sa, 1H); 4.15-4.08 (m, 2H); 3.73 (s, 3H); 3.60-3.45 (m, 2H); 2.96-2.85 (m, 2H); 2.47-2.39 (m, 1H); 2.29 (s, 3H); 2.27 (s, 3H); 2.17-2.08 (m, 1H); 2.02 (s, 3H).

$^{13}$C-RMN (75 MHz, CDCl$_3$): δ 169.0, 156.4, 156.1, 146.0, 142.9, 141.3, 141.1, 131.8, 130.1, 129.0, 121.7, 120.8, 115.1, 114.6, 102.1, 81.1, 68.4, 62.2, 60.4, 57.2, 56.1, 53.1, 42.5, 32.1, 32.0, 29.6, 28.1, 22.9, 20.7, 14.3, 9.8

ESI-MS m/z: Calcd. for C$_{31}$H$_{32}$F$_3$N$_3$O$_{10}$S: 695.2. Found (M−H$_2$O+H)$^+$: 678.4.

Example 44
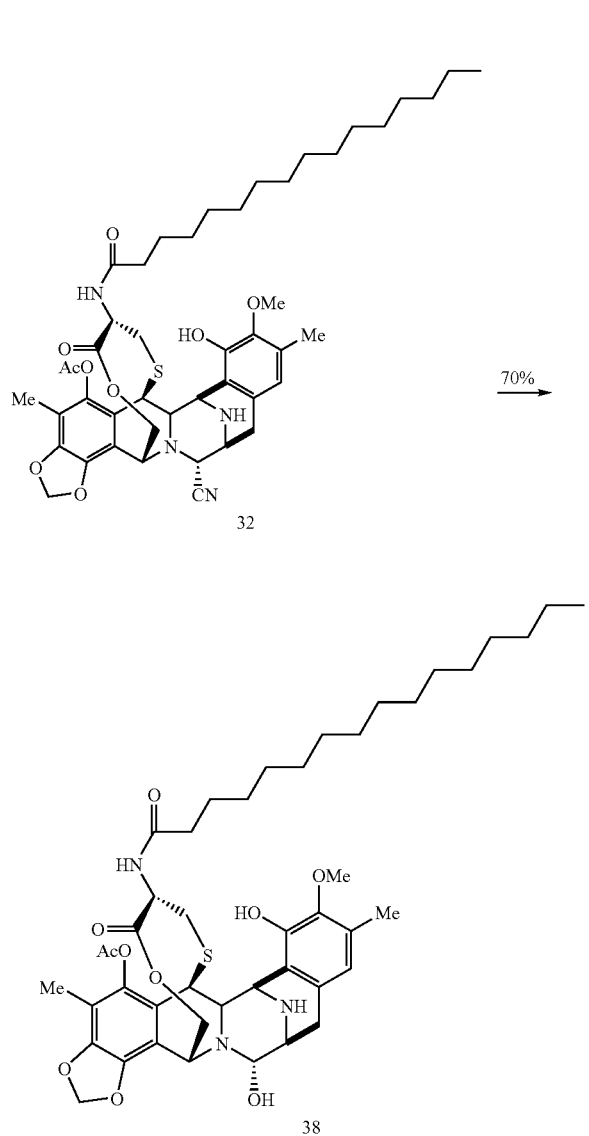
$R_f$: 0.4 (CH$_2$Cl$_2$/MeOH 16:1)
$^1$H-RMN (300 MHz, CDCl$_3$): δ 6.57 (s, 1H); 6.06 (d, 1H); 5.96 (d, 1H); 5.53 (d, 1H); 5.15 (d, 1H); 4.78 (s, 1H); 4.59-4.56 (m, 1H); 4.48-4.42 (m, 1H); 4.35 (d, 1H); 4.07 (dd, 1H); 3.98 (dd, 1H); 3.76 (s, 3H); 3.60-3.57 (m, 1H); 3.52 (d, 1H); 3.02-2.79 (m, 2H); 2.31 (s, 3H); 2.28 (s, 3H); 2.17-2.05 (m, 1H); 2.01 (s, 3H); 1.70-1.63 (m, 2H), 1.36-1.24 (m, 24H), 0.87 (t, 3H).
$^{13}$C-RMN (75 MHz, CDCl$_3$): δ 172.2, 170.7, 146.1, 145.8, 142.9, 141.2, 141.0, 132.1, 129.2, 125.5, 125.0, 121.4, 121.0, 115.4, 112.8, 102.0, 81.2, 61.8, 60.6, 57.0, 56.1, 52.0, 51.3, 48.1, 42.4, 36.6, 32.5, 32.1, 30.0, 29.9, 29.8, 29.7, 29.6, 28.0, 27.4, 25.6, 22.9, 20.8, 16.2, 14.3, 9.8
ESI-MS m/z: Calcd. for C$_{45}$H$_{63}$N$_3$O$_{10}$S: 837.4. Found (M–H$_2$O+H)$^+$: 820.8.
Example 45
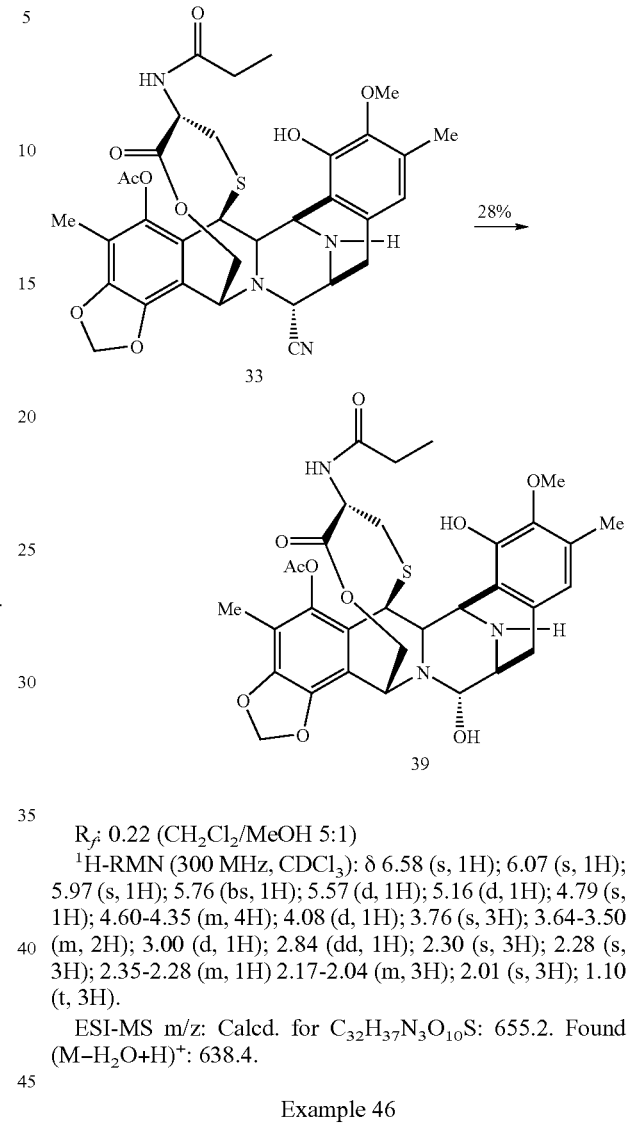
$R_f$: 0.22 (CH$_2$Cl$_2$/MeOH 5:1)
$^1$H-RMN (300 MHz, CDCl$_3$): δ 6.58 (s, 1H); 6.07 (s, 1H); 5.97 (s, 1H); 5.76 (bs, 1H); 5.57 (d, 1H); 5.16 (d, 1H); 4.79 (s, 1H); 4.60-4.35 (m, 4H); 4.08 (d, 1H); 3.76 (s, 3H); 3.64-3.50 (m, 2H); 3.00 (d, 1H); 2.84 (dd, 1H); 2.30 (s, 3H); 2.28 (s, 3H); 2.35-2.28 (m, 1H) 2.17-2.04 (m, 3H); 2.01 (s, 3H); 1.10 (t, 3H).
ESI-MS m/z: Calcd. for C$_{32}$H$_{37}$N$_3$O$_{10}$S: 655.2. Found (M–H$_2$O+H)$^+$: 638.4.
Example 46
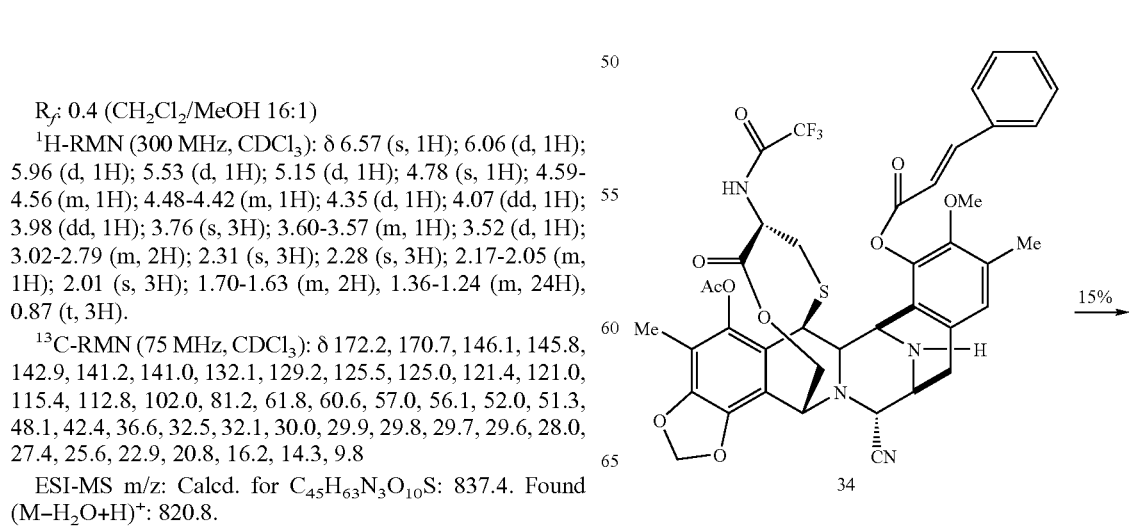

-continued

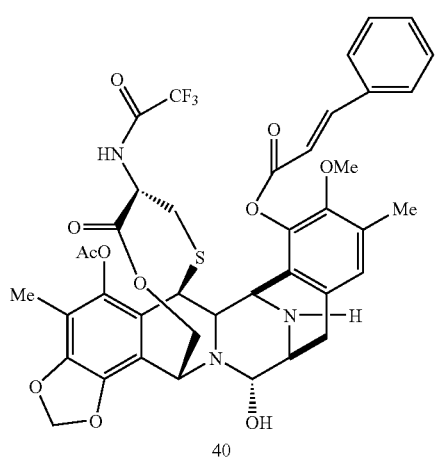

40

$R_f$: 0.35 (CH$_2$Cl$_2$/MeOH 16:1)

$^1$H-RMN (300 MHz, CDCl$_3$): δ 7.94 (d, 1H); 7.62-7.59 (m, 2H); 7.46-7.44 (m, 3H); 6.87 (s, 1H); 6.65 (d, 1H); 6.45 (d, 1H); 6.09 (d, 1H); 6.00 (d, 1H); 5.15 (d, 1H); 4.83 (s, 1H); 4.52-4.49 (m, 2H); 4.35 (sa, 1H); 4.15-4.08 (m, 2H); 3.73 (s, 3H); 3.60-3.45 (m, 2H); 2.96-2.85 (m, 2H); 2.47-2.39 (m, 1H); 2.29 (s, 3H); 2.27 (s, 3H); 2.17-2.08 (m, 1H); 2.02 (s, 3H).

ESI-MS m/z: Calcd. for C$_{40}$H$_{38}$F$_3$N$_3$O$_{11}$S: 825.2. Found (M−H$_2$O+H)$^+$: 809.5.

Example 47

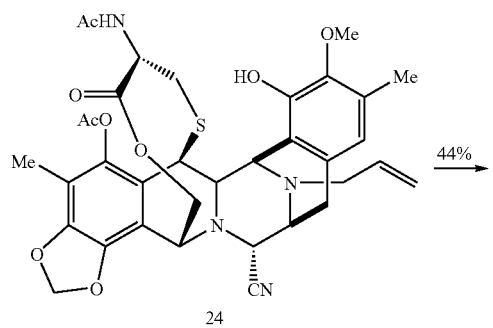

24

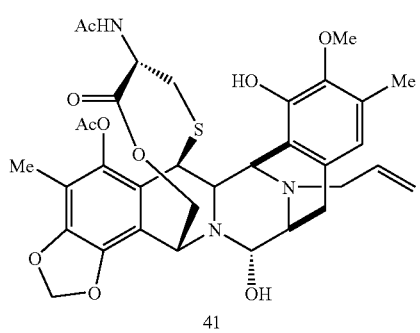

41

$R_f$: 0.2 (CH$_2$Cl$_2$/MeOH 60:1)

$^1$H-RMN (300 MHz, CDCl$_3$): δ 6.58 (s, 1H), 6.02 (d, 2H), 5.83-5.69 (m, 1H), 5.69 (s, 1H), 5.59 (d, 1H), 5.17-4.96 (m, 3H), 4.78 (s, 1H), 4.57-4.53 (m, 1H), 4.47-4.25 (m, 3H), 4.09 (dd, 1H), 3.77 (s, 3H), 3.47 (d, 1H), 3.34-3.31 (m, 1H), 2.92-2.73 (m, 4H), 2.32-2.27 (m, 1H), 2.32 (s, 3H), 2.27 (s, 3H), 2.14 (d, 1H), 2.01 (s, 3H), 1.88 (s, 3H).

ESI-MS m/z: Calcd. for C$_{34}$H$_{39}$N$_3$O$_{10}$S: 681.2. Found (M−H$_2$O+H)$^+$: 664.6.

Example 48

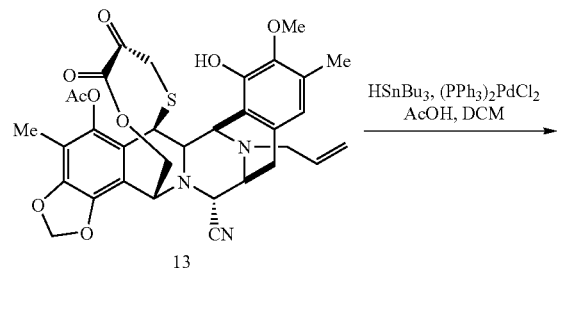

To a solution of compound 13 (39 mg, 0.06 mmol) in CH$_2$Cl$_2$ (1.5 mL, 0.040 M) were added (PPh$_3$)$_2$PdCl$_2$ (3.4 mg, 0.004 mmol), acetic acid (0.02 mL, 0.30 mmol) and finally HsnBu$_3$ (0.05 mL, 0.2 mmol). After 30 min at 23° C. the reaction was poured onto a column. Chromatography (hexane/ethyl acete in gradient from 4:1 to 1:2) gives pure compound 42 (31 mg, 86%).

$R_f$: 0.38 (hexane/ethyl acete 3:4)

$^1$H-RMN (300 MHz, CDCl$_3$): δ 6.58 (s, 1H); 6.51 (s, 1H); 6.11 (d, 1H); 6.08 (d, 1H); 6.02 (d, 1H); 5.99 (d, 1H); 5.78 (sa, 2H); 5.10 (d, 1H); 5.05 (d, 1H); 4.65 (s, 1H); 4.54 (s, 1H); 4.50 (d, 1H); 4.47 (d, 1H); 4.40 (s, 1H); 4.26 (s, 1H); 4.24 (s, 1H); 4.20 (s, 1H); 4.18 (d, 1H); 4.01 (dd, 1H); 3.87-3.81 (m, 2H); 3.76 (s, 3H); 3.74 (s, 3H); 3.56 (d, 1H); 3.42 (d, 1H); 3.13-2.81 (m, 6H); 2.57 (d, 2H); 2.32 (s, 3H); 3.31 (s, 3H); 2.28 (s, 3H); 2.24 (s, 3H); 2.19-2.15 (m, 1H); 2.04 (s, 3H); 2.03 (s, 3H).

ESI-MS m/z: Calcd. for $C_{30}H_{29}N_3O_9S$: 607.2. Found (M+H)+: 608.3.

Example 49

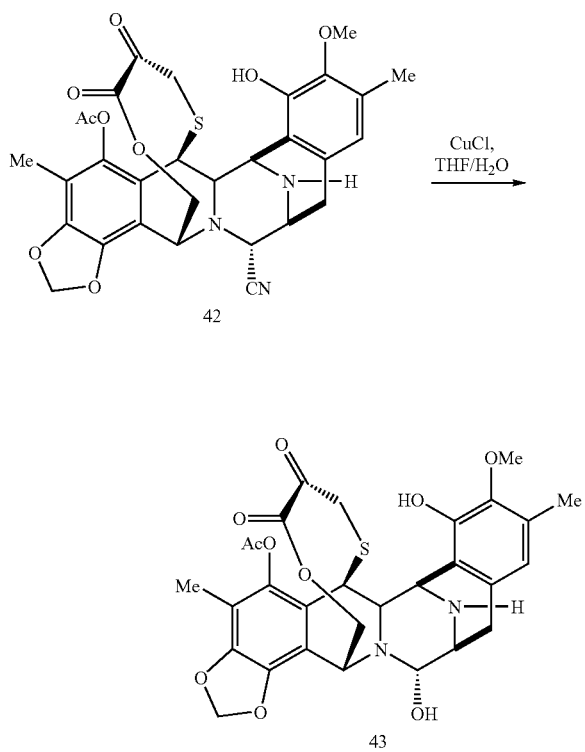

Example 50

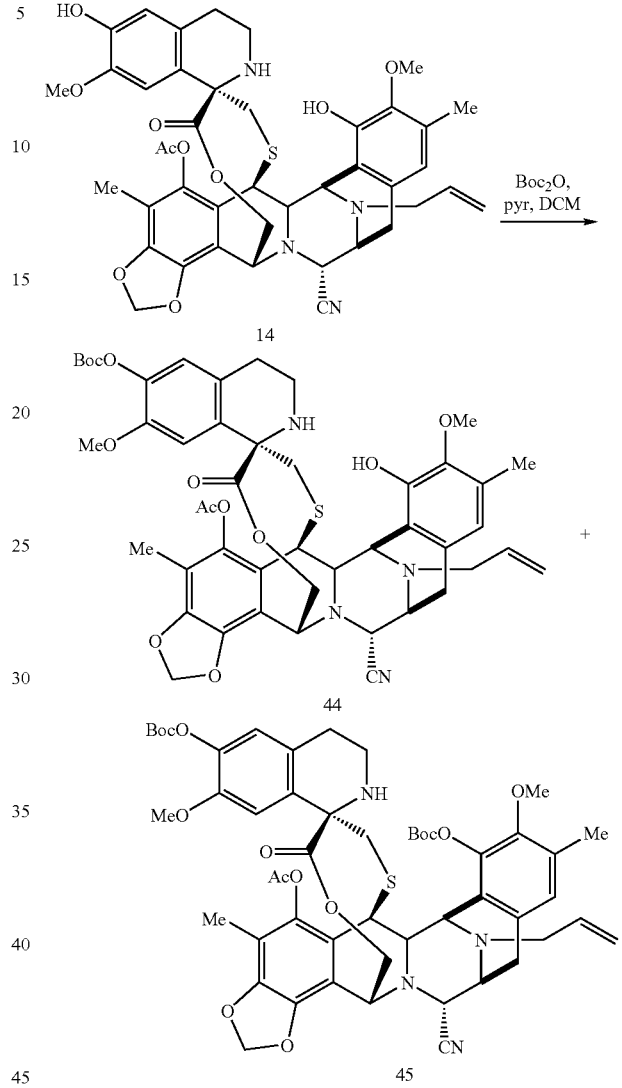

To a solution of compound 42 (30 mg, 0.05 mmol) in THF/$H_2O$ 4:1 (1.7 mL, 0.009M) was added CuCl (49 mg, 0.5 mmol). After 24 h at 23° C. the reaction mixture was quenched with an aqueous saturated solution of $NH_4Cl$, diluted with $CH_2Cl_2$ and washed with brine and an aqueous saturated solution of $NaHCO_3$ and the aqueous phase was extracted with $CH_2Cl_2$. The organic layer was dried over $Na_2SO_4$. Chromatography ($CH_2Cl_2$/MeOH 16:1) gives pure compound 43 (3 mg, 10%).

$R_f$: 0.2 ($CH_2Cl_2$/MeOH 16:1)

1H-RMN (300 MHz, $CDCl_3$): δ 6.58 (s, 1H); 6.05 (d, 1H); 5.96 (d, 1H); 5.78 (sa, 1H); 5.17 (d, 1H); 4.78 (s, 1H); 4.51-4.35 (m, 3H); 4.07 (dd, 1H); 4.00 (m, 2H); 3.77 (s, 3H); 3.64-3.53 (m, 2H); 3.07-2.80 (m, 3H); 2.31 (s, 3H); 2.17-2.10 (m, 1H); 2.02 (s, 3H).

ESI-MS m/z: Calcd. for $C_{29}H_{30}N_2O_{10}S$: 598.2. Found 583.1 (M+−H2O+Me)

To a solution of compound 14 (414 mg, 0.5 mmol) in $CH_2Cl_2$ (9.5 mL, 0.032M) under Argon were added $Boc_2O$ (113 mg, 0.5 mmol) and pyridine (0.04 mL, 0.5 mmol). After 2 h at 23° C. more $Boc_2O$ (113 mg, 0.5 mmol) and pyridine (0.04 mL, 0.05 mmol) were added. Additional $Boc_2O$ (113 mg, 0.5 mmol) and pyridine (0.04 mL, 0.05 mmol) were added after 3 h. Total reaction time: 6 hours. The reaction mixture was quenched with an aqueous saturated solution of $NaHCO_3$, the aqueous phase was extracted with $CH_2Cl_2$ and the organic layers dried over $Na_2SO_4$. Flash chromatography (hexane/ethyl acetate 1:1) gives pure compounds 44 (365 mg, 78%) and 45 (105 mg, 20%).

Compound 44

$R_f$: 0.5 (hexane/ethyl acete 1:1)

1H-RMN (300 MHz, $CDCl_3$): δ 6.68 (s, 1H); 6.59 (s, 1H); 6.57 (s, 1H); 6.03 (d, 1H); 5.96 (d, 1H); 5.93-5.80 (m, 1H);

5.73 (s, 1H); 5.13-5.07 (m, 2H); 5.00 (d, 1H); 4.55 (s, 1H); 4.36 (d, 1H); 4.32 (s, 1H); 4.18 (d, 1H); 4.09 (dd, 1H); 3.78 (s, 3H); 3.58 (s, 3H); 3.57-3.49 (m, 2H); 3.14-3.05 (m, 1H); 2.98-2.76 (m, 4H); 2.68-2.59 (m, 1H); 2.50-2.45 (m, 1H); 2.35-2.14 (m, 2H); 2.31 (s, 3H); 2.26 (s, 3H); 2.02 (s, 3H); 1.50 (s, 9H).

ESI-MS m/z: Calcd. for $C_{47}H_{52}N_4O_{12}S$: 896.3. Found $(M+H)^+$: 897.0.

Compound 45

$R_f$: 0.6 (hexane/ethyl acete 1:1)

$^1$H-RMN (300 MHz, $CDCl_3$): δ 6.92 (s, 1H); 6.68 (s, 1H); 6.55 (s, 1H); 6.03 (d, 1H); 5.96 (d, 1H); 5.87-5.75 (m, 1H); 5.22-5.07 (m, 2H); 5.00 (d, 1H); 4.55 (s, 1H); 4.33 (s, 1H); 4.18 (d, 1H); 4.10 (dd, 1H); 4.06 (d, 1H); 3.80 (s, 3H); 3.58 (s, 3H); 3.52 (d, 1H); 3.12-3.00 (m, 1H); 2.93-2.75 (m, 4H); 2.68-2.58 (m, 1H); 2.51-2.46 (m, 1H); 2.32 (s, 3H); 2.31 (s, 3H); 2.27-2.23 (m, 2H); 2.05 (s, 3H); 1.50 (s, 9H); 1,49 (s, 9H).

ESI-MS m/z: Calcd. for $C_{52}H_{60}N_4O_{14}S$: 996.4. Found $(M+H)^+$: 997.7.

Example 51

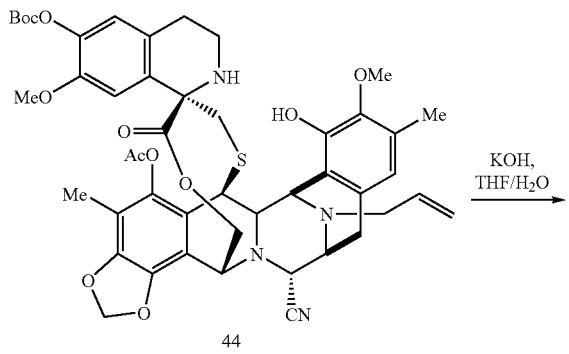

44

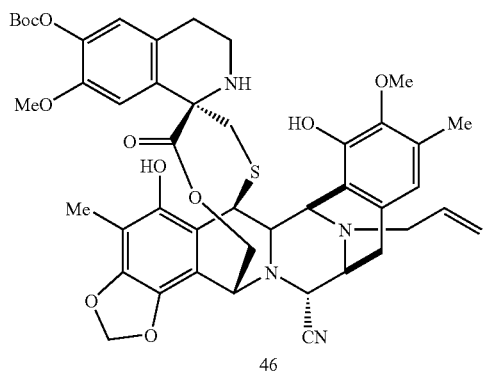

46

To a solution of compound 44 (275 mg, 0.30 mmol) in THF/$H_2O$ 2:1 (15 mL, 0.027M) was added an aqueous solution of KOH (4 mL, 1.1 M). The reaction mixture was stirred at 23° C. for 2 h. After this time the reaction was quenched with brine and extracted with $CH_2Cl_2$. The organic layer was dried over $Na_2SO_4$. Chromatography (hexane/ethyl acete 1:1) gives pure compound 46 (216 mg, 82%).

$R_f$: 0.48 (hexane/ethyl acete 1:1)

$^1$H-RMN (300 MHz, $CDCl_3$): δ 6.70 (s, 1H); 6.59 (s, 1H); 6.55 (s, 1H); 6.25 (s, 1H); 5.95 (d, 1H); 5.89 (d, 1H); 5.87-5.77 (m, 1H); 5.72 (s, 1H); 5.10-5.03 (m, 2H); 4.99 (d, 1H); 4.49 (d, 1H); 4.38-4.36 (m, 2H); 4.17 (d, 1H); 4.05 (dd, 1H); 3.68 (s, 3H); 3.59-3.53 (m, 2H); 3.56 (s, 3H); 3.13-3.04 (m, 1H); 2.99-2.71 (m, 4H); 2.68-2.46 (m, 3H); 2.40 (d, 1H); 2.30 (s, 3H); 2.16 (s, 3H); 1.50 (s, 9H).

ESI-MS m/z: Calcd. for $C_{45}H_{50}N_4O_{11}S$: 854.3. Found $(M+H)^+$: 855.6.

Example 52

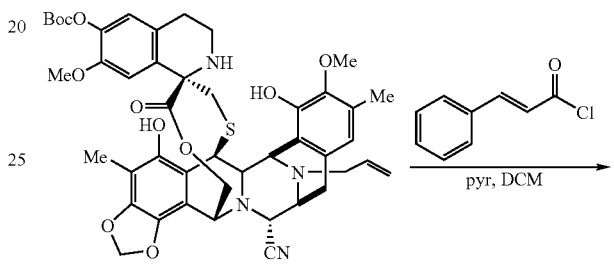

46

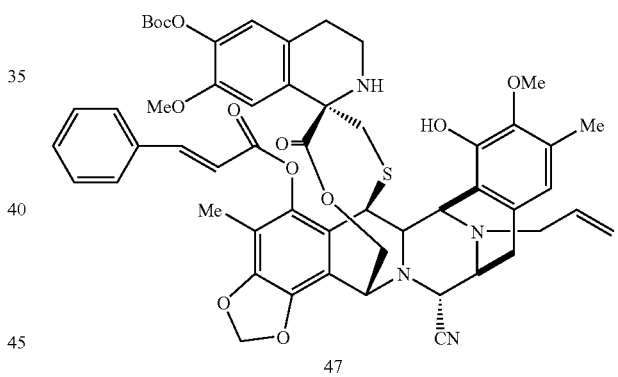

47

To a solution of compound 46 (108 mg, 0.13 mmol) in $CH_2Cl_2$ (4 mL, 0.032M) under Argon atmosphere at 23° C. were added pyridine (0.02 mL, 0.26 mmol) and the cinnamoyl chloride (21 mg, 0.13 mmol). The reaction mixture was left for 2 hours at 23° C. and quenched after this time with an aqueous saturated solution of $NaHCO_3$, the aqueous phase extracted with $CH_2Cl_2$ and the organic layers dried over $Na_2SO_4$. Flash chromatography (hexane/ethyl acetate 2:1) gives pure compound 47 (53 mg, 43%)

$R_f$: 0.67 (hexane/ethyl acete 1:1)

$^1$H-RMN (300 MHz, $CDCl_3$): δ 7.88 (d, 1H); 7.59-7.57 (m, 2H); 7.44-7.39 (m, 3H); 6.71 (s, 1H); 6.589 (d, 1H); 6.58 (s, 1H); 6.54 (s, 1H); 6.06 (d, 1H); 5.97 (d, 1H); 5.92-5.79 (m, 1H); 5.46 (s, 1H); 5.13-5.05 (m, 2H); 5.01 (d, 1H); 4.57 (s, 1H); 4.37-4.34 (m, 2H); 4.20 (s, 1H); 4.11 (d, 1H); 3.61 (s, 3H); 3.55 (d, 2H); 3.45 (s, 3H); 3.15-3.09 (m, 1H); 2.96-2.62 (m, 4H); 2.51-2.31 (m, 3H); 2.25 (s, 3H); 2.09 (s, 3H); 1.51 (s, 9H)

ESI-MS m/z: Calcd. for $C_{55}H_{56}N_4O_{12}S$: 984.4. Found (M+H)$^+$: 986.0.

ESI-MS m/z: Calcd. for $C_{53}H_{64}N_4O_{12}S$: 980.4. Found (M+H)$^+$: 982.0.

Example 53

Example 54

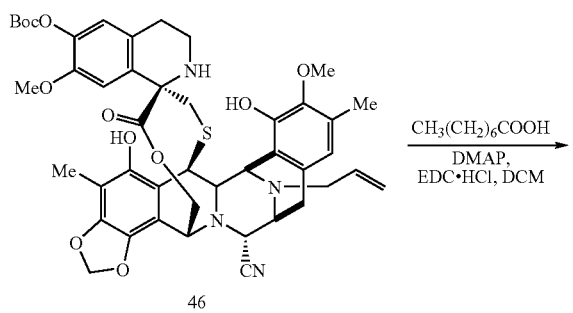

46

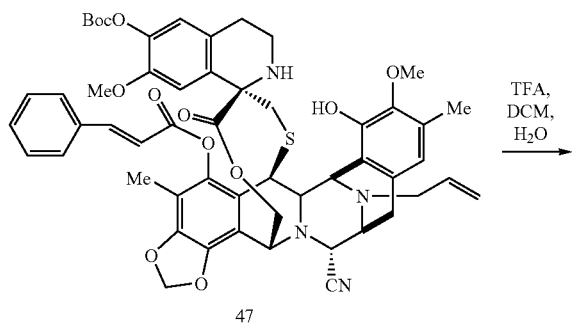

47

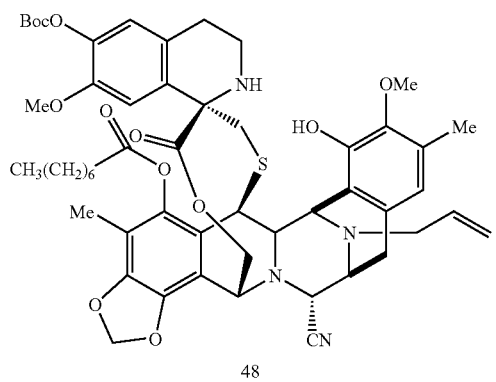

48

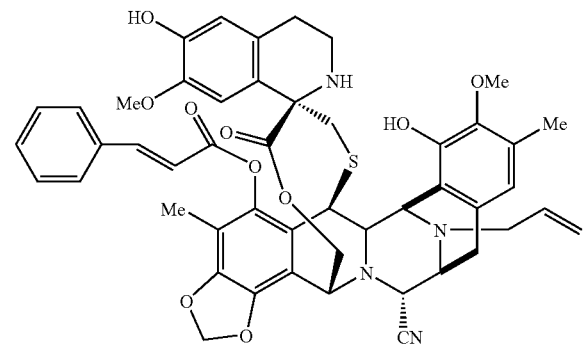

49

To a solution of compound 46 (108 mg, 0.13 mmol) in $CH_2Cl_2$ (4 mL, 0.032M) under Argon atmosphere were added octanoic acid (0.02 mL, 0.13 mmol), DMAP (31 mg, 0.26 mmol) and EDC.HCl (48 mg, 0.26 mmol). The reaction was stirred at 23° C. for 2 h. After this time the reaction mixture was diluted with $CH_2Cl_2$, washed with brine and the organic layer dried over $Na_2SO_4$. Flash chromatography (hexane/ethyl acetate 2:1) gives pure compound 48 (86 mg, 69%).

$R_f$: 0.85 (hexane/ethyl acete 1:1)

$^1$H-RMN (300 MHz, CDCl$_3$): δ 6.68 (s, 1H); 6.58 (s, 1H); 6.56 (s, 1H); 6.03 (d, 1H); 5.95 (d, 1H); 5.93-5.79 (m, 1H); 5.65 (s, 1H); 5.13-5.07 (m, 2H); 5.00 (d, 1H); 4.53 (d, 1H); 4.36-4.32 (m, 2H); 4.17 (d, 1H); 4.09 (dd, 1H); 3.76 (s, 3H); 3.58 (s, 3H); 3.57-3.50 (m, 2H); 3.14-3.06 (m, 1H); 2.97-2.75 (m, 4H); 2.68-2.45 (m, 3H); 2.35-2.14 (m, 2H); 2.31 (s, 3H); 2.01 (s, 3H); 1.75-1.71 (m, 2H); 1.50 (s, 9H); 1.36-1.24 (m, 10H); 0.89 (t, 3H).

A solution of compound 47 (38 mg, 0.03 mmol) in $CH_2Cl_2$/$H_2O$/TFA 2:1:3.3 (3.1 mL, 0.013M) was stirred at 23° C. for 64 h. The reaction mixture was neutralised with an aqueous saturated solution of NaHCO$_3$, extracted with $CH_2Cl_2$ and the organic layers dried over $Na_2SO_4$. Flash chromatography (hexane/ethyl acetate 3:2) gives pure compound 49 (34 mg, 99%).

$R_f$: 0.56 (hexane/ethyl acete 1:1)

$^1$H-RMN (300 MHz, CDCl$_3$): δ 7.86 (d, 1H); 7.58-7.54 (m, 2H); 7.46-7.44 (m, 3H); 6.57 (d, 1H); 6.55 (s, 1H); 6.49 (s, 1H); 6.45 (s, 1H); 6.07 (d, 1H); 5.99 (d, 1H); 5.90-5.79 (m, 1H); 5.42 (s, 1H); 5.13-5.04 (m, 2H); 5.03 (d, 1H); 4.60 (s, 1H); 4.37-4.34 (m, 2H); 4.23-4.20 (m, 2H); 4.13 (d, 1H); 3.64 (s, 3H); 3.55 (d, 2H); 3.44 (s, 3H); 3.15-3.06 (m, 1H); 2.97-2.77 (m, 4H); 2.64-2.34 (m, 4H); 2.24 (s, 3H); 2.09 (s, 3H).

ESI-MS m/z: Calcd. for $C_{49}H_{48}N_4O_{10}S$: 884.3. Found (M+H)$^+$: 885.0.

Example 55

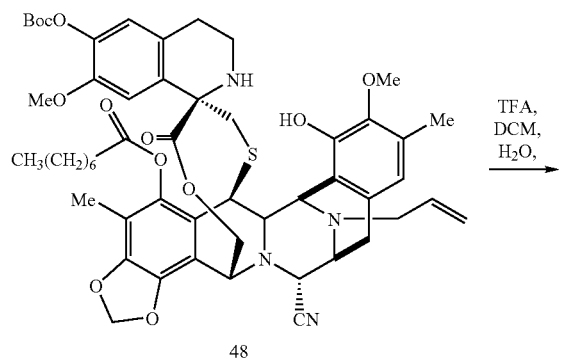

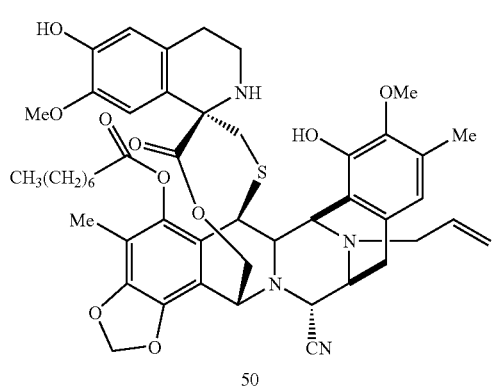

A solution of compound 48 (65 mg, 0.06 mmol) in CH$_2$Cl$_2$/H$_2$O/TFA 2:1:3.3 (5.3 mL, 0.013M) was stirred at 23° C. for 64 h. The reaction mixture was neutralised with an aqueous saturated solution of NaHCO$_3$, extracted with CH$_2$Cl$_2$ and the organic layer dried over Na$_2$SO$_4$. Flash chromatography (hexane/ethyl acetate 3:2) gives pure compound 50 (57 mg, 99%).

R$_f$: 0.64 (hexane/ethyl acete 1:1)

$^1$H-RMN (300 MHz, CDCl$_3$): δ 6.59 (s, 1H); 6.47 (s, 1H); 6.43 (s, 1H); 6.04 (d, 1H); 5.96 (d, 1H); 5.91-5.80 (m, 1H); 5.64 (s, 1H); 5.14-5.07 (m, 2H); 5.00 (d, 1H); 4.55 (d, 1H); 4.36-4.33 (m, 2H); 4.20 (d, 1H); 4.11 (dd, 1H); 3.77 (s, 3H); 3.62 (s, 3H); 3.58-3.50 (m, 2H); 3.12-3.07 (m, 1H); 2.98-2.76 (m, 4H); 2.63-2.43 (m, 3H); 2.36-2.10 (m, 2H); 2.31 (s, 3H); 2.02 (s, 3H); 1.73-1.65 (m, 2H); 1.34-1.20 (m, 10H); 0.89 (t, 3H).

ESI-MS m/z: Calcd. for C$_{48}$H$_{56}$N$_4$O$_{10}$S: 880.4. Found (M+H)$^+$: 882.0.

Synthesis of Compounds 51 and 52 Following the General Experimental Procedure for Deallylation Reactions

Example 56

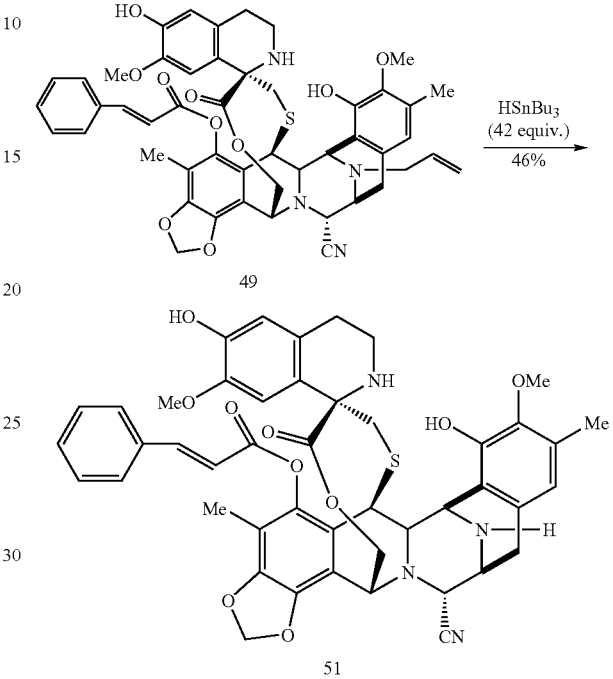

R$_f$: 0.26 (hexane/ethyl acetate 1:1)

$^1$H NMR (300 MHz, CDCl$_3$): 7.87 (d, 1H); 7.59-7.54 (m, 4H); 7.51-7.44 (m, 6H); 6.60-6.43 (m, 8H); 6.07 (d, 2H); 5.97 (d, 2H); 5.03 (d, 2H); 4.59 (s, 2H); 4.50 (d, 1H); 4.37-4.34 (m, 2H); 4.23-4.09 (m, 4H); 3.84 (d, 2H); 3.65 (s, 3H); 3.64 (s, 3H); 3.61 (s, 6H); 3.57-3.52 (m, 2H); 3.43-3.40 (m, 2H); 3.14-2.97 (m, 6H); 2.93-2.80 (m, 6H); 2.68-2.58 (m, 2H); 2.48-2.20 (m, 4H); 2.29 (s, 3H); 2.23 (s, 3H); 2.09 (s, 3H); 1.94 (s, 3H).

ESI-MS m/z: Calcd. for C$_{46}$H$_{44}$N$_4$O$_{10}$S: 844.3. Found (M+H)$^+$: 845.0.

Example 57

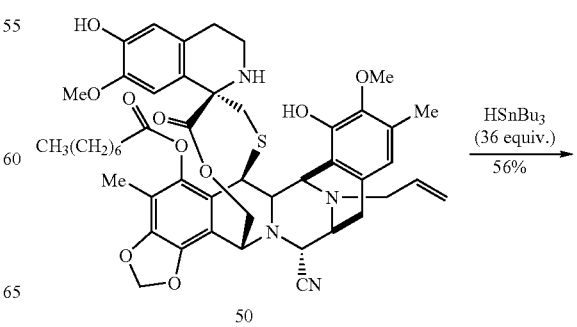

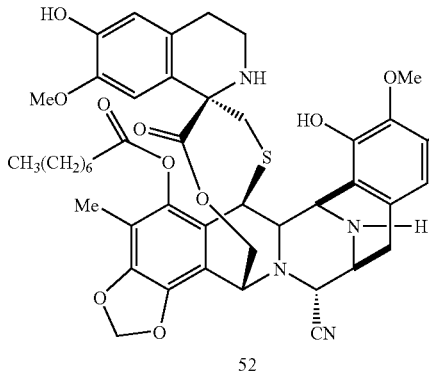

52

$R_f$: 0.36 (hexane/ethyl acete 1:1)

¹H-NMR (300 MHz, CDCl₃) δ: 6.61 (s, 1H); 6.47 (s, 1H); 6.43 (s, 1H); 6.05 (d, 1H); 5.97 (d, 1H); 5.72 (s, 1H); 5.02 (d, 1H); 4.55 (d, 1H); 4.50 (d, 1H); 4.33 (s, 1H); 4.19 (d, 1H); 4.11 (dd, 1H); 3.85 (d, 1H); 3.76 (s, 3H); 3.61 (s, 3H); 3.52 (d, 1H); 3.14-2.97 (m, 3H); 2.81-2.76 (m, 1H); 2.67-2.48 (m, 3H); 2.43-2.33 (m, 1H); 2.30 (s, 3H); 2.17-2.09 (m, 1H); 2.02 (s, 3H); 1.74-1.70 (m, 2H); 1.38-1.20 (m, 10H); 0.89 (t, 3H)

ESI-MS m/z: Calcd. for: $C_{45}H_{52}N_4O_{10}S$; 840.3. Found $(M+H)^+$; 841.1.

General Experimental Procedure for the Synthesis of Compounds 53 and 54. Interconversion of the Nitrile Group into the Hydroxyl Group.

To a solution of starting material in CH₃CN/H₂O 3:2 (0.015M) was added AgNO₃ (30 equiv). After 24 h at 23° C., the reaction was quenched with a mixture 1:1 of saturated aqueous solutions of brine and NaHCO₃, stirred for 10 min, diluted and extracted with CH₂Cl₂. The organic layer was dried over Na₂SO₄. Chromatography (mixtures of CH₂Cl₂: MeOH) gives pure compounds 53 and 54.

Example 58

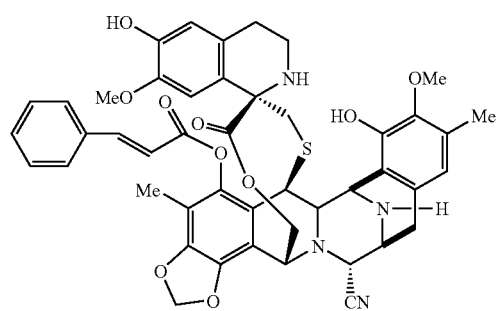

51

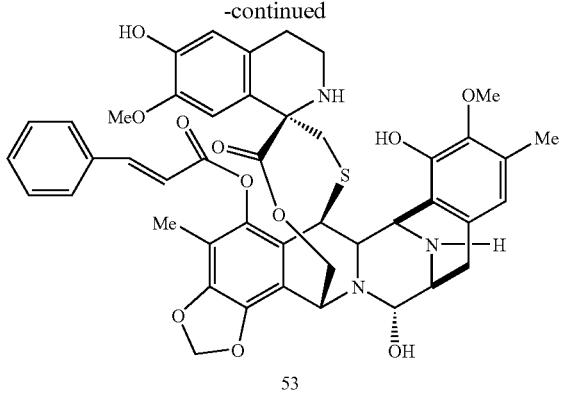

53

$R_f$: 0.46 (CH₂Cl₂/MeOH 8:0.5)

¹H-NMR (300 MHz, CDCl₃): δ 7.87 (d, 1H); 7.59-7.54 (m, 4H); 7.51-7.44 (m, 6H); 6.60-6.43 (m, 8H); 6.05 (d, 2H); 5.97 (d, 2H); 5.14 (d, 2H); 4.87 (s, 2H); 4.54-4.37 (m, 4H); 4.06-4.02 (m, 2H); 3.74-3.60 (m, 4H); 3.64 (s, 3H); 3.63 (s, 3H); 3.61 (s, 3H); 3.48 (s, 3H); 3.48-3.43 (m, 2H); 3.18-3.01 (m, 6H); 2.91-2.83 (m, 6H); 2.70-2.58 (m, 2H); 2.49-2.22 (m, 4H); 2.29 (s, 3H); 2.24 (s, 3H); 2.08 (s, 3H); 1.93 (s, 3H).

¹³C-RMN (75 MHz, CDCl₃): δ 145.7, 144.6, 144.5, 131.1, 129.4, 129.0, 128.9, 128.5, 127.1, 126.7, 125.0, 121.6, 117.3, 114.9, 114.2, 110.0, 101.9, 81.5, 68.4, 61.4, 60.6, 57.3, 56.2, 55.3, 51.4, 48.0, 42.4, 40.0, 38.9, 37.3, 36.0, 33.0, 32.1, 32.0, 31.2, 30.5, 29.6, 29.1, 27.6, 27.3, 23.9, 23.2, 22.9, 20.0, 16.0, 14.4, 11.2, 9.8

ESI-MS m/z: Calcd. for: $C_{45}H_{45}N_3O_{11}S$: 835.3. Found $(M+H)^+$: 836.0.

Example 59

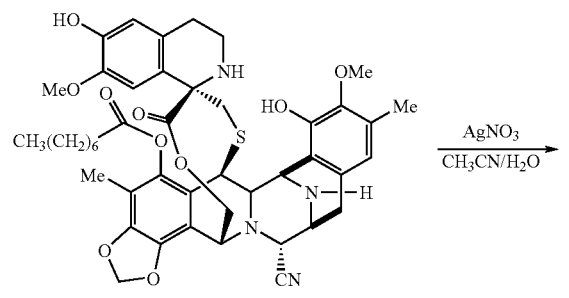

52

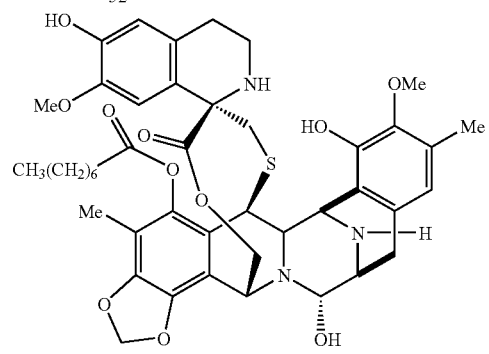

54

$R_f$: 0.31 ($CH_2Cl_2$/MeOH 8:0.5)

$^1$H-NMR (300 MHz, $CDCl_3$) δ: 6.60 (s, 1H); 6.45 (s, 1H); 6.42 (s, 1H); 6.02 (d, 1H); 5.95 (d, 1H); 5.12 (d, 1H); 4.83 (s, 1H); 4.52 (d, 1H); 4.45 (s, 1H); 4.40-4.36 (m, 1H); 4.06-3.99 (m, 2H); 3.76 (s, 1H); 3.63-3.60 (m, 2H); 3.61 (s, 3H); 3.46 (d, 1H); 3.15-3.00 (m, 3H); 2.90-2.77 (m, 2H); 2.63-2.49 (m, 3H); 2.43-2.35 (m, 1H); 2.30 (s, 3H); 2.18-2.06 (m, 1H); 2.00 (s, 3H); 1.74-1.70 (m, 2H); 1.34-1.20 (m, 10H); 0.89 (t, 3H).

ESI-MS m/z: Calcd. for: $C_{44}H_{53}N_3O_{11}S$: 831.3 Found $(M+H)^+$: 832.0.

General Experimental Procedure for Introduction of the Tryptamine Moiety, Pictect-Spengler Reaction; Synthesis of Compounds 55, 56, 57 and 58.

To a solution of compound 13 in acetic acid (0.5 $10^{-4}$M) under Argon atmosphere at 23° C. was added the tryptamine reagent. The reaction mixture was stirred for 24 h at 23° C. (for compounds 57 and 58 temperature reaction 60° C.) and then the acetic acid was evaporated. An aqueous saturated solution of $NaHCO_3$ was added and the mixture was extracted with $CH_2Cl_2$ and the organic layers were dried over $Na_2SO_4$. Flash chromatography (mixtures of hexane/ethyl acetate) gives pure compounds.

Example 60

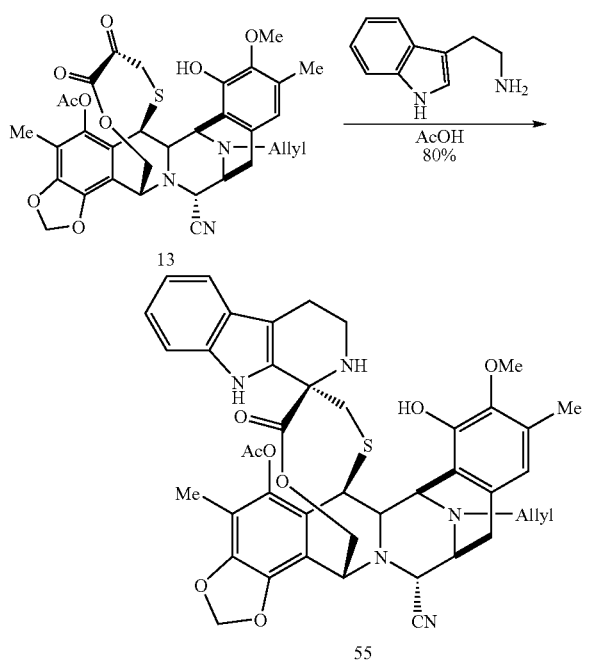

55

$R_f$: 0.45 (hexane/ethyl acete 1:1)

$^1$H-RMN (300 MHz, $CDCl_3$): δ 7.74 (s, 1H); 7.38 (d, 1H); 7.24 (d, 1H); 7.09 (t, 1H); 7.00 (t, 1H); 6.66 (s, 1H); 6.22 (d, 1H); 6.01 (d, 1H); 5.94-5.80 (m, 1H); 5.78 (s, 1H); 5.15-5.07 (m, 3H); 4.56 (s, 1H); 4.37 (d, 1H); 4.33 (s, 1H); 4.23 (d, 1H); 4.19 (dd, 1H); 3.80 (s, 3H); 3.55 (d, 1H); 3.44 (d, 1H); 3.17-2.80 (m, 6H); 2.71-2.52 (m, 3H); 2.37 (s, 3H); 2.25 (s, 3H); 2.06 (s, 3H).

ESI-MS m/z: Calcd. for $C_{43}H_{43}N_5O_8S$: 789.3. Found $(M+H)^+$: 790.0.

Example 61

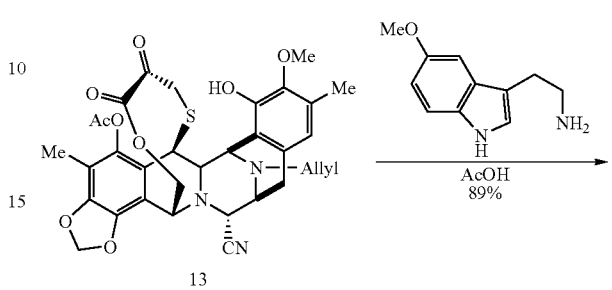

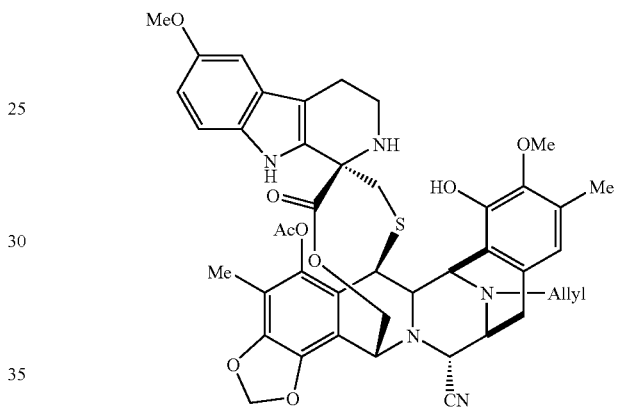

56

$R_f$: 0.18 (Hex/ethyl acetate 1:1)

$^1$H-RMN (300 MHz, $CDCl_3$): δ 7.65 (s, 1H); 7.11 (d, 1H); 6.81 (d, 1H); 6.73 (dd, 1H); 6.66 (s, 1H); 6.19 (d, 1H); 5.99 (d, 1H); 5.92-5.83 (m, 1H); 5.78 (s, 1H); 5.15-5.06 (m, 3H); 4.55 (s, 1H); 4.36 (d, 1H); 4.32 (s, 1H); 4.22 (d, 1H); 4.18 (dd, 1H); 3.81 (s, 3H); 3.79 (s, 3H); 3.54 (d, 1H); 3.44 (d, 1H); 3.16-3.03 (m, 2H); 2.96-2.78 (m, 4H); 2.65-2.50 (m, 3H); 2.38 (s, 3H); 2.25 (s, 3H); 2.05 (s, 3H).

ESI-MS m/z: Calcd. for $C_{44}H_{45}N_5O_9S$: 819.3. Found $(M+H)^+$: 820.5.

Example 62

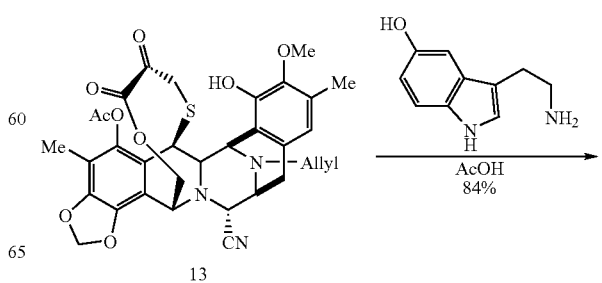

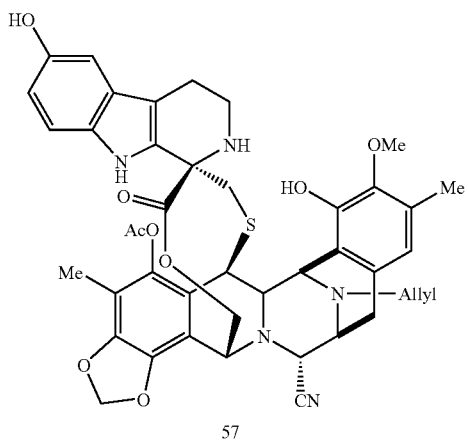

57

R$_f$: 0.10 (Hex/ethyl acetate 1:1)

$^1$H-RMN (300 MHz, CDCl$_3$): δ 7.72 (s, 1H); 6.88 (d, 1H); 6.65 (d, 1H); 6.60 (d, 1H); 6.52 (dd, 1H); 6.10 (s, 1H); 5.94 (s, 1H); 5.94-5.81 (m, 1H); (s, 1H); 5.14-5.03 (m, 3H); 4.53 (s, 1H); 4.35 (d, 1H); 4.29 (s, 1H); 4.20 (d, 1H); 4.17 (dd, 1H); 3.80 (s, 3H); 3.53 (d, 1H); 3.41 (d, 1H); 3.09-3.01 (m, 2H); 2.91-2.72 (m, 5H); 2.56-2.51 (m, 2H); 2.37 (s, 3H); 2.23 (s, 3H); 2.03 (s, 3H).

ESI-MS m/z: Calcd. for C$_{43}$H$_{43}$N$_5$O$_9$S: 805.3. Found (M+H)$^+$: 806.5.

Example 63

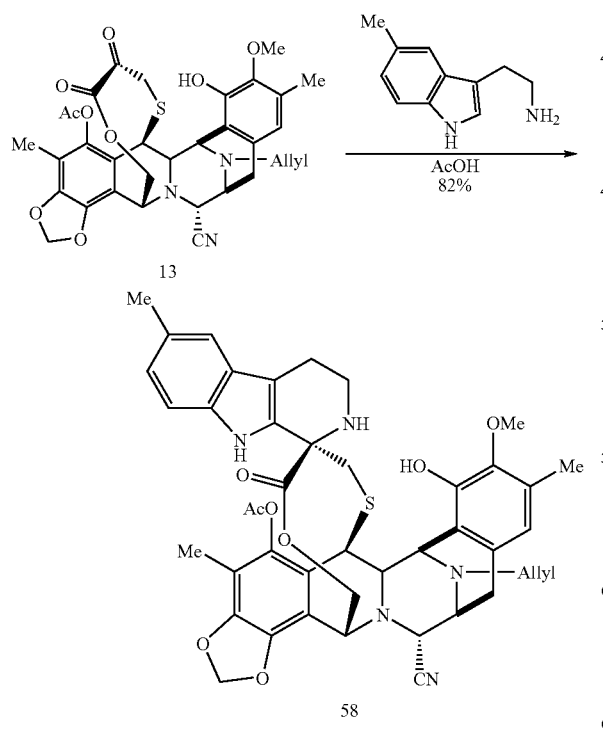

R$_f$: 0.48 (Hex/ethyl acetate 1:1)

$^1$H-RMN (300 MHz, CDCl$_3$): δ 7.66 (s, 1H); 7.14 (S, 1H); 7.13 (d, 1H); 6.91 (d, 1H); 6.66 (S, 1H); 6.21 (s, 1H); 6.00 (s, 1H); 5.92-5.81 (m, 1H); 5.80 (s, 1H); 5.15-5.06 (m, 3H); 4.55 (s, 1H); 4.37 (d, 1H); 4.32 (s, 1H); 4.21 (d, 1H); 4.16 (d, 1H); 3.81 (s, 3H); 3.54 (d, 1H); 3.43 (d, 1H); 3.17-3.03 (m, 2H); 2.96-2.77 (m, 5H); 2.68-2.42 (m, 4H); 2.37 (s, 3H); 2.25 (s, 3H); 2.06 (s, 3H).

ESI-MS m/z: Calcd. for C$_{44}$H$_{45}$N$_5$O$_8$S: 803.3. Found (M+H)$^+$: 804.4.

Synthesis of Compounds 59, 60, 61 and 62 Following the General Experimental Procedure for Deallylation Reactions

Example 64

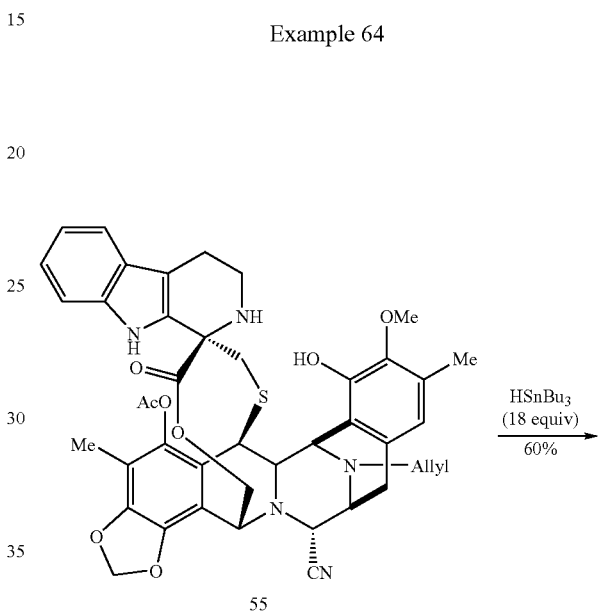

R$_f$: 0.21 (Hex/ethyl acetate 1:1)

$^1$H-RMN (300 MHz, CDCl$_3$): δ 7.74 (s, 1H); 7.38 (d, 1H); 7.24 (d, 1H); 7.09 (t, 1H); 7.00 (t, 1H); 6.68 (s, 1H); 6.23 (d, 1H); 6.02 (d, 1H); 5.10 (d, 1H); 4.55 (s, 1H); 4.51 (d, 1H); 4.33 (s, 1H); 4.23 (d, 1H); 4.19 (dd, 1H); 3.84 (d, 1H); 3.80 (s, 3H); 3.45 (d, 1H); 3.25-2.79 (m, 6H); 2.71-2.53 (m, 3H); 2.36 (s, 3H); 2.26 (s, 3H); 2.07 (s, 3H).

ESI-MS m/z: Calcd. for $C_{40}H_{39}N_5O_8S$: 749.3. Found (M+H)$^+$: 749.9.
ESI-MS m/z: Calcd. for $C_{41}H_{41}N_5O_9S$: 779.3. Found (M+H)$^+$: 780.0.
Example 65
Example 66
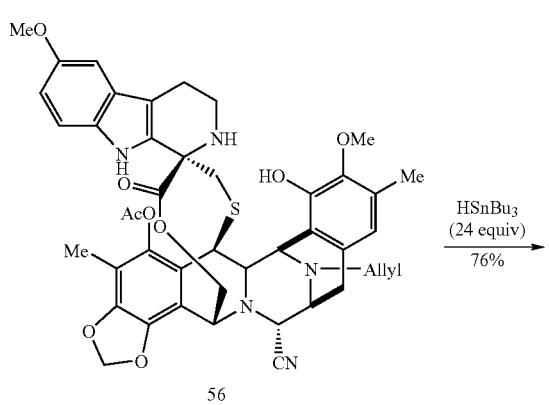
56
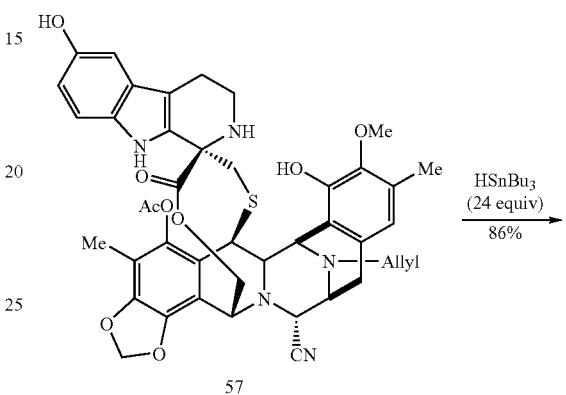
57
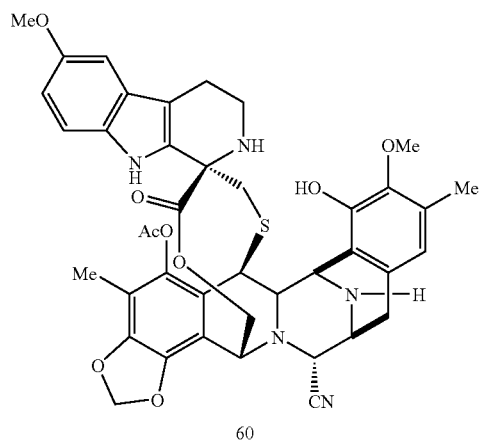
60
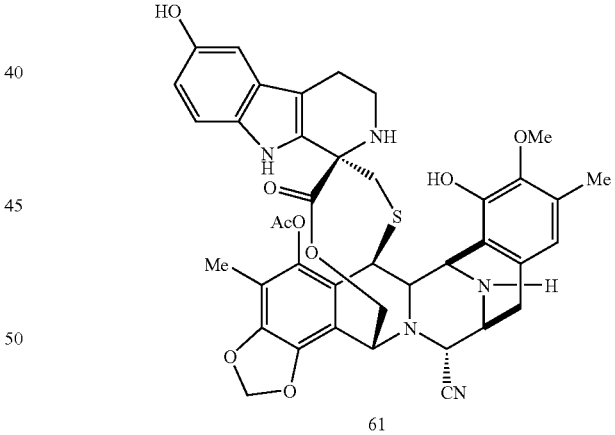
61
$R_f$: 0.15 (Hex/ethyl acetate 1:2)
$^1$H-RMN (300 MHz, CDCl$_3$): δ 7.65 (s, 1H); 7.12 (d, 1H); 6.81 (d, 1H); 6.73 (dd, 1H); 6.67 (s, 1H); 6.20 (s, 1H); 6.00 (s, 1H); 5.08 (d, 1H); 4.55 (s, 1H); 4.49 (d, 1H); 4.31 (s, 1H); 4.31-4.16 (m, 2H); 3.83 (d, 1H); 3.80 (s, 3H); 3.79 (s, 3H); 3.44 (d, 1H); 3.24-3.11 (m, 2H); 3.03-2.94 (m, 1H); 2.83-2.80 (m, 1H); 2.65-2.50 (m, 4H); 2.36 (s, 3H); 2.26 (s, 3H); 2.06 (s, 3H).
$R_f$: 0.10 (Hex/ethyl acetate 1:2)
$^1$H-RMN (300 MHz, CDCl$_3$): δ 7.67 (s, 1H); 6.93 (d, 1H); 6.66 (s, 2H); (dd, 1H); 6.15 (s, 1H); 5.98 (s, 1H); 5.06 (d, 1H); 4.53 (s, 1H); 4.48 (d, 1H); 4.29 (s, 1H); 4.19 (d, 1H); 3.82 (d, 1H); 3.78 (s, 3H); 3.42 (d, 1H); 3.22-2.96 (m, 5H); 2.76-2.73 (m, 2H); 2.57-2.43 (m, 3H); 2.35 (s, 3H); 2.25 (s, 3H); 2.04 (s, 3H).

ESI-MS m/z: Calcd. for $C_{40}H_{39}N_5O_9S$: 765.3. Found (M+H)$^+$: 766.4.

Example 67

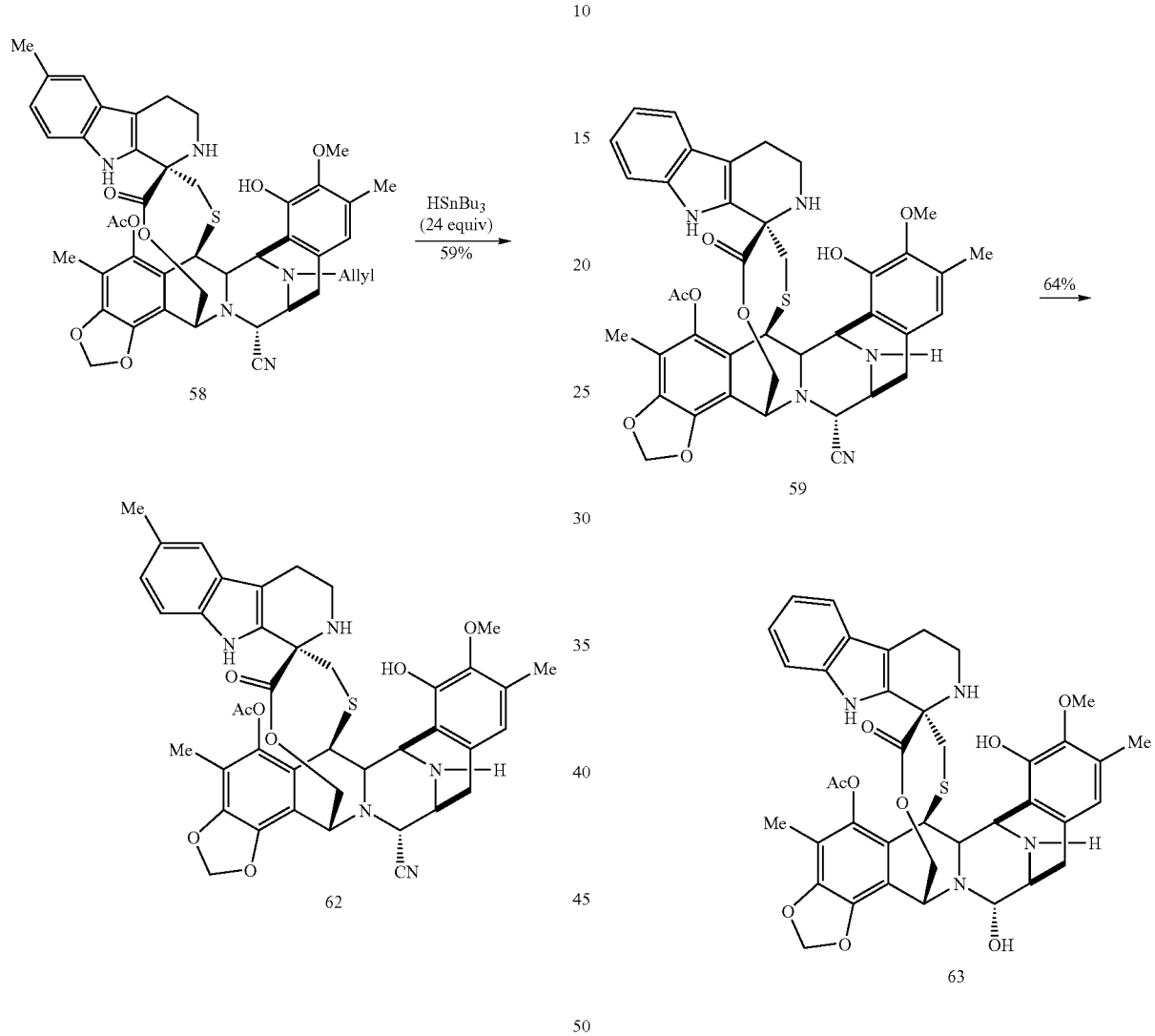

$R_f$: 0.35 (Hex/ethyl acetate 1:2)

$^1$H-RMN (300 MHz, CDCl$_3$): δ 7.63 (s, 1H); 7.26 (s, 1H); 7.15 (d, 1H); 6.91 (d, 1H); 6.68 (s, 1H); 6.22 (d, 1H); 6.02 (d, 1H); 5.09 (d, 1H); 4.55 (s, 1H); 4.50 (d, 1H); 4.32 (s, 1H); 4.22 (d, 1H); 4.18 (dd, 1H); 3.83 (d, 1H); 3.80 (s, 3H); 3.44 (d, 1H); 3.25-3.10 (m, 3H); 3.03-2.94 (m, 1H); 2.83-2.77 (m, 1H); 2.66-2.51 (m, 4H); 2.37 (s, 3H); 2.36 (s, 3H); 2.26 (s, 3H); 2.07 (s, 3H).

ESI-MS m/z: Calcd. for $C_{41}H_{41}N_5O_8S$: 763.3. Found (M+H)$^+$: 764.0.

General Experimental Procedure for the Synthesis of Compounds 63, 64, 65, 66 and 67. Interconversion of the Nitrile Group into the Hydroxyl Group.

To a solution of starting material in CH$_3$CN/H$_2$O 3:2 (0.015M) was added AgNO$_3$ (30 equiv). After 24 h at 23° C., the reaction was quenched with a mixture 1:1 of saturated aqueous solutions of brine and NaHCO$_3$, stirred for 10 min, diluted and extracted with CH$_2$Cl$_2$. The organic layer was dried over Na$_2$SO$_4$. Chromatography (mixtures of CH$_2$Cl$_2$: MeOH) gave pure compounds 63, 64, 65, 66 and 67.

Example 68

$R_f$: 0.13 (CH$_2$Cl$_2$/MeOH 16:1)

$^1$H-RMN (300 MHz, CDCl$_3$): δ 7.72 (s, 1H); 7.38 (d, 1H); 7.24 (d, 1H); (t, 1H); 7.00 (t, 1H); 6.68 (s, 1H); 6.21 (d, 1H); 6.00 (d, 1H); 5.21 (d, 1H); 4.85 (s, 1H); 4.53-4.38 (m, 3H); 4.13-4.08 (m, 2H); 3.80 (s, 3H); 3.64-3.57 (m, 3H); 3.17-3.08 (m, 2H); 2.91-2.82 (m, 2H); 2.69-2.54 (m, 3H); 2.36 (s, 3H); 2.25 (s, 3H); 2.08 (s, 3H).

$^{13}$C-RMN (75 MHz, CDCl$_3$): δ 171.7, 146.0, 145.7, 142.8, 141.4, 140.9, 135.7, 132.0, 131.1, 129.5, 127.1, 125.0, 124.6, 122.1, 121.8, 121.5, 119.4, 118.6, 115.7, 111.2, 110.4, 102.0, 81.7, 62.6, 62.1, 60.6, 57.2, 56.1, 51.4, 48.1, 42.6, 40.0, 39.4, 29.9, 27.4, 21.8, 20.8, 16.0, 9.9

ESI-MS m/z: Calcd. for $C_{39}H_{40}N_4O_9S$: 740.3. Found $(M-H_2O+H)^+$: 723.0.
ESI-MS m/z: Calcd. for $C_{40}H_{42}N_4O_{10}S$: 770.3. Found $(M-H_2O+H)^+$: 753.2.
Example 69
Example 70
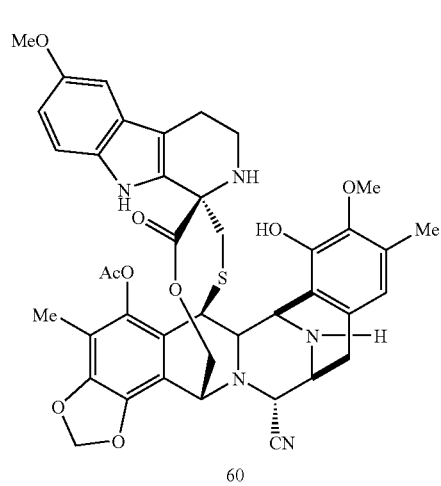
60
68% →
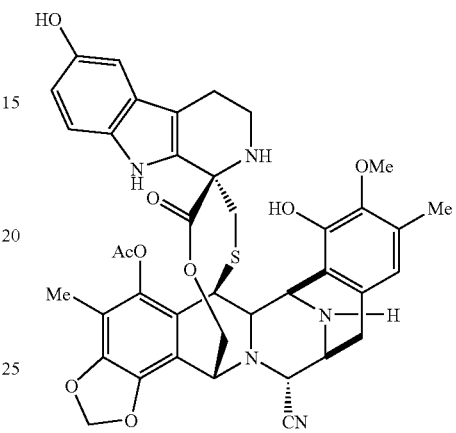
61
70% →
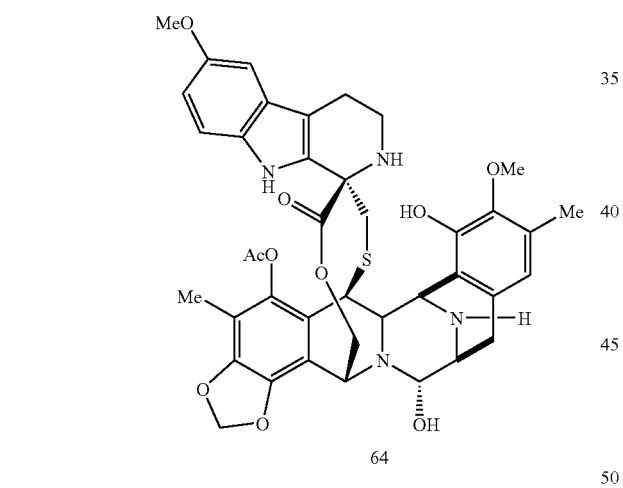
64
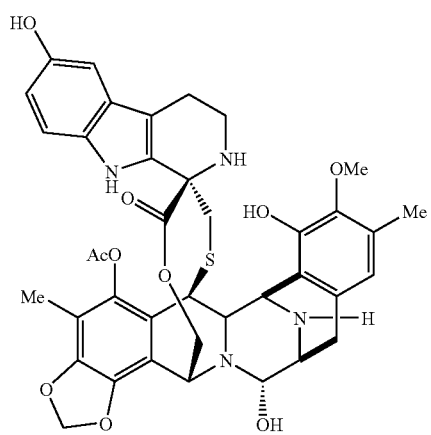
65
$R_f$: 0.36 ($CH_2Cl_2$/MeOH 8:1)
$^1$H-RMN (300 MHz, $CDCl_3$): δ 7.60 (s, 1H); 7.12 (d, 1H); 6.81 (d, 1H); 6.74 (dd, 1H); 6.68 (s, 1H); 6.19 (s, 1H); 6.00 (dd, 1H); 5.20 (d, 1H); 4.84 (s, 1H); 4.53-4.37 (m, 3H); 4.12-4.07 (m, 2H); 3.80 (s, 3H); 3.78 (s, 3H); 3.60-3.53 (m, 3H); 3.18-3.11 (m, 2H); 2.90-2.79 (m, 2H); 2.66-2.49 (m, 3H); 2.36 (s, 3H); 2.25 (s, 3H); 2.05 (s, 3H).
$^{13}$C-RMN (75 MHz, $CDCl_3$): δ 171.7; 168.9; 154.0; 146.1; 145.7; 142.9; 141.4; 140.9; 134.0; 131.9; 130.9; 129.6; 129.3; 127.4; 124.5; 121.8; 121.5; 115.7; 113.1; 111.9; 110.1; 102.1; 100.6; 81.7; 62.6; 62.0; 60.6; 57.1; 56.1; 51.4; 48.0; 42.6; 40.1; 39.4; 29.9; 27.4; 21.8; 20.8; 16.0; 9.9.
$R_f$: 0.15 ($CH_2Cl_2$/MeOH 8:1)
$^1$H-RMN (300 MHz, $CDCl_3$): δ 7.59 (s, 1H); 7.03 (d, 1H); 6.72 (d, 1H); 6.68 (t, 1H); 7.00 (t, 1H); 6.68 (s, 1H); 6.61 (dd, 1H); 6.18 (s, 1H); 5.97 (s, 1H); 5.20 (d, 1H); 4.84 (s, 1H); 4.52-4.36 (m, 3H); 4.12-4.09 (m, 2H); 3.80 (s, 3H); 3.60-3.48 (m, 3H); 3.16-3.10 (m, 3H); 2.91-2.77 (m, 2H); 2.57-2.43 (m, 3H); 2.36 (s, 3H); 2.26 (s, 3H); 2.05 (s, 3H).
$^{13}$C-RMN (75 MHz, $CDCl_3$): δ 171.7; 169.2; 149.6; 146.1; 142.8; 141.3; 141.0; 132.1; 132.0; 131.1; 131.0; 129.6; 129.0; 127.7; 124.6; 121.8; 121.5; 115.7; 113.1; 111.7; 109.8; 103.4; 102.1; 81.7; 68.3; 62.0; 60.6; 57.1; 56.1; 51.4; 48.0; 42.5; 40.0; 39.2; 32.1; 27.4; 20.8; 16.0; 9.9.

ESI-MS m/z: Calcd. for $C_{39}H_{40}N_4O_{10}S$: 756.3. Found $(M-H_2O+H)^+$: 739.0.

Example 71

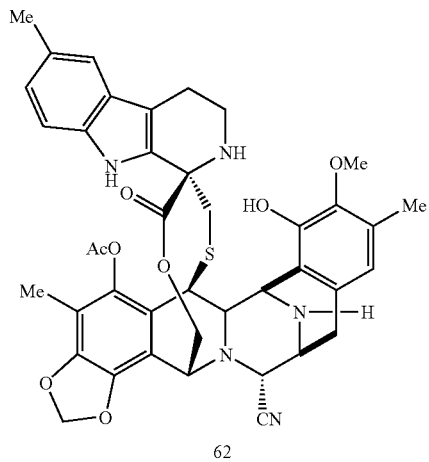
62

71%

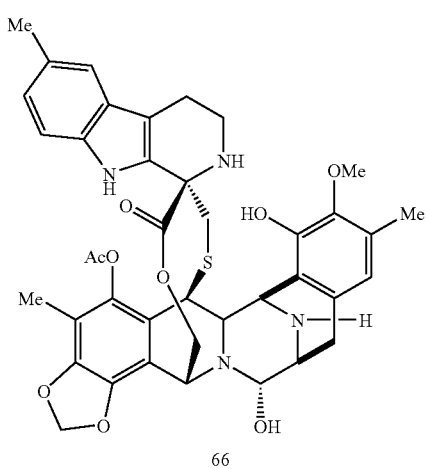
66

$R_f$: 0.47 (CH$_2$Cl$_2$/MeOH 8:1)

$^1$H-RMN (300 MHz, CDCl$_3$): δ 7.61 (s, 1H); 7.14 (s, 1H); 7.13 (d, 1H); (d, 1H); 6.66 (s, 1H); 6.20 (s, 1H); 6.01 (d, 1H); 5.19 (d, 1H); 4.85 (s, 1H); 4.54-4.40 (m, 3H); 4.12-4.08 (m, 2H); 3.80 (s, 3H); 3.62 (d, 2H); (m, 1H); 3.17-3.08 (m, 2H); 2.90-2.78 (m, 2H); 2.64-2.47 (m, 3H); 2.37 (s, 3H); 2.36 (s, 3H); 2.25 (s, 3H); 2.06 (s, 3H).

$^{13}$C-RMN (75 MHz, CDCl$_3$): δ 171.7; 168.9; 146.2; 145.7; 142.9; 141.4; 140.9; 134.1; 132.4; 132.3; 131.2; 129.6; 128.6; 127.3; 123.7; 121.7; 121.4; 118.4; 115.7; 113.1; 110.8; 109.9; 102.1; 81.6; 62.0; 60.6; 56.1; 51.4; 48.0; 42.5; 39.4; 32.1; 29.2; 28.1; 27.3; 21.8; 20.8; 16.0; 13.8; 9.9.

ESI-MS m/z: Calcd. for $C_{40}H_{42}N_4O_9S$: 754.3. Found $(M-H_2O+H)^+$: 737.3.

Example 72

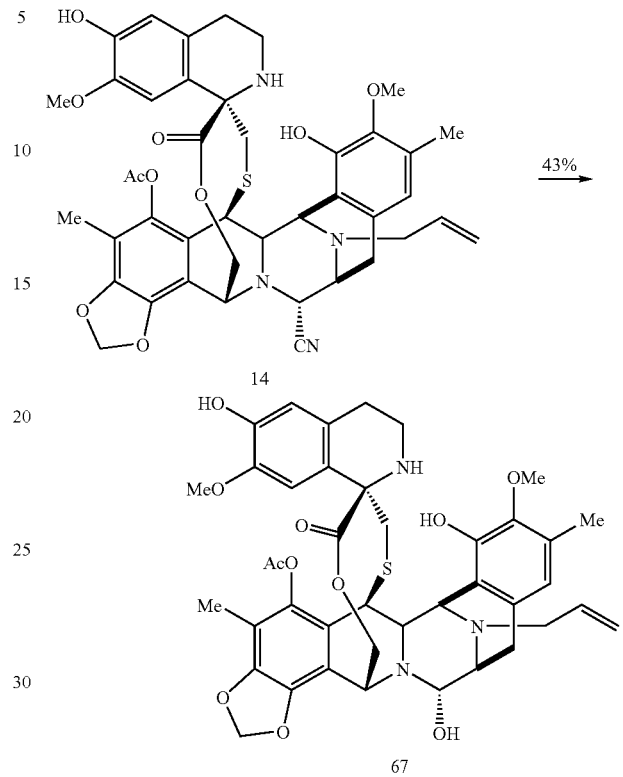
14

43%

67

$R_f$: 0.26 (CH$_2$Cl$_2$/MeOH 30:1)

$^1$H-RMN (300 MHz, CDCl$_3$): δ 6.62 (s, 1H), 6.47 (s, 1H), 6.45 (s, 1H), 6.03 (s, 1H), 5.95 (s, 1H), 5.78 (m, 1H), 5.67 (s, 1H), 5.38 (m, 1H), 5.14 (d, 2H), 5.05 (bs, 1H), 4.99 (bs, 1H), 4.83 (bs, 1H), 4.49 (bs, 1H), 4.28 (bs, 1H), 4.05 (d, 1H), 3.79 (s, 3H), 3.61 (s, 3H), 3.57 (m, 1H), 3.35 (m, 1H), 3.12 (m, 1H), 2.85 (m, 4H), 2.60 (m, 2H), 2.51 (m, 1H), 2.32 (s, 3H), 2.26 (s, 3H), 2.18 (m, 4H), 2.03 (s, 3H)

ESI-MS m/z: Calcd. for $C_{41}H_{45}N_3O_{11}S$: 787.8. Found $(M-H_2O+H)^+$: 770.4.

Example 73

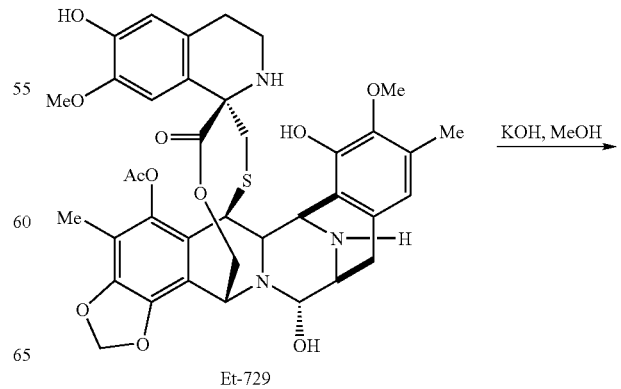
Et-729

KOH, MeOH

-continued

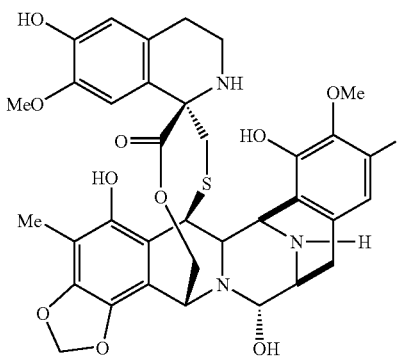

68

A solution of Et-729 (19.9 mg, 0.03 mmol) in a methanolic solution of KOH (5.21 ml, 0.95 mmol, 0.1817M) was stirred under argon at 23° C. After 1 h the reaction was diluted with CH$_2$Cl$_2$ and extracted. The organic layer was dried over Na$_2$SO$_4$. Chromatography gives pure compound.

R$_f$: 0.18 (CH$_2$Cl$_2$/MeOH 10:1)

$^1$H-RMN (300 MHz, CD$_3$OD): δ 6.61 (s, 1H); 6.39 (s, 1H); 6.33 (s, 1H); 6.03 (s, 1H); 5.88 (s, 1H); 5-45-5.44 (m, 1H); 5.13 (d, 1H); 4.81 (s, 1H); 4.71-6.67 (m, 2H); 4.30 (d, 1H); 4.08 (dd, 1H); 3.92 (d, 1H); 3.79 (d, 1H); 3.73 (s, 3H), 3.55 (s, 3H); 3.18-3.05 (m, 3H); 2.83-2.79 (m, 1H); 2-70-2.56 (m, 1H); 2.38 (d, 1H); 2.30 (s, 3H); 2.20 (d, 1H); 2.14 (s, 3H).

ESI-MS m/z: Calcd. for C$_{36}$H$_{39}$N$_3$O$_{10}$S: 705.2. Found (M−H$_2$O+H)$^+$: 688.4.

Example 74

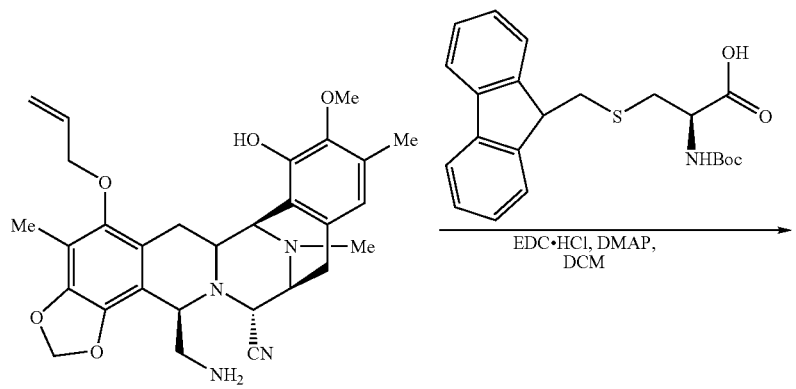

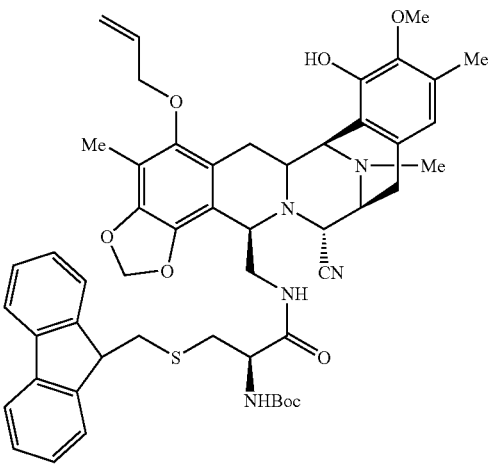

69

To a solution of intermediate 1 (1.17 g, 2.26 mmol) and cysteine derivative (0.9 g, 2.26 mmol) in anhydrous dichloromethane (45 mL, 0.05M) was added at 23° C. under Argon atmosphere EDC.HCl (0.87 g, 4.52 mmol) and DMAP (0.55 g, 4.52 mmol). The reaction mixture was left at 23° C. under Argon atmosphere for 1 hour. A saturated aqueous solution of sodium bicarbonate was added and the aqueous phase was extracted with dichloromethane, the combined organic layers were dried over sodium sulphate, filtered and the solvent was eliminated under reduced pressure. The crude was purified by flash column chromatography (eluent mixtures of dichloromethane/methanol in gradient from 100:0 to 80:1) to afford intermediate 69 (1.43 g, 70%) as a yellow solid.

$R_f$: 0.5 (dichloromethane/MeOH 60:1)

$^1$H-RMN (CDCl$_3$, 300 MHz) δ 7.63 (d, 2H), 7.47 (dd, 2H), 7.34 (m, 2H), 7.23 (m, 2H), 6.35 (s, 1H), 6.09 (d, 1H), 5.91 (m, 2H), 5.85 (d, 1H), 5.62 (m, 1H), 5.58 (s, 1H), 5.30 (dd, 1H), 5.20 (dd, 1H), 4.15 (d, 1H), 4.06-3.91 (m, 4H), 3.78 (dd, 1H), 3.69 (broad t, 1H), 3.49 (s, 3H), 3.44 (m, 2H), 3.30 (d, 1H), 3.18 (dd, 1H), 3.07 (m, 3H), 2.81 (m, 2H), 2.29-2.21 (m, 1H), 2.22 (s, 3H), 2.15 (s, 3H), 2.08 (s, 3H), 1.45 (s, 9H), 1.44 (m, 1H).

$^{13}$C-RMN (CDCl$_3$, 75 MHz) δ 169.95, 154.83, 148.77, 146.74, 145.06, 144.19, 142.48, 141.30, 141.22, 138.49, 134.24, 131.47, 128.76, 127.46, 127.33, 126.98, 126.76, 124.36, 124.09, 121.29, 121.08, 119.82, 119.62, 118.03, 116.76, 116.41, 112.89, 112.44, 101.03, 79.65, 73.46, 60.38, 58.76, 57.85, 56.21, 55.27, 51.76, 46.66, 41.49, 38.59, 34.48, 33.85, 31.55, 28.37, 26.41, 24.29, 22.61, 15.51, 14.08, 9.53.

ESI-MS m/z: Calcd. for C$_{51}$H$_{57}$N$_5$O$_8$S: 899.4. Found (M+H)$^+$: 900.4.

Example 75

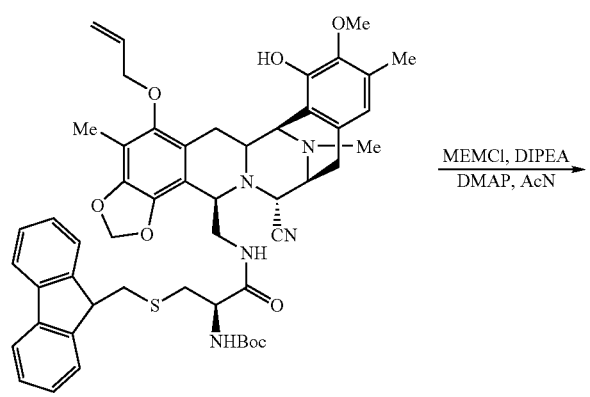

69

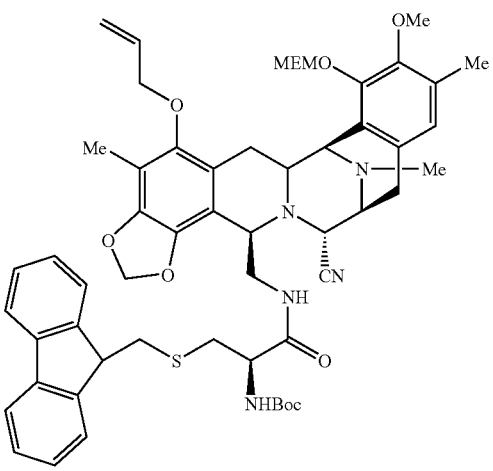

70

To a solution of intermediate 69 (1.37 g, 1.52 mmol) in anhydrous acetonitrile (8 mL, 0.19 M) was added at 0° C. under Argon atmosphere DIPEA (5.31 mL, 30.4 mmol), MEMCl (2.59 mL, 22.8 mmol) and DMAP (18.63 mg, 0.15 mmol). The reaction mixture was left at 23° C. under Argon atmosphere for 5 hours. A saturated aqueous solution of ammonium chloride was added, the aqueous phase was extracted with dichloromethane, the combined organic layers were dried over sodium sulphate, filtered and the solvent was eliminated under reduced pressure. The crude was purified by flash column chromatography (eluent ethyl acetate/hexane 2:3) to afford intermediate 70 (1.38 g, 92%) as a yellow solid. Other fraction with 130 mg was isolated after column as a mixture of starting material and compound 70 in a ratio 2:1.

$R_f$: 0.48 (ethyl acetate/hexane 2:3)

$^1$H-RMN (CDCl$_3$, 300 MHz): δ 7.62 (d, 2H), 7.50 (d, 1H), 7.40 (t, 1H), 7.33 (m, 2H), 7.21 (m, 2H), 6.55 (s, 1H), 6.08 (d, 1H), 5.97 (m, 1H), 5.95-5.86 (m, 1H), 5.84 (d, 1H), 5.66 (broad d, 1H), 5.31 (dd, 1H), 5.21 (dd, 1H), 5.14 (d, 1H), 5.04 (d, 1H), 4.16 (d, 1H), 4.06-3.92 (m, 3H), 3.87 (m, 2H), 3.73 (m, 4H), 3.54 (m, 2H), 3.41 (s, 3H), 3.34 (s, 3H), 3.30 (m, 2H), 3.20 (dd, 1H), 3.04 (m, 3H), 2.82 (m, 2H), 2.27 (m, 1H), 2.24 (s, 3H), 2.09 (s, 3H), 2.07 (s, 3H), 1.49 (s, 9H), 1.43 (m, 1H).

$^{13}$C-RMN (CDCl$_3$, 75 MHz): δ 170.19, 155.14, 148.96, 148.83, 148.31, 145.37, 145.23, 144.43, 141.61, 141.55, 138.70, 134.42, 131.13, 131.02, 127.76, 127.59, 127.23, 127.127.01, 125.58, 124.58, 124.27, 123.93, 121.42, 120.09, 119.88, 118.29, 116.82, 113.03, 112.68, 101.31, 98.34, 95.88, 92.55, 79.97, 73.50, 71.98, 71.88, 69.54, 67.68, 67.01, 59.73, 59.27, 58.94, 58.27, 56.86, 56.35, 55.52, 51.90, 46.95, 41.63, 38.37, 34.87, 33.67, 28.65, 26.70, 24.47, 15.83, 9.73.

ESI-MS m/z: Calcd. for $C_{55}H_{65}N_5O_{10}S$: 987.4. Found $(M+1)^+$: 988.6.

Example 76

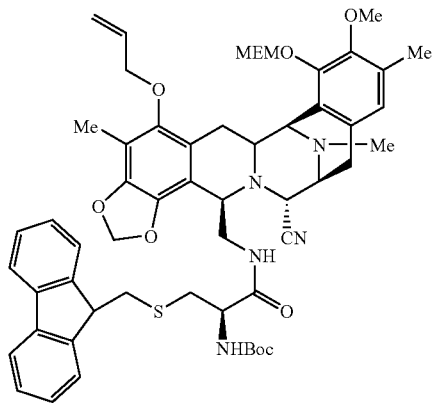

70

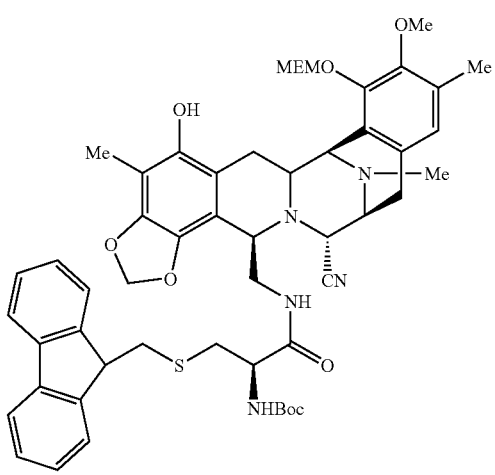

71

To a solution of intermediate 70 (1.38 g, 1.39 mmol) in anhydrous dichloromethane (36 mL, 0.04 M) was added at 23° C. under Argon atmosphere, $(PPh_3)_2PdCl_2$ (0.11 g, 8% in weight), acetic acid (0.39 mL, 6.98 mmol) and tributyltin hydride (1.31 mL, 4.88 mmol). The reaction mixture was left at 23° C. under Argon atmosphere for 30 minutes, diluted with hexane and poured onto column (eluent mixtures ethyl acetate/hexane in gradient from 0:100 to 3:2) to afford intermediate 71 (1.16 g, 87%) as a yellow solid.

$R_f$: 0.28 (ethyl acetate/hexane 1:1)

$^1$H-RMN (CDCl$_3$, 300 MHz): δ 7.69 (t, 2H), 7.54 (t, 2H), 7.39-7.23 (m 4H), 6.61 (s, 1H), 5.98 (m, 1H), 5.96 (s, 1H), 5.87 (s, 1H), 5.80 (s, 1H), 5.39 (t, 2H), 5.21 (d, 1H), 4.11 (m, 3H), 4.01 (m, 1H), 3.92 (m, 3H), 3.66 (s, 3H), 3.55 (m, 2H), 3.39 (s, 3H), 3.37 (m, 3H), 3.26-3.12 (m, 4H), 2.90 (d, 1H), 2.88 (m, 1H), 2.78 (d, 1H), 2.27 (s, 3H), 2.15 (s, 3H), 2.06 (s, 3H), 1.73 (dd, 1H), 1.39 (s, 9H).

ESI-MS m/z: Calcd. for $C_{52}H_{61}N_5O_{10}S$: 947.4. Found $(M+1)^+$: 948.8.

Example 77

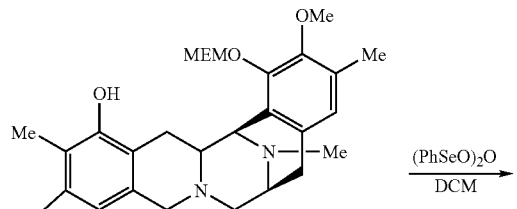

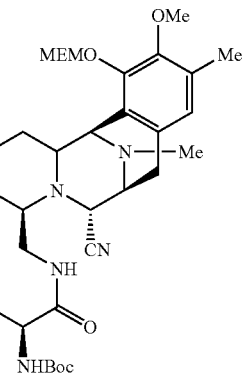

71

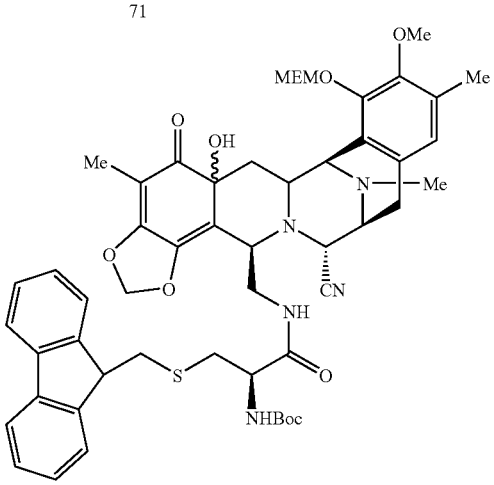

72

To a solution of compound 71 (39 mg, 0.041 mmol) in anhydrous CH$_2$Cl$_2$ (1.2 mL, 0.03M) was added at −10° C. under Argon atmosphere a solution of benceneseleninic anhydride (21.14 mg, 0.041 mmol) in anhydrous CH$_2$Cl$_2$ (0.6 mL). The reaction mixture was stirred at −10° C. under Argon atmosphere for 30 minutes. The reaction was diluted with CH$_2$Cl$_2$ and quenched with an aqueous saturated solution of sodium bicarbonate, the aqueous phase was extracted with CH$_2$Cl$_2$ and the organic layers were dried over sodium sulphate. The solvent was eliminated under reduced pressure and the crude of the reaction was purified by flash column chromatography to afford compound 72 (33 mg, 83%) as a pale yellow solid and a mixture of isomers in ratio 1.3:1 by $^1$H-RMN.

$R_f$: 0.21 and 0.11 (ethyl acetate/hexane 2:1)

$^1$H-RMN (CDCl$_3$, 300 MHz) δ 7.74 (d, 4H), 7.70-7.62 (m, 4H), 7.39 (t, 4H), 7.31 (t, 4H), 6.72 (m, 2H), 6.61 (s, 1H), 6.46 (s, 1H), 5.78 (s, 1H), 5.77 (s, 1H), 5.61 (s, 1H), 5.58 (s, 1H), 5.38 (broad d, 1H), 5.23 (d, 1H), 5.12 (d, 2H), 5.04 (d, 1H), 4.83 (s, 1H), 4.41 (s, 1H), 4.11 (m, 2H), 4.03 (m, 4H), 3.90-3.86 (m, 2H), 3.86 (s, 3H), 3.78-3.71 (m, 5H), 3.55 (m, 6H), 3.52 (s, 3H), 3.38 (s, 3H), 3.35 (s, 3H), 3.27 (m, 4H), 3.12 (m, 3H), 2.81 (m, 6H), 2.44 (m, 4H), 2.26 (s, 3H), 2.22 (s, 3H), 2.14 (s, 3H), 2.14-2.10 (m, 2H), 2.04 (s, 3H), 1.78 (s, 3H), 1.77 (s, 3H), 1.39 (s, 9H), 1.34 (s, 9H).

ESI-MS m/z: Calcd. for $C_{52}H_{61}N_5O_{11}S$: 963.4. Found $(M+1)^+$: 964.9.

Example 78

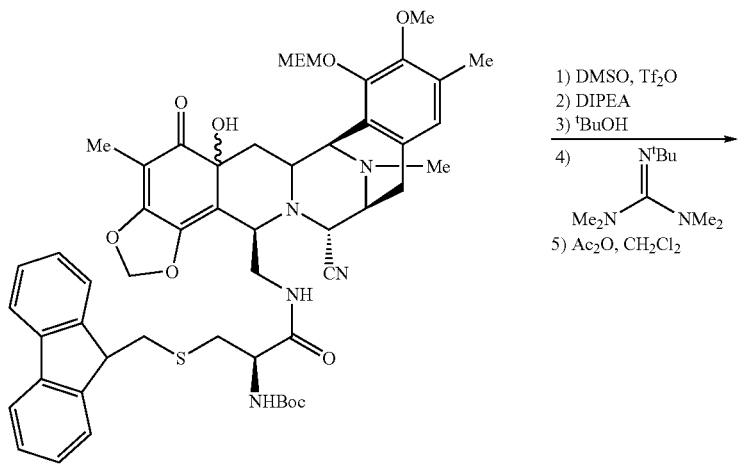

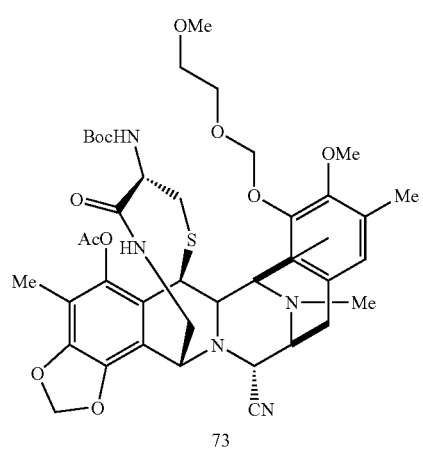

The reaction flask was flamed twice, purged vacuum/Argon several times and kept under Argon atmosphere for the reaction. To a solution of DMSO (220.8 µL) in anhydrous CH$_2$Cl$_2$ (20.7 mL) was dropwise added triflic anhydride (104.7 µL) at −78° C. The reaction mixture was stirred at −78° C. for 20 minutes, then a solution of 72 (300 mg, 0.31 mmol) in anhydrous CH$_2$Cl$_2$ (10.4 mL) at −78° C. was added via canula. During the addition the temperature was kept at −78° C. in both flasks. The reaction mixture was stirred at −40° C. for 35 minutes. After this time, $^i$Pr$_2$NEt (812.9 µL) was dropwise added and the reaction mixture was kept at 0° C. for 45 minutes. Then $^t$BuOH (293.4 µL) and guanidine (534.9 µL) were dropwise added and the reaction mixture was stirred at 23° C. for 40 minutes. After this time, acetic anhydride (441.1 µL) was dropwise added and the reaction mixture was kept at 23° C. for 1 hour more. Then the reaction mixture was diluted with CH$_2$Cl$_2$ and washed with an aqueous saturated solution of NH$_4$Cl, NaHCO$_3$ and NaCl. The combined organic layers were dried over Na$_2$SO$_4$, filtered and concentrated.

The residue was purified by a flash column chromatography (eluent mixtures of ethyl acetate/hexane in gradient from 1:4 to 1:1) to afford 73 (160 mg, 64%) as a pale yellow solid.

R$_f$: 0.13 (ethyl acetate/hexane 1:1)

$^1$H-RMN (300 MHz, CDCl$_3$): δ 6.76 (s, 1H), 6.06 (d, 1H), 5.98 (s, 1H), 5.32 (d, 1H), 5.17 (d, 1H), 4.81 (s, 1H), 4.48 (broad s, 1H), 4.36 (broad d, 1H), 4.18 (s, 1H), 3.95-3.82 (m, 3H), 3.75 (s, 3H), 3.72-3.68 (m, 1H), 3.59-3.52 (m, 4H), 3.37 (s, 3H), 3.36 (s, 3H), 2.96 (m, 2H), 2.56 (broad d, 1H), 2.29 (s, 3H), 2.28 (s, 3H), 2.19 (s, 3H), 1.98 (s, 3H), 1.69 (m, 1H), 1.42-1.37 (m, 1H), 1.38 (s, 9H).

ESI-MS m/z: Calcd. for C$_{40}$H$_{51}$N$_5$O$_{11}$S: 809.3. Found (M+1)$^+$: 810.2.

Example 79

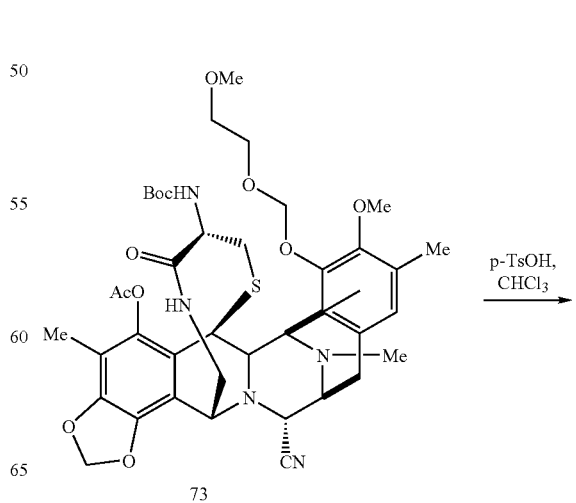

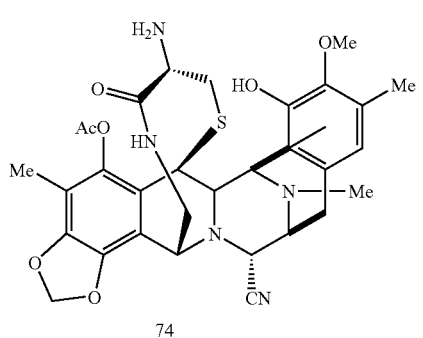

74

To a solution of intermediate 73 (169 mg, 0.21 mmol) in CHCl$_3$ (11 mL, 0.02 M) was added at 23° C. p-TsOH (243 mg, 1.25 mmol). The reaction mixture was left at 23° C. and under Argon atmosphere for 14 hours. The reaction was diluted with dichloromethane and a saturated solution of sodium bicarbonate was added. The aqueous phase was extracted with dichloromethane, the combined organic layers were dried over sodium sulphate, filtered and the solvent was eliminated under reduced pressure. The crude was purified by flash column chromatography (eluent mixtures of methylene chloride/methyl alcohol in gradient from 100:0 to 9:1) to afford intermediate 74 (123 mg, 95%) as a orange solid.

R$_f$: 0.17 (methylene chloride/methyl alcohol 95:5)

$^1$H-RMN (300 MHz, CDCl$_3$): δ 6.81 (broad s, 1H), 6.49 (s, 1H), 6.06 (d, 1H), 6.00 (d, 1H), 4.43 (broad s, 1H), 4.27 (d, 2H), 4.17 (s, 1H), 4.04 (d, 1H), 3.77 (s, 3H), 3.62 (d, 1H), 3.39 (d, 1H), 3.18 (m, 1H), 3.00 (dd, 2H), 2.65 (d, 1H), 2.57 (m, 1H), 2.33 (s, 3H), 2.27 (s, 3H), 2.17 (s, 3H), 1.97 (s, 3H), 1.80 (d, 1H).

ESI-MS m/z: Calcd. for C$_{31}$H$_{35}$N$_5$O$_7$S: 621.2. Found (M+1)$^+$: 622.2.

Example 80

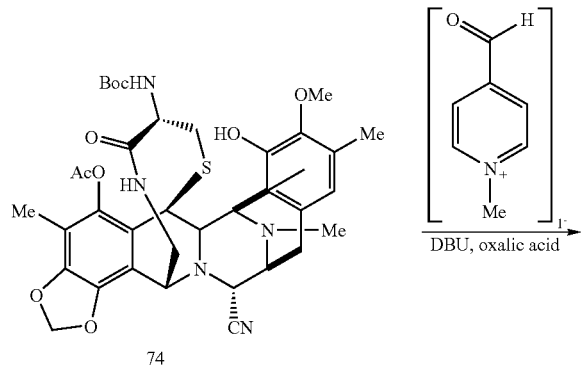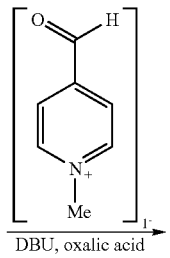

74

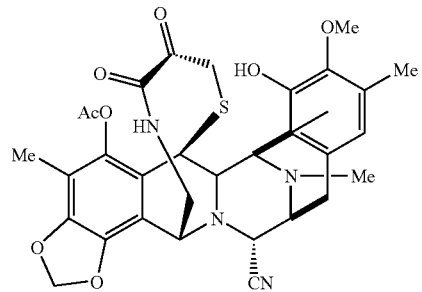

75

To a solution of the pyiridinium salt (285 mg, 1.14 mmol) in DMF (6 mL) was added at 23° C. a solution of intermediate 74 (71 mg, 0.114 mmol) in dichloromethane (6 mL, 0.01 M final concentration). The reaction mixture was left at 23° C. and under Argon atmosphere for 4 hours and 15 minutes, then DBU (0.17 mL, 1.14 mmol) was added and the solution was stirred at 23° C. and under Argon atmosphere for 15 minutes. After this time a saturated solution of oxalic acid (11 mL) was added, and the reaction mixture was left at 23° C. under Argon atmosphere for 30 minutes. The reaction mixture was cooled at 0° C., was diluted with Et$_2$O and a saturated solution of sodium bicarbonate was added until to reach pH=5. The aqueous phase was extracted with Et$_2$O (×4), further basified with more sodium bicarbonate and extracted with more Et$_2$O (×4). The combined organic layers were dried over sodium sulphate, filtered and the solvent was eliminated under reduced pressure. The crude was purified by flash column chromatography (eluent mixtures methylene chloride/methyl alcohol in gradient from 100:0 to 20:1) to afford intermediate 75 (38 mg, 55%) as a yellow solid.

R$_f$: 0.7 and 0.5 (methylene chloride/methyl alcohol 8:1)

$^1$H-RMN (300 MHz, CDCl$_3$): δ (major isomer) 6.49 (s, 1H), 6.06 (d, 1H), 6.01 (d, 1H), 5.78 (s, 1H), 4.55 (s, 1H), 4.37-4.23 (m, 3H), 4.05 (d, 1H), 3.80 (s, 3H), 3.65 (d, 1H), 3.40 (broad d, 1H), 3.06-3.00 (m, 2H), 2.66 (dd, 2H), 2.34 (s, 3H), 2.29 (s, 3H), 2.18 (s, 3H), 1.99 (s, 3H).

ESI-MS m/z: Calcd. for C$_{31}$H$_{32}$N$_4$O$_8$S: 620.2. Found (M+1)$^+$: 621.1.

Example 81

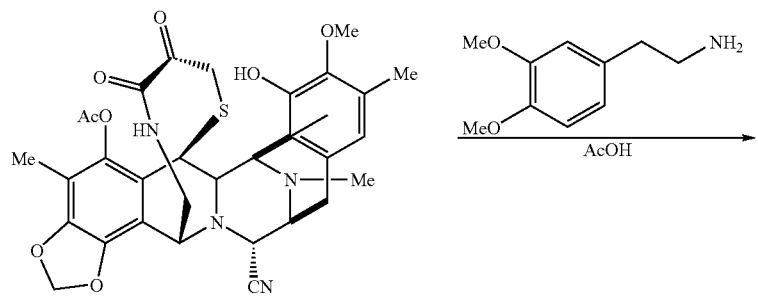

To a solution of intermediate 75 (23 mg, 0.037 mmol) in acetic acid (1.3 mL) was added after 1 hour dopamine derivative (25 mg, 0.10 mmol). The reaction mixture was left at 23° C. and under Argon atmosphere for 50 hours. The solvent of the reaction was eliminated under reduced pressure and the residue was diluted with $CH_2Cl_2$, washed with an aqueous saturated solution of sodium bicarbonate. The organic phase was dried over sodium sulphate, the solvent was eliminated under reduced pressure and the crude was purified by flash column chromatography (eluent mixtures of $CH_2Cl_2$/ethyl acetate in gradient from 100:0 to 1:2) to afford intermediate 76 (18 mg, 63%) as a pale yellow solid and a mixture of isomers.

$R_f$: 0.26 ($CH_2Cl_2$/ethyl acetate 1:3)

$^1$H-RMN (300 MHz, $CDCl_3$): δ 6.54 (s, 1H), 6.48 (d, 1H), 6.43 (s, 1H), 6.08 (d, 1H), 6.06 (d, 1H), 6.04 (d, 1H), 6.01 (d, 1H), 5.80 (s, 1H), 5.75 (s, 1H), 5.41 (m, 1H), 4.60-4.16 (m, 7H), 4.04 (m, 2H), 3.80 (s, 3H), 3.79 (s, 3H), 3.77 (s, 3H), 3.76 (s, 3H), 3.65 (d, 2H), 3.42 (m, 2H), 3.07-2.84 (m, 5H), 2.70 (d, 2H), 2.61-2.47 (m, 4H), 2.36 (s, 3H), 2.34 (s, 3H), 2.31 (s, 3H), 2.19 (s, 3H), 2.16 (s, 3H), 2.04 (s, 3H), 2.00 (s, 3H), 1.99 (s, 3H), 1.66 (m, 2H).

ESI-MS m/z: Calcd. for $C_{40}H_{43}N_5O_9S$: 769.3. Found (M+1)$^+$: 770.0.

Example 82

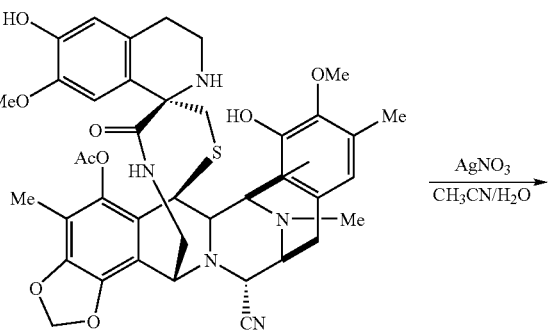

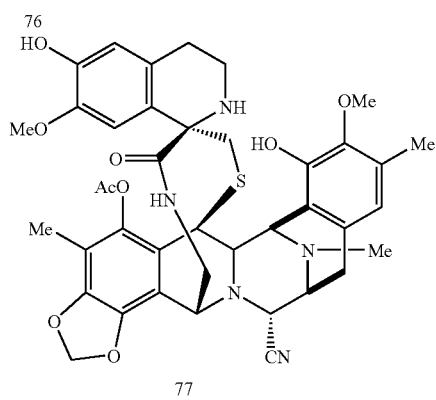

To a solution of intermediate 76 (7 mg, 0.009 mmol) in acetonitrile (0.6 mL) was added at 23° C. water (0.4 mL, 0.015 M, final concentration) and AgNO$_3$ (46 mg, 0.27 mmol). The reaction mixture was left under Argon atmosphere at 23° C. for 31 hours. The reaction was diluted with dichloromethane and a saturated solution of sodium bicarbonate and a saturated solution of sodium chloride was added. The aqueous phase was extracted with dichloromethane and the combined organic layers were dried over sodium sulphate, filtered and the solvent was eliminated under reduced pressure. The crude was purified by flash column chromatography (eluent dichloromethane/ethyl acetate in gradient from 1/9 to 100% in ethyl acetate) to afford the final product 77 (4 mg, 58%) as a pale yellow solid.

R$_f$: 0.17 (dichloromethane/ethyl acetate 1:9)

$^1$H-RMN (300 MHz, CDCl$_3$): δ 6.54 (s, 1H), 6.20 (m, 1H), 6.03 (d, 1H), 6.01 (d, 1H), 5.72 (s, 1H), 5.41 (broad s, 1H), 4.65 (broad s, 1H), 4.40-4.29 (m, 3H), 4.16 (d, 2H), 3.83 (m, 1H), 3.77 (s, 3H), 3.76 (s, 3H), 3.49 (s, 1H), 3.21 (m, 2H), 2.94 (m, 4H), 2.66 (d, 1H), 2.51 (d, 2H), 2.36 (m, 2H), 2.31 (s, 6H), 2.17 (s, 3H), 2.00 (s, 3H).

ESI-MS m/z: Calcd. for C$_{39}$H$_{44}$N$_4$O$_{10}$S: 760.3. Found (M−H$_2$O+1)$^+$: 743.0.

Bioassays for Antitumor Screening

The finality of these assays is to interrupt the growth of a "in vitro" tumor cell culture by means a continued exhibition of the cells to the sample to be testing.

| CELL LINES | | | | |
|---|---|---|---|---|
| Name | N° ATCC | Species | Tissue | Characteristics |
| P-388 | CCL-46 | mouse | ascites fluid | lymphoid neoplasm |
| K-562 | CCL-243 | human | leukemia | erythroleukemia (pleural effusion) |
| A-549 | CCL-185 | human | lung | lung carcinoma "NSCL" |
| SK-MEL-28 | HTB-72 | human | melanoma | malignant melanoma |
| HT-29 | HTB-38 | human | colon | colon adeno-carcinoma |
| LoVo | CCL-229 | human | colon | colon adeno-carcinoma |
| LoVo-Dox | | human | colon | colon adeno-carcinoma (MDR) |
| SW620 | CCL-228 | human | colon | colon adenocarcinoma (lymph node metastasis) |
| DU-145 | HTB-81 | human | prostate | prostate carcinoma, not androgen receptors |
| LNCaP | CRL-1740 | human | prostate | prostate adenocarcinoma, with androgen receptors |
| SK-BR-3 | HTB-30 | human | breast | breast adenocarcinoma, Her2/neu+, (pleural effusion) |
| MCF-7 | HTB-22 | human | breast | breast adenocarcinoma, (pleural effusion) |
| MDA-MB-231 | HTB-26 | human | breast | breast adenocarcinoma, Her2/neu+, (pleural effusion) |
| IGROV-1 | | human | ovary | ovary adenocarcinoma |
| IGROV-ET | | human | ovary | ovary adenocarcinoma, characterized as ET-743 resistant cells |
| SK-OV-3 | HTB-77 | human | ovary | ovary adenocarcinoma (malignant ascites) |
| OVCAR-3 | HTB-161 | human | ovary | ovary adenocarcinoma |
| HeLa | CCL-2 | human | cervix | cervix epitheloid carcinoma |
| HeLa-APL | CCL-3 | human | cervix | cervix epitheloid carcinoma, characterized as aplidine resistant cells |
| A-498 | HTB-44 | human | kidney | kidney carcinoma |
| PANC-1 | CRL-1469 | human | pancreas | pancreatic epitheloid carcinoma |
| HMEC1 | | human | endothelium | |

1°.—Inhibition of Cell Growth by Counting Cells.

This form of the assay employs 24 well multidishes of 16 mm diameter (Bergeron, 1984; Schroeder, 1981). The tumor cell lines employed are: P-388 (ATCC CCL 46), suspension culture of a lymphoid neoplasm from a DBA/2 mouse; A-549 (ATCC CCL 185), monolayer culture of a human lung carcinoma; HT-29 (ATCC HTB-38), monolayer culture of a human colon carcinoma; MEL-28 (ATCC HTB-72), monolayer culture of a human melanoma and DU-145 (ATCC HTB-81), monolayer culture of a human prostate carcinoma.

Cells were maintained, in logarithmic phase of growth in Eagle's Minimum Essential Medium, with Earle's Balanced Salts, with non-essential amino acids, with 2.0 mM L-Glutamine, without sodium bicarbonate (EMEM/neaa), supplemented with 10% Fetal Calf Serum (FCS), 10$^{-2}$ M. sodium bicarbonate and 0.1 U/l penicillin G+0.1 g/l streptomycin sulfate. For the experiments, cells are harvested from subconfluent cultures using trypsin and resuspended in fresh medium before plating.

P-388 cells were seeded into 16 mm diameter wells at 1×10$^4$ cells per well in 1 ml aliquots of EMEM 5% FCS containing different concentrations of the sample to be tested. A separate set of cultures without drug was seeded as control of growth, to ensure that cells remained in exponential phase of growth. All determinations are carrying out in duplicate. After three days of incubation at 37° C., 5% CO$_2$ in a 98% humid atmosphere, an approximately IC50 was determined by comparing the growth in wells with drug to the growth in wells control.

A-549, HT-29, MEL-28 and DU-145 cells were seeded into 16 mm diameter wells at 1×10$^4$ cells per well in 1 ml aliquots of EMEM 5% FCS containing different concentrations of the sample to be tested. A separate set of cultures without drug was seeded as control of growth, to ensure that cells remained in exponential phase of growth. All determinations are carrying out in duplicate. After three days of incubation at 37° C., 5% CO$_2$ in a 98% humid atmosphere cells were stained with 0.1% crystal violet. An approximately IC50 was determined by comparing the growth in wells with drug to the growth in wells control.

For quantifying the activity, after the incubation time, cells are trypsinized and counted in a Coulter Counter ZM. All counts (net cells per well), represent the average of duplicate wells. % G, percent of growth relative to cultures without drug. The results of these assays are used to generate dose-response curves from which more precise IC50 values are determined (sample concentration which produces 50% cell growth inhibition).

Obtained results may predict the usefulness of a certain drug as a potential cancer treatment. For this technique, compounds which show IC50 values smaller than 1 µg/ml are selected to continue with further studies. IC50's data allow to predict that not only if a drug could be cystostatic, but also if it could have a potential in terms of tumor reduction.

2°.—Inhibition of Cells Growth by Colorimetric Assay.

A calorimetric type of assay, using sulforhodamine B (SRB) reaction has been adapted for a quantitative measurement of cell growth and viability [following the technique described by Philip Skehan, et al. (1990), New colorimetric cytotoxicity assay for anticancer drug screening, *J. Natl. Cancer Inst.*, 82:1107-1112]

This form of the assay employs 96 well cell culture microplates of 9 mm diameter (Faircloth, 1988; Mosmann, 1983). Most of the cell lines are obtained from American Type Culture Collection (ATCC) derived from different human cancer types.

Cells are maintained in RPMI 1640 10% FBS, supplemented with 0.1 g/l penicillin and 0.1 g/l streptomycin sulfate and then incubated at 37° C., 5% $CO_2$ and 98% humidity. For the experiments, cells were harvested from subconfluent cultures using trypsin and resuspended in fresh medium before plating.

Cells are seeded in 96 well microtiter plates, at $5 \times 10^3$ cells per well in aliquots of 195 μl medium, and they are allowed to attach to the plate surface by growing in drug free medium for 18 hours. Afterward, samples are added in aliquots of 5 μl in a ranging from 10 to $10^{-8}$ μg/ml, dissolved in DMSO/EtOH/PBS (0.5:0.5:99). After 48 hours exposure, the antitumor effect are measured by the SRB methodology: cells are fixed by adding 50 μl of cold 50% (wt/vol) trichloroacetic acid (TCA) and incubating for 60 minutes at 4° C. Plates are washed with deionized water and dried. One hundred μl of SRB solution (0.4% wt/vol in 1% acetic acid) is added to each microtiter well and incubated for 10 minutes at room temperature. Unbound SRB is removed by washing with 1% acetic acid. Plates are air dried and bound stain is solubilized with Tris buffer. Optical densities are read on a automated spectrophotometric plate reader at a single wavelength of 490 nm.

The values for mean+/−SD of data from triplicate wells are calculated. Some parameters for cellular responses can be calculated: GI=growth inhibition, TGI=total growth inhibition (cytostatic effect) and LC=cell killing (cytotoxic effect).

Obtained results may predict the usefulness of a certain drug as a potential cancer treatment. For this technique, compounds which show GI50 values smaller than 10 μg/ml are selected to continue with further studies. GI50's data allow to predict that not only could a drug be cystostatic, but also it could have a potential in terms of tumor reduction.

Activity Data (Molar)

| $IC_{50}$ | 16 | 19 |
|---|---|---|
| p388 | 1.63E−08 | 7.53E−10 |
| a549 | 1.63E−08 | 7.53E−10 |
| ht29 | 1.63E−08 | 7.53E−10 |
| mel28 | 1.63E−08 | 7.53E−10 |
| du145 | | 7.53E−10 |

| | | 1 | 2 | 3 | 4 | 5 | 6 |
|---|---|---|---|---|---|---|---|
| A549 | $GI_{50}$ | 1.53E−06 | 6.33E−07 | 4.18E−06 | 2.36E−06 | 7.21E−07 | 6.65E−06 |
| | TGI | 6.07E−06 | 1.39E−06 | 1.30E−05 | 8.27E−06 | 2.40E−06 | 1.26E−05 |
| | $LC_{50}$ | 1.92E−05 | 9.11E−06 | 1.32E−05 | 1.18E−05 | 8.41E−06 | 1.26E−05 |
| HT29 | $GI_{50}$ | 1.11E−06 | 1.06E−06 | 4.01E−06 | 5.91E−07 | 4.81E−07 | 1.25E−05 |
| | TGI | 1.92E−05 | 1.42E−05 | 1.23E−05 | 1.18E−06 | 1.20E−06 | 1.26E−05 |
| | $LC_{50}$ | 1.92E−05 | 1.92E−05 | 1.32E−05 | 1.18E−05 | 6.01E−06 | 1.26E−05 |
| SW-620 | $GI_{50}$ | | | | | | |
| | TGI | | | | | | |
| | $LC_{50}$ | | | | | | |
| MEL-28 | $GI_{50}$ | 5.61E−07 | 5.98E−07 | | | | |
| | TGI | 1.15E−06 | 1.27E−06 | | | | |
| | $LC_{50}$ | 6.07E−06 | 5.31E−06 | | | | |
| OVCAR | $GI_{50}$ | | | | | | |
| | TGI | | | | | | |
| | $LC_{50}$ | | | | | | |
| A498 | $GI_{50}$ | | | | | | |
| | TGI | | | | | | |
| | $LC_{50}$ | | | | | | |
| DU145 | $GI_{50}$ | 5.67E−07 | 8.97E−07 | | | | |
| | TGI | 1.07E−06 | 3.13E−06 | | | | |
| | $LC_{50}$ | 1.92E−06 | 1.92E−05 | | | | |
| MCF | $GI_{50}$ | | | | | | |
| | TGI | | | | | | |
| | $LC_{50}$ | | | | | | |
| MB231 | $GI_{50}$ | | | | | | |
| | TGI | | | | | | |
| | $LC_{50}$ | | | | | | |
| H-MEC-1 | $GI_{50}$ | | | | | | |
| | TGI | | | | | | |
| | $LC_{50}$ | | | | | | |
| LNCAP | $GI_{50}$ | 4.34E−07 | 5.92E−07 | | | | |
| | TGI | 7.47E−07 | 1.11E−06 | | | | |
| | $LC_{50}$ | 1.29E−06 | 2.76E−06 | | | | |
| SK-OV3 | $GI_{50}$ | | | | | | |
| | TGI | | | | | | |
| | $LC_{50}$ | | | | | | |

-continued

| | | | |
|---|---|---|---|
| IGROV | $GI_{50}$ | 9.01E−07 | 9.26E−07 |
| | TGI | 2.59E−06 | 2.26E−06 |
| | $LC_{50}$ | 1.92E−05 | 1.82E−05 |
| IGROV-ET | $GI_{50}$ | 9.70E−07 | 1.06E−06 |
| | TGI | 1.92E−05 | 1.92E−05 |
| | $LC_{50}$ | 1.92E−05 | 1.92E−05 |
| SK-BR3 | $GI_{50}$ | 1.01E−06 | 7.78E−07 |
| | TGI | 3.96E−06 | 1.75E−06 |
| | $LC_{50}$ | 1.92E−05 | 1.92E−05 |
| K562 | $GI_{50}$ | 3.61E−07 | 5.16E−07 |
| | TGI | 7.99E−07 | 1.22E−06 |
| | $LC_{50}$ | 1.77E−06 | 4.79E−06 |
| PANC-1 | $GI_{50}$ | 8.87E−07 | 8.90E−07 |
| | TGI | 4.36E−06 | 3.26E−06 |
| | $LC_{50}$ | 1.92E−05 | 1.92E−05 |
| LOVO | $GI_{50}$ | 9.32E−07 | 5.33E−07 |
| | TGI | 4.00E−06 | 1.07E−06 |
| | $LC_{50}$ | 1.92E−05 | 1.92E−06 |
| LOVO-DOX | $GI_{50}$ | 6.17E−06 | 9.24E−07 |
| | TGI | 1.92E−05 | 1.92E−05 |
| | $LC_{50}$ | 1.92E−05 | 1.92E−05 |
| HELA | $GI_{50}$ | 1.08E−06 | 7.63E−07 |
| | TGI | 2.84E−06 | 1.45E−06 |
| | $LC_{50}$ | 1.81E−05 | 9.80E−06 |
| HELA-APL | $GI_{50}$ | 7.17E−07 | 4.79E−07 |
| | TGI | 1.63E−06 | 8.44E−07 |
| | $LC_{50}$ | 7.51E−06 | 1.49E−06 |

| | | 7 | 8 | 9 | 10 | 11 | 12 |
|---|---|---|---|---|---|---|---|
| A549 | $GI_{50}$ | 1.87E−06 | 1.18E−05 | 1.64E−05 | 1.01E−03 | 1.19E−05 | 3.38E−07 |
| | TGI | 3.51E−06 | 1.18E−05 | 1.64E−05 | 1.01E−03 | 1.19E−05 | 6.24E−07 |
| | $LC_{50}$ | 6.61E−06 | 1.18E−05 | 1.64E−05 | 1.01E−03 | 1.19E−05 | 1.16E−06 |
| HT29 | $GI_{50}$ | 9.18E−07 | 7.82E−06 | 1.64E−05 | 1.01E−03 | 1.19E−05 | 5.03E−07 |
| | TGI | 2.40E−06 | 1.18E−05 | 1.64E−05 | 1.01E−03 | 1.19E−05 | 1.27E−06 |
| | $LC_{50}$ | 5.46E−06 | 1.18E−05 | 1.64E−05 | 1.01E−03 | 1.19E−05 | 1.54E−05 |
| SW-620 | $GI_{50}$ | | | | | | |
| | TGI | | | | | | |
| | $LC_{50}$ | | | | | | |
| MEL-28 | $GI_{50}$ | | | | | 1.19E−05 | 3.50E−07 |
| | TGI | | | | | 1.19E−05 | 6.03E−07 |
| | $LC_{50}$ | | | | | 1.19E−05 | 1.03E−06 |
| OVCAR | $GI_{50}$ | | | | | | |
| | TGI | | | | | | |
| | $LC_{50}$ | | | | | | |
| A498 | $GI_{50}$ | | | | | | |
| | TGI | | | | | | |
| | $LC_{50}$ | | | | | | |
| DU145 | $GI_{50}$ | | | | | 1.19E−05 | 5.35E−07 |
| | TGI | | | | | 1.19E−05 | 1.02E−06 |
| | $LC_{50}$ | | | | | 1.19E−05 | 4.22E−06 |
| MCF | $GI_{50}$ | | | | | | |
| | TGI | | | | | | |
| | $LC_{50}$ | | | | | | |
| MB231 | $GI_{50}$ | | | | | | |
| | TGI | | | | | | |
| | $LC_{50}$ | | | | | | |
| H-MEC-1 | $GI_{50}$ | | | | 2.15E−06 | | |
| | TGI | | | | 4.06E−06 | | |
| | $LC_{50}$ | | | | 7.63E−06 | | |
| LNCAP | $GI_{50}$ | | | | | 5.84E−06 | 8.25E−08 |
| | TGI | | | | | 1.19E−05 | 2.51E−07 |
| | $LC_{50}$ | | | | | 1.19E−05 | 7.11E−07 |
| SK-OV3 | $GI_{50}$ | | | | | | |
| | TGI | | | | | | |
| | $LC_{50}$ | | | | | | |
| IGROV | $GI_{50}$ | | | | | 1.19E−05 | 2.25E−07 |
| | TGI | | | | | 1.19E−05 | 4.86E−07 |
| | $LC_{50}$ | | | | | 1.19E−05 | 1.05E−06 |
| IGROV-ET | $GI_{50}$ | | | | | 1.19E−05 | 6.35E−07 |
| | TGI | | | | | 1.19E−05 | 1.07E−06 |
| | $LC_{50}$ | | | | | 1.19E−05 | 3.82E−06 |
| SK-BR3 | $GI_{50}$ | | | | | 1.19E−05 | 2.56E−07 |
| | TGI | | | | | 1.19E−05 | 5.01E−07 |
| | $LC_{50}$ | | | | | 1.19E−05 | 9.79E−07 |
| K562 | $GI_{50}$ | | | | | 4.76E−06 | 1.10E−07 |
| | TGI | | | | | 1.19E−05 | 2.51E−06 |
| | $LC_{50}$ | | | | | 1.19E−05 | 1.54E−05 |

-continued

| | | | | | | | |
|---|---|---|---|---|---|---|---|
| PANC-1 | $GI_{50}$ | | | | | 1.19E−05 | 4.72E−07 |
| | TGI | | | | | 1.19E−05 | 9.53E−07 |
| | $LC_{50}$ | | | | | 1.19E−05 | 4.07E−06 |
| LOVO | $GI_{50}$ | | | | | 1.19E−05 | 3.99E−07 |
| | TGI | | | | | 1.19E−05 | 8.08E−07 |
| | $LC_{50}$ | | | | | 1.19E−05 | 3.21E−06 |
| LOVO-DOX | $GI_{50}$ | | | | | 1.19E−05 | 5.04E−07 |
| | TGI | | | | | 1.19E−05 | 9.71E−07 |
| | $LC_{50}$ | | | | | 1.19E−05 | 1.22E−05 |
| HELA | $GI_{50}$ | | | | | 1.19E−05 | 3.44E−07 |
| | TGI | | | | | 1.19E−05 | 6.21E−07 |
| | $LC_{50}$ | | | | | 1.19E−05 | 1.12E−06 |
| HELA-APL | $GI_{50}$ | | | | | 1.19E−05 | 2.44E−07 |
| | TGI | | | | | 1.19E−05 | 4.72E−07 |
| | $LC_{50}$ | | | | | 1.19E−05 | 9.14E−07 |

| | | 13 | 14 | 15 | 17 | 18 | 20 |
|---|---|---|---|---|---|---|---|
| A549 | $GI_{50}$ | 3.94E−06 | 2.23E−06 | 2.00E−09 | 2.29E−08 | 1.61E−07 | 2.52E−08 |
| | TGI | 7.36E−06 | 5.11E−06 | 7.35E−09 | 5.21E−08 | 6.43E−07 | 4.91E−08 |
| | $LC_{50}$ | 1.37E−05 | 1.17E−05 | 1.76E+07 | 1.19E−07 | 8.04E−06 | 9.55E−08 |
| HT29 | $GI_{50}$ | 6.02E−06 | 1.77E−06 | 4.84E−10 | 3.91E−08 | 8.04E−08 | 6.50E−09 |
| | TGI | 1.54E−05 | 6.39E−06 | 5.35E−09 | 8.60E−08 | 6.43E−07 | 5.36E−08 |
| | $LC_{50}$ | 1.54E−05 | 1.25E−05 | 3.13E−06 | 1.27E−05 | 8.04E−05 | 6.67E−06 |
| SW-620 | $GI_{50}$ | | | | | | |
| | TGI | | | | | | |
| | $LC_{50}$ | | | | | | |
| MEL-28 | $GI_{50}$ | | | | | | 2.45E−08 |
| | TGI | | | | | | 4.71E−08 |
| | $LC_{50}$ | | | | | | 9.11E−08 |
| OVCAR | $GI_{50}$ | | | | | | |
| | TGI | | | | | | |
| | $LC_{50}$ | | | | | | |
| A498 | $GI_{50}$ | | | | | | |
| | TGI | | | | | | |
| | $LC_{50}$ | | | | | | |
| DU145 | $GI_{50}$ | | | | | | 1.59E−08 |
| | TGI | | | | | | 3.99E−08 |
| | $LC_{50}$ | | | | | | 1.47E−06 |
| MCF | $GI_{50}$ | | | | | | |
| | TGI | | | | | | |
| | $LC_{50}$ | | | | | | |
| MB231 | $GI_{50}$ | | | | | | |
| | TGI | | | | | | |
| | $LC_{50}$ | | | | | | |
| H-MEC-1 | $GI_{50}$ | 4.74E−06 | 3.00E−06 | 5.56E−10 | | | |
| | TGI | 1.54E−05 | 1.25E−05 | 1.32E−08 | | | |
| | $LC_{50}$ | 1.54E−05 | 1.25E−05 | 4.44E−06 | | | |
| LNCAP | $GI_{50}$ | | | | | | 7.28E−09 |
| | TGI | | | | | | 2.28E−08 |
| | $LC_{50}$ | | | | | | 5.89E−08 |
| SK-OV3 | $GI_{50}$ | | | | | | |
| | TGI | | | | | | |
| | $LC_{50}$ | | | | | | |
| IGROV | $GI_{50}$ | | | | | | 2.59E−08 |
| | TGI | | | | | | 5.63E−08 |
| | $LC_{50}$ | | | | | | 1.22E−07 |
| IGROV-ET | $GI_{50}$ | | | | | | 2.77E−07 |
| | TGI | | | | | | 5.76E−07 |
| | $LC_{50}$ | | | | | | 1.20E−06 |
| SK-BR3 | $GI_{50}$ | | | | | | 5.22E−09 |
| | TGI | | | | | | 1.45E−08 |
| | $LC_{50}$ | | | | | | 9.83E−08 |
| K562 | $GI_{50}$ | | | | | | 1.52E−09 |
| | TGI | | | | | | 9.11E−09 |
| | $LC_{50}$ | | | | | | 4.04E−07 |
| PANC-1 | $GI_{50}$ | | | | | | 3.71E−08 |
| | TGI | | | | | | 9.46E−08 |
| | $LC_{50}$ | | | | | | 3.11E−06 |
| LOVO | $GI_{50}$ | | | | | | 2.87E−08 |
| | TGI | | | | | | 5.76E−08 |
| | $LC_{50}$ | | | | | | 1.15E−07 |
| LOVO-DOX | $GI_{50}$ | | | | | | 5.02E−07 |
| | TGI | | | | | | 1.83E−06 |
| | $LC_{50}$ | | | | | | 1.47E−05 |
| HELA | $GI_{50}$ | | | | | | 3.45E−09 |
| | TGI | | | | | | 7.09E−09 |
| | $LC_{50}$ | | | | | | 1.46E−08 |
| HELA-APL | $GI_{50}$ | | | | | | 3.89E−09 |

-continued

|   |   | | | | | 21 | 22 |
|---|---|---|---|---|---|---|---|
|   | TGI |   |   |   |   |   | 8.09E−09 |
|   | LC$_{50}$ |   |   |   |   |   | 2.28E−08 |

|   |   | 21 | 22 | 23 | 24 | 25 | 26 |
|---|---|---|---|---|---|---|---|
| A549 | GI$_{50}$ | 3.45E−06 | 2.67E−08 | 6.06E−08 | 2.19E−08 | 9.27E−07 | 1.16E−05 |
|   | TGI | 6.15E−06 | 5.90E−08 | 2.11E−07 | 4.62E−08 | 3.45E−06 | 1.16E−05 |
|   | LC$_{50}$ | 1.10E−05 | 1.31E−07 | 7.85E−07 | 9.74E−08 | 1.15E−05 | 1.16E−05 |
| HT29 | GI$_{50}$ | 4.06E−06 | 2.97E−08 | 5.12E−08 | 5.17E−09 | 1.64E−06 | 1.16E−05 |
|   | TGI | 8.86E−06 | 8.25E−08 | 2.15E−07 | 1.39E−08 | 8.57E−06 | 1.16E−05 |
|   | LC$_{50}$ | 1.57E−05 | 1.31E−05 | 1.29E−05 | 1.45E−05 | 1.39E−05 | 1.16E−05 |
| SW-620 | GI$_{50}$ |   |   |   |   |   |   |
|   | TGI |   |   |   |   |   |   |
|   | LC$_{50}$ |   |   |   |   |   |   |
| MEL-28 | GI$_{50}$ | 3.02E−06 | 3.02E−08 | 2.47E−07 | 2.01E−08 | 6.32E−07 | 1.16E−05 |
|   | TGI | 5.35E−06 | 5.55E−08 | 4.60E−07 | 4.27E−08 | 1.77E−06 | 1.16E−05 |
|   | LC$_{50}$ | 9.49E−06 | 1.02E−07 | 8.57E−07 | 9.09E−08 | 5.65E−06 | 1.16E−05 |
| OVCAR | GI$_{50}$ |   |   |   |   |   |   |
|   | TGI |   |   |   |   |   |   |
|   | LC$_{50}$ |   |   |   |   |   |   |
| A498 | GI$_{50}$ |   |   |   |   |   |   |
|   | TGI |   |   |   |   |   |   |
|   | LC$_{50}$ |   |   |   |   |   |   |
| DU145 | GI$_{50}$ | 3.40E−06 | 2.96E−08 | 5.85E−08 | 2.78E−08 | 8.61E−07 | 1.16E−05 |
|   | TGI | 6.07E−06 | 8.68E−08 | 1.43E−07 | 5.23E−08 | 2.20E−06 | 1.16E−05 |
|   | LC$_{50}$ | 1.09E−05 | 1.31E−06 | 4.45E−06 | 1.25E−07 | 6.57E−06 | 1.16E−05 |
| MCF | GI$_{50}$ |   |   |   |   |   |   |
|   | TGI |   |   |   |   |   |   |
|   | LC$_{50}$ |   |   |   |   |   |   |
| MB231 | GI$_{50}$ |   |   |   |   |   |   |
|   | TGI |   |   |   |   |   |   |
|   | LC$_{50}$ |   |   |   |   |   |   |
| H-MEC-1 | GI$_{50}$ |   |   |   |   |   |   |
|   | TGI |   |   |   |   |   |   |
|   | LC$_{50}$ |   |   |   |   |   |   |
| LNCAP | GI$_{50}$ | 2.58E−06 | 6.15E−09 | 1.53E−07 | 8.40E−09 | 3.23E−07 | 3.82E−06 |
|   | TGI | 4.72E−06 | 2.11E−08 | 3.18E−07 | 2.53E−08 | 7.57E−07 | 1.16E−05 |
|   | LC$_{50}$ | 8.64E−06 | 5.50E−08 | 6.57E−07 | 6.44E−08 | 2.55E−06 | 1.16E−05 |
| SK-OV3 | GI$_{50}$ |   |   |   |   |   |   |
|   | TGI |   |   |   |   |   |   |
|   | LC$_{50}$ |   |   |   |   |   |   |
| IGROV | GI$_{50}$ | 3.81E−06 | 1.91E−08 | 3.50E−07 | 8.21E−09 | 6.60E−07 | 6.84E−06 |
|   | TGI | 7.17E−06 | 4.46E−08 | 6.27E−07 | 3.18E−08 | 1.43E−06 | 1.16E−05 |
|   | LC$_{50}$ | 1.35E−05 | 1.04E−07 | 1.13E−06 | 1.10E−07 | 8.01E−06 | 1.16E−05 |
| IGROV-ET | GI$_{50}$ | 3.56E−06 | 5.22E−08 | 4.56E−07 | 2.95E−08 | 1.61E−06 | 1.16E−05 |
|   | TGI | 6.51E−06 | 1.04E−07 | 7.60E−07 | 6.20E−08 | 4.41E−06 | 1.16E−05 |
|   | LC$_{50}$ | 1.19E−05 | 1.31E−07 | 1.26E−06 | 1.30E−07 | 1.21E−05 | 1.16E−05 |
| SK-BR3 | GI$_{50}$ | 3.85E−06 | 5.77E−09 | 1.31E−08 | 2.48E−08 | 5.55E−07 | 4.23E−06 |
|   | TGI | 7.33E−06 | 2.23E−08 | 8.77E−08 | 6.38E−08 | 1.06E−06 | 9.20E−06 |
|   | LC$_{50}$ | 1.39E−05 | 1.20E−07 | 6.45E−07 | 2.69E−07 | 8.64E−06 | 1.16E−05 |
| K562 | GI$_{50}$ | 3.52E−06 | 5.92E−09 | 2.03E−08 | 4.07E−09 | 3.16E−07 | 2.30E−06 |
|   | TGI | 7.76E−04 | 4.24E−08 | 7.33E−08 | 1.71E−08 | 7.75E−07 | 4.94E−06 |
|   | LC$_{50}$ | 1.57E−05 | 8.40E−07 | 1.40E−06 | 9.38E−08 | 3.78E−06 | 1.06E−05 |
| PANC-1 | GI$_{50}$ | 3.21E−06 | 2.96E−08 | 5.09E−07 | 3.01E−08 | 1.37E−06 | 1.16E−05 |
|   | TGI | 6.62E−06 | 7.38E−08 | 1.26E−06 | 9.19E−08 | 3.90E−06 | 1.16E−05 |
|   | LC$_{50}$ | 1.37E−05 | 8.54E−07 | 1.29E−05 | 1.45E−05 | 1.10E−05 | 1.16E−05 |
| LOVO | GI$_{50}$ | 3.30E−06 | 2.03E−08 | 2.76E−07 | 2.61E−08 | 9.38E−07 | 1.16E−05 |
|   | TGI | 6.20E−06 | 4.11E−08 | 5.22E−07 | 8.21E−08 | 3.16E−06 | 1.16E−05 |
|   | LC$_{50}$ | 1.16E−05 | 9.65E−08 | 9.83E−07 | 1.45E−05 | 9.27E−06 | 1.16E−05 |
| LOVO-DOX | GI$_{50}$ | 4.88E−06 | 8.74E−08 | 6.61E−07 | 1.15E−07 | 9.04E−07 | 1.16E−05 |
|   | TGI | 1.24E−05 | 5.24E−07 | 7.46E−06 | 1.74E−06 | 3.77E−06 | 1.16E−05 |
|   | LC$_{50}$ | 1.57E−05 | 1.31E−05 | 1.29E−05 | 1.45E−05 | 1.39E−05 | 1.16E−05 |
| HELA | GI$_{50}$ | 3.40E−06 | 3.32E−08 | 3.82E−08 | 2.03E−08 | 1.50E−06 | 1.16E−05 |
|   | TGI | 5.90E−06 | 5.66E−08 | 6.60E−08 | 4.76E−08 | 3.48E−06 | 1.16E−05 |
|   | LC$_{50}$ | 1.02E−05 | 1.58E−07 | 1.14E−07 | 1.12E−07 | 8.11E−06 | 1.16E−05 |
| HELA-APL | GI$_{50}$ | 3.24E−06 | 2.11E−08 | 3.56E−08 | 2.03E−08 | 9.39E−07 | 1.16E−05 |
|   | TGI | 5.98E−06 | 4.44E−08 | 6.03E−08 | 4.65E−08 | 2.78E−06 | 1.16E−05 |
|   | LC$_{50}$ | 1.11E−05 | 9.35E−08 | 1.02E−07 | 1.07E−07 | 7.69E−06 | 1.16E−05 |

|   |   | 27 | 28 | 29 | 30 | 31 | 32 |
|---|---|---|---|---|---|---|---|
| A549 | GI$_{50}$ | 6.26E−08 | 5.25E−08 | 4.80E−06 | 3.47E−09 | 1.83E−09 | 2.38E−06 |
|   | TGI | 2.06E−07 | 1.63E−07 | 1.14E−05 | 1.05E−08 | 5.97E−09 | 4.29E−06 |
|   | LC$_{50}$ | 1.89E−06 | 2.27E−06 | 1.14E−05 | 8.90E−08 | 9.21E−08 | 7.70E−06 |
| HT29 | GI$_{50}$ | 7.56E−08 | 7.65E−08 | 1.14E−05 | 2.03E−09 | 1.97E−09 | 3.48E−06 |
|   | TGI | 1.42E−06 | 2.05E−06 | 1.14E−05 | 1.35E−08 | 1.62E−08 | 6.10E−06 |
|   | LC$_{50}$ | 1.42E−05 | 1.22E−05 | 1.14E−05 | 1.54E−05 | 3.68E−06 | 1.07E−05 |

-continued

|  |  |  |  |  |  |  |  |
|---|---|---|---|---|---|---|---|
| SW-620 | GI$_{50}$ |  |  |  |  |  |  |
|  | TGI |  |  |  |  |  |  |
|  | LC$_{50}$ |  |  |  |  |  |  |
| MEL-28 | GI$_{50}$ | 6.14E−08 | 5.68E−08 | 3.74E−06 | 1.09E−09 | 8.32E−10 | 2.41E−06 |
|  | TGI | 1.34E−07 | 1.35E−07 | 1.14E−05 | 3.66E−09 | 2.54E−09 | 4.14E−06 |
|  | LC$_{50}$ | 5.94E−07 | 6.92E−07 | 1.14E−05 | 1.07E−08 | 8.06E−09 | 7.13E−06 |
| OVCAR | GI$_{50}$ |  |  |  |  |  |  |
|  | TGI |  |  |  |  |  |  |
|  | LC$_{50}$ |  |  |  |  |  |  |
| A498 | GI$_{50}$ |  |  |  |  |  |  |
|  | TGI |  |  |  |  |  |  |
|  | LC$_{50}$ |  |  |  |  |  |  |
| DU145 | GI$_{50}$ | 7.55E−08 | 3.58E−08 | 2.30E−06 | 2.63E−09 | 4.44E−10 | 2.48E−06 |
|  | TGI | 8.48E−07 | 1.27E−06 | 7.93E−06 | 7.44E−09 | 9.51E−10 | 4.83E−06 |
|  | LC$_{50}$ | 1.42E−05 | 1.22E−05 | 1.14E−05 | 1.41E−05 | 2.23E−06 | 9.39E−06 |
| MCF | GI$_{50}$ |  |  |  |  |  |  |
|  | TGI |  |  |  |  |  |  |
|  | LC$_{50}$ |  |  |  |  |  |  |
| MB231 | GI$_{50}$ |  |  |  |  |  |  |
|  | TGI |  |  |  |  |  |  |
|  | LC$_{50}$ |  |  |  |  |  |  |
| H-MEC-1 | GI$_{50}$ |  |  |  |  |  |  |
|  | TGI |  |  |  |  |  |  |
|  | LC$_{50}$ |  |  |  |  |  |  |
| LNCAP | GI$_{50}$ | 2.61E−08 | 2.29E−08 | 8.78E−07 | 9.68E−08 | 4.19E−10 | 1.77E−06 |
|  | TGI | 6.46E−08 | 5.04E−08 | 6.07E−06 | 1.20E−07 | 1.63E−08 | 3.36E−06 |
|  | LC$_{50}$ | 2.61E−07 | 1.11E−07 | 1.14E−05 | 1.47E−07 | 9.07E−08 | 6.41E−06 |
| SK-OV3 | GI$_{50}$ |  |  |  |  |  |  |
|  | TGI |  |  |  |  |  |  |
|  | LC$_{50}$ |  |  |  |  |  |  |
| IGROV | GI$_{50}$ | 4.07E−08 | 4.90E−08 | 2.19E−06 | 6.95E−10 | 4.13E−10 | 1.97E−06 |
|  | TGI | 1.02E−07 | 1.55E−07 | 1.14E−05 | 3.32E−09 | 1.07E−09 | 3.91E−06 |
|  | LC$_{50}$ | 1.02E−06 | 1.57E−06 | 1.14E−05 | 2.31E−07 | 1.26E−07 | 7.74E−06 |
| IGROV-ET | GI$_{50}$ | 1.65E−07 | 1.38E−07 | 3.12E−06 | 2.54E−08 | 2.91E−09 | 2.85E−06 |
|  | TGI | 3.87E−07 | 3.52E−07 | 1.14E−05 | 8.24E−08 | 7.49E−09 | 5.24E−06 |
|  | LC$_{50}$ | 9.15E−07 | 8.98E−07 | 1.14E−05 | 1.54E−05 | 2.09E−06 | 9.67E−06 |
| SK-BR3 | GI$_{50}$ | 5.58E−08 | 4.73E−08 | 8.89E−07 | 5.27E−10 | 3.96E−10 | 2.63E−07 |
|  | TGI | 1.97E−07 | 1.64E−07 | 7.98E−06 | 2.29E−09 | 1.22E−09 | 1.66E−06 |
|  | LC$_{50}$ | 1.05E−06 | 1.22E−06 | 1.14E−05 | 2.67E−07 | 6.07E−08 | 7.52E−06 |
| K562 | GI$_{50}$ | 2.17E−08 | 2.83E−08 | 6.29E−07 | 3.12E−10 | 2.26E−10 | 6.94E−07 |
|  | TGI | 5.66E−08 | 1.35E−07 | 3.90E−06 | 2.49E−09 | 7.92E−08 | 2.20E−06 |
|  | LC$_{50}$ | 2.06E−07 | 2.69E−06 | 1.14E−05 | 9.51E−06 | 1.26E−07 | 6.81E−06 |
| PANC-1 | GI$_{50}$ | 9.28E−08 | 5.92E−08 | 6.55E−06 | 2.89E−09 | 8.07E−10 | 2.56E−06 |
|  | TGI | 1.45E−06 | 1.97E−07 | 1.14E−05 | 1.55E−08 | 6.68E−09 | 4.75E−06 |
|  | LC$_{50}$ | 1.42E−05 | 1.22E−05 | 1.14E−05 | 1.54E−05 | 1.77E−06 | 8.79E−06 |
| LOVO | GI$_{50}$ | 8.04E−08 | 6.63E−08 | 2.85E−06 | 2.00E−08 | 6.88E−10 | 1.89E−06 |
|  | TGI | 2.36E−07 | 2.12E−07 | 1.14E−05 | 8.07E−09 | 3.49E−09 | 3.76E−06 |
|  | LC$_{50}$ | 7.07E−07 | 6.87E−07 | 1.14E−05 | 1.54E−05 | 1.82E−06 | 7.39E−06 |
| LOVO-DOX | GI$_{50}$ | 4.31E−07 | 3.62E−07 | 4.09E−06 | 2.07E−07 | 9.05E−09 | 8.02E−07 |
|  | TGI | 1.42E−05 | 1.22E−06 | 1.14E−05 | 2.07E−06 | 1.48E−06 | 2.48E−06 |
|  | LC$_{50}$ | 1.42E−05 | 1.22E−05 | 1.14E−05 | 1.54E−05 | 7.21E−06 | 6.76E−06 |
| HELA | GI$_{50}$ | 9.78E−08 | 3.86E−08 | 6.30E−06 | 1.15E−09 | 6.78E−10 | 2.53E−07 |
|  | TGI | 2.75E−07 | 7.55E−08 | 1.14E−05 | 4.53E−09 | 2.04E−09 | 4.18E−07 |
|  | LC$_{50}$ | 7.86E−07 | 2.89E−07 | 1.14E−05 | 2.17E−08 | 1.12E−08 | 6.89E−07 |
| HELA-APL | GI$_{50}$ | 9.51E−08 | 5.59E−08 | 4.29E−06 | 1.86E−09 | 5.76E−10 | 3.39E−08 |
|  | TGI | 3.04E−07 | 1.30E−07 | 1.14E−05 | 5.50E−09 | 1.96E−09 | 6.05E−08 |
|  | LC$_{50}$ | 9.51E−07 | 6.82E−07 | 1.14E−05 | 1.95E−08 | 9.96E−09 | 1.08E−07 |

|  |  | 33 | 34 | 35 | 36 | 37 | 38 |
|---|---|---|---|---|---|---|---|
| A549 | GI$_{50}$ | 2.62E−08 | 5.53E−08 | 2.93E−06 | 5.56E−09 | 2.64E−08 | 4.73E−07 |
|  | TGI | 6.24E−08 | 1.84E−07 | 5.96E−06 | 2.29E−08 | 7.13E−08 | 1.42E−06 |
|  | LC$_{50}$ | 1.49E−07 | 6.11E−07 | 1.21E−05 | 8.38E−08 | 8.75E−07 | 4.71E−06 |
| HT29 | GI$_{50}$ | 1.73E−08 | 6.20E−08 | 6.02E−07 | 2.73E−09 | 2.90E−08 | 6.53E−07 |
|  | TGI | 2.71E−07 | 1.65E−07 | 8.18E−06 | 1.17E−08 | 2.62E−07 | 1.67E−06 |
|  | LC$_{50}$ | 9.81E−06 | 1.64E−06 | 1.44E−05 | 1.56E−05 | 1.05E−05 | 4.73E−06 |
| SW-620 | GI$_{50}$ |  |  |  |  |  |  |
|  | TGI |  |  |  |  |  |  |
|  | LC$_{50}$ |  |  |  |  |  |  |
| MEL-28 | GI$_{50}$ | 1.28E−08 | 3.27E−08 | 3.90E−07 | 1.84E−09 | 1.41E−08 | 2.72E−07 |
|  | TGI | 3.67E−08 | 6.03E−08 | 8.63E−07 | 4.01E−09 | 3.42E−08 | 4.83E−07 |
|  | LC$_{50}$ | 9.79E−08 | 1.11E−07 | 3.19E−06 | 8.71E−09 | 8.21E−08 | 8.60E−07 |
| OVCAR | GI$_{50}$ |  |  |  |  |  |  |
|  | TGI |  |  |  |  |  |  |
|  | LC$_{50}$ |  |  |  |  |  |  |
| A498 | GI$_{50}$ |  |  |  |  |  |  |
|  | TGI |  |  |  |  |  |  |
|  | LC$_{50}$ |  |  |  |  |  |  |

-continued

| | | | | | | | |
|---|---|---|---|---|---|---|---|
| DU145 | GI$_{50}$ | 8.02E−09 | 5.11E−08 | 5.70E−07 | 3.58E−09 | 7.50E−09 | 2.86E−07 |
| | TGI | 1.56E−08 | 9.87E−08 | 1.20E−06 | 9.55E−09 | 1.48E−08 | 5.64E−07 |
| | LC$_{50}$ | 4.41E−06 | 5.37E−08 | 1.03E−05 | 1.04E−05 | 4.43E−06 | 1.11E−06 |
| MCF | GI$_{50}$ | | | | | | |
| | TGI | | | | | | |
| | LC$_{50}$ | | | | | | |
| MB231 | GI$_{50}$ | | | | | | |
| | TGI | | | | | | |
| | LC$_{50}$ | | | | | | |
| H-MEC-1 | GI$_{50}$ | | | | | | |
| | TGI | | | | | | |
| | LC$_{50}$ | | | | | | |
| LNCAP | GI$_{50}$ | 2.86E−09 | 2.20E−08 | 1.89E−07 | 4.60E−10 | 2.86E−09 | 3.38E−07 |
| | TGI | 5.64E−09 | 5.21E−08 | 3.97E−07 | 1.37E−09 | 5.26E−09 | 5.18E−07 |
| | LC$_{50}$ | 1.11E−08 | 1.47E−07 | 8.34E−07 | 5.06E−09 | 9.67E−09 | 7.96E−07 |
| SK-OV3 | GI$_{50}$ | | | | | | |
| | TGI | | | | | | |
| | LC$_{50}$ | | | | | | |
| IGROV | GI$_{50}$ | 9.85E−08 | 2.92E−08 | 4.20E−07 | 1.12E−09 | 7.24E−09 | 3.81E−07 |
| | TGI | 4.26E−07 | 5.83E−08 | 1.69E−06 | 3.79E−09 | 2.63E−08 | 7.86E−07 |
| | LC$_{50}$ | 1.58E−06 | 1.17E−07 | 8.63E−06 | 1.04E−08 | 1.81E−06 | 4.18E−06 |
| IGROV-ET | GI$_{50}$ | | 8.95E−08 | 2.30E−06 | 2.77E−08 | 2.99E−08 | 3.65E−07 |
| | TGI | | 2.62E−07 | 6.35E−06 | 7.17E−08 | 1.04E−07 | 6.75E−07 |
| | LC$_{50}$ | | 8.60E−07 | 1.44E−05 | 1.56E−06 | 5.71E−06 | 1.48E−06 |
| SK-BR3 | GI$_{50}$ | 4.83E−09 | 1.27E−08 | 3.96E−07 | 2.87E−09 | 4.15E−09 | 1.94E−07 |
| | TGI | 1.39E−08 | 7.01E−08 | 1.10E−06 | 6.65E−09 | 1.01E−08 | 4.57E−07 |
| | LC$_{50}$ | 3.85E−07 | 6.26E−07 | 9.35E−06 | 1.54E−08 | 4.01E−07 | 1.07E−06 |
| K562 | GI$_{50}$ | 5.49E−09 | 1.62E−08 | 1.93E−07 | 2.46E−10 | 5.05E−09 | 1.93E−07 |
| | TGI | 1.59E−07 | 4.50E−08 | 1.13E−06 | 7.00E−10 | 1.37E−08 | 5.10E−07 |
| | LC$_{50}$ | 2.83E−06 | 1.46E−07 | 9.77E−06 | 5.11E−09 | 7.37E−07 | 1.54E−06 |
| PANC-1 | GI$_{50}$ | 1.99E−08 | 5.11E−08 | 4.71E−07 | 2.82E−09 | 3.09E−08 | 6.16E−07 |
| | TGI | 1.22E−07 | 1.23E−07 | 1.41E−06 | 9.72E−09 | 9.57E−08 | 1.38E−06 |
| | LC$_{50}$ | 4.51E−06 | 8.41E−07 | 1.44E−05 | 2.60E−06 | 2.69E−06 | 4.50E−06 |
| LOVO | GI$_{50}$ | 1.99E−08 | 2.87E−08 | 5.64E−07 | 2.12E−09 | 1.62E−08 | 3.58E−07 |
| | TGI | 5.36E−08 | 5.32E−08 | 2.14E−06 | 5.91E−09 | 1.18E−07 | 7.93E−07 |
| | LC$_{50}$ | 1.45E−07 | 9.86E−08 | 1.44E−05 | 1.56E−08 | 6.40E−06 | 2.51E−06 |
| LOVO-DOX | GI$_{50}$ | 3.67E−07 | 1.40E−07 | 5.75E−06 | 2.46E−07 | 8.68E−08 | 1.54E−06 |
| | TGI | 9.40E−07 | 4.10E−07 | 1.44E−05 | 1.09E−06 | 8.97E−07 | 3.08E−06 |
| | LC$_{50}$ | 5.90E−06 | 1.20E−05 | 1.44E−05 | 1.56E−05 | 6.96E−06 | 6.15E−06 |
| HELA | GI$_{50}$ | 5.02E−09 | 3.35E−08 | 3.96E−07 | 1.46E−09 | 4.04E−09 | 3.17E−07 |
| | TGI | 1.61E−08 | 6.24E−08 | 8.37E−07 | 3.85E−09 | 8.55E−09 | 5.45E−07 |
| | LC$_{50}$ | 9.69E−08 | 1.16E−07 | 3.39E−06 | 9.82E−09 | 4.73E−08 | 9.35E−07 |
| HELA-APL | GI$_{50}$ | 5.24E−09 | 3.39E−08 | 4.58E−07 | 1.85E−09 | 7.10E−09 | 2.95E−07 |
| | TGI | 1.91E−08 | 6.05E−08 | 1.09E−06 | 4.30E−09 | 2.06E−08 | 5.49E−07 |
| | LC$_{50}$ | 1.15E−07 | 1.08E−07 | 5.92E−06 | 1.00E−08 | 7.70E−08 | 1.02E−06 |

| | | 39 | 40 | 41 | 42 | 43 | 44 |
|---|---|---|---|---|---|---|---|
| A549 | GI$_{50}$ | 8.49E−09 | 1.95E−07 | 4.31E−08 | 5.74E−08 | 2.61E−08 | 2.74E−08 |
| | TGI | 4.51E−08 | 4.47E−07 | 7.35E−08 | 1.47E−07 | 6.21E−08 | 5.67E−08 |
| | LC$_{50}$ | 1.49E−06 | 1.03E−06 | 1.25E−07 | 2.37E−06 | 1.48E−07 | 4.70E−07 |
| HT29 | GI$_{50}$ | 5.34E−09 | 3.37E−07 | 4.27E−08 | 3.97E−08 | 2.42E−08 | 3.88E−08 |
| | TGI | 1.97E−07 | 1.05E−06 | 1.20E−07 | 1.31E−07 | 1.90E−07 | 1.54E−06 |
| | LC$_{50}$ | 3.77E−06 | 3.84E−06 | 1.47E−05 | 1.65E−05 | 1.67E−05 | 1.11E−05 |
| SW-620 | GI$_{50}$ | | | | | | |
| | TGI | | | | | | |
| | LC$_{50}$ | | | | | | |
| MEL-28 | GI$_{50}$ | 3.03E−09 | 1.62E−07 | 3.37E−08 | 3.01E−08 | 9.09E−09 | 2.34E−08 |
| | TGI | 5.43E−09 | 3.34E−07 | 6.45E−08 | 5.68E−08 | 3.27E−08 | 4.59E−08 |
| | LC$_{50}$ | 9.76E−09 | 6.88E−07 | 1.23E−07 | 1.07E−07 | 9.10E−08 | 9.01E−08 |
| OVCAR | GI$_{50}$ | | | | | | |
| | TGI | | | | | | |
| | LC$_{50}$ | | | | | | |
| A498 | GI$_{50}$ | | | | | | |
| | TGI | | | | | | |
| | LC$_{50}$ | | | | | | |
| DU145 | GI$_{50}$ | 3.52E−09 | 5.63E−06 | 4.53E−08 | 3.74E−08 | 1.36E−08 | 2.34E−08 |
| | TGI | 9.85E−09 | 1.60E−07 | 7.55E−08 | 8.25E−08 | 6.70E−08 | 7.19E−08 |
| | LC$_{50}$ | 2.01E−06 | 1.63E−06 | 2.74E−07 | 2.47E−07 | 2.92E−06 | 1.11E−05 |
| MCF | GI$_{50}$ | | | | | | |
| | TGI | | | | | | |
| | LC$_{50}$ | | | | | | |
| MB231 | GI$_{50}$ | | | | | | |
| | TGI | | | | | | |
| | LC$_{50}$ | | | | | | |
| H-MEC-1 | GI$_{50}$ | | | | | | |
| | TGI | | | | | | |
| | LC$_{50}$ | | | | | | |

-continued

|   |   |   |   |   |   |   |   |
|---|---|---|---|---|---|---|---|
| LNCAP | GI$_{50}$ | 7.35E−10 | 4.81E−08 | 9.50E−40 | 5.96E−09 | 6.58E−09 | 4.53E−09 |
|  | TGI | 2.49E−09 | 1.62E−07 | 3.14E−08 | 2.24E−08 | 2.02E−08 | 2.04E−08 |
|  | LC$_{50}$ | 6.73E−09 | 5.09E−07 | 9.28E−08 | 6.37E−08 | 8.87E−08 | 4.80E−08 |
| SK-OV3 | GI$_{50}$ |  |  |  |  |  |  |
|  | TGI |  |  |  |  |  |  |
|  | LC$_{50}$ |  |  |  |  |  |  |
| IGROV | GI$_{50}$ | 3.13E−09 | 9.13E−08 | 1.57E−08 | 2.86E−08 | 1.06E−08 | 3.26E−08 |
|  | TGI | 7.47E−09 | 3.17E−07 | 4.37E−08 | 6.63E−08 | 4.96E−08 | 7.80E−08 |
|  | LC$_{50}$ | 5.26E−07 | 1.28E−06 | 1.21E−07 | 1.53E−07 | 3.84E−07 | 1.11E−05 |
| IGROV-ET | GI$_{50}$ | 4.19E−08 | 2.89E−07 | 4.18E−08 | 2.80E−07 | 6.85E−08 | 4.92E−08 |
|  | TGI | 8.86E−08 | 5.33E−07 | 8.71E−08 | 1.02E−06 | 3.69E−07 | 4.43E−07 |
|  | LC$_{50}$ | 2.44E−06 | 9.80E−07 | 1.47E−05 | 1.65E−05 | 5.80E−06 | 1.11E−05 |
| SK-BR3 | GI$_{50}$ | 2.68E−09 | 4.26E−08 | 3.23E−08 |  | 5.83E−09 | 3.27E−09 |
|  | TGI | 6.98E−09 | 9.76E−08 | 7.22E−08 |  | 2.42E−08 | 1.19E−08 |
|  | LC$_{50}$ | 5.57E−08 | 5.24E−07 | 3.52E−07 |  | 1.64E−07 | 7.61E−08 |
| K562 | GI$_{50}$ | 1.06E−09 | 4.14E−08 | 2.04E−08 | 1.78E−08 | 3.11E−09 | 7.97E−09 |
|  | TGI | 5.58E−09 | 1.31E−07 | 5.05E−08 | 5.96E−08 | 1.38E−08 | 7.79E−08 |
|  | LC$_{50}$ | 6.98E−07 | 7.76E−07 | 1.25E−07 | 6.94E−07 | 8.95E−07 | 1.11E−05 |
| PANC-1 | GI$_{50}$ | 4.91E−09 | 3.21E−07 | 3.77E−08 | 3.90E−08 | 2.29E−08 | 7.52E−08 |
|  | TGI | 1.47E−08 | 7.47E−07 | 1.00E−07 | 1.15E−08 | 8.27E−08 | 3.44E−07 |
|  | LC$_{50}$ | 2.36E−06 | 2.57E−06 | 1.47E−05 | 5.27E−06 | 2.15E−06 | 1.11E−05 |
| LOVO | GI$_{50}$ | 3.72E−09 | 2.13E−07 | 3.78E−08 | 3.77E−08 | 3.12E−08 | 3.39E−08 |
|  | TGI | 9.00E−09 | 5.52E−07 | 9.40E−08 | 7.26E−08 | 8.67E−08 | 1.43E−07 |
|  | LC$_{50}$ | 9.71E−07 | 1.68E−06 | 1.47E−05 | 2.93E−06 | 1.67E−06 | 1.11E−05 |
| LOVO-DOX | GI$_{50}$ | 3.26E−07 | 3.54E−07 | 2.70E−07 | 5.15E−07 | 4.23E−07 | 2.97E−07 |
|  | TGI | 9.12E−07 | 8.10E−07 | 1.18E−06 | 1.44E−06 | 1.15E−06 | 9.19E−07 |
|  | LC$_{50}$ | 4.12E−06 | 2.79E−06 | 1.47E−05 | 1.65E−05 | 1.67E−05 | 1.11E−05 |
| HELA | GI$_{50}$ | 2.84E−09 | 1.11E−07 | 2.82E−08 | 2.81E−08 | 9.39E−09 | 2.02E−08 |
|  | TGI | 5.69E−09 | 2.76E−07 | 5.81E−08 | 6.25E−08 | 3.99E−08 | 4.20E−08 |
|  | LC$_{50}$ | 1.14E−08 | 6.61E−07 | 1.20E−07 | 1.39E−07 | 1.45E−07 | 8.75E−08 |
| HELA-APL | GI$_{50}$ | 2.76E−09 | 1.53E−07 | 3.01E−08 | 3.46E−08 | 2.41E−08 | 2.50E−08 |
|  | TGI | 5.20E−09 | 3.44E−07 | 6.31E−08 | 6.70E−08 | 7.32E−08 | 5.96E−08 |
|  | LC$_{50}$ | 9.82E−09 | 7.75E−07 | 1.32E−07 | 1.30E−07 | 4.23E−07 | 3.52E−07 |

|   |   | 45 | 46 | 47 | 48 | 49 | 50 |
|---|---|---|---|---|---|---|---|
| A549 | GI$_{50}$ | 1.62E−07 | 2.89E−08 | 1.02E−05 | 8.10E−06 | 1.84E−07 | 3.76E−06 |
|  | TGI | 4.13E−07 | 6.18E−08 | 1.02E−05 | 1.02E−05 | 4.31E−07 | 1.13E−05 |
|  | LC$_{50}$ | 1.50E−06 | 2.77E−06 | 1.02E−05 | 1.02E−05 | 1.01E−06 | 1.13E−05 |
| HT29 | GI$_{50}$ | 8.36E−08 | 4.29E−08 | 1.02E−05 | 6.71E−06 | 1.94E−07 | 8.90E−06 |
|  | TGI | 1.41E−06 | 1.17E−07 | 1.02E−05 | 1.02E−05 | 5.88E−07 | 1.13E−05 |
|  | LC$_{50}$ | 1.00E−05 | 1.17E−05 | 1.02E−05 | 1.02E−05 | 1.13E−05 | 1.13E−05 |
| SW-620 | GI$_{50}$ |  |  |  |  |  |  |
|  | TGI |  |  |  |  |  |  |
|  | LC$_{50}$ |  |  |  |  |  |  |
| MEL-28 | GI$_{50}$ | 1.17E−07 | 2.96E−08 | 8.70E−06 | 3.19E−06 | 1.81E−07 | 2.53E−06 |
|  | TGI | 2.85E−07 | 5.64E−08 | 1.02E−05 | 1.02E−05 | 3.56E−07 | 8.36E−06 |
|  | LC$_{50}$ | 6.89E−07 | 1.07E−07 | 1.02E−05 | 1.02E−05 | 7.01E−07 | 1.13E−05 |
| OVCAR | GI$_{50}$ |  |  |  |  |  |  |
|  | TGI |  |  |  |  |  |  |
|  | LC$_{50}$ |  |  |  |  |  |  |
| A498 | GI$_{50}$ |  |  |  |  |  |  |
|  | TGI |  |  |  |  |  |  |
|  | LC$_{50}$ |  |  |  |  |  |  |
| DU145 | GI$_{50}$ | 3.59E−08 | 2.34E−08 | 4.12E−06 | 2.55E−06 | 1.07E−07 | 1.80E−06 |
|  | TGI | 1.03E−07 | 4.96E−08 | 1.02E−05 | 6.26E−06 | 1.25E−06 | 9.18E−04 |
|  | LC$_{50}$ | 1.00E−05 | 1.05E−07 | 1.02E−05 | 1.02E−05 | 1.13E−05 | 1.13E−03 |
| MCF | GI$_{50}$ |  |  |  |  |  |  |
|  | TGI |  |  |  |  |  |  |
|  | LC$_{50}$ |  |  |  |  |  |  |
| MB231 | GI$_{50}$ |  |  |  |  |  |  |
|  | TGI |  |  |  |  |  |  |
|  | LC$_{50}$ |  |  |  |  |  |  |
| H-MEC-1 | GI$_{50}$ |  |  |  |  |  |  |
|  | TGI |  |  |  |  |  |  |
|  | LC$_{50}$ |  |  |  |  |  |  |
| LNCAP | GI$_{50}$ | 3.83E−09 | 1.47E−08 | 4.49E−07 | 1.67E−06 | 4.05E−08 | 9.48E−07 |
|  | TGI | 1.73E−08 | 2.96E−08 | 2.92E−06 | 3.24E−06 | 1.75E−07 | 3.68E−06 |
|  | LC$_{50}$ | 5.15E−08 | 5.92E−08 | 1.02E−05 | 6.31E−06 | 4.42E−07 | 1.13E−05 |
| SK-OV3 | GI$_{50}$ |  |  |  |  |  |  |
|  | TGI |  |  |  |  |  |  |
|  | LC$_{50}$ |  |  |  |  |  |  |
| IGROV | GI$_{50}$ | 5.69E−08 | 2.99E−08 | 4.22E−06 | 3.52E−06 | 1.65E−07 | 2.42E−06 |
|  | TGI | 3.92E−07 | 7.24E−08 | 1.02E−05 | 1.02E−05 | 4.32E−07 | 1.13E−05 |
|  | LC$_{50}$ | 1.00E−05 | 1.17E−05 | 1.02E−05 | 1.02E−05 | 1.13E−06 | 1.13E−03 |
| IGROV-ET | GI$_{50}$ | 8.65E−08 | 2.85E−07 | 4.92E−06 | 3.72E−06 | 2.80E−07 | 3.29E−06 |
|  | TGI | 4.97E−07 | 1.35E−06 | 1.02E−05 | 1.02E−05 | 6.16E−07 | 1.13E−05 |
|  | LC$_{50}$ | 1.00E−05 | 1.17E−05 | 1.02E−05 | 1.02E−05 | 1.13E−05 | 1.13E−05 |

-continued

| | | | | | | | |
|---|---|---|---|---|---|---|---|
| SK-BR3 | GI$_{50}$ | 2.83E−09 | 1.86E−08 | 3.01E−07 | 6.82E−07 | 4.96E−08 | 1.31E−05 |
| | TGI | 7.56E−09 | 5.32E−08 | 1.37E−06 | 4.00E−06 | 1.86E−06 | 1.13E−05 |
| | LC$_{50}$ | 1.33E−07 | 2.47E−07 | 1.02E−05 | 1.02E−05 | 1.13E−05 | 1.13E−05 |
| K562 | GI$_{50}$ | 1.76E−08 | 2.30E−08 | 1.73E−07 | 5.15E−07 | 3.77E−07 | 8.91E−07 |
| | TGI | 1.50E−07 | 6.48E−08 | 2.32E−06 | 2.73E−06 | 3.11E−07 | 1.13E−05 |
| | LC$_{50}$ | 1.00E−05 | 4.25E−06 | 1.02E−05 | 1.02E−05 | 5.10E−06 | 1.13E−05 |
| PANC-1 | GI$_{50}$ | 2.29E−07 | 6.19E−08 | 1.02E−05 | 4.42E−06 | 1.79E−07 | 2.45E−06 |
| | TGI | 1.24E−06 | 3.98E−07 | 1.02E−05 | 1.02E−05 | 5.64E−07 | 1.13E−05 |
| | LC$_{50}$ | 1.00E−05 | 1.17E−05 | 1.02E−05 | 1.02E−05 | 3.92E−06 | 1.13E−05 |
| LOVO | GI$_{50}$ | 1.30E−07 | 5.53E−08 | 9.16E−06 | 4.01E−06 | 2.50E−07 | 4.94E−06 |
| | TGI | 2.83E−07 | 3.04E−07 | 1.02E−05 | 1.02E−05 | 4.71E−07 | 1.13E−05 |
| | LC$_{50}$ | 6.14E−07 | 1.17E−05 | 1.02E−05 | 1.02E−05 | 8.90E−07 | 1.13E−05 |
| LOVO-DOX | GI$_{50}$ | 4.79E−07 | 4.26E−07 | 1.02E−05 | 1.02E−05 | 6.72E−07 | 1.01E−05 |
| | TGI | 3.14E−06 | 1.35E−06 | 1.02E−05 | 1.02E−05 | 1.13E−05 | 1.13E−05 |
| | LC$_{50}$ | 1.00E−05 | 1.17E−05 | 1.02E−05 | 1.02E−05 | 1.13E−05 | 1.13E−05 |
| HELA | GI$_{50}$ | 1.64E−08 | 2.64E−08 | 4.10E−06 | 2.17E−06 | 1.89E−07 | 3.75E−06 |
| | TGI | 3.62E−08 | 5.01E−08 | 1.02E−05 | 5.11E−06 | 4.18E−07 | 1.13E−05 |
| | LC$_{50}$ | 7.97E−08 | 9.74E−08 | 1.02E−05 | 1.02E−05 | 9.29E−07 | 1.13E−05 |
| HELA-APL | GI$_{50}$ | 2.84E−08 | 2.77E−08 | 3.74E−06 | 1.87E−06 | 1.82E−07 | 3.11E−06 |
| | TGI | 1.21E−07 | 5.20E−08 | 1.02E−05 | 3.83E−06 | 3.57E−07 | 1.13E−05 |
| | LC$_{50}$ | 7.83E−07 | 9.78E−08 | 1.02E−05 | 7.87E−06 | 7.01E−07 | 1.13E−05 |

| | | 51 | 52 | 53 | 54 | 55 | 56 |
|---|---|---|---|---|---|---|---|
| A549 | GI$_{50}$ | 2.85E−09 | 8.01E−09 | 3.34E−09 | 2.02E−08 | 6.84E−08 | 3.02E−08 |
| | TGI | 6.59E−09 | 5.78E−08 | 8.17E−09 | 6.63E−08 | 2.86E−07 | 6.87E−08 |
| | LC$_{50}$ | 5.42E−07 | 9.73E−07 | 2.21E−06 | 6.36E−07 | 1.22E−06 | 7.05E−07 |
| HT29 | GI$_{50}$ | 5.24E−09 | 6.14E−09 | 4.33E−09 | 2.99E−08 | 7.57E−08 | 4.88E−08 |
| | TGI | 2.37E−06 | 1.25E−06 | 1.83E−08 | 1.23E−07 | 1.81E−06 | 5.71E−07 |
| | LC$_{50}$ | 1.18E−08 | 7.78E−06 | 2.74E−06 | 1.20E−05 | 1.27E−05 | 1.20E−05 |
| SW-620 | GI$_{50}$ | | | | | | |
| | TGI | | | | | | |
| | LC$_{50}$ | | | | | | |
| MEL-28 | GI$_{50}$ | 2.71E−09 | 4.07E−09 | 2.21E−09 | 1.55E−08 | 8.86E−08 | 2.63E−08 |
| | TGI | 4.64E−09 | 1.55E−08 | 4.00E−09 | 3.61E−08 | 2.65E−07 | 4.90E−08 |
| | LC$_{50}$ | 7.94E−09 | 5.27E−08 | 7.20E−09 | 8.39E−08 | 6.98E−07 | 9.14E−08 |
| OVCAR | GI$_{50}$ | | | | | | |
| | TGI | | | | | | |
| | LC$_{50}$ | | | | | | |
| A498 | GI$_{50}$ | | | | | | |
| | TGI | | | | | | |
| | LC$_{50}$ | | | | | | |
| DU145 | GI$_{50}$ | 5.24E−09 | 4.92E−09 | 3.58E−09 | 3.76E−09 | 5.90E−08 | 4.10E−08 |
| | TGI | 1.63E−08 | 1.93E−08 | 2.43E−08 | 2.20E−08 | 2.47E−07 | 1.01E−07 |
| | LC$_{50}$ | 1.18E−05 | 5.14E−06 | 3.04E−06 | 1.20E−05 | 1.27E−05 | 1.20E−05 |
| MCF | GI$_{50}$ | | | | | | |
| | TGI | | | | | | |
| | LC$_{50}$ | | | | | | |
| MB231 | GI$_{50}$ | | | | | | |
| | TGI | | | | | | |
| | LC$_{50}$ | | | | | | |
| H-MEC-1 | GI$_{50}$ | | | | | | |
| | TGI | | | | | | |
| | LC$_{50}$ | | | | | | |
| LNCAP | GI$_{50}$ | 2.31E−09 | 2.39E−09 | 1.87E−09 | 7.42E−09 | 1.71E−08 | 1.22E−08 |
| | TGI | 3.96E−09 | 4.66E−09 | 3.95E−09 | 2.93E−08 | 3.60E−08 | 2.88E−08 |
| | LC$_{50}$ | 6.82E−09 | 9.06E−09 | 8.33E−09 | 1.09E−07 | 7.57E−08 | 6.77E−08 |
| SK-OV3 | GI$_{50}$ | | | | | | |
| | TGI | | | | | | |
| | LC$_{50}$ | | | | | | |
| IGROV | GI$_{50}$ | 3.35E−09 | 7.32E−09 | 2.74E−09 | 6.56E−09 | 6.92E−08 | 3.42E−08 |
| | TGI | 6.45E−09 | 4.33E−08 | 6.72E−09 | 3.94E−08 | 2.71E−07 | 6.93E−08 |
| | LC$_{50}$ | 1.18E−04 | 3.06E−06 | 2.74E−06 | 3.37E−06 | 1.58E−06 | 1.06E−06 |
| IGROV-ET | GI$_{50}$ | 4.36E−08 | 3.95E−08 | 1.02E−08 | 3.70E−08 | 2.48E−07 | 4.02E−08 |
| | TGI | 1.18E−07 | 1.19E−07 | 1.40E−06 | 1.20E−07 | 6.24E−07 | 7.97E−08 |
| | LC$_{50}$ | 1.18E−05 | 8.53E−06 | 6.45E−06 | 1.20E−05 | 4.18E−06 | 1.20E−05 |
| SK-BR3 | GI$_{50}$ | 5.05E−09 | 6.18E−09 | 2.95E−09 | 1.27E−08 | | 5.71E−09 |
| | TGI | 3.44E−07 | 2.58E−07 | 2.99E−08 | 1.54E−07 | | 1.86E−08 |
| | LC$_{50}$ | 1.18E−05 | 1.19E−05 | 1.82E−06 | 1.20E−05 | | 4.22E−07 |
| K562 | GI$_{50}$ | 3.15E−09 | 4.51E−09 | 1.54E−09 | 1.88E−09 | 5.84E−08 | 6.89E−09 |
| | TGI | 7.75E−09 | 2.13E−08 | 1.30E−08 | 5.18E−09 | 2.72E−07 | 8.68E−08 |
| | LC$_{50}$ | 6.53E−07 | 8.06E−08 | 5.83E−07 | 2.70E−06 | 1.04E−06 | 1.20E−05 |
| PANC-1 | GI$_{50}$ | 3.53E−09 | 2.15E−08 | 3.36E−09 | 2.30E−08 | 1.48E−07 | 9.02E−08 |
| | TGI | 7.73E−09 | 6.24E−08 | 1.01E−08 | 6.48E−08 | 1.90E−06 | 9.53E−07 |
| | LC$_{50}$ | 5.20E−07 | 6.10E−07 | 1.44E−06 | 5.31E−06 | 1.27E−05 | 1.20E−05 |
| LOVO | GI$_{50}$ | 3.93E−09 | 9.17E−09 | 3.82E−09 | 3.85E−09 | 1.51E−07 | 2.30E−08 |
| | TGI | 8.86E−09 | 2.96E−08 | 8.54E−09 | 1.44E−08 | 3.56E−07 | 4.82E−08 |
| | LC$_{50}$ | 1.18E−05 | 8.57E−08 | 2.94E−06 | 1.20E−05 | 8.37E−07 | 1.01E−07 |

-continued

| | | | | | | | |
|---|---|---|---|---|---|---|---|
| LOVO-DOX | $GI_{50}$ | 3.52E−07 | 2.73E−07 | 5.79E−08 | 3.38E−07 | 3.33E−07 | 3.33E−07 |
| | TGI | 1.18E−05 | 1.19E−05 | 1.45E−06 | 1.20E−05 | 1.57E−06 | 1.33E−06 |
| | $LC_{50}$ | 1.18E−05 | 1.19E−05 | 5.24E−06 | 1.20E−05 | 1.27E−05 | 1.20E−05 |
| HELA | $GI_{50}$ | 3.43E−09 | 5.98E−09 | 3.12E−09 | 2.19E−08 | 1.48E−07 | 2.71E−08 |
| | TGI | 6.63E−09 | 2.25E−08 | 7.55E−09 | 6.41E−08 | 3.63E−07 | 5.31E−08 |
| | $LC_{50}$ | 1.55E−08 | 1.85E−06 | 8.39E−08 | 3.76E−07 | 8.87E−07 | 1.04E−07 |
| HELA-APL | $GI_{50}$ | 3.49E−09 | 7.05E−09 | 2.99E−09 | 1.33E−08 | 1.11E−07 | 2.59E−08 |
| | TGI | 6.18E−09 | 2.14E−08 | 1.22E−08 | 1.43E−07 | 3.23E−07 | 5.83E−08 |
| | $LC_{50}$ | 1.09E−08 | 9.23E−08 | 3.89E−08 | 4.59E−07 | 9.15E−07 | 2.04E−07 |

| | | 57 | 58 | 59 | 60 | 61 | 62 |
|---|---|---|---|---|---|---|---|
| A549 | $GI_{50}$ | 3.74E−08 | 2.16E−07 | 1.59E−08 | 3.60E−09 | 2.43E−08 | 4.56E−09 |
| | TGI | 1.01E−07 | 5.17E−07 | 4.85E−08 | 1.31E−08 | 5.01E−08 | 1.65E−08 |
| | $LC_{50}$ | 1.50E−06 | 1.24E−06 | 2.73E−07 | 7.60E−08 | 1.04E−07 | 3.34E−07 |
| HT29 | $GI_{50}$ | 4.46E−08 | 2.97E−07 | 3.83E−09 | 2.28E−09 | 6.58E−09 | 4.03E−09 |
| | TGI | 4.38E−06 | 1.54E−06 | 1.60E−08 | 1.31E−08 | 1.40E−06 | 2.83E−07 |
| | $LC_{50}$ | 1.22E−05 | 1.24E−05 | 4.28E−06 | 1.28E−05 | 1.31E−05 | 1.25E−05 |
| SW-620 | $GI_{50}$ | | | | | | |
| | TGI | | | | | | |
| | $LC_{50}$ | | | | | | |
| MEL-28 | $GI_{50}$ | 2.93E−08 | 2.41E−07 | 3.56E−09 | 1.91E−09 | 6.19E−09 | 2.46E−09 |
| | TGI | 5.56E−08 | 4.69E−07 | 1.10E−08 | 4.27E−09 | 1.88E−08 | 4.92E−09 |
| | $LC_{50}$ | 1.06E−07 | 9.69E−07 | 3.04E−06 | 9.55E−09 | 6.07E−08 | 9.78E−09 |
| OVCAR | $GI_{50}$ | | | | | | |
| | TGI | | | | | | |
| | $LC_{50}$ | | | | | | |
| A498 | $GI_{50}$ | | | | | | |
| | TGI | | | | | | |
| | $LC_{50}$ | | | | | | |
| DU145 | $GI_{50}$ | 5.21E−08 | 4.68E−08 | 4.09E−09 | 1.80E−09 | 5.14E−09 | 3.30E−09 |
| | TGI | 1.22E−05 | 8.88E−08 | 1.02E−08 | 1.36E−06 | 9.34E−09 | 1.04E−08 |
| | $LC_{50}$ | 1.22E−05 | 1.24E−05 | 1.64E−06 | 7.13E−06 | 7.97E−06 | 3.59E−06 |
| MCF | $GI_{50}$ | | | | | | |
| | TGI | | | | | | |
| | $LC_{50}$ | | | | | | |
| MB231 | $GI_{50}$ | | | | | | |
| | TGI | | | | | | |
| | $LC_{50}$ | | | | | | |
| H-MEC-1 | $GI_{50}$ | | | | | | |
| | TGI | | | | | | |
| | $LC_{50}$ | | | | | | |
| LNCAP | $GI_{50}$ | 1.51E−08 | 2.99E−08 | 1.03E−09 | 4.15E−10 | 1.17E−09 | 3.01E−09 |
| | TGI | 3.23E−08 | 7.16E−08 | 2.67E−09 | 1.42E−09 | 2.94E−09 | 5.03E−09 |
| | $LC_{50}$ | 6.93E−08 | 2.40E−07 | 6.43E−09 | 5.03E−09 | 6.92E−09 | 8.40E−09 |
| SK-OV3 | $GI_{50}$ | | | | | | |
| | TGI | | | | | | |
| | $LC_{50}$ | | | | | | |
| IGROV | $GI_{50}$ | 2.88E−08 | 9.39E−08 | 3.01E−09 | 1.38E−09 | 4.82E−09 | 2.59E−09 |
| | TGI | 6.60E−08 | 3.05E−07 | 7.33E−09 | 4.03E−09 | 9.64E−09 | 6.55E−09 |
| | $LC_{50}$ | 6.48E−06 | 1.04E−06 | 1.10E−07 | 1.18E−08 | 5.25E−07 | 3.90E−06 |
| IGROV-ET | $GI_{50}$ | 2.52E−07 | 1.88E−07 | 4.48E−09 | 2.09E−08 | 2.25E−07 | 2.66E−08 |
| | TGI | 5.44E−07 | 4.22E−07 | 1.07E−07 | 5.31E−08 | 7.12E−07 | 6.95E−08 |
| | $LC_{50}$ | 1.17E−06 | 9.49E−07 | 3.04E−06 | 2.89E−06 | 4.77E−06 | 2.92E−06 |
| SK-BR3 | $GI_{50}$ | 6.42E−09 | 2.09E−08 | | 4.31E−10 | 4.28E−09 | 1.01E−09 |
| | TGI | 3.18E−08 | 7.50E−08 | | 1.22E−09 | 9.00E−09 | 4.74E−09 |
| | $LC_{50}$ | 3.82E−07 | 2.55E−06 | | 4.22E−08 | 2.45E−07 | 1.03E−07 |
| K562 | $GI_{50}$ | 8.82E−09 | 2.64E−08 | 1.80E−09 | 8.09E−10 | 2.56E−09 | 1.94E−09 |
| | TGI | 8.88E−08 | 9.42E−08 | 9.83E−09 | 1.32E−08 | 8.62E−09 | 1.10E−08 |
| | $LC_{50}$ | 1.22E−05 | 1.24E−05 | 3.29E−06 | 8.57E−06 | 6.42E−06 | 6.02E−06 |
| PANC-1 | $GI_{50}$ | 5.29E−08 | 3.79E−07 | 4.76E−09 | 3.31E−09 | 4.69E−09 | 3.86E−09 |
| | TGI | 1.34E−06 | 1.27E−06 | 4.23E−08 | 1.19E−08 | 1.54E−08 | 1.35E−08 |
| | $LC_{50}$ | 1.22E−05 | 1.24E−05 | 3.75E−06 | 1.28E−05 | 1.31E−05 | 4.75E−06 |
| LOVO | $GI_{50}$ | 8.59E−08 | 1.39E−07 | 5.80E−09 | 3.27E−09 | 1.71E−08 | 5.03E−09 |
| | TGI | 2.74E−07 | 2.85E−07 | 2.33E−08 | 8.23E−09 | 7.09E−08 | 1.79E−08 |
| | $LC_{50}$ | 8.77E−07 | 5.81E−07 | 1.19E−06 | 2.90E−06 | 8.23E−06 | 1.54E−06 |
| LOVO-DOX | $GI_{50}$ | 7.74E−07 | 4.83E−07 | 1.23E−07 | 1.63E−07 | 4.95E−07 | 1.36E−07 |
| | TGI | 6.22E−06 | 2.26E−06 | 7.09E−07 | 7.57E−07 | 1.76E−06 | 5.58E−07 |
| | $LC_{50}$ | 1.22E−05 | 1.24E−05 | 3.93E−06 | 1.28E−05 | 1.31E−05 | 1.31E−05 |
| HELA | $GI_{50}$ | 2.68E−08 | 3.94E−08 | 2.44E−09 | 1.03E−09 | 3.56E−09 | 2.37E−09 |
| | TGI | 5.64E−08 | 7.08E−08 | 5.08E−09 | 3.41E−09 | 6.49E−09 | 5.11E−09 |
| | $LC_{50}$ | 1.12E−07 | 1.65E−07 | 1.06E−08 | 1.28E−08 | 1.18E−08 | 1.10E−08 |
| HELA-APL | $GI_{50}$ | 2.23E−08 | 6.10E−08 | 3.32E−09 | 1.37E−09 | 2.98E−09 | 2.30E−09 |
| | TGI | 5.05E−08 | 1.90E−07 | 7.69E−09 | 3.58E−09 | 5.60E−09 | 4.88E−09 |
| | $LC_{50}$ | 1.15E−07 | 1.16E−06 | 5.92E−08 | 9.27E−09 | 1.05E−08 | 1.03E−08 |

-continued

|  |  | 63 | 64 | 65 | 66 | 67 | 68 |
|---|---|---|---|---|---|---|---|
| A549 | $GI_{50}$ | 2.40E−08 | 5.19E−09 | 2.29E−08 | 7.62E−09 | 3.27E−08 | 2.81E−08 |
|  | TGI | 6.14E−08 | 3.66E−08 | 5.60E−08 | 3.97E−08 | 6.87E−08 | 1.13E−07 |
|  | $LC_{50}$ | 2.73E−07 | 1.12E−06 | 3.13E−07 | 8.74E−07 | 7.97E−07 | 6.29E−06 |
| HT29 | $GI_{50}$ | 9.17E−09 | 3.58E−09 | 4.51E−09 | 5.86E−09 | 3.79E−08 | 6.66E−09 |
|  | TGI | 3.27E−07 | 1.32E−08 | 1.96E−07 | 1.81E−07 | 1.02E−07 | 1.50E−08 |
|  | $LC_{50}$ | 1.35E−05 | 1.30E−05 | 1.32E−05 | 1.32E−05 | 1.19E−05 | 1.42E−05 |
| SW-620 | $GI_{50}$ |  |  |  |  |  |  |
|  | TGI |  |  |  |  |  |  |
|  | $LC_{50}$ |  |  |  |  |  |  |
| MEL-28 | $GI_{50}$ | 5.64E−09 | 2.65E−09 | 3.78E−09 | 5.34E−09 | 2.04E−08 | 5.45E−09 |
|  | TGI | 1.70E−08 | 6.24E−09 | 1.08E−08 | 1.89E−08 | 4.53E−08 | 1.57E−08 |
|  | $LC_{50}$ | 5.26E−08 | 2.05E−08 | 4.20E−08 | 7.45E−08 | 1.00E−07 | 5.21E−08 |
| OVCAR | $GI_{50}$ |  |  |  |  |  |  |
|  | TGI |  |  |  |  |  |  |
|  | $LC_{50}$ |  |  |  |  |  |  |
| A498 | $GI_{50}$ |  |  |  |  |  |  |
|  | TGI |  |  |  |  |  |  |
|  | $LC_{50}$ |  |  |  |  |  |  |
| DU145 | $GI_{50}$ | 3.48E−09 | 2.89E−09 | 2.63E−09 | 3.39E−09 | 3.59E−08 | 4.68E−09 |
|  | TGI | 7.24E−09 | 1.53E−07 | 6.45E−09 | 1.60E−09 | 7.54E−08 | 1.50E−09 |
|  | $LC_{50}$ | 4.40E−06 | 1.30E−05 | 4.77E−06 | 3.86E−06 | 3.50E−06 | 1.42E−05 |
| MCF | $GI_{50}$ |  |  |  |  |  |  |
|  | TGI |  |  |  |  |  |  |
|  | $LC_{50}$ |  |  |  |  |  |  |
| MB231 | $GI_{50}$ |  |  |  |  |  |  |
|  | TGI |  |  |  |  |  |  |
|  | $LC_{50}$ |  |  |  |  |  |  |
| H-MEC-1 | $GI_{50}$ |  |  |  |  |  |  |
|  | TGI |  |  |  |  |  |  |
|  | $LC_{50}$ |  |  |  |  |  |  |
| LNCAP | $GI_{50}$ | 2.86E−09 | 1.02E−09 | 8.75E−10 | 1.99E−09 | 3.00E−09 | 1.59E−09 |
|  | TGI | 5.36E−09 | 2.67E−09 | 2.54E−09 | 3.83E−09 | 9.00E−09 | 3.70E−09 |
|  | $LC_{50}$ | 1.00E−08 | 6.12E−09 | 6.16E−09 | 7.39E−09 | 3.74E−08 | 8.64E−09 |
| SK-OV3 | $GI_{50}$ |  |  |  |  |  |  |
|  | TGI |  |  |  |  |  |  |
|  | $LC_{50}$ |  |  |  |  |  |  |
| IGROV | $GI_{50}$ | 5.40E−09 | 1.78E−09 | 4.07E−09 | 2.99E−09 | 3.12E−08 | 3.94E−09 |
|  | TGI | 1.50E−08 | 4.41E−09 | 1.14E−08 | 6.76E−09 | 7.86E−08 | 8.01E−09 |
|  | $LC_{50}$ | 4.49E−09 | 1.09E−08 | 2.99E−06 | 1.60E−07 | 6.85E−07 | 3.51E−08 |
| IGROV-ET | $GI_{50}$ | 7.59E−08 | 3.48E−08 | 7.60E−08 | 3.83E−08 | 2.68E−08 | 2.90E−07 |
|  | TGI | 5.37E−07 | 1.71E−07 | 4.06E−07 | 1.79E−07 | 6.27E−08 | 1.66E−06 |
|  | $LC_{50}$ | 1.33E−05 | 8.30E−06 | 3.30E−06 | 5.59E−06 | 2.68E−06 | 8.63E−06 |
| SK-BR3 | $GI_{50}$ | 3.93E−09 | 7.17E−10 | 2.97E−09 | 6.50E−09 | 8.71E−09 | 7.20E−09 |
|  | TGI | 8.98E−09 | 1.50E−07 | 7.66E−09 | 3.31E−07 | 3.74E−08 | 1.53E−07 |
|  | $LC_{50}$ | 1.98E−07 | 1.30E−05 | 2.09E−07 | 1.32E−05 | 2.84E−07 | 1.42E−05 |
| K562 | $GI_{50}$ | 3.86E−09 | 8.60E−10 | 1.22E−09 | 4.33E−09 | 3.39E−08 | 2.65E−09 |
|  | TGI | 7.92E−09 | 4.71E−09 | 1.39E−08 | 1.25E−08 | 3.97E−08 | 6.60E−09 |
|  | $LC_{50}$ | 6.34E−07 | 8.12E−07 | 7.80E−06 | 4.84E−07 | 2.09E−06 | 2.34E−07 |
| PANC-1 | $GI_{50}$ | 4.60E−09 | 2.46E−09 | 3.99E−09 | 4.57E−09 | 2.74E−08 | 3.90E−09 |
|  | TGI | 1.74E−08 | 1.09E−08 | 1.23E−08 | 2.34E−08 | 9.27E−08 | 1.28E−08 |
|  | $LC_{50}$ | 4.27E−06 | 1.30E−05 | 4.25E−06 | 6.40E−06 | 2.78E−06 | 2.07E−06 |
| LOVO | $GI_{50}$ | 8.63E−09 | 4.15E−09 | 6.78E−09 | 5.27E−09 | 2.86E−08 | 1.20E−08 |
|  | TGI | 5.48E−08 | 1.03E−08 | 3.69E−08 | 2.09E−08 | 7.30E−08 | 4.80E−08 |
|  | $LC_{50}$ | 1.35E−05 | 1.25E−05 | 2.96E−06 | 4.35E−06 | 1.06E−05 | 1.93E−06 |
| LOVO-DOX | $GI_{50}$ | 3.98E−07 | 3.20E−07 | 3.99E−07 | 3.70E−07 | 3.68E−07 | 4.72E−07 |
|  | TGI | 1.09E−06 | 2.76E−06 | 1.05E−06 | 1.89E−06 | 9.75E−07 | 1.42E−05 |
|  | $LC_{50}$ | 1.35E−05 | 1.30E−05 | 1.32E−05 | 1.32E−05 | 1.27E−05 | 1.42E−05 |
| HELA | $GI_{50}$ | 3.16E−09 | 2.40E−09 | 2.34E−09 | 2.41E−09 | 3.02E−08 | 4.00E−09 |
|  | TGI | 6.29E−09 | 4.89E−09 | 4.82E−09 | 4.68E−09 | 6.74E−08 | 7.06E−09 |
|  | $LC_{50}$ | 1.25E−08 | 1.00E−08 | 9.99E−09 | 9.07E−09 | 3.95E−07 | 1.24E−08 |
| HELA-APL | $GI_{50}$ | 1.10E−08 | 2.39E−09 | 2.00E−09 | 3.05E−09 | 2.97E−08 | 3.81E−09 |
|  | TGI | 3.98E−08 | 4.80E−09 | 4.10E−09 | 6.24E−09 | 6.47E−08 | 6.32E−09 |
|  | $LC_{50}$ | 1.50E−07 | 9.63E−09 | 8.46E−09 | 1.27E−08 | 3.27E−07 | 1.04E−08 |

|  |  | 69 | 70 | 71 | 72 | 73 | 74 |
|---|---|---|---|---|---|---|---|
| A549 | $GI_{50}$ | 5.57E−06 | 5.06E−06 | 2.11E−06 | 5.19E−08 | 3.25E−06 | 2.64E−06 |
|  | TGI | 2.23E−05 | 5.06E−05 | 1.05E−05 | 1.04E−07 | 6.05E−06 | 7.09E−06 |
|  | $LC_{50}$ | 5.57E−05 | 5.06E−05 | 3.16E−05 | 4.15E−06 | 1.13E−05 | 1.61E−05 |
| HT29 | $GI_{50}$ | 1.11E−06 | 1.01E−05 | 5.27E−06 | 1.04E−06 | 5.65E−06 | 5.32E−07 |
|  | TGI | 1.11E−06 | 1.01E−05 | 5.27E−06 | 1.04E−06 | 1.23E−05 | 1.61E−05 |
|  | $LC_{50}$ | 1.11E−05 | 5.06E−05 | 5.27E−05 | 5.19E−06 | 1.23E−05 | 1.61E−05 |
| SW-620 | $GI_{50}$ |  |  |  |  |  |  |
|  | TGI |  |  |  |  |  |  |
|  | $LC_{50}$ |  |  |  |  |  |  |

-continued

| | | | | | | | |
|---|---|---|---|---|---|---|---|
| MEL-28 | GI$_{50}$ | | | | | | |
| | TGI | | | | | | |
| | LC$_{50}$ | | | | | | |
| OVCAR | GI$_{50}$ | | | | | | |
| | TGI | | | | | | |
| | LC$_{50}$ | | | | | | |
| A498 | GI$_{50}$ | | | | | | |
| | TGI | | | | | | |
| | LC$_{50}$ | | | | | | |
| DU145 | GI$_{50}$ | | | | | | |
| | TGI | | | | | | |
| | LC$_{50}$ | | | | | | |
| MCF | GI$_{50}$ | | | | | | |
| | TGI | | | | | | |
| | LC$_{50}$ | | | | | | |
| MB231 | GI$_{50}$ | | | | | | |
| | TGI | | | | | | |
| | LC$_{50}$ | | | | | | |
| H-MEC-1 | GI$_{50}$ | | | | | 6.65E−06 | 2.64E−07 |
| | TGI | | | | | 1.23E−05 | 4.33E−06 |
| | LC$_{50}$ | | | | | 1.23E−05 | 1.61E−05 |
| LNCAP | GI$_{50}$ | | | | | | |
| | TGI | | | | | | |
| | LC$_{50}$ | | | | | | |
| SK-OV3 | GI$_{50}$ | | | | | | |
| | TGI | | | | | | |
| | LC$_{50}$ | | | | | | |
| IGROV | GI$_{50}$ | | | | | | |
| | TGI | | | | | | |
| | LC$_{50}$ | | | | | | |
| IGROV-ET | GI$_{50}$ | | | | | | |
| | TGI | | | | | | |
| | LC$_{50}$ | | | | | | |
| SK-BR3 | GI$_{50}$ | | | | | | |
| | TGI | | | | | | |
| | LC$_{50}$ | | | | | | |
| K562 | GI$_{50}$ | | | | | | |
| | TGI | | | | | | |
| | LC$_{50}$ | | | | | | |
| PANC-1 | GI$_{50}$ | | | | | | |
| | TGI | | | | | | |
| | LC$_{50}$ | | | | | | |
| LOVO | GI$_{50}$ | | | | | | |
| | TGI | | | | | | |
| | LC$_{50}$ | | | | | | |
| LOVO-DOX | GI$_{50}$ | | | | | | |
| | TGI | | | | | | |
| | LC$_{50}$ | | | | | | |
| HELA | GI$_{50}$ | | | | | | |
| | TGI | | | | | | |
| | LC$_{50}$ | | | | | | |
| HELA-APL | GI$_{50}$ | | | | | | |
| | TGI | | | | | | |
| | LC$_{50}$ | | | | | | |

| | | 75 | 76 | 77 | ET729 | ET594 | ET770 |
|---|---|---|---|---|---|---|---|
| A549 | GI$_{50}$ | 8.89E−07 | 4.13E−07 | 3.01E−07 | 1.82E−08 | 4.90E−08 | 3.24E−09 |
| | TGI | 4.01E−06 | 8.40E−07 | 7.28E−07 | 5.71E−08 | 1.31E−07 | 6.98E−09 |
| | LC$_{50}$ | 1.27E−05 | 4.65E−06 | 3.65E−06 | 1.34E−06 | 6.54E−07 | 5.20E−06 |
| HT29 | GI$_{50}$ | 3.30E−07 | 6.27E−07 | 1.89E−07 | 2.05E−09 | 4.90E−08 | 5.86E−09 |
| | TGI | 9.33E−07 | 1.30E−06 | 9.08E−07 | 1.91E−08 | 9.80E−08 | 1.30E−08 |
| | LC$_{50}$ | 1.61E−05 | 1.30E−05 | 1.31E−05 | 1.34E−05 | 1.63E−06 | 1.30E−05 |
| SW-620 | GI$_{50}$ | | | | | 3.27E−08 | |
| | TGI | | | | | 9.80E−08 | |
| | LC$_{50}$ | | | | | 3.27E−06 | |
| MEL-28 | GI$_{50}$ | | 2.38E−07 | 6.31E−08 | 7.52E−10 | 3.27E−08 | 2.63E−09 |
| | TGI | | 5.49E−07 | 1.75E−07 | 2.11E−09 | 6.54E−08 | 5.34E−09 |
| | LC$_{50}$ | | 1.27E−06 | 7.56E−07 | 7.07E−09 | 1.31E−07 | 1.08E−08 |
| OVCAR | GI$_{50}$ | | | | | 3.27E−08 | |
| | TGI | | | | | 1.14E−07 | |
| | LC$_{50}$ | | | | | 1.63E−05 | |
| A498 | GI$_{50}$ | | | | | 8.17E−08 | |
| | TGI | | | | | 3.27E−07 | |
| | LC$_{50}$ | | | | | 1.14E−05 | |
| DU145 | GI$_{50}$ | | 4.92E−07 | 3.01E−07 | 5.68E−10 | 3.27E−08 | 4.16E−09 |
| | TGI | | 1.34E−06 | 1.16E−06 | 3.17E−09 | 8.17E−08 | 3.20E−08 |
| | LC$_{50}$ | | 1.30E−05 | 1.31E−05 | 1.34E−05 | 1.63E−07 | 1.30E−05 |

-continued

| | | | | | | |
|---|---|---|---|---|---|---|
| MCF | $GI_{50}$ | | | | 3.27E−08 | |
| | TGI | | | | 9.80E−08 | |
| | $LC_{50}$ | | | | 3.27E−06 | |
| MB231 | $GI_{50}$ | | | | 3.27E−08 | |
| | TGI | | | | 1.14E−07 | |
| | $LC_{50}$ | | | | 1.63E−06 | |
| H-MEC-1 | $GI_{50}$ | 2.79E−07 | | | | |
| | TGI | 1.64E−06 | | | | |
| | $LC_{50}$ | 1.61E−05 | | | | |
| LNCAP | $GI_{50}$ | | 4.66E−08 | 4.35E−08 | 3.69E−10 | 1.48E−09 |
| | TGI | | 8.07E−08 | 7.10E−08 | 8.68E−10 | 3.06E−09 |
| | $LC_{50}$ | | 2.57E−07 | 1.18E−07 | 3.77E−09 | 6.34E−09 |
| SK-OV3 | $GI_{50}$ | | 5.47E−07 | 4.39E−07 | | |
| | TGI | | 1.90E−06 | 4.86E−06 | | |
| | $LC_{50}$ | | 1.30E−05 | 1.31E−05 | | |
| IGROV | $GI_{50}$ | | 1.97E−07 | 5.80E−08 | 4.13E−10 | 3.32E−09 |
| | TGI | | 6.48E−07 | 2.72E−07 | 9.86E−10 | 8.51E−09 |
| | $LC_{50}$ | | 5.25E−06 | 6.32E−06 | 7.45E−09 | 1.30E−05 |
| IGROV-ET | $GI_{50}$ | | 5.13E−07 | 6.52E−07 | 2.54E−08 | 1.21E−08 |
| | TGI | | 9.24E−07 | 1.70E−06 | 6.19E−08 | 4.50E−06 |
| | $LC_{50}$ | | 1.30E−06 | 1.31E−05 | 1.34E−05 | 1.30E−05 |
| SK-BR3 | $GI_{50}$ | | | | 3.98E−40 | 9.86E−10 |
| | TGI | | | | 8.60E−10 | 9.48E−08 |
| | $LC_{50}$ | | | | 7.11E−09 | 1.30E−05 |
| K562 | $GI_{50}$ | | 2.69E−08 | 1.66E−08 | 5.99E−10 | 1.65E−09 |
| | TGI | | 1.30E−07 | 1.01E−07 | 2.97E−09 | 8.02E−09 |
| | $LC_{50}$ | | 1.30E−05 | 1.31E−05 | 2.74E−06 | 6.63E−06 |
| PANC-1 | $GI_{50}$ | | 6.95E−07 | 4.18E−07 | 1.05E−09 | 5.53E−09 |
| | TGI | | 4.97E−06 | 2.72E−06 | 5.32E−09 | 1.15E−07 |
| | $LC_{50}$ | | 1.30E−05 | 1.31E−05 | 1.34E−06 | 1.30E−05 |
| LOVO | $GI_{50}$ | | 2.74E−07 | 2.41E−07 | 2.01E−09 | 3.09E−09 |
| | TGI | | 6.83E−07 | 9.17E−07 | 6.50E−09 | 5.93E−09 |
| | $LC_{50}$ | | 1.30E−06 | 1.31E−05 | 1.34E−05 | 1.14E−08 |
| LOVO-DOX | $GI_{50}$ | | 2.66E−06 | 9.29E−07 | 2.05E−07 | 7.41E−08 |
| | TGI | | 8.13E−06 | 5.66E−06 | 6.98E−07 | 1.30E−05 |
| | $LC_{50}$ | | 1.30E−05 | 1.31E−05 | 1.34E−05 | 1.30E−05 |
| HELA | $GI_{50}$ | | | | 3.33E−10 | 5.09E−09 |
| | TGI | | | | 6.75E−10 | 1.26E−08 |
| | $LC_{50}$ | | | | 1.78E−09 | 1.86E−07 |
| HELA-APL | $GI_{50}$ | | | | 3.41E−10 | 2.96E−09 |
| | TGI | | | | 6.79E−10 | 6.01E−09 |
| | $LC_{50}$ | | | | 1.58E−09 | 1.22E−08 |

| | | ET743 | ET745 | ET759B | ET637-quinone | ET594-quinone | ET736-quinone |
|---|---|---|---|---|---|---|---|
| A549 | $GI_{50}$ | 2.52E−09 | 7.43E−07 | 2.62E−08 | 4.42E−09 | 2.35E−06 | 2.56E−08 |
| | TGI | 5.51E−09 | 4.77E−06 | 6.13E−08 | 1.09E−08 | 4.91E−06 | 5.29E−08 |
| | $LC_{50}$ | 1.21E−08 | 1.34E−05 | 7.02E−07 | 5.15E−08 | 1.03E−05 | 1.09E−07 |
| HT29 | $GI_{50}$ | 3.41E−09 | 5.22E−07 | 4.19E−08 | 3.32E−09 | 6.53E−07 | 5.12E−08 |
| | TGI | 1.11E−08 | 2.65E−06 | 2.29E−06 | 7.78E−09 | 1.71E−06 | 1.28E−07 |
| | $LC_{50}$ | 1.31E−05 | 1.34E−05 | 1.29E−05 | 2.26E−06 | 1.63E−05 | 1.30E−05 |
| SW-620 | $GI_{50}$ | | | | | | |
| | TGI | | | | | | |
| | $LC_{50}$ | | | | | | |
| MEL-28 | $GI_{50}$ | 7.42E−10 | 6.02E−07 | 1.97E−08 | 2.96E−09 | 4.13E−07 | 1.23E−07 |
| | TGI | 3.06E−09 | 2.21E−06 | 4.91E−08 | 5.34E−09 | 7.38E−07 | 3.00E−07 |
| | $LC_{50}$ | 1.12E−08 | 8.62E−06 | 1.23E−07 | 9.61E−09 | 1.32E−06 | 7.18E−07 |
| OVCAR | $GI_{50}$ | | | | | | |
| | TGI | | | | | | |
| | $LC_{50}$ | | | | | | |
| A498 | $GI_{50}$ | | | | | | |
| | TGI | | | | | | |
| | $LC_{50}$ | | | | | | |
| DU145 | $GI_{50}$ | 6.18E−10 | 4.88E−07 | 3.91E−07 | 3.74E−09 | 1.99E−06 | 4.51E−08 |
| | TGI | 1.29E−09 | 2.67E−06 | 3.20E−06 | 6.30E−09 | 5.39E−06 | 7.63E−08 |
| | $LC_{50}$ | 4.33E−06 | 1.34E−05 | 1.19E−05 | 1.53E−08 | 1.46E−05 | 1.29E−07 |
| MCF | $GI_{50}$ | | | | | | |
| | TGI | | | | | | |
| | $LC_{50}$ | | | | | | |
| MB231 | $GI_{50}$ | | | | | | |
| | TGI | | | | | | |
| | $LC_{50}$ | | | | | | |
| H-MEC-1 | $GI_{50}$ | 9.03E−09 | 6.34E−07 | | | | |
| | TGI | 6.88E−08 | 3.67E−06 | | | | |
| | $LC_{50}$ | 1.31E−05 | 1.34E−05 | | | | |
| LNCAP | $GI_{50}$ | 2.30E−10 | 6.52E−07 | 4.64E−09 | 1.78E−09 | 2.74E−07 | 2.48E−08 |
| | TGI | 5.29E−10 | 2.39E−06 | 1.67E−08 | 3.64E−09 | 4.98E−07 | 4.46E−08 |
| | $LC_{50}$ | 1.22E−09 | 9.81E−06 | 5.22E−08 | 7.44E−09 | 9.01E−07 | 7.99E−08 |

-continued

| | | | | | | | |
|---|---|---|---|---|---|---|---|
| SK-OV3 | $GI_{50}$ | 1.31E−09 | 1.32E−06 | | | | |
| | TGI | 1.30E−08 | 5.48E−06 | | | | |
| | $LC_{50}$ | 1.31E−05 | 1.34E−05 | | | | |
| IGROV | $GI_{50}$ | 5.79E−10 | 7.74E−07 | 2.29E−08 | 2.76E−09 | 4.52E−07 | 6.71E−08 |
| | TGI | 2.60E−09 | 3.26E−06 | 6.52E−08 | 5.80E−09 | 9.58E−07 | 2.15E−07 |
| | $LC_{50}$ | 1.03E−08 | 1.34E−05 | 1.00E−05 | 1.21E−08 | 3.64E−06 | 7.35E−07 |
| IGROV-ET | $GI_{50}$ | 4.29E−09 | 3.70E−06 | 5.82E−08 | 3.42E−08 | 4.37E−06 | 5.10E−07 |
| | TGI | 7.86E−09 | 8.45E−06 | 2.73E−07 | 6.91E−08 | 9.11E−06 | 7.82E−07 |
| | $LC_{50}$ | 1.86E−08 | 1.34E−05 | 1.71E−06 | 1.39E−07 | 1.63E−05 | 1.20E−06 |
| SK-BR3 | $GI_{50}$ | 4.79E−10 | 6.29E−07 | 5.37E−09 | 7.58E−40 | 3.02E−07 | 5.33E−09 |
| | TGI | 1.72E−09 | 3.15E−06 | 1.16E−08 | 2.67E−09 | 5.93E−07 | 1.13E−08 |
| | $LC_{50}$ | 8.57E−09 | 1.34E−05 | 8.81E−08 | 8.51E−09 | 1.16E−06 | 1.92E−07 |
| K562 | $GI_{50}$ | 3.47E−10 | 8.84E−07 | 6.00E−09 | 5.66E−40 | 1.37E−07 | 4.96E−09 |
| | TGI | 6.05E−10 | 3.90E−06 | 3.79E−08 | 1.97E−09 | 4.78E−07 | 1.37E−08 |
| | $LC_{50}$ | 1.06E−09 | 1.34E−05 | 1.29E−05 | 1.44E−08 | 1.62E−06 | 1.05E−07 |
| PANC-1 | $GI_{50}$ | 1.59E−09 | 1.32E−06 | 3.55E−08 | 3.72E−09 | 1.58E−06 | 3.94E−07 |
| | TGI | 6.34E−09 | 9.22E−06 | 1.22E−07 | 8.24E−09 | 4.86E−06 | 9.57E−07 |
| | $LC_{50}$ | 3.99E−08 | 1.34E−05 | 1.10E−05 | 3.42E−09 | 1.49E−05 | 1.30E−05 |
| LOVO | $GI_{50}$ | 1.56E−09 | 5.55E−06 | 3.27E−07 | 3.98E−09 | 7.59E−07 | 2.65E−07 |
| | TGI | 4.23E−09 | 1.34E−05 | 6.21E−08 | 8.51E−09 | 2.91E−06 | 5.96E−07 |
| | $LC_{50}$ | 1.14E−08 | 1.34E−05 | 1.18E−07 | 6.08E−06 | 1.63E−05 | 1.30E−06 |
| LOVO-DOX | $GI_{50}$ | 2.95E−08 | 6.25E−06 | 1.92E−07 | 2.62E−07 | 6.27E−06 | 7.47E−07 |
| | TGI | 1.10E−07 | 1.34E−05 | 6.25E−07 | 9.62E−08 | 1.31E−05 | 3.28E−06 |
| | $LC_{50}$ | 1.31E−05 | 1.34E−05 | 1.29E−05 | 9.00E−08 | 1.63E−05 | 1.30E−05 |
| HELA | $GI_{50}$ | | | 2.13E−08 | 2.24E−08 | 3.43E−07 | 3.32E−06 |
| | TGI | | | 6.42E−08 | 4.88E−09 | 6.20E−08 | 6.14E−06 |
| | $LC_{50}$ | | | 5.27E−07 | 1.06E−08 | 1.12E−06 | 1.14E−07 |
| HELA-APL | $GI_{50}$ | | | 3.59E−08 | 2.39E−09 | 3.98E−07 | 5.55E−08 |
| | TGI | | | 1.02E−07 | 5.12E−09 | 6.74E−07 | 7.84E−08 |
| | $LC_{50}$ | | | 1.04E−06 | 1.09E−08 | 1.14E−06 | 1.11E−07 |

The invention claimed is:

1. A compound of formula:

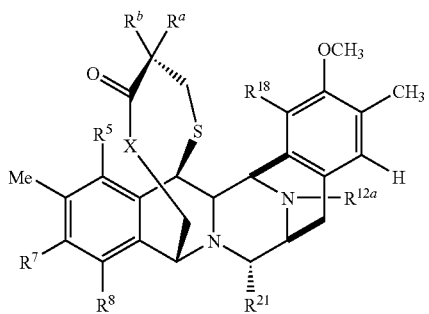

wherein $R^a$ and $R^b$ together with the carbon to which they are attached form a group of formula:

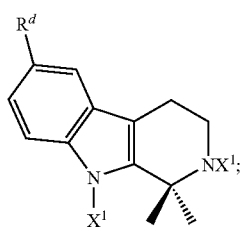

where $R^d$ is a substituted or unsubstituted R', OR', —(C=O)R', substituted or unsubstituted alkyl, substituted or unsubstituted alkoxy, substituted or unsubstituted alkenyl, substituted or unsubstituted alkynyl, substituted or unsubstituted aryl, or substituted or unsubstituted aralkyl; wherein R' is selected from the group consisting of OH, $NO_2$, $NH_2$, SH, CN, halogen, C(=O)H, C(=O)$CH_3$, $CO_2H$, $CO_2CH_3$, $C_1$-$C_6$ alkyl, alkenyl, alkynyl, aryl, aralkyl and heterocyclic;

each $X^1$ in:

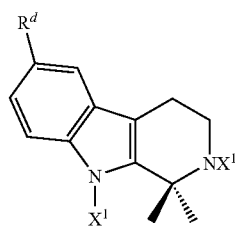

is independently selected from hydrogen or substituted or unsubstituted R', OR', —(C=O)R', substituted or unsubstituted alkyl, substituted or unsubstituted alkoxy, substituted or unsubstituted alkenyl, substituted or unsubstituted alkynyl, substituted or unsubstituted aryl, and substituted or unsubstituted aralkyl; wherein R' is selected from the group consisting of H, OH, $NO_2$, $NH_2$, SH, CN, halogen, C(=O)H, C(=O)$CH_3$, $CO_2H$, $CO_2CH_3$, $C_1$-$C_6$ alkyl, alkenyl, alkynyl, aryl, aralkyl and heterocyclic;

$R^7$ is —$OCH_3$ and $R^8$ is —OH or $R^7$ and $R^8$ together form a group —O—$CH_2$—O—;

$R^{12a}$ is hydrogen, acyl, alkenyl, or alkyl-O—CO—;

$R^{21}$ is —H, OH or CN;

X is —O— or —NH—;

$R^5$ and $R^{18}$ are each —$OX^1$, wherein each $X^1$ is independently selected from hydrogen, substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, or —C(=O)R' wherein R' is selected from hydrogen, OH, $NO_2$, $NH_2$, SH, CN, halogen, $C_1$-$C_6$ alkyl, alkenyl, alkynyl, aryl, aralkyl, and heterocyclic.

2. A compound according to claim 1 wherein each $X^1$ in:

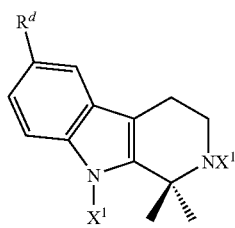

is, independently, hydrogen or $C_1$-$C_6$ alkyl.

3. A compound according to claim 1 wherein $R^d$ is substituted or unsubstituted alkyl, substituted or unsubstituted alkoxy, substituted or unsubstituted alkenyl, substituted or unsubstituted alkynyl, substituted or unsubstituted aryl, or substituted or unsubstituted aralkyl.

4. A compound according to claim 3 wherein $R^d$ is alkyl or alkoxy.

5. A compound according to claim 4 wherein $R^d$ is methyl or methoxy.

6. A compound according to claim 1 wherein $R^5$ is an acyloxy group.

7. A compound according to claim 6 wherein $R^5$ is acetyloxy.

8. A compound according to claim 1 wherein $R^7$ and $R^8$ together form a group —O—$CH_2$—O—.

9. A compound according to claim 1 wherein $R^{12a}$ is hydrogen, alkyl-CO—, allyl, or t-BOC.

10. A compound according to claim 1 wherein $R^{21}$ is —OH.

11. A compound according to claim 1, wherein $R^{21}$ is —CN.

12. A compound according to claim 1, wherein X is —O—.

13. A compound according to claim 1, wherein $R^{18}$ is OH.

14. A compound according to claim 1, wherein $R^5$ and $R^{18}$ are each —$OX^1$, wherein each $X^1$ is independently selected from hydrogen, substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, or —C(=O)R' wherein R' is selected from $C_1$-$C_6$ alkyl, alkenyl, alkynyl, aryl, aralkyl, and heterocyclic.

15. A compound according to claim 1, of formula:

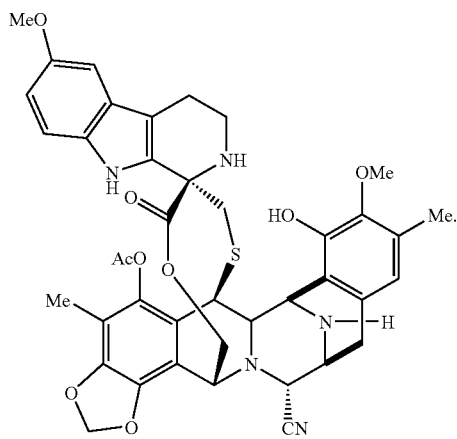

16. A compound according to claim 1, of formula:

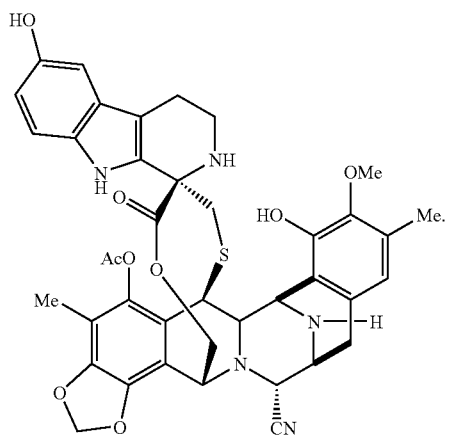

17. A compound according to claim 1, of formula:

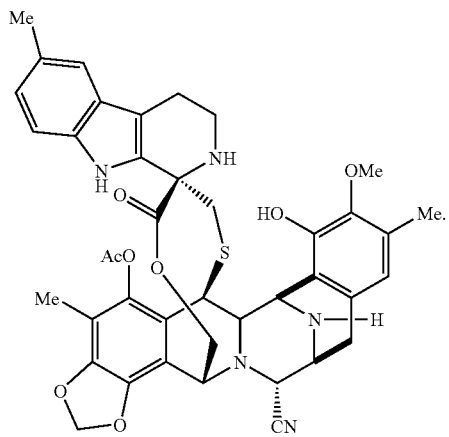

18. A compound according to claim 1 of formula:

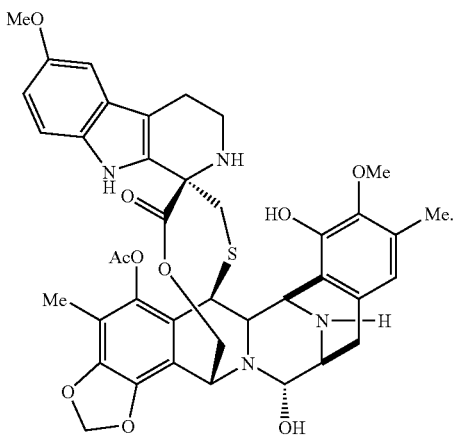

19. A compound according to claim 1, of formula:

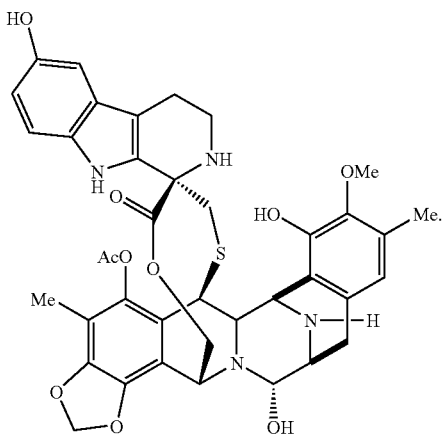

20. A compound according to claim 1, of formula:

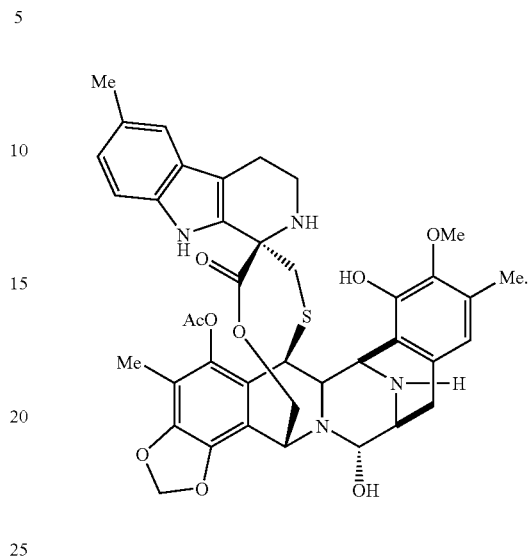

21. A pharmaceutical composition comprising a compound according to claim 1, and a pharmaceutical carrier.

22. A method for the treatment of cancer in a mammal affected by cancer, the method comprising administering to the mammal a therapeutically effective amount of a compound of claim 1 or a pharmaceutical composition of claim 21, wherein said cancer is selected from the group consisting of leukaemia, lung cancer, colon cancer, kidney cancer, melanoma, prostate cancer, ovarian cancer, breast cancer, pancreatic epitheloid carcinoma, and cervix epitheloid carcinoma.

* * * * *